US012774323B2

(12) United States Patent
Quiroz et al.

(10) Patent No.: US 12,774,323 B2
(45) Date of Patent: Oct. 27, 2026

(54) ANTI-APOLIPOPROTEIN E (APOE) ANTIBODIES AND POLYNUCLEOTIDES THEREOF

(71) Applicants: The General Hospital Corporation, Boston, MA (US); Banner Health, Phoenix, AZ (US); Massachusetts Eye and Ear Infirmary, Boston, MA (US)

(72) Inventors: Yakeel T. Quiroz, Charlestown, MA (US); Joseph F. Arboleda-Velasquez, Newton, MA (US); Eric Reiman, Phoenix, AZ (US); Francisco Lopera, Medellin (CO)

(73) Assignees: The General Hospital Corporation, Boston, MA (US); Banner Health, Boston, MA (US); Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 18/611,325

(22) Filed: Mar. 20, 2024

(65) Prior Publication Data

US 2024/0287165 A1 Aug. 29, 2024

Related U.S. Application Data

(63) Continuation of application No. 17/614,008, filed as application No. PCT/US2020/034978 on May 28, 2020, now Pat. No. 12,384,834.

(60) Provisional application No. 62/873,019, filed on Jul. 11, 2019, provisional application No. 62/853,676, filed on May 28, 2019.

(51) Int. Cl.

| | |
|---|---|
| ***A61K 39/00*** | (2006.01) |
| ***A61K 39/395*** | (2006.01) |
| ***A61P 25/28*** | (2006.01) |
| ***C07K 14/775*** | (2006.01) |
| ***C07K 16/00*** | (2006.01) |
| ***C07K 16/18*** | (2006.01) |
| ***C12N 15/00*** | (2006.01) |
| ***C12N 15/62*** | (2006.01) |

(52) U.S. Cl.

CPC ............ *C07K 16/18* (2013.01); *A61K 39/395* (2013.01); *A61P 25/28* (2018.01); *C07K 14/775* (2013.01); *C12N 15/00* (2013.01); *C12N 15/62* (2013.01); *A61K 2039/505* (2013.01); *A61K 2039/515* (2013.01); *A61K 2039/6018* (2013.01); *C07K 2317/24* (2013.01); *C07K 2317/34* (2013.01); *C07K 2317/56* (2013.01); *C07K 2317/565* (2013.01); *C07K 2317/92* (2013.01); *C07K 2319/30* (2013.01)

(58) Field of Classification Search

CPC .......... C07K 2317/622; C07K 2317/24; C07K 2317/34; C07K 16/18; C07K 14/775; A61K 2039/505; A61K 39/0012; A61P 25/28; A61P 25/00

See application file for complete search history.

(56) References Cited

U.S. PATENT DOCUMENTS

| | | | |
|---|---|---|---|
| 4,399,216 A | 8/1983 | Axel et al. | |
| 4,522,811 A | 6/1985 | Eppstein et al. | |
| 4,634,665 A | 1/1987 | Axel et al. | |
| 5,057,313 A | 10/1991 | Shih et al. | |
| 5,156,840 A | 10/1992 | Goers et al. | |
| 5,179,017 A | 1/1993 | Axel et al. | |
| 5,508,167 A | 4/1996 | Roses et al. | |
| 5,641,640 A | 6/1997 | Hanning | |
| 5,869,046 A | 2/1999 | Presta et al. | |
| 6,468,798 B1 | 10/2002 | Debs et al. | |
| 6,503,713 B1 | 1/2003 | Rana | |
| 8,058,016 B2 | 11/2011 | Nordstedt et al. | |
| 8,741,298 B2 | 6/2014 | Schenk et al. | |
| 2005/0079574 A1 | 4/2005 | Bond | |
| 2006/0073104 A1 | 4/2006 | Mahley et al. | |
| 2007/0104715 A1 | 5/2007 | Nordstedt et al. | |
| 2012/0100140 A1 | 4/2012 | Reyes et al. | |
| 2012/0204275 A1 | 8/2012 | Schenk et al. | |
| 2022/0227852 A1* | 7/2022 | Quiroz | C07K 16/18 |
| 2024/0301044 A1* | 9/2024 | Quiroz | A61P 25/28 |

FOREIGN PATENT DOCUMENTS

| | | |
|---|---|---|
| EP | 3309550 | 4/2018 |
| JP | 2008-502311 | 1/2008 |
| JP | 2020-531010 A | 11/2020 |
| WO | WO 1988/009344 | 12/1988 |
| WO | WO 1989/009622 | 10/1989 |
| WO | WO 1990/007861 | 7/1990 |
| WO | WO 1991/010741 | 7/1991 |
| WO | WO 1994/002602 | 2/1994 |
| WO | WO 1996/033735 | 10/1996 |
| WO | WO 1996/034096 | 10/1996 |
| WO | WO 2007/067809 | 6/2007 |
| WO | WO 2012/075422 | 6/2012 |

(Continued)

OTHER PUBLICATIONS

MacCallum et al., J. Mol. Biol., 1996; 262: 732-745.*

(Continued)

*Primary Examiner* — Chang-Yu Wang

(74) *Attorney, Agent, or Firm* — Fish & Richardson P.C.

(57) ABSTRACT

Methods and compositions for preventing or treating cognitive decline associated with dementia and/or mild cognitive impairment and/or neurodegeneration using antibodies, peptides, fusion proteins, or genome editing systems that modulate HSPG/heparin binding affinities of ApoE.

9 Claims, 58 Drawing Sheets

Specification includes a Sequence Listing.

(56) References Cited

FOREIGN PATENT DOCUMENTS

| | | | |
|---|---|---|---|
| WO | WO 2013/181618 | | 12/2013 |
| WO | WO 2015/054653 | | 4/2015 |
| WO | WO 2018/026976 | | 2/2018 |
| WO | WO 2018/081642 | A1 | 5/2018 |
| WO | WO 2019/197676 | | 10/2019 |

OTHER PUBLICATIONS

Pascalis et al.,The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al., J of Cell Bio. 1990, 111:2129-2138.*
Pawson et al., 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Office Action in Japanese Appln. No. 2021-570726, dated May 7, 2024, 10 pages (with English translation).
Yamada and Itoh, "Epitope Analysis of Anti-Serum Protein Antibodies and its Application for Amyloidosis Research," Jpn J Clin Pathol, May 1998, 46(5):456-460 (with English abstract).
Yamada et al., "Further Characterization of a Monoclonal Antibody Recognizing Apolipoprotein E Peptides in Amyloid Deposits," Annals of Clinical and Laboratory Science, 1997, 27(4):.276-281.
Office Action in Chinese Appln. No. 202080054661.6, dated Jun. 19, 2024, 9 pages (with English translation).
Alaoui-Ismaili et al., "Design of second generation therapeutic recombinant bone morphogenetic proteins," Cytokine Growth Factor Rev., Oct.-Dec. 2009, 20(5-6-):501-507.
Antibody Engineering, 2nd ed., Kontermann et al. (eds), 2010, 578 pages.
Bowie et al., "Deciphering the message in protein sequences: tolerance to amino acid substitutions," Science, Mar. 1990, 247(4948):1306-1310.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol., 1990, 111(5):2129-2138.
Casset et al., "A peptide mimetic of an anti-CD4 monoclonal antibody by rational design," BBRC, Jul. 2003, 307(1):198-205.
Chen et al., "Selection and analysis of an optimized anti-VEGF antibody: crystal structure of an affinity-matured Fab in complex with antigen," J. Mol. Bio., Nov. 1999, 293(4):865-881.
De Pascalis et al., "Grafting of "abbreviated" complementarity-determining regions containing specificity-determining residues essential for ligand contact to engineer a less immunogenic humanized monoclonal antibody," The Journal of Immunology, Sep. 2002, 169(6):3076-3084.
Guo et al., "Protein tolerance to random amino acid change," PNAS, Jun. 2004, 101(25):9205-9210.
Holm et al., "Functional mapping and single chain construction of the anti-cytokeratin 8 monoclonal antibody TS1," Mol. Immunol., Feb. 2007, 44(6):1075-1084.
MacCallum et al., "Antibody-antigen interactions: contact analysis and binding site topography," J. Mol. Biol., 1996, 262(5):732-745.
Pawson et al., "Assembly of cell regulatory systems through protein interaction domains," Science, Apr. 2003, 300(5618):445-452.
Rudikoff et al., "Single amino acid substitution altering antigen-binding specificity," Proc. Natl. Acad. Sci. USA, Mar. 1982, 79(6):1979-83.
Vajdos et al., "Comprehensive Functional Maps of the Antigen-binding Site of an Anti-ErbB2 Antibody Obtained with Shotgun Scanning Mutagenesis," J. Mol. Biol., Jul. 2002, 320(2):415-428.
Wu et al., "Humanization of a murine monoclonal antibody by simultaneous optimization of framework and CDR residues," J. Mol. Biol., Nov. 1999, 294(1):151-162.
Acosta-Baena et al., "Pre-dementia clinical stages in presenilin 1 E280A familial early-onset Alzheimer's disease: a retrospective cohort study," Lancet Neurol, Mar. 2011, 10(3):213-220.
Aguirre-Acevedo et al., "English Abstract: Validity and reliability of the CERAD-Col neuropsychological battery," Rev Neurol, Dec. 2007, 45(11):655-660, 1 page (English Abstract Only).
Alberer et al., "Safety and immunogenicity of a mRNA rabies vaccine in healthy adults: an open-label, non-randomised, prospective, first-in-human phase 1 clinical trial," Lancet, Sep. 2017, 390(10101):1511-1520, 10 pages.
Albert et al., "The diagnosis of mild cognitive impairment due to Alzheimer's disease: recommendations from the National Institute on Aging-Alzheimer's Association workgroups on diagnostic guidelines for Alzheimer's disease," Alzheimers Dement, 2011, 7(3): 270-279.
Allocca et al., "Novel adeno-associated virus serotypes efficiently transduce murine photoreceptors," J. Viral., Oct. 2007, 81(20):11372-11380.
Amariglio et al., "Subjective cognitive concerns, amyloid-β, and neurodegeneration in clinically normal elderly," Neurology, 2015, 85:56-62.
Arboleda-Velasquez et al., "Resistance to autosomal dominant Alzheimer's disease in an APOE3 Christchurch homozygote: a case report," Nature Medicine, Nov. 2019, 25(11):1680-1683.
Asokan et al., "The AAV Vector Toolkit: Poised at the Clinical Crossroads," Mol Ther., Apr. 2012, 20(4):699-708.
Baek et al., "GalaxyHomomer: a web server for protein homo-oligomer structure prediction from a monomer sequence or structure," Nucleic Acids Res, Jul. 2017, 45(W1):W320-W324.
Bateman et al., "Autosomal-dominant Alzheimer's disease: a review and proposal for the prevention of Alzheimer's disease," Alzheimer's Research & Therapy, Jan. 2011, 3(1): 13 pages.
Becker et al., "Amyloid-β associated cortical thinning in clinically normal elderly," Ann Neural., Jun. 2011, 69(6):1032-42.
Beecham et al., "Genome-Wide Association Meta-analysis of Neuropathologic Features of Alzheimer's Disease and Related Dementias," PLoS Genet., Sep. 2014, 10(9):e1004606, 15 pages.
Berlau et al., "APOE ε2 is associated with intact cognition but increased Alzheimer pathology in the oldest old," Neurology, Mar. 2009, 72(9):829-34.
Bettcher et al., "MCP-1 and eotaxin-1 selectively and negatively associate with memory in MCI and Alzheimer's disease dementia phenotypes," Alzheimers Dement (Arnst), Jun. 2016, 3:91-7.
Better et al., "*Escherichia coli* Secretion of an Active Chimeric Antibody Fragment," Science, May 1988, 240(4855):1041-1043.
Better et al., "Expression of engineered antibodies and antibody fragments in microorganisms," Methods in Enzymology, 1989, 178(33):476-496.
Bird et al., "Single chain antibody variable regions," TIBTECH, Apr. 1991, 9(1):132-137.
Braak et al., "Diagnostic Criteria for Neuropathologic Assessment of Alzheimer's Disease," Neurobiol Aging, Jul.-Aug. 1997, 18(4 Suppl):S85-88.
Braak et al., "Vulnerability of cortical neurons to Alzheimer's and Parkinson's diseases," J Alzheimers Dis., 2006, 9(3 Suppl):35-44.
Breslow et al., "Studies of familial type III hyperlipoproteinemia using as a genetic marker the apoE phenotype E2/2," J Lipid Res., Nov. 1982, 23(8):1224-35.
Bugiani et al., "Frontotemporal dementia and corticobasal degeneration in a family with a P301S mutation in tau," J Neuripathol Exp Neurol., 1999, 58(6):667-77.
Burgess et al., "ApoE of the HepG2 Cell Surface Includes a Major Pool Associated with Chondroitin Sulfate Proteoglycans," Biochemistry, Dec. 1998, 38(2):524-531.
Cacace et al., "Molecular genetics of early-onset Alzheimer's disease revisited," Alzheimers Dement., Jun. 2016, 12(6):733-748.
Candas-Estebanez et al., "APOE Variants E2, E3, and E4 Can Be Miscalled By Classical PCR-RFLP When The Christchurch Variant Is Also Present," J Clin Lab Anal., Mar. 2017, 31(2):e22040, 3 pages.

(56) References Cited

OTHER PUBLICATIONS

Carter et al., "High Level *Escherichia coli* Expression and Production of a Bivalent Humanized Antibody Fragment," BioTechnology, Feb. 1992, 10(2):163-167.
Carter et al., "Improved oligonucleotide site-directed mutagenesis using M13 vectors," Nucl. Acids Res., Jun. 1985, 13(12):4431-4443.
Carvajal-Carmona et al., "Strong Amerind/White Sex Bias and a Possible Sephardic Contribution among the Founders of a Population in Northwest Colombia," Am J Hum Genet., Nov. 2000, 67(5):1287-95.
Castellano et al., "Human apoE Isoforms Differentially Regulate Brain Amyloid-β Peptide Clearance," Sci Transl Med., Jun. 2011, 3(89):89ra57, 13 pages.
Chavez-Gutierrez et al., "The mechanism of gamma-Secretase dysfunction in familial Alzheimer disease," EMBO J., May 2012, 31(10):2261-74.
Chen et al., "Topology of human apolipoprotein E3 uniquely regulates its diverse biological functions," PNAS, Sep. 2011, 108(36):14813-14818.
Chien et al., "Early Clinical PET Imaging Results with the Novel PHF-Tau Radioligand [F-18]-T807," J Alzheimers Dis., 2014, 34(1):457-468.
Co et al., "A humanized antibody specific for the platelet integrin gpIIb/IIIa," J. Immunol., Mar. 1994, 152(6):2968-2976.
Cokol et al., "Finding nuclear localization signals," EMBO Rep., Nov. 2000, 1(5):411-415.
Corder et al., "Gene dose of apolipoprotein E type 4 allele and the risk of Alzheimer's disease in late onset families," Science, Aug. 1993, 261(5123):921-923.
Corder et al., "Protective effect of apolipoprotein E type 2 allele for late onset Alzheimer disease," Nat Genet., Jun. 1994, 7(2):180-184.
Czarnik, "Encoding methods for combinatorial chemistry," Curr. Opin. Chem. Bio., Jun. 1997, 1(1):60-6.
Davies et al., "Single antibody domains as small recognition units: design and in vitro antigen selection of camelized, human VH domains with improved protein stability," Protein Eng., Jun. 1996, 9(6):531-7.
De Strooper et al., "Deficiency of presenilin-1 inhibits the normal cleavage of amyloid precursor protein," Nature, Jan. 1998, 391(6665):387-90.
Deng et al., "The Structure of Dimeric Apolipoprotein A-IV and Its Mechanism of Self-Association," Structure, May 2012, 20(5):767-79.
Deyle et al., "Adeno-associated virus vector integration," Curr Opin Mol Ther., Aug. 2009, 11(4):442-447, 11 pages.
Dominguez et al., "Nanoparticles and blood-brain barrier: the key to central nervous system diseases," J Nanosci nanotechnol., Jan. 2014, 14(1):766-79.
Ebrahimi et al., "Drug Delivery using genetically modified Mesenchymal Stem Cells: A promising targeted-delivery method," J.D.Med., Apr. 2013, 5(1):90-104.
Extended European Search Report in European Appln. No. 20815122.5, dated Oct. 9, 2023, 31 pages.
Farrer et al., "Effects of age, sex, and ethnicity on the association between apolipoprotein E genotype and Alzheimer disease. A meta-analysis. APOE and Alzheimer Disease Meta Analysis Consortium," JAMA, Oct. 1997, 278(16):1349-1356.
Fisher et al., "A scalable, fully automated process for construction of sequence-ready human exome targeted capture libraries," Genome Biol., 2011, 12(1):R1, 15 pages.
Fleisher et al., "Associations Between Biomarkers and Age in the Presenilin 1 E280A Autosomal Dominant Alzheimer Disease Kindred: A Cross-sectional Study," JAMA Neurol., Mar. 2015, 72(3):316-324.
Freitas et al., "Mechanisms and Signals for the Nuclear Import of Proteins," Curr Genomics, Dec. 2009, 10(8):550-557.
Frieden et al., "Structural differences between apoE3 and apoE4 may be useful in developing therapeutic agents for Alzheimer's disease," PNSA, Apr. 2012, 109(23):8913-8918.
Futamura et al., "Two-step Mechanism of Binding of Apolipoprotein E to Heparin," The Journal of Biological Chemistry, Feb. 2005, 280(7):5414-5422.
Garrison et al., "Haplotype-based variant detection from short-read sequencing," arXiv:12073907 [q-bioGN], Jul. 2012, 9 pages.
Gaudelli et al., "Programmable base editing of A•T to G•C in genomic DNA without DNA cleavage," Nature, Nov. 2017, 551(7681), 464-471.
Georgiadou et al., "Biophysical Analysis of Apolipoprotein E3 Variants Linked with Development of Type III Hyperlipoproteinemia," PLoS One, 2011, 6(11):e27037, 11 pages.
Ghiselli et al., "Type III hyperlipoproteinemia associated with apolipoprotein E deficiency," Science, Dec. 1981, 214(4526):1239-1241.
Harmsen et al., "Properties, production, and applications of camelid single-domain antibody fragments," Appl. Microbiol. Biotechnol., Nov. 2007, 77(1):13-22.
Hashimoto et al., "Apolipoprotein E, especially apolipoprotein E4, increases the oligomerization of amyloid beta peptide," J Neurosci., Oct. 2021, 32(43):15181-15192.
Hauser et al., "Impact of apolipoprotein E on Alzheimer's disease," Cure Alzheimer Res, Oct. 2013, 10(8):809-817, 17 pages.
He et al., "Towards improvements for penetrating the blood-brain barrier—recent progress from a material and pharmaceutical perspective," Cells, 2018, 7(4):24, 21 pages.
Hedden et al., "Disruption of functional connectivity in clinically normal older adults harboring amyloid burden," J Neurosci, Oct. 2009, 29(40):12686-12694.
Hofman et al., "Atherosclerosis, apolipoprotein E, and prevalence of dementia and Alzheimer's disease in the Rotterdam Study," Lancet, Jan. 1997, 349(9046):151-4.
Hollingworth et al., "Common variants at ABCA7, MS4A6A/MS4A4E, EPHA1, CD33 and CD2AP are associated with Alzheimer's disease," Nat Genet, Apr. 2011, 43(5):429-35.
Huang and Mahley, "Apolipoprotein E: structure and function in lipid metabolism, neurobiology, and Alzheimer's diseases," Neurobiol Dis, 2014, 72(Pt A):3-12.
Huang et al., "ApoE2, ApoE3, and ApoE4 Differentially Stimulate APP Transcription and Abeta Secretion," Cell, Jan. 2017, 168(3):427-441.e21, 37 pages.
Hudry et al., "Gene transfer of human Apoe isoforms results in differential modulation of amyloid deposition and neurotoxicity in mouse brain," Sci Transl Med, 2013, 5:212ra161, 23 pages.
Huynh et al., "Age-Dependent Effects of apoE Reduction Using Antisense Oligonucleotides in a Model of beta-amyloidosis," Neuron, Dec. 2017, 96(5):1013-1023.e4.
International Preliminary Report on Patentability in International Appln. No. PCT/US2020/034978, mailed on Dec. 9, 2021, 8 pages.
International Search Report and Written Opinion in International Appln. No. PCT/US2020/034978, mailed on Oct. 26, 2021, 13 pages.
Jiang et al., "ApoE promotes the proteolytic degradation of Abeta," Neuron, Jun. 2008, 58(5):681-93.
Jiang et al., "Apolipoprotein E Mediates Attachment of Clinical Hepatitis C Virus to Hepatocytes by Binding to Cell Surface Heparan Sulfate Proteoglycan Receptors," PLoS One, Jul. 2013, 8(7):e67982, 8 pages.
Johnson et al., "Tau positron emission tomographic imaging in aging and early Alzheimer disease," Ann Neurol, Jan. 2016, 79(1):110-9.
Johnson et al., "The Alzheimer's A beta-peptide is deposited at sites of complement activation in pathologic deposits associated with aging and age-related macular degeneration," PNAS, Sep. 2002, 99(18):11830-11835.
Kanekiyo et al., "ApoE and Aβ in Alzheimer's disease: accidental encounters or partners?," Neuron, Feb. 2014, 81(4):740-54.
Kaufman and Sharp, "Amplification and expression of sequences cotransfected with a modular dihydrofolate reductase complementary DNA gene," J. Mol. Biol., Aug. 1982, 159(4):601-621.
Khani et al., "AAV-mediated expression targeting of rod and cone photoreceptors with a human rhodopsin kinase promoter," Invest Ophthalmol Vis Sci., Sep. 2007, 48(9):3954-61.

(56) References Cited

OTHER PUBLICATIONS

Köhler and Milstein, "Continuous cultures of fused cells secreting antibody of predefined specificit," Nature, Aug. 1975, 256(5517):495-7.
Köhler and Milstein, "Derivation of specific antibody-producing tissue culture and tumor lines by cell fusion," Eur. J. Immunol., Jul. 1976, 6(7):511-9.
Köhler et al., "The Human Phenotype Ontology project: linking molecular biology and disease through phenotype data," Nucleic Acids Res, 2014, 42:D966-974.
Komor et al., "Programmable editing of a target base in genomic DNA without double-stranded DNA cleavage," Nature, May 2016, 533(7603):420-424, 17 pages.
Kunik et al., "Structural Consensus among Antibodies Defines the Antigen Binding Site," PLoS Comput Biol., Feb. 2012, 8(2):e1002388, 12 pages.
Kunkel, "Rapid and efficient site-specific mutagenesis without phenotypic selection," Proc. Natl. Acad Sci. USA, Jan. 1985, 82:488-492.
Lalazar et al., "Site-specific mutagenesis of human apolipoprotein E. Receptor binding activity of variants with single amino acid substitutions," J Biol Chem, Mar. 1988, 263(8):3542-3545.
Lalli et al., "Whole-genome sequencing suggests a chemokine gene cluster that modifies age at onset in familial Alzheimer's disease," Mol Psychiatry, 2015, 20:1294-1300.
Lamoyi, "[62] Preparation of $F(ab')_2$ fragments from mouse IgG of various subclasses," Methods in Enzymology, 1986, 121:652-663.
Lefevre et al., "Syndecan 4 is involved in mediating HCV entry through interaction with lipoviral particle-associated apolipoprotein E," PLoS One, Apr. 2014, 9(4):e95550, 8 pages.
Lei et al., "Characterization of the Erwinia carotovora pelB gene and its product pectate lyase," J Bacterial., Sep. 1987, 169(9):4379-83.
Lek et al., "Analysis of protein-coding genetic variation in 60,706 humans," Nature, Aug. 2016, 536(7616):285-291, 13 pages.
Lemere et al., "The E280A presenilin 1 Alzheimer mutation produces increased A beta 42 deposition and severe cerebellar pathology," Nature Medicine, Oct. 1996, 2(10):1146-50.
Lendon et al., "E280A PS-1 mutation causes Alzheimer's disease but age of onset is not modified by ApoE alleles," Hum Mutat, 1997, 10(3):186-195.
Li, "Aligning sequence reads, clone sequences and assembly contigs with BWA-MEM," arXiv, published on Mar. 16, 2013, arXiv:1303.3997 [q-bio.GN], 3 pages.
Libeu et al., "New insights into the heparan sulfate proteoglycan-binding activity of apolipoprotein E," J Biol Chem., Oct. 2001, 276(42):39138-44.
Logan et al., Graphical analysis of reversible radioligand binding from time-activity measurements applied to [N-11 C-methyl ]-(−)-cocaine PET studies in human subjects, J Cereb Blood Flow Metab, Sep. 1990, 10(5):740-747.
Lopera et al., "Clinical features of early-onset Alzheimer disease in a large kindred with an E280A presenilin-1 mutation," JAMA, Mar. 1997, 277(10):793-799.
Mahley et al., "Pathogenesis of type III hyperlipoproteinemia (dysbetalipoproteinemia). Questions, quandaries, and paradoxes," J Lipid Res, Nov. 1999, 40(11):1933-1949.
Mahley, "Apolipoprotein E: from cardiovascular disease to neurodegenerative disorders," J Mol Med (Berl), Jul. 2016, 94(7):739-46, 8 pages.
Malmborg and Borrebaeck, "BIAcore as a tool in antibody engineering," J. Immunol. Methods, Jun. 1995, 183(1):7-13.
McCall et al., "Pathogen-inspired drug delivery to the central nervous system" Tissue Barriers, Aug. 2014, 2(4):e944449, 12 pages.
McKinnon, "Glaucoma: Ocular Alzheimer's disease?," Frontiers in Bioscience, Oct. 2003, 8(1-3):s1140-1156.
Milne et al., "Characterization of monoclonal antibodies against human apolipoprotein E," J Clin Invest., Jul. 1981, 68(1):111-117.
Mingozzi and High, "Therapeutic in vivo gene transfer for genetic disease using AAV: progress and challenges," Nature Reviews Genetics, May 2011, 12(5):341-355.
Miyake et al., "Bypassing the blood-brian barrier using established skull base reconstruction techniques," World J Otorhinolaryngol Head Neck Surg., Oct. 2015, 1(1):11-16.
Mizushima et al., "pEF-BOS, a powerful mammalian expression vector," Nucleic Acids Res., Sep. 1990, 18(17):5322.
Möller et al., "Intracellular activation of interferon regulatory factor-1 by nanobodies to the multifunctional (Mf1) domain," J Biol. Chem., Dec. 2010, 285(49):38348-38361.
Mondal et al., "ApoE: In Vitro Studies of a Small Molecule Effector," Biochemistry, May 2016, 55(18):2613-21, 20 pages.
Mulligan et al., "Synthesis of rabbit beta-globin in cultured monkey kidney cells following infection with a SV40 beta-globin recombinant genome," Nature, Jan. 1979, 277(5692):108-14.
Muzyczka, "Use of adeno-associated virus as a general transduction vector for mammalian cells," Curr. Topics in Micro and Immunol., 1992, 158:97-129.
Office Action in Chinese Appln. No. 202080054661.6, dated Aug. 11, 2023, 15 pages (with English translation).
Ophir et al., "Abstract: Neutralization of apoE4 phenotypes with apoE4 specific antibodies," Neural Plasticity, Jan. 2003, 10(3):222.
Pandey et al., "Blood brain barrier: An overview on strategies in drug delivery, realistic in vitro modeling and in vivo live tracking," Tissue Barriers, Feb. 2016, 4(1):e1129476, 14 pages.
Pang et al., "Comparative analysis of in vivo and in vitro AAV vector transduction in the neonatal mouse retina: effects of serotype and site of administration," Vision Research, Feb. 2008, 48(3):377-385.
Pardridge, "Drug transport across the blood-brain barrier," J Cereb Blood Flow Metab, Nov. 2012, 32(11):1959-1972.
Partial European Search Report in European Appln. No. 20815122.5, dated Jan. 12, 2023, 28 pages.
PCR Protocols: a Guide to Methods and Applications, 1st ed., Innis et al. (eds.), 1990, Chapter 22, pp. 177-183.
Pérez De La Lastra et al., "Epitope mapping of 10 monoclonal antibodies against the pig analogue of human membrane cofactor protein (MCP)," Immunology, Apr. 1999, 96(4):663-70.
Plückthun and Skerra, "[34] Expression of functional antibody Fv and Fab fragments in *Escherichia coli*," Methods in Enzymology, 1989, 178:497-515.
Powers et al., "Expression of single-chain Fv-Fc fusions in Pichia pastoris," J Immunol Methods, May 2001, 251(1-2):123-35.
Quiroz et al., "Association Between Amyloid and Tau Accumulation in Young Adults With Autosomal Dominant Alzheimer Disease," JAMA Neurol, May 2018, 75(5):548-556.
Raffai et al., "Molecular characterization of two monoclonal antibodies specific for the LDL receptor-binding site of human apolipoprotein E," J Lipid Res., Sep. 1995, 36(9):1905-18.
Rauch et al., "Tau internalization is regulated by 6-O sulfation on heparan sulfate proteoglycans (HSPGs)," Sci Rep., Apr. 2018, 8(1):6382, 10 pages.
Reiman et al., "Exceptionally low likelihood of Alzheimer's dementia in APOE2 homozygotes from a 5,000-person neuropathological study," Nat Commun, 2020, 11:667, 11 pages.
Reisberg, "Functional assessment staging (FAST)," Psychopharmacol Bull, 1988, 24(4):653-659.
Reisberg, "Global measures: utility in defining and measuring treatment response in dementia," Int Psychogeriatr., Jun. 2007, 19(3):421-56.
Roger et al., "Mesenchymal stem cells as cellular vehicles for delivery of nanoparticles to brain tumors," Biomaterials, Nov. 2010, 31(23):8393-8401.
Romeo et al., "Population-based resequencing of ANGPTL4 uncovers variations that reduce triglycerides and increase HDL," Nat Genet, Apr. 2007, 39(4):513-6.
Rose et al., "NGL viewer: web-based molecular graphics for large complexes," Bioinformatics, Nov. 2018, 34(21):3755-3758.
Rosenberg et al., "AAVrh. 10-Mediated APOE2 Central Nervous System Gene Therapy for APOE4-Associated Alzheimer's Disease," Hum Gene Ther Clin Dev, Mar. 2018, 29(1):24-47.

(56) References Cited

OTHER PUBLICATIONS

Rousseaux et al., "[63] Optimal conditions for the preparation of proteolytic fragments from monoclonal IgG of different rat IgG subclasses," Methods in Enzymology, 1986, 121:663-669.
Saito et al., "Characterization of the heparin binding sites in human apolipoprotein E," J Biol. Chem., Apr. 2003, 278(17):14782-7.
Sanchez-Covarrubias et al., "Transporters at CNS barrier sites: obstacles or opportunities for drug delivery?," Curr Pharm Des., 2014, 20(10):1422-49, 59 pages.
Saura et al., "Loss of presenilin function causes impairments of memory and synaptic plasticity followed by age-dependent neurodegeneration," Neuron, Apr. 2004, 42(1):23-36.
Schier and Marks, "Efficient in vitro affinity maturation of phage antibodies using BIAcore guided selections," Human Antibodies Hybridomas, 1996, 7(3):97-105.
Sherrington et al., "Cloning of a gene bearing missense mutations in early-onset familial Alzheimer's disease," Nature, Jun. 1995, 375(6534):754-60.
Shi and Holtzman, "Interplay between innate immunity and Alzheimer disease: APOE and TREM2 in the spotlight," Nat Rev Immunol., Dec. 2018, 18(12):759-772, 14 pages.
Shi et al., "ApoE4 markedly exacerbates tau-mediated neurodegeneration in a mouse model of tauopathy," Nature, Sep. 2017, 549(7673):523-7, 20 pages.
Sivak, "The aging eye: common degenerative mechanisms between the Alzheimer's brain and retinal disease," Investigative Ophthalmology & Visual Science, 2013, 54(1):871-880.
Smedley et al., "A Whole-Genome Analysis Framework for Effective Identification of Pathogenic Regulatory Variants in Mendelian Disease," Am J Hum Genet, Sep. 2016, 99:595-606.
Sun et al., "Analysis of 138 pathogenic mutations in presenilin-1 on the in vitro production of Abeta42 and Abeta40 peptides by gamma-secretase," Proc Natl Acad Sci U S A, 2017, 114(4):E476-E85.
Tzioras et al., "APOE at the interface of inflammation, neurodegeneration and pathological protein spread in Alzheimer's disease," Neuropathology and Applied Neurobiology, Jun. 2019, 45(4):327-346, 21 pages.
Urlaub and Chasin, "Isolation of Chinese hamster cell mutants deficient in dihydrofolate reductase activity," Proc. Natl. Acad Sci. USA, Jul. 1980, 77(7):4216-4220.
Utermann et al., "Familial hyperlipoproteinemia type III: deficiency of a specific apolipoprotein (apo E-III) in the very-low-density lipoproteins," FEBS Lett, Aug. 1975, 56(2):352-5.
Vafa et al., "An engineered Fc variant of an IgG eliminates all immune effector functions via structural perturbations," Methods, Jan. 2014, 65(1):114-26.
Vallette et al., "Construction of mutant and chimeric genes using the polymerase chain reaction," Nucl. Acids Res., Jan. 1989, 17(2):723-733.
Vélez et al., "APOE*E2 allele delays age of onset in PSEN1 E280A Alzheimer's disease," Mol Psychiatry, 2016, 21:916-24.
Walsh et al., "Naturally secreted oligomers of amyloid beta protein potently inhibit hippocampal long-term potentiation in vivo," Nature, Apr. 2002, 416(6880):535-539.
Wang et al., "Evaluation of Tau Imaging in Staging Alzheimer Disease and Revealing Interactions Between beta-Amyloid and Tauopathy," JAMA Neurol, Sep. 2016, 73(9):1070-1077.
Wang et al., "IgG Fc engineering to modulate antibody effector functions," Protein Cell, Jan. 2018, 9(1):63-73.
Ward et al., "Binding activities of a repertoire of single immunoglobulin variable domains secreted from *Escherichia coli*," Nature, Oct. 1989, 341(6242):544-546.
Wardell et al., "Apolipoprotein E2-Christchurch (136 Arg—Ser). New variant of human apolipoprotein E in a patient with type III hyperlipoproteinemia," J Clin Invest, Aug. 1987, 80(2):483-90.
Weisgraber et al., "Human apolipoprotein E. Determination of the heparin binding sites of apolipoprotein E3," J Biol Chem, Feb. 1986, 261(5):2068-76.
Wells et al., "Cassette mutagenesis: an efficient method for generation of multiple mutations at defined sites," Gene, 1985, 34(2-3):315-323.
Yesavage, "Opportunities for and obstacles to treatments for dementias," J Am Geriatr Soc, Jan. 1983, 31(1):59-60.
Yoshiyama et al., "Synapse loss and microglial activation precede tangles in a P301S tauopathy mouse model," Neuron, Feb. 2007, 53(3):337-51, 18 pages.
Zalocusky et al., "An Alzheimer's-disease-protective APOE mutation," Nat Med., Nov. 2019, 25(11):1648-1649.
Zangi et al., "Modified mRNA directs the fate of heart progenitor cells and induces vascular regeneration after myocardial infarction," Nat Biotechnol., Sep. 2013, 31(10):898-907.
Zhong et al., "A rapid and cost-effective method for genotyping apolipoprotein E gene polymorphism," Mol Neurodegener, 2016, 11:2, 8 pages.
Zhou et al., "Dominant negative effect of the loss-of-function gamma-secretase mutants on the wild- type enzyme through heterooligomerization," Proc Natl Acad Sci U S A, Nov. 2017, 114(48):12731-6.
Office Action in Japanese Appln. No. 2021-570726, mailed on Nov. 12, 2024, 7 pages (with English translation).
Atwood et al., "A unified hypothesis of early-and late-onset Alzheimer's disease pathogenesis," J. Alzheimer's Disease, 2015, 47:33-47.
Falkenburger et al., "Limitations of cellular models in Parkinson's disease research," J. Neural Transm. Suppl., 2006, 2006(70):261-268.
Henstridge et al., "Beyond the neuron-cellular interactions early in Alzheimer disease pathogenesis," Nat. Rev. Neurosci., Feb. 2019, 20(2):94-108.
Office Action in Australian Appln. No. 2020282792, mailed on May 19, 2025, 5 pages.
Sarter, "Animal cognition: defining the issues," Neurosci. Biobehav. Rev., Nov. 2004, 28(7):645-650, 4 pages.
Swerdlow, "Pathogenesis of Alzheimer's disease," Clin. Interv. Aging, 2007, 2(3):347-359.
Tayebati, "Animal models of cognitive dysfunction," Mech. Ageing Dev., Feb. 2006, 127(2):100-8.
Mahley, "Apolipoprotein E: cholesterol transport protein with expanding role in cell biology," Science, Apr. 1988, 240(4852):622-630.
Notice of Acceptance in Australian Appln. No. 2020282792, mailed on Nov. 25, 2025, 4 pages.
Office Action in Canadian Application No. 3,141,988, mailed on Nov. 7, 2025, 8 pages.
Marino et al., "APOE Christchurch-mimetic therapeutic antibody reduces APOE-mediated toxicity and tau phosphorylation," Alzheimer's & Dementia, Feb. 2024, 20(2):819-836.
Office Action in Japanese Appln. No. 2025-039014, mailed on Feb. 24, 2026, 8 pages (with English translation).
Schroeder et al., "Regulation of the antibody repertoire through control of HCDR3 diversity," Vaccine, Aug. 1998, 16(14-15):1383-1390, 15 pages (Accepted Manuscript).
Yu et al., "Immunoglobulin Fc domain fusion to apolipoprotein(a) kringle V significantly prolongs plasma half-life without affecting its anti-angiogenic activity," Protein Engineering Design & Selection, Apr. 2013, 26(6):425-432.

* cited by examiner

23B2

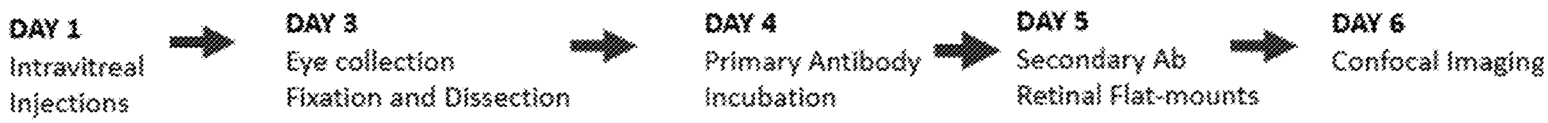
FIG. 42A
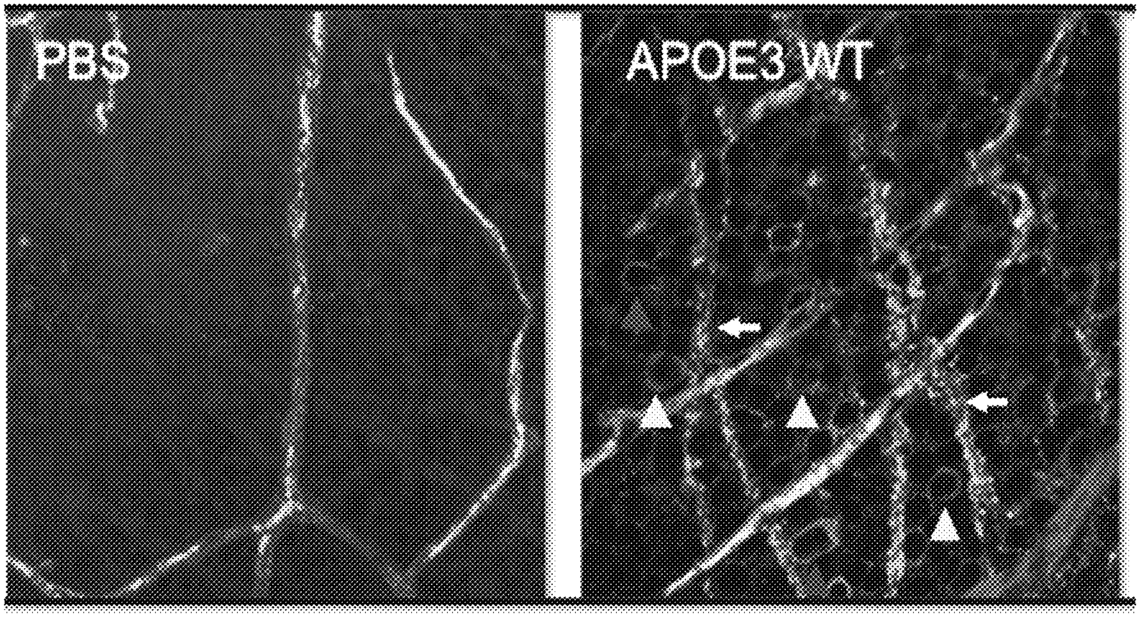
FIG. 42B
FIG. 42C

SEQUENCE LISTING

```
Sequence total quantity: 117
SEQ ID NO: 1            moltype = AA  length = 299
FEATURE                 Location/Qualifiers
source                  1..299
                        mol_type = protein
                        organism = Homo sapiens
SEQUENCE: 1
KVEQAVETEP EPELRQQTEW QSGQRWELAL GRFWDYLRWV QTLSEQVQEE LLSSQVTQEL  60
RALMDETMKE LKAYKSELEE QLTPVAEETR ARLSKELQAA QARLGADMED VCGRLVQYRG  120
EVQAMLGQST EELRVRLASH LRKLRKRLLR DADDLQKRLA VYQAGAREGA ERGLSAIRER  180
LGPLVEQGRV RAATVGSLAG QPLQERAQAW GERLRARMEE MGSRTRDRLD EVKEQVAEVR  240
AKLEEQAQQI RLQAEAFQAR LKSWFEPLVE DMQRQWAGLV EKVQAAVGTS AAPVPSDNH   299

SEQ ID NO: 2            moltype = AA  length = 14
FEATURE                 Location/Qualifiers
source                  1..14
                        mol_type = protein
                        organism = synthetic construct
SEQUENCE: 2
TEELRVSLAS HLRK                                                    14

SEQ ID NO: 3            moltype = AA  length = 14
FEATURE                 Location/Qualifiers
source                  1..14
                        mol_type = protein
                        organism = synthetic construct
SEQUENCE: 3
TEELRVRLAS HLRK                                                    14

SEQ ID NO: 4            moltype = AA  length = 15
FEATURE                 Location/Qualifiers
source                  1..15
                        mol_type = protein
                        organism = synthetic construct
SEQUENCE: 4
KASQSVDYDG DSYMN                                                   15

SEQ ID NO: 5            moltype = AA  length = 7
FEATURE                 Location/Qualifiers
source                  1..7
```

```
                         mol_type = protein
                         organism = synthetic construct
SEQUENCE: 5
AASNLES                                                              7

SEQ ID NO: 6             moltype = AA  length = 9
FEATURE                  Location/Qualifiers
source                   1..9
                         mol_type = protein
                         organism = synthetic construct
SEQUENCE: 6
QQSNEDPWT                                                            9

SEQ ID NO: 7             moltype = AA  length = 5
FEATURE                  Location/Qualifiers
source                   1..5
                         mol_type = protein
                         organism = synthetic construct
SEQUENCE: 7
SYTMS                                                                5

SEQ ID NO: 8             moltype = AA  length = 17
FEATURE                  Location/Qualifiers
source                   1..17
                         mol_type = protein
                         organism = synthetic construct
SEQUENCE: 8
KIRNGGGITY YLDTLKG                                                   17

SEQ ID NO: 9             moltype = AA  length = 11
FEATURE                  Location/Qualifiers
source                   1..11
                         mol_type = protein
                         organism = synthetic construct
SEQUENCE: 9
HYYGSEDYFD Y                                                         11

SEQ ID NO: 10            moltype = DNA  length = 393
FEATURE                  Location/Qualifiers
source                   1..393
                         mol_type = other DNA
                         organism = synthetic construct
SEQUENCE: 10
atggagacag acacaatcct gctatgggtg ctgctgctct gggttccagg ctccactggt  60
gacaatgtgc tgacccaatc tccagcttct ttggctgtgt ctctagggca gagggccacc  120
atctcctgca aggccagcca aagtgttgat tatgatggtg atagttatat gaactggtac  180
caacagaaac caggacagcc acccaaagtc ttcatctatg ctgcatccaa tctagaatct  240
gggatcccag ccaggtttag tggcagtggg tctgggacag acttcaccct caacatccat  300
cctgtggagg aggaggatgc tgcaacctat tactgtcagc aaagtaatga ggatccgtgg  360
acgttcggtg gaggcaccaa gctggaaatc aaa                                 393

SEQ ID NO: 11            moltype = DNA  length = 417
FEATURE                  Location/Qualifiers
source                   1..417
                         mol_type = other DNA
                         organism = synthetic construct
SEQUENCE: 11
atgaatttcg ggctcagctt gattttcctt gtccttgttt taaaaggtgt cctgtgtgaa  60
gtgaagctgg tggaatctgg gggaggtgtg gtgcagcctg gagggtccct gaaactctcc  120
tgtgcagcct ctggattcac tttcagtagc tataccatgt cttgggttcg tcagactcca  180
gagaagaggc tggagtgggt cgcaaaaatt cgtaatggtg gtggtatcac ctactattta  240
gacactttaa agggccgatt caccatctcc agagacaacg ccaagaacac cctatacctg  300
caaatgagca gtctgaagtc tgaagacacg gccatttatt tctgtgcaag acattactac  360
ggtagcgagg actactttga ctactggggc caaggcacca ctctcacagt ctcctca     417

SEQ ID NO: 12            moltype = AA  length = 131
FEATURE                  Location/Qualifiers
source                   1..131
                         mol_type = protein
                         organism = synthetic construct
SEQUENCE: 12
METDTILLWV LLLWVPGSTG DNVLTQSPAS LAVSLGQRAT ISCKASQSVD YDGDSYMNWY  60
QQKPGQPPKV FIYAASNLES GIPARFSGSG SGTDFTLNIH PVEEEDAATY YCQQSNEDPW  120
TFGGGTKLEI K                                                         131

SEQ ID NO: 13            moltype = AA  length = 139
FEATURE                  Location/Qualifiers
source                   1..139
                         mol_type = protein
```

```
                        organism = synthetic construct
SEQUENCE: 13
MNFGLSLIFL VLVLKGVLCE VKLVESGGGV VQPGGSLKLS CAASGFTFSS YTMSWVRQTP  60
EKRLEWVAKI RNGGGITYYL DTLKGRFTIS RDNAKNTLYL QMSSLKSEDT AIYFCARHYY  120
GSEDYFDYWG QGTTLTVSS                                               139

SEQ ID NO: 14           moltype = AA  length = 15
FEATURE                 Location/Qualifiers
source                  1..15
                        mol_type = protein
                        organism = synthetic construct
SEQUENCE: 14
KASQSVDYDG DSYMN                                                   15

SEQ ID NO: 15           moltype = AA  length = 7
FEATURE                 Location/Qualifiers
source                  1..7
                        mol_type = protein
                        organism = synthetic construct
SEQUENCE: 15
AASNLES                                                            7

SEQ ID NO: 16           moltype = AA  length = 9
FEATURE                 Location/Qualifiers
source                  1..9
                        mol_type = protein
                        organism = synthetic construct
SEQUENCE: 16
QQSNEDPWT                                                          9

SEQ ID NO: 17           moltype = AA  length = 5
FEATURE                 Location/Qualifiers
source                  1..5
                        mol_type = protein
                        organism = synthetic construct
SEQUENCE: 17
RYTMS                                                              5

SEQ ID NO: 18           moltype = AA  length = 17
FEATURE                 Location/Qualifiers
source                  1..17
                        mol_type = protein
                        organism = synthetic construct
SEQUENCE: 18
KIRNVGGITY YPDTVKG                                                 17

SEQ ID NO: 19           moltype = AA  length = 11
FEATURE                 Location/Qualifiers
source                  1..11
                        mol_type = protein
                        organism = synthetic construct
SEQUENCE: 19
HYYGSEDYFD Y                                                       11

SEQ ID NO: 20           moltype = DNA  length = 417
FEATURE                 Location/Qualifiers
source                  1..417
                        mol_type = other DNA
                        organism = synthetic construct
SEQUENCE: 20
atgaatttcg ggctcagcgt gattttcctt gtccttgttt taaaaggtgt cctgtgtgaa  60
gtgaagctgg tggagtctgg gggaggttta gtgcagcctg gagggtccct gaaactctcc  120
tgtgcagcct ctggattcac tttcagtagg tataccatgt cttgggttcg gcagactcca  180
gagaagaggc tggagtgggt cgcaaaaatt cgtaatgttg gtggtatcac ctactatcca  240
gacactgtaa agggccgatt caccatctcc agagacaacg ccaagaacac cctttacctg  300
caaatgagca gtctgaagtc tgaagacacg gccatgtatt actgtgcaag acattattac  360
ggtagcgagg actactttga ctactggggc caaggcacca ctctcacagt ctcctca     417

SEQ ID NO: 21           moltype = DNA  length = 393
FEATURE                 Location/Qualifiers
source                  1..393
                        mol_type = other DNA
                        organism = synthetic construct
SEQUENCE: 21
atggagacag acacaatcct gctatgggtg ctgctgctct gggttccagg ctccactggt  60
gacaatgtgc tgacccaatc tccagcttct ttggctgtgt ctctagggca gagggccacc  120
atctcctgca aggccagcca aagtgttgat tatgatggtg atagttatat gaactggtac  180
caacagaaac caggacagcc acccaaagtc ttcatctatg ctgcatccaa tctagaatct  240
gggatcccag ccaggtttag tggcagtggg tctgggacaa acttcaccct caacatccat  300
```

-continued

```
cctgtggagg aggaggatgc tgcaacctat tactgtcagc aaagtaatga ggatccgtgg  360
acgttcggtg gaggcaccaa gctggaaatc aaa                               393

SEQ ID NO: 22          moltype = AA  length = 139
FEATURE                Location/Qualifiers
source                 1..139
                       mol_type = protein
                       organism = synthetic construct
SEQUENCE: 22
MNFGLSVIFL VLVLKGVLCE VKLVESGGGL VQPGGSLKLS CAASGFTFSR YTMSWVRQTP  60
EKRLEWVAKI RNVGGITYYP DTVKGRFTIS RDNAKNTLYL QMSSLKSEDT AMYYCARHYY  120
GSEDYFDYWG QGTTLTVSS                                               139

SEQ ID NO: 23          moltype = AA  length = 131
FEATURE                Location/Qualifiers
source                 1..131
                       mol_type = protein
                       organism = synthetic construct
SEQUENCE: 23
METDTILLWV LLLWVPGSTG DNVLTQSPAS LAVSLGQRAT ISCKASQSVD YDGDSYMNWY  60
QQKPGQPPKV FIYAASNLES GIPARFSGSG SGTNFTLNIH PVEEEDAATY YCQQSNEDPW  120
TFGGGTKLEI K                                                       131

SEQ ID NO: 24          moltype = AA  length = 15
FEATURE                Location/Qualifiers
source                 1..15
                       mol_type = protein
                       organism = synthetic construct
SEQUENCE: 24
KASQSVDYDG DSYMN                                                   15

SEQ ID NO: 25          moltype = AA  length = 7
FEATURE                Location/Qualifiers
source                 1..7
                       mol_type = protein
                       organism = synthetic construct
SEQUENCE: 25
AASNLES                                                            7

SEQ ID NO: 26          moltype = AA  length = 9
FEATURE                Location/Qualifiers
source                 1..9
                       mol_type = protein
                       organism = synthetic construct
SEQUENCE: 26
QQSNVDPWT                                                          9

SEQ ID NO: 27          moltype = AA  length = 5
FEATURE                Location/Qualifiers
source                 1..5
                       mol_type = protein
                       organism = synthetic construct
SEQUENCE: 27
DYHMH                                                              5

SEQ ID NO: 28          moltype = AA  length = 17
FEATURE                Location/Qualifiers
source                 1..17
                       mol_type = protein
                       organism = synthetic construct
SEQUENCE: 28
WIDPENGNTM YDPKFQG                                                 17

SEQ ID NO: 29          moltype = AA  length = 9
FEATURE                Location/Qualifiers
source                 1..9
                       mol_type = protein
                       organism = synthetic construct
SEQUENCE: 29
GTARASFDY                                                          9

SEQ ID NO: 30          moltype = DNA  length = 393
FEATURE                Location/Qualifiers
source                 1..393
                       mol_type = other DNA
                       organism = synthetic construct
SEQUENCE: 30
atggagacag acacaatcct gctatgggtg ctgctgctct gggttccagg ctccactggt  60
gacattgtgc tgacccaatc tccagcttct ttggctgtgt ctctagggca gagggccacc  120
```

-continued

```
atctcctgca aggccagcca aagtgttgat tatgatggtg atagttatat gaattggtac  180
caacagaaat caggacagcc acccaaactc ctcatctatg ctgcatccaa tctagaatct  240
gggatcccag ccaggtttag tggcagtggg tctgggacag acttcaccct caacatccat  300
cctgtggagg aggaggatgc tgcaacctat tactgtcagc aaagtaatgt ggatccgtgg  360
acgttcggtg gaggcaccaa gctggaaatc aaa                               393

SEQ ID NO: 31          moltype = DNA  length = 411
FEATURE                Location/Qualifiers
source                 1..411
                       mol_type = other DNA
                       organism = synthetic construct
SEQUENCE: 31
atgaaatgca gctgggtcat cttcttcctg atggcagtgg ttacaggggt caattcagag  60
gttcagctgc agcagtctgg ggctgagctt gtgaggccag ggccttagt caagttgtcc   120
tgcaaagctt ctggcttcaa cattaaagac taccatatgc actgggtgaa ggagaggcct  180
gaacagggcc tggagtggat tggatggatt gatcctgaga atggtaatac tatgtatgac  240
ccgaagttcc agggcaaggc cagtataaca gcagacacat cctccaacac agcctacctg  300
cagctcagca gcctgacatc tgaggacact gccgtctatt actgtgttag ggggacagct  360
cgggcttcct ttgactactg gggccaaggc accactctca cagtctcctc a          411

SEQ ID NO: 32          moltype = AA  length = 131
FEATURE                Location/Qualifiers
source                 1..131
                       mol_type = protein
                       organism = synthetic construct
SEQUENCE: 32
METDTILLWV LLLWVPGSTG DIVLTQSPAS LAVSLGQRAT ISCKASQSVD YDGDSYMNWY  60
QQKSGQPPKL LIYAASNLES GIPARFSGSG SGTDFTLNIH PVEEEDAATY YCQQSNVDPW  120
TFGGGTKLEI K                                                       131

SEQ ID NO: 33          moltype = AA  length = 137
FEATURE                Location/Qualifiers
source                 1..137
                       mol_type = protein
                       organism = synthetic construct
SEQUENCE: 33
MKCSWVIFFL MAVVTGVNSE VQLQQSGAEL VRPGALVKLS CKASGFNIKD YHMHWVKERP  60
EQGLEWIGWI DPENGNTMYD PKFQGKASIT ADTSSNTAYL QLSSLTSEDT AVYYCVRGTA  120
RASFDYWGQG TTLTVSS                                                 137

SEQ ID NO: 34          moltype = AA  length = 15
FEATURE                Location/Qualifiers
source                 1..15
                       mol_type = protein
                       organism = synthetic construct
SEQUENCE: 34
KASQSVDYDG DTYMN                                                   15

SEQ ID NO: 35          moltype = AA  length = 7
FEATURE                Location/Qualifiers
source                 1..7
                       mol_type = protein
                       organism = synthetic construct
SEQUENCE: 35
TASNLES                                                            7

SEQ ID NO: 36          moltype = AA  length = 9
FEATURE                Location/Qualifiers
source                 1..9
                       mol_type = protein
                       organism = synthetic construct
SEQUENCE: 36
QQSNEDPWT                                                          9

SEQ ID NO: 37          moltype = AA  length = 5
FEATURE                Location/Qualifiers
source                 1..5
                       mol_type = protein
                       organism = synthetic construct
SEQUENCE: 37
DYHIH                                                              5

SEQ ID NO: 38          moltype = AA  length = 17
FEATURE                Location/Qualifiers
source                 1..17
                       mol_type = protein
                       organism = synthetic construct
SEQUENCE: 38
WIDPEIDKTL YDPKFQG                                                 17
```

```
SEQ ID NO: 39          moltype = AA  length = 9
FEATURE                Location/Qualifiers
source                 1..9
                       mol_type = protein
                       organism = synthetic construct
SEQUENCE: 39
GTARASFDY                                                    9

SEQ ID NO: 40          moltype = DNA  length = 393
FEATURE                Location/Qualifiers
source                 1..393
                       mol_type = other DNA
                       organism = synthetic construct
SEQUENCE: 40
atggagacag acacaatcct gctatgggtg ctgctgctct gggttccagg ctccactggt  60
gacattgtgc tgacccaatc tccagcttct ttggctgtgt ctctagggca gagggccacc  120
atctcctgca aggccagcca aagtgttgat tatgatggtg atacttatat gaactggtac  180
caacagaaac caggacagcc acccaaactc ctcatctata ctgcatccaa tctagaatct  240
gggatcccag ccaggtttag tggcagtggg tctgggacag acttcaccct caacatccat  300
cctgtggagg aggtggatgc tgcaacctat tactgtcagc aaagtaatga ggatccatgg  360
acgttcggtg gaggcaccaa gctggaaatc aaa                              393

SEQ ID NO: 41          moltype = DNA  length = 411
FEATURE                Location/Qualifiers
source                 1..411
                       mol_type = other DNA
                       organism = synthetic construct
SEQUENCE: 41
atgaaatgca gctgggtcat cttcttcctg atggcagtgg ttacaggggt caattcagag  60
gttcagctgc agcagtctgg ggctgagctt gtgaggccag gggccttagt caagtggtcc  120
tgcaaagctt ctggcttcaa cattaaagac taccatatac actgggtgaa acagaggcct  180
gaacagggcc tggactggat tggatggatt gatcctgaga ttgataaaac tctatatgac  240
ccgaagtttc agggcaaggc cagaataaca gcagacacat cctccaatac agcctacctg  300
cagctcagca gcctgacatc tgaagacact gccgtctatt actgtgccag ggggacagct  360
cgggcttcct ttgactactg gggccaaggc accactctca cagtctcctc a          411

SEQ ID NO: 42          moltype = AA  length = 131
FEATURE                Location/Qualifiers
source                 1..131
                       mol_type = protein
                       organism = synthetic construct
SEQUENCE: 42
METDTILLWV LLLWVPGSTG DIVLTQSPAS LAVSLGQRAT ISCKASQSVD YDGDTYMNWY  60
QQKPGQPPKL LIYTASNLES GIPARFSGSG SGTDFTLNIH PVEEVDAATY YCQQSNEDPW  120
TFGGGTKLEI K                                                 131

SEQ ID NO: 43          moltype = AA  length = 137
FEATURE                Location/Qualifiers
source                 1..137
                       mol_type = protein
                       organism = synthetic construct
SEQUENCE: 43
MKCSWVIFFL MAVVTGVNSE VQLQQSGAEL VRPGALVKWS CKASGFNIKD YHIHWVKQRP  60
EQGLDWIGWI DPEIDKTLYD PKFQGKARIT ADTSSNTAYL QLSSLTSEDT AVYYCARGTA  120
RASFDYWGQG TTLTVSS                                           137

SEQ ID NO: 44          moltype = AA  length = 15
FEATURE                Location/Qualifiers
source                 1..15
                       mol_type = protein
                       organism = synthetic construct
SEQUENCE: 44
KASQSVDYDG ENYMN                                             15

SEQ ID NO: 45          moltype = AA  length = 7
FEATURE                Location/Qualifiers
source                 1..7
                       mol_type = protein
                       organism = synthetic construct
SEQUENCE: 45
VASNLES                                                      7

SEQ ID NO: 46          moltype = AA  length = 9
FEATURE                Location/Qualifiers
source                 1..9
                       mol_type = protein
                       organism = synthetic construct
SEQUENCE: 46
```

```
QQSNLDPWT                                                       9

SEQ ID NO: 47          moltype = AA  length = 7
FEATURE                Location/Qualifiers
source                 1..7
                       mol_type = protein
                       organism = synthetic construct
SEQUENCE: 47
GFNIKDY                                                         7

SEQ ID NO: 48          moltype = AA  length = 6
FEATURE                Location/Qualifiers
source                 1..6
                       mol_type = protein
                       organism = synthetic construct
SEQUENCE: 48
DPENGN                                                          6

SEQ ID NO: 49          moltype = AA  length = 9
FEATURE                Location/Qualifiers
source                 1..9
                       mol_type = protein
                       organism = synthetic construct
SEQUENCE: 49
GTARASFDY                                                       9

SEQ ID NO: 50          moltype = AA  length = 317
FEATURE                Location/Qualifiers
source                 1..317
                       mol_type = protein
                       organism = synthetic construct
SEQUENCE: 50
MKVLWAALLV TFLAGCQAKV EQAVETEPEP ELRQQTEWQS GQRWELALGR FWDYLRWVQT  60
LSEQVQEELL SSQVTQELRA LMDETMKELK AYKSELEEQL TPVAEETRAR LSKELQAAQA  120
RLGADMEDVC GRLVQYRGEV QAMLGQSTEE LRVSLASHLR KLRKRLLRDA DDLQKRLAVY  180
QAGAREGAER GLSAIRERLG PLVEQGRVRA ATVGSLAGQP LQERAQAWGE RLRARMEEMG  240
SRTRDRLDEV KEQVAEVRAK LEEQAQQIRL QAEAFQARLK SWFEPLVEDM QRQWAGLVEK  300
VQAAVGTSAA PVPSDNH                                              317

SEQ ID NO: 51          moltype =   length =
SEQUENCE: 51
000

SEQ ID NO: 52          moltype = AA  length = 218
FEATURE                Location/Qualifiers
source                 1..218
                       mol_type = protein
                       organism = synthetic construct
SEQUENCE: 52
DIVLTQSPAS LAVSLGQRAT ISCKASQSVD YDGENYMNWY QQKPGQSPKL LIYVASNLES  60
GIPARFSGSG SGTDFTLNIH PVEEEDAATY YCQQSNLDPW TFGGGTKLEI KRADAAPTVS  120
IFPPSSEQLT SGGASVVCFL NNFYPKDINV KWKIDGSERQ NGVLNSWTDQ DSKDSTYSMS  180
STLTLTKDEY ERHNSYTCEA THKTSTSPIV KSFNRNEC                        218

SEQ ID NO: 53          moltype = AA  length = 442
FEATURE                Location/Qualifiers
source                 1..442
                       mol_type = protein
                       organism = synthetic construct
SEQUENCE: 53
EVQLQQSGAE LVRPGALVKL SCKASGFNIK DYHLHWVKQR PEQGLEWIGW IDPENGNVIY  60
DPKFQGKATM TVVTSSNTAY LQLRSLTSED TAVYFCTRGT ARASFDYWGQ GTSLTVSSAK  120
TTPPSVYPLA PGSAAQTNSM VTLGCLVKGY FPEPVTVTWN SGSLSSGVHT FPAVLQSDLY  180
TLSSSVTVPS STWPSETVTC NVAHPASSTK VDKKIVPRDC GCKPCICTVP EVSSVFIFPP  240
KPKDVLTITL TPKVTCVVVD ISKDDPEVQF SWFVDDVEVH TAQTQPREEQ FNSTFRSVSE  300
LPIMHQDWLN GKEFKCRVNS AAFPAPIEKT ISKTKGRPKA PQVYTIPPPK EQMAKDKVSL  360
TCMITDFFPE DITVEWQWNG QPAENYKNTQ PIMDTDGSYF VYSKLNVQKS NWEAGNTFTC  420
SVLHEGLHNH HTEKSLSHSP GK                                        442

SEQ ID NO: 54          moltype = AA  length = 15
FEATURE                Location/Qualifiers
source                 1..15
                       mol_type = protein
                       organism = synthetic construct
SEQUENCE: 54
CTEELRVRLA SHLRK                                                15

SEQ ID NO: 55          moltype = AA  length = 15
FEATURE                Location/Qualifiers
```

```
source                  1..15
                        mol_type = protein
                        organism = synthetic construct
SEQUENCE: 55
CTEELRVSLA SHLRK                                                   15

SEQ ID NO: 56           moltype = DNA  length = 954
FEATURE                 Location/Qualifiers
source                  1..954
                        mol_type = other DNA
                        organism = synthetic construct
SEQUENCE: 56
atgaaggttc tgtgggctgc gttgctggtc acattcctgg caggatgcca ggccaaggtg  60
gagcaagcgg tggagacaga gccggagccc gagctgcgcc agcagaccga gtggcagagc  120
ggccagcgct gggaactggc actgggtcgc ttttgggatt acctgcgctg ggtgcagaca  180
ctgtctgagc aggtgcagga ggagctgctc agctcccagg tcacccagga actgagggcg  240
ctgatggacg agaccatgaa ggagttgaag gcctacaaat cggaactgga ggaacaactg  300
accccggtgg cggaggagac gcgggcacgg ctgtccaagg agctgcaggc ggcgcaggcc  360
cggctgggcg cggacatgga ggacgtgtgc ggccgcctgg tgcagtaccg cggcgaggtg  420
caggccatgc tcggccagag caccgaggag ctgcgggtga gcctcgcctc ccacctgcgc  480
aagctgcgta agcggctcct ccgcgatgcc gatgacctgc agaagcgcct ggcagtgtac  540
caggccgggg cccgcgaggg cgccgagcgc ggcctcagcg ccatccgcga gcgcctgggg  600
cccctggtgg aacagggccg cgtgcgggcc gccactgtgg gctccctggc cggccagccg  660
ctacaggagc gggcccaggc ctggggcgag cggctgcgcg cgcggatgga ggagatgggc  720
agccggaccc gcgaccgcct ggacgaggtg aaggagcagg tggcggaggt gcgcgccaag  780
ctggaggagc aggcccagca gatacgcctg caggccgagg ccttccaggc ccgcctcaag  840
agctggttcg agcccctggt ggaagacatg cagcgccagt gggccgggct ggtggagaag  900
gtgcaggctg ccgtgggcac cagcgccgcc cctgtgccca gcgacaatca ctga        954

SEQ ID NO: 57           moltype = AA  length = 29
FEATURE                 Location/Qualifiers
source                  1..29
                        mol_type = protein
                        organism = Homo sapiens
SEQUENCE: 57
STEELRVRLA SHLRKLRKRL LRDADDLQK                                    29

SEQ ID NO: 58           moltype = AA  length = 29
FEATURE                 Location/Qualifiers
source                  1..29
                        mol_type = protein
                        organism = synthetic construct
SEQUENCE: 58
STEELRVSLA SHLRKLRKRL LRDADDLQK                                    29

SEQ ID NO: 59           moltype = AA  length = 31
FEATURE                 Location/Qualifiers
source                  1..31
                        mol_type = protein
                        organism = Homo sapiens
SEQUENCE: 59
RLVQYRGEVQ AMLGQSTEEL RVRLASHLRK L                                 31

SEQ ID NO: 60           moltype = AA  length = 31
FEATURE                 Location/Qualifiers
source                  1..31
                        mol_type = protein
                        organism = synthetic construct
SEQUENCE: 60
RLVQYRGEVQ AMLGQSTEEL RVSLASHLRK L                                 31

SEQ ID NO: 61           moltype = AA  length = 7
FEATURE                 Location/Qualifiers
REGION                  1..7
                        note = Description of Unknown: nuclear localization sequence
source                  1..7
                        mol_type = protein
                        organism = unidentified
SEQUENCE: 61
PKKKRKV                                                            7

SEQ ID NO: 62           moltype = AA  length = 7
FEATURE                 Location/Qualifiers
source                  1..7
                        mol_type = protein
                        organism = Simian immunodeficiency virus
SEQUENCE: 62
PKKKRRV                                                            7
```

```
SEQ ID NO: 63          moltype = AA  length = 16
FEATURE                Location/Qualifiers
REGION                 1..16
                       note = Description of Unknown: nucleoplasmin NLS sequence
source                 1..16
                       mol_type = protein
                       organism = unidentified
SEQUENCE: 63
KRPAATKKAG QAKKKK                                                 16

SEQ ID NO: 64          moltype = DNA  length = 60
FEATURE                Location/Qualifiers
source                 1..60
                       mol_type = other DNA
                       organism = synthetic construct
SEQUENCE: 64
tagcaataaa ggatcgttta ttttcattgg aagcgtgtgt tggtttttg atcaggcgcg  60

SEQ ID NO: 65          moltype = DNA  length = 127
FEATURE                Location/Qualifiers
source                 1..127
                       mol_type = other DNA
                       organism = synthetic construct
SEQUENCE: 65
cgcctggtgc agtaccgcgg cgaggtgcag gccatgctcg gccagagcac agaggagctc  60
cgcgtgagtc tcgcaagcca cctgcgcaag ctgcgtaagc ggctcctccg cgatgccgat  120
gacctgc                                                           127

SEQ ID NO: 66          moltype = DNA  length = 264
FEATURE                Location/Qualifiers
source                 1..264
                       mol_type = genomic DNA
                       organism = Homo sapiens
SEQUENCE: 66
aaggtcgggc aggaagaggg cctatttccc atgattcctt catatttgca tatacgatac  60
aaggctgtta gagagataat tagaattaat ttgactgtaa acacaaagat attagtacaa  120
aatacgtgac gtagaaagta ataatttctt gggtagtttg cagttttaaa attatgtttt  180
aaaatggact atcatatgct taccgtaact tgaaagtatt tcgatttctt ggctttatat  240
atcttgtgga aaggacgaaa cacc                                        264

SEQ ID NO: 67          moltype = DNA  length = 25
FEATURE                Location/Qualifiers
source                 1..25
                       mol_type = other DNA
                       organism = synthetic construct
SEQUENCE: 67
agcccttctc cccgcctccc actgt                                       25

SEQ ID NO: 68          moltype = DNA  length = 25
FEATURE                Location/Qualifiers
source                 1..25
                       mol_type = other DNA
                       organism = synthetic construct
SEQUENCE: 68
ctccgccacc tgctccttca cctcg                                       25

SEQ ID NO: 69          moltype = DNA  length = 20
FEATURE                Location/Qualifiers
source                 1..20
                       mol_type = other DNA
                       organism = synthetic construct
SEQUENCE: 69
cttacgcagc ttgcgcaggt                                             20

SEQ ID NO: 70          moltype = DNA  length = 20
FEATURE                Location/Qualifiers
source                 1..20
                       mol_type = other DNA
                       organism = synthetic construct
SEQUENCE: 70
gcttgcgcag gtgggaggcg                                             20

SEQ ID NO: 71          moltype = DNA  length = 20
FEATURE                Location/Qualifiers
source                 1..20
                       mol_type = other DNA
                       organism = synthetic construct
SEQUENCE: 71
acgcagcttg cgcaggtggg                                             20
```

-continued

```
SEQ ID NO: 72          moltype = DNA  length = 20
FEATURE                Location/Qualifiers
source                 1..20
                       mol_type = other DNA
                       organism = synthetic construct
SEQUENCE: 72
ccagagcacc gaggagctgc                                       20

SEQ ID NO: 73          moltype = DNA  length = 20
FEATURE                Location/Qualifiers
source                 1..20
                       mol_type = other DNA
                       organism = synthetic construct
SEQUENCE: 73
gccagagcac cgaggagctg                                       20

SEQ ID NO: 74          moltype = DNA  length = 20
FEATURE                Location/Qualifiers
source                 1..20
                       mol_type = other DNA
                       organism = synthetic construct
SEQUENCE: 74
gaggcgcacc cgcagctcct                                       20

SEQ ID NO: 75          moltype = DNA  length = 20
FEATURE                Location/Qualifiers
source                 1..20
                       mol_type = other DNA
                       organism = synthetic construct
SEQUENCE: 75
agctgcgcca gcagaccgag                                       20

SEQ ID NO: 76          moltype = DNA  length = 20
FEATURE                Location/Qualifiers
source                 1..20
                       mol_type = other DNA
                       organism = synthetic construct
SEQUENCE: 76
ccaggccaag gtggagcaag                                       20

SEQ ID NO: 77          moltype = DNA  length = 20
FEATURE                Location/Qualifiers
source                 1..20
                       mol_type = other DNA
                       organism = synthetic construct
SEQUENCE: 77
cacaggatgc caggccaagg                                       20

SEQ ID NO: 78          moltype = DNA  length = 20
FEATURE                Location/Qualifiers
source                 1..20
                       mol_type = other DNA
                       organism = synthetic construct
SEQUENCE: 78
acagtgtctg cacccagcgc                                       20

SEQ ID NO: 79          moltype = DNA  length = 20
FEATURE                Location/Qualifiers
source                 1..20
                       mol_type = other DNA
                       organism = synthetic construct
SEQUENCE: 79
ggccaaggtg gagcaagcgg                                       20

SEQ ID NO: 80          moltype = DNA  length = 20
FEATURE                Location/Qualifiers
source                 1..20
                       mol_type = other DNA
                       organism = synthetic construct
SEQUENCE: 80
gaggcgcacc cgcagctcct                                       20

SEQ ID NO: 81          moltype = DNA  length = 4290
FEATURE                Location/Qualifiers
source                 1..4290
                       mol_type = other DNA
                       organism = synthetic construct
SEQUENCE: 81
```

-continued

```
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cggcacctct cgagcgcaaa tctagtgtcg  660
agtgcccacc gtgcccagca ccacctgtgg caggaccgtc agtcttcctc ttccccccaa  720
aacccaagga caccctcatg atctcccgga cccctgaggt cacgtgcgtg gtggtggacg  780
tgagccacga agaccccgag gtccagttca actggtacgt ggacggcgtg gaggtgcata  840
atgccaagac aaagccacgg gaggagcagt tcaacagcac gttccgtgtg gtcagcgtcc  900
tcaccgttgt gcaccaggac tggctgaacg gcaaggagta caagtgcaag gtctccaaca  960
aaggcctccc agcccccatc gagaaaacca tctccaaaac caaagggcag ccccgagaac  1020
cacaggtgta caccctgccc ccatcccggg aggagatgac caagaaccag gtcagcctga  1080
cctgcctggt caaaggcttc taccccagcg acatcgccgt ggagtgggag agcaatgggc  1140
agccggagaa caactacaag accacgcctc ccatgctgga ctccgacggc tccttcttcc  1200
tctacagcaa gctcaccgtg gacaagagca ggtggcagca ggggaacgtc ttctcatgct  1260
ccgtgatgca tgaggctctg cacaaccact acacgcagaa gagcctctcc ctgtctccgg  1320
gtgcacgtac gcgcctggtg cagtaccgcg gcgaggtgca ggccatgctc ggccagagca  1380
ccgaggagct gcgggtgcgc ctcgcctccc acctgcgcaa gctgtgatat ctcgagctag  1440
ctggccagac atgataagat acattgatga gtttggacaa accacaacta gaatgcagtg  1500
aaaaaaatgc tttatttgtg aaatttgtga tgctattgct ttatttgtaa ccattataag  1560
ctgcaataaa caagttaaca acaacaattg cattcatttt atgtttcagg ttcaggggga  1620
ggtgtgggag gtttttttaaa gcaagtaaaa cctctacaaa tgtggtatgg aattaattct  1680
aaaatacagc atagcaaaac tttaacctcc aaatcaagcc tctacttgaa tccttttctg  1740
agggatgaat aaggcatagg catcaggggc tgttgccaat gtgcattagc tgtttgcagc  1800
ctcaccttct ttcatggagt ttaagatata gtgtattttc ccaaggtttg aactagctct  1860
tcatttcttt atgttttaaa tgcactgacc tcccacattc ccttttttagt aaaatattca  1920
gaaataattt aaatacatca ttgcaatgaa aataaatgtt ttttattagg cagaatccag  1980
atgctcaagg cccttcataa tatcccccag tttagtagtt ggacttaggg aacaaaggaa  2040
cctttaatag aaattggaca gcaagaaagc gagcttctag cttatcctca gtcctgctcc  2100
tctgccacaa agtgcacgca gttgccggcc gggtcgcgca gggcgaactc ccgcccccac  2160
ggctgctcgc cgatctcggt catggccggc ccggaggcgt cccggaagtt cgtggacacg  2220
acctccgacc actcggcgta cagctcgtcc aggccgcgca cccacaccca ggccagggtg  2280
ttgtccggca ccacctggtc ctggaccgcg ctgatgaaca gggtcacgtc gtcccggacc  2340
acaccggcga agtcgtcctc cacgaagtcc cgggagaacc cgagccggtc ggtccagaac  2400
tcgaccgctc cggcgacgtc gcgcgcggtg agcaccggaa cggcactggt caacttggcc  2460
atgatggctc ctcctgtcag gagaggaaag agaagaaggt tagtacaatt gctatagtga  2520
gttgtattat actatgcaga tatactatgc caatgattaa ttgtcaaact agggctgcag  2580
ggttcatagt gccacttttc ctgcactgcc ccatctcctg cccacccttt cccaggcata  2640
gacagtcagt gacttaccaa actcacagga gggagaaggc agaagcttga gacagacccg  2700
cgggaccgcc gaactgcgag gggacgtggc tagggcggct tcttttatgg tgcgccggcc  2760
ctcggaggca gggcgctcgg ggaggcctag cggccaatct gcggtggcag gaggcggggc  2820
cgaaggccgt gcctgaccaa tccggagcac ataggagtct cagccccccg ccccaaagca  2880
aggggaagtc acgcgcctgt agcgccagcg tgttgtgaaa tgggggcttg ggggggttgg  2940
ggccctgact agtcaaaaca aactcccatt gacgtcaatg gggtggagac ttggaaatcc  3000
ccgtgagtca aaccgctatc cacgcccatt gatgtactgc caaaaccgca tcatcatggt  3060
aatagcgatg actaatacgt agatgtactg ccaagtagga aagtcccata aggtcatgta  3120
ctgggcataa tgccaggcgg gccatttacc gtcattgacg tcaatagggg gcgtacttgg  3180
catatgatac acttgatgta ctgccaagtg ggcagtttac cgtaaatact ccacccattg  3240
acgtcaatgg aaagtcccta ttggcgttac tatgggaaca tacgtcatta ttgacgtcaa  3300
tgggcggggg tcgttgggcg gtcagccagg cgggccattt accgtaagtt atgtaacgcc  3360
tgcaggttaa ttaagaacat gtgagcaaaa ggccagcaaa aggccaggaa ccgtaaaaag  3420
gccgcgttgc tggcgttttt ccataggctc cgccccccctg acgagcatca caaaaatcga  3480
cgctcaagtc agaggtggcg aaacccgaca ggactataaa gataccaggc gtttccccct  3540
ggaagctccc tcgtgcgctc tcctgttccg accctgccgc ttaccggata cctgtccgcc  3600
tttctccctt cgggaagcgt ggcgctttct catagctcac gctgtaggta tctcagttcg  3660
gtgtaggtcg ttcgctccaa gctgggctgt gtgcacgaac cccccgttca gcccgaccgc  3720
tgcgccttat ccggtaacta tcgtcttgag tccaacccgg taagacacga cttatcgcca  3780
ctggcagcag ccactggtaa caggattagc agagcgaggt atgtaggcgg tgctacagag  3840
ttcttgaagt ggtggcctaa ctacggctac actagaagaa cagtatttgg tatctgcgct  3900
ctgctgaagc cagttacctt cggaaaaaga gttggtagct cttgatccgg caaacaaacc  3960
accgctggta gcggtggttt ttttgtttgc aagcagcaga ttacgcgcag aaaaaaagga  4020
tctcaagaag atcctttgat cttttctacg gggtctgacg ctcagtggaa cgaaaactca  4080
cgttaaggga ttttggtcat ggctagttaa ttaacattta aatcagcggc cgcaataaaa  4140
tatctttatt ttcattacat ctgtgtgttg gttttttgtg tgaatcgtaa ctaacatacg  4200
ctctccatca aaacaaaacg aaacaaaaca aactagcaaa ataggctgtc cccagtgcaa  4260
gtgcaggtgc cagaacattt ctctatcgaa                                4290
```

```
SEQ ID NO: 82          moltype = AA  length = 284
FEATURE                Location/Qualifiers
source                 1..284
                       mol_type = protein
                       organism = synthetic construct
SEQUENCE: 82
```

-continued

```
MYRMQLLSCI ALSLALVTNS APLERKSSVE CPPCPAPPVA GPSVFLFPPK PKDTLMISRT  60
PEVTCVVVDV SHEDPEVQFN WYVDGVEVHN AKTKPREEQF NSTFRVVSVL TVVHQDWLNG  120
KEYKCKVSNK GLPAPIEKTI SKTKGQPREP QVYTLPPSRE EMTKNQVSLT CLVKGFYPSD  180
IAVEWESNGQ PENNYKTTPP MLDSDGSFFL YSKLTVDKSR WQQGNVFSCS VMHEALHNHY  240
TQKSLSLSPG ARTRLVQYRG EVQAMLGQST EELRVRLASH LRKL                  284

SEQ ID NO: 83          moltype = DNA  length = 4290
FEATURE                Location/Qualifiers
source                 1..4290
                       mol_type = other DNA
                       organism = synthetic construct
SEQUENCE: 83
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cggcacctct cgagcgcaaa tctagtgtcg  660
agtgcccacc gtgcccagca ccacctgtgg caggaccgtc agtcttcctc ttccccccaa  720
aacccaagga caccctcatg atctcccgga cccctgaggt cacgtgcgtg gtggtggacg  780
tgagccacga agaccccgag gtccagttca actggtacgt ggacggcgtg gaggtgcata  840
atgccaagac aaagccacgg gaggagcagt tcaacagcac gttccgtgtg gtcagcgtcc  900
tcaccgttgt gcaccaggac tggctgaacg gcaaggagta caagtgcaag gtctccaaca  960
aaggcctccc agcccccatc gagaaaacca tctccaaaac caaagggcag ccccgagaac  1020
cacaggtgta caccctgccc ccatcccggg aggagatgac caagaaccag gtcagcctga  1080
cctgcctggt caaaggcttc taccccagcg acatcgccgt ggagtgggag agcaatgggc  1140
agccggagaa caactacaag accacgcctc ccatgctgga ctccgacggc tccttcttcc  1200
tctacagcaa gctcaccgtg gacaagagca ggtggcagca ggggaacgtc ttctcatgct  1260
ccgtgatgca tgaggctctg cacaaccact acacgcagaa gagcctctcc ctgtctccgg  1320
gtgcacgtac gcgcctggtg cagtaccgcg gcgaggtgca ggccatgctc ggccagagca  1380
ccgaggagct gcgggtgagc ctcgcctccc acctgcgcaa gctgtgatat ctcgagctag  1440
ctggccagac atgataagat acattgatga gtttggacaa accacaacta gaatgcagtg  1500
aaaaaaatgc tttatttgtg aaatttgtga tgctattgct ttatttgtaa ccattataag  1560
ctgcaataaa caagttaaca acaacaattg cattcatttt atgtttcagg ttcaggggga  1620
ggtgtgggag gttttttaaa gcaagtaaaa cctctacaaa tgtggtatgg aattaattct  1680
aaaatacagc atagcaaaac tttaacctcc aaatcaagcc tctacttgaa tccttttctg  1740
agggatgaat aaggcatagg catcaggggc tgttgccaat gtgcattagc tgtttgcagc  1800
ctcaccttct ttcatggagt ttaagatata gtgtattttc ccaaggtttg aactagctct  1860
tcatttcttt atgttttaaa tgcactgacc tcccacattc ccttttttagt aaaatattca  1920
gaaataattt aaatacatca ttgcaatgaa aataaatgtt ttttattagg cagaatccag  1980
atgctcaagg cccttcataa tatcccccag tttagtagtt ggacttaggg aacaaaggaa  2040
cctttaatag aaattggaca gcaagaaagc gagcttctag cttatcctca gtcctgctcc  2100
tctgccacaa agtgcacgca gttgccggcc gggtcgcgca gggcgaactc ccgcccccac  2160
ggctgctcgc cgatctcggt catggccggc ccggaggcgt cccggaagtt cgtggacacg  2220
acctccgacc actcggcgta cagctcgtcc aggccgcgca cccacaccca ggccagggtg  2280
ttgtccggca ccacctggtc ctggaccgcg ctgatgaaca gggtcacgtc gtcccggacc  2340
acaccggcga agtcgtcctc cacgaagtcc cgggagaacc cgagccggtc ggtccagaac  2400
tcgaccgctc cggcgacgtc gcgcgcggtg agcaccggaa cggcactggt caacttggcc  2460
atgatggctc ctcctgtcag gagaggaaag agaagaaggt tagtacaatt gctatagtga  2520
gttgtattat actatgcaga tatactatgc caatgattaa ttgtcaaact agggctgcag  2580
ggttcatagt gccacttttc ctgcactgcc ccatctcctg cccacccttt cccaggcata  2640
gacagtcagt gacttaccaa actcacagga gggagaaggc agaagcttga gacagacccg  2700
cgggaccgcc gaactgcgag gggacgtggc tagggcggct tcttttatgg tgcgccggcc  2760
ctcggaggca gggcgctcgg ggaggcctag cggccaatct gcggtggcag gaggcggggc  2820
cgaaggccgt gcctgaccaa tccggagcac ataggagtct cagccccccg ccccaaagca  2880
aggggaagtc acgcgcctgt agcgccagcg tgttgtgaaa tgggggcttg ggggggttgg  2940
ggccctgact agtcaaaaca aactcccatt gacgtcaatg gggtggagac ttggaaatcc  3000
ccgtgagtca aaccgctatc cacgcccatt gatgtactgc caaaaccgca tcatcatggt  3060
aatagcgatg actaatacgt agatgtactg ccaagtagga aagtcccata aggtcatgta  3120
ctgggcataa tgccaggcgg gccatttacc gtcattgacg tcaatagggg gcgtacttgg  3180
catatgatac acttgatgta ctgccaagtg ggcagtttac cgtaaatact ccacccattg  3240
acgtcaatgg aaagtcccta ttggcgttac tatgggaaca tacgtcatta ttgacgtcaa  3300
tgggcggggg tcgttgggcg gtcagccagg cgggccattt accgtaagtt atgtaacgcc  3360
tgcaggttaa ttaagaacat gtgagcaaaa ggccagcaaa aggccaggaa ccgtaaaaag  3420
gccgcgttgc tggcgttttt ccataggctc cgcccccctg acgagcatca caaaaatcga  3480
cgctcaagtc agaggtggcg aaacccgaca ggactataaa gataccaggc gtttccccct  3540
ggaagctccc tcgtgcgctc tcctgttccg accctgccgc ttaccggata cctgtccgcc  3600
tttctccctt cgggaagcgt ggcgctttct catagctcac gctgtaggta tctcagttcg  3660
gtgtaggtcg ttcgctccaa gctgggctgt gtgcacgaac cccccgttca gcccgaccgc  3720
tgcgccttat ccggtaacta tcgtcttgag tccaacccgg taagacacga cttatcgcca  3780
ctggcagcag ccactggtaa caggattagc agagcgaggt atgtaggcgg tgctacagag  3840
ttcttgaagt ggtggcctaa ctacggctac actagaagaa cagtatttgg tatctgcgct  3900
ctgctgaagc cagttacctt cggaaaaaga gttggtagct cttgatccgg caaacaaacc  3960
accgctggta gcggtggttt ttttgtttgc aagcagcaga ttacgcgcag aaaaaaagga  4020
```

-continued

```
tctcaagaag atcctttgat cttttctacg gggtctgacg ctcagtggaa cgaaaactca  4080
cgttaaggga ttttggtcat ggctagttaa ttaacattta aatcagcggc cgcaataaaa  4140
tatctttatt ttcattacat ctgtgtgttg gttttttgtg tgaatcgtaa ctaacatacg  4200
ctctccatca aaacaaaacg aaacaaaaca aactagcaaa ataggctgtc cccagtgcaa  4260
gtgcaggtgc cagaacattt ctctatcgaa                                  4290

SEQ ID NO: 84          moltype = AA  length = 284
FEATURE                Location/Qualifiers
source                 1..284
                       mol_type = protein
                       organism = synthetic construct
SEQUENCE: 84
MYRMQLLSCI ALSLALVTNS APLERKSSVE CPPCPAPPVA GPSVFLFPPK PKDTLMISRT  60
PEVTCVVVDV SHEDPEVQFN WYVDGVEVHN AKTKPREEQF NSTFRVVSVL TVVHQDWLNG  120
KEYKCKVSNK GLPAPIEKTI SKTKGQPREP QVYTLPPSRE EMTKNQVSLT CLVKGFYPSD  180
IAVEWESNGQ PENNYKTTPP MLDSDGSFFL YSKLTVDKSR WQQGNVFSCS VMHEALHNHY  240
TQKSLSLSPG ARTRLVQYRG EVQAMLGQST EELRVSLASH LRKL                  284

SEQ ID NO: 85          moltype = DNA  length = 4284
FEATURE                Location/Qualifiers
source                 1..4284
                       mol_type = other DNA
                       organism = synthetic construct
SEQUENCE: 85
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cgatacgcct ggtgcagtac cgcggcgagg  660
tgcaggccat gctcggccag agtactgagg agctgcgggt gcgcctcgcc tcccacctgc  720
gcaagctgat atcggccatg gttagatctg tggagtgccc accttgccca gcaccacctg  780
tggcaggacc ttcagtcttc ctcttccccc caaaacccaa ggacaccctg atgatctcca  840
gaacccctga ggtcacgtgc gtggtggtgg acgtgagcca cgaagacccc gaggtccagt  900
tcaactggta cgtggacggc atggaggtgc ataatgccaa gacaaagcca cgggaggagc  960
agttcaacag cacgttccgt gtggtcagcg tcctcaccgt cgtgcaccag gactggctga  1020
acggcaagga gtacaagtgc aaggtctcca acaaaggcct cccagccccc atcgagaaaa  1080
ccatctccaa aaccaaaggg cagccccgag aaccacaggt gtacaccctg cccccatccc  1140
gggaggagat gaccaagaac caggtcagcc tgacctgcct ggtcaaaggc ttctacccca  1200
gcgacatcgc cgtggagtgg gagagcaatg ggcagccgga gaacaactac aagaccacac  1260
ctcccatgct ggactccgac ggctccttct tcctctacag caagctcacc gtggacaaga  1320
gcaggtggca gcaggggaac gtcttctcat gctccgtgat gcatgaggct ctgcacaacc  1380
actacacaca gaagagcctc tccctgtctc cgggtaaatg agtgccacgg ctagctggcc  1440
agacatgata agatacattg atgagtttgg acaaaccaca actagaatgc agtgaaaaaa  1500
atgctttatt tgtgaaattt gtgatgctat tgctttattt gtaaccatta taagctgcaa  1560
taaacaagtt aacaacaaca attgcattca ttttatgttt caggttcagg gggaggtgtg  1620
ggaggttttt taaagcaagt aaaacctcta caaatgtggt atggaattaa ttctaaaata  1680
cagcatagca aaactttaac ctccaaatca agcctctact tgaatccttt tctgagggat  1740
gaataaggca taggcatcag gggctgttgc caatgtgcat tagctgtttg cagcctcacc  1800
ttctttcatg gagtttaaga tatagtgtat tttcccaagg tttgaactag ctcttcattt  1860
ctttatgttt taaatgcact gacctcccac attccctttt tagtaaaata ttcagaaata  1920
atttaaatac atcattgcaa tgaaaataaa tgttttttat taggcagaat ccagatgctc  1980
aaggcccttc ataatatccc ccagtttagt agttggactt agggaacaaa ggaaccttta  2040
atagaaattg gacagcaaga aagcgagctt ctagcttatc ctcagtcctg ctcctctgcc  2100
acaaagtgca cgcagttgcc ggccgggtcg cgcagggcga actcccgccc ccacggctgc  2160
tcgccgatct cggtcatggc cggcccggag gcgtcccgga agttcgtgga cacgacctcc  2220
gaccactcgg cgtacagctc gtccaggccg cgcacccaca cccaggccag ggtgttgtcc  2280
ggcaccacct ggtcctggac cgcgctgatg aacagggtca cgtcgtcccg gaccacaccg  2340
gcgaagtcgt cctccacgaa gtcccgggag aacccgagcc ggtcggtcca gaactcgacc  2400
gctccggcga cgtcgcgcgc ggtgagcacc ggaacggcac tggtcaactt ggccatgatg  2460
gctcctcctg tcaggagagg aaagagaaga aggttagtac aattgctata gtgagttgta  2520
ttatactatg cagatatact atgccaatga ttaattgtca aactagggct gcagggttca  2580
tagtgccact tttcctgcac tgccccatct cctgcccacc ctttcccagg catagacagt  2640
cagtgactta ccaaactcac aggagggaga aggcagaagc ttgagacaga cccgcgggac  2700
cgccgaactg cgaggggacg tggctagggc ggcttctttt atggtgcgcc ggccctcgga  2760
ggcagggcgc tcggggaggc ctagcggcca atctgcggtg gcaggaggcg ggccgaagg  2820
ccgtgcctga ccaatccgga gcacatagga gtctcagccc cccgccccaa agcaagggga  2880
agtcacgcgc ctgtagcgcc agcgtgttgt gaaatggggg cttgggggg ttggggccct  2940
gactagtcaa aacaaactcc cattgacgtc aatggggtgg agacttggaa atccccgtga  3000
gtcaaaccgc tatccacgcc cattgatgta ctgccaaaac cgcatcatca tggtaatagc  3060
gatgactaat acgtagatgt actgccaagt aggaaagtcc cataaggtca tgtactgggc  3120
ataatgccag gcgggccatt taccgtcatt gacgtcaata gggggcgtac ttggcatatg  3180
atacacttga tgtactgcca agtgggcagt ttaccgtaaa tactccaccc attgacgtca  3240
atggaaagtc cctattggcg ttactatggg aacatacgtc attattgacg tcaatgggcg  3300
```

-continued

```
ggggtcgttg ggcggtcagc caggcgggcc atttaccgta agttatgtaa cgcctgcagg  3360
ttaattaaga acatgtgagc aaaaggccag caaaaggcca ggaaccgtaa aaaggccgcg  3420
ttgctggcgt ttttccatag gctccgcccc cctgacgagc atcacaaaaa tcgacgctca  3480
agtcagaggt ggcgaaaccc gacaggacta taaagatacc aggcgtttcc ccctggaagc  3540
tccctcgtgc gctctcctgt tccgaccctg ccgcttaccg gatacctgtc cgcctttctc  3600
ccttcgggaa gcgtggcgct ttctcatagc tcacgctgta ggtatctcag ttcggtgtag  3660
gtcgttcgct ccaagctggg ctgtgtgcac gaaccccccg ttcagcccga ccgctgcgcc  3720
ttatccggta actatcgtct tgagtccaac ccggtaagac acgacttatc gccactggca  3780
gcagccactg gtaacaggat tagcagagcg aggtatgtag gcggtgctac agagttcttg  3840
aagtggtggc ctaactacgg ctacactaga agaacagtat ttggtatctg cgctctgctg  3900
aagccagtta ccttcggaaa aagagttggt agctcttgat ccggcaaaca aaccaccgct  3960
ggtagcggtg gtttttttgt ttgcaagcag cagattacgc gcagaaaaaa aggatctcaa  4020
gaagatcctt tgatcttttc tacggggtct gacgctcagt ggaacgaaaa ctcacgttaa  4080
gggattttgg tcatggctag ttaattaaca tttaaatcag cggccgcaat aaaatatctt  4140
tattttcatt acatctgtgt gttggttttt tgtgtgaatc gtaactaaca tacgctctcc  4200
atcaaaacaa aacgaaacaa aacaaactag caaaataggc tgtccccagt gcaagtgcag  4260
gtgccagaac atttctctat cgaa                                        4284

SEQ ID NO: 86          moltype = AA  length = 282
FEATURE                Location/Qualifiers
source                 1..282
                       mol_type = protein
                       organism = synthetic construct
SEQUENCE: 86
MYRMQLLSCI ALSLALVTNS IRLVQYRGEV QAMLGQSTEE LRVRLASHLR KLISAMVRSV  60
ECPPCPAPPV AGPSVFLFPP KPKDTLMISR TPEVTCVVVD VSHEDPEVQF NWYVDGMEVH  120
NAKTKPREEQ FNSTFRVVSV LTVVHQDWLN GKEYKCKVSN KGLPAPIEKT ISKTKGQPRE  180
PQVYTLPPSR EEMTKNQVSL TCLVKGFYPS DIAVEWESNG QPENNYKTTP PMLDSDGSFF  240
LYSKLTVDKS RWQQGNVFSC SVMHEALHNH YTQKSLSLSP GK                    282

SEQ ID NO: 87          moltype = DNA  length = 4284
FEATURE                Location/Qualifiers
source                 1..4284
                       mol_type = other DNA
                       organism = synthetic construct
SEQUENCE: 87
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cgatacgcct ggtgcagtac cgcggcgagg  660
tgcaggccat gctcggccag agtactgagg agctgcgggt gagcctcgcc tcccacctgc  720
gcaagctgat atcggccatg gttagatctg tggagtgccc accttgccca gcaccacctg  780
tggcaggacc ttcagtcttc ctcttccccc caaaacccaa ggacaccctg atgatctcca  840
gaacccctga ggtcacgtgc gtggtggtgg acgtgagcca cgaagacccc gaggtccagt  900
tcaactggta cgtggacggc atggaggtgc ataatgccaa gacaaagcca cgggaggagc  960
agttcaacag cacgttccgt gtggtcagcg tcctcaccgt cgtgcaccag gactggctga  1020
acggcaagga gtacaagtgc aaggtctcca acaaaggcct cccagccccc atcgagaaaa  1080
ccatctccaa aaccaaaggg cagccccgag aaccacaggt gtacaccctg cccccatccc  1140
gggaggagat gaccaagaac caggtcagcc tgacctgcct ggtcaaaggc ttctacccca  1200
gcgacatcgc cgtggagtgg gagagcaatg ggcagccgga gaacaactac aagaccacac  1260
ctcccatgct ggactccgac ggctccttct tcctctacag caagctcacc gtggacaaga  1320
gcaggtggca gcaggggaac gtcttctcat gctccgtgat gcatgaggct ctgcacaacc  1380
actacacaca gaagagcctc tccctgtctc cgggtaaatg agtgccacgg ctagctggcc  1440
agacatgata agatacattg atgagtttgg acaaaccaca actagaatgc agtgaaaaaa  1500
atgctttatt tgtgaaattt gtgatgctat tgctttattt gtaaccatta taagctgcaa  1560
taaacaagtt aacaacaaca attgcattca ttttatgttt caggttcagg gggaggtgtg  1620
ggaggttttt taaagcaagt aaaacctcta caaatgtggt atggaattaa ttctaaaata  1680
cagcatagca aaactttaac ctccaaatca agcctctact tgaatccttt tctgagggat  1740
gaataaggca taggcatcag gggctgttgc caatgtgcat tagctgtttg cagcctcacc  1800
ttctttcatg gagtttaaga tatagtgtat tttcccaagg tttgaactag ctcttcattt  1860
ctttatgttt taaatgcact gacctcccac attccctttt tagtaaaata ttcagaaata  1920
atttaaatac atcattgcaa tgaaaataaa tgttttttat taggcagaat ccagatgctc  1980
aaggcccttc ataatatccc ccagtttagt agttggactt agggaacaaa ggaaccttta  2040
atagaaattg gacagcaaga aagcgagctt ctagcttatc ctcagtcctg ctcctctgcc  2100
acaaagtgca cgcagttgcc ggccgggtcg cgcagggcga actcccgccc ccacggctgc  2160
tcgccgatct cggtcatggc cggcccggag gcgtcccgga agttcgtgga cacgacctcc  2220
gaccactcgg cgtacagctc gtccaggccg cgcacccaca cccaggccag ggtgttgtcc  2280
ggcaccacct ggtcctggac cgcgctgatg aacagggtca cgtcgtcccg gaccacaccg  2340
gcgaagtcgt cctccacgaa gtcccgggag aacccgagcc ggtcggtcca gaactcgacc  2400
gctccggcga cgtcgcgcgc ggtgagcacc ggaacggcac tggtcaactt ggccatgatg  2460
gctcctcctg tcaggagagg aaagagaaga aggttagtac aattgctata gtgagttgta  2520
ttatactatg cagatatact atgccaatga ttaattgtca aactagggct gcagggttca  2580
```

-continued

```
tagtgccact tttcctgcac tgccccatct cctgcccacc ctttcccagg catagacagt  2640
cagtgactta ccaaactcac aggagggaga aggcagaagc ttgagacaga cccgcgggac  2700
cgcccgaactg cgaggggacg tggctagggc ggcttctttt atggtgcgcc ggccctcgga  2760
ggcagggcgc tcggggaggc ctagcggcca atctgcggtg gcaggaggcg gggccgaagg  2820
ccgtgcctga ccaatccgga gcacatagga gtctcagccc cccgccccaa agcaagggga  2880
agtcacgcgc ctgtagcgcc agcgtgttgt gaaatggggg cttgggggg ttggggccct  2940
gactagtcaa aacaaactcc cattgacgtc aatggggtgg agacttggaa atccccgtga  3000
gtcaaaccgc tatccacgcc cattgatgta ctgccaaaac cgcatcatca tggtaatagc  3060
gatgactaat acgtagatgt actgccaagt aggaaagtcc cataaggtca tgtactgggc  3120
ataatgccag gcgggccatt taccgtcatt gacgtcaata gggggcgtac ttggcatatg  3180
atacacttga tgtactgcca agtgggcagt ttaccgtaaa tactccaccc attgacgtca  3240
atggaaagtc cctattggcg ttactatggg aacatacgtc attattgacg tcaatgggcg  3300
ggggtcgttg ggcggtcagc caggcgggcc atttaccgta agttatgtaa cgcctgcagg  3360
ttaattaaga acatgtgagc aaaaggccag caaaaggcca ggaaccgtaa aaaggccgcg  3420
ttgctggcgt ttttccatag gctccgcccc cctgacgagc atcacaaaaa tcgacgctca  3480
agtcagaggt ggcgaaaccc gacaggacta taaagatacc aggcgtttcc ccctggaagc  3540
tccctcgtgc gctctcctgt tccgaccctg ccgcttaccg gatacctgtc cgcctttctc  3600
ccttcgggaa gcgtggcgct ttctcatagc tcacgctgta ggtatctcag ttcggtgtag  3660
gtcgttcgct ccaagctggg ctgtgtgcac gaaccccccg ttcagcccga ccgctgcgcc  3720
ttatccggta actatcgtct tgagtccaac ccggtaagac acgacttatc gccactggca  3780
gcagccactg gtaacaggat tagcagagcg aggtatgtag gcggtgctac agagttcttg  3840
aagtggtggc ctaactacgg ctacactaga agaacagtat ttggtatctg cgctctgctg  3900
aagccagtta ccttcggaaa aagagttggt agctcttgat ccggcaaaca aaccaccgct  3960
ggtagcggtg gtttttttgt ttgcaagcag cagattacgc gcagaaaaaa aggatctcaa  4020
gaagatcctt tgatcttttc tacggggtct gacgctcagt ggaacgaaaa ctcacgttaa  4080
gggattttgg tcatggctag ttaattaaca tttaaatcag cggccgcaat aaaatatctt  4140
tattttcatt acatctgtgt gttggttttt tgtgtgaatc gtaactaaca tacgctctcc  4200
atcaaaacaa aacgaaacaa aacaaactag caaaataggc tgtccccagt gcaagtgcag  4260
gtgccagaac atttctctat cgaa                                         4284

SEQ ID NO: 88          moltype = AA  length = 282
FEATURE                Location/Qualifiers
source                 1..282
                       mol_type = protein
                       organism = synthetic construct
SEQUENCE: 88
MYRMQLLSCI ALSLALVTNS IRLVQYRGEV QAMLGQSTEE LRVSLASHLR KLISAMVRSV  60
ECPPCPAPPV AGPSVFLFPP KPKDTLMISR TPEVTCVVVD VSHEDPEVQF NWYVDGMEVH  120
NAKTKPREEQ FNSTFRVVSV LTVVHQDWLN GKEYKCKVSN KGLPAPIEKT ISKTKGQPRE  180
PQVYTLPPSR EEMTKNQVSL TCLVKGFYPS DIAVEWESNG QPENNYKTTP PMLDSDGSFF  240
LYSKLTVDKS RWQQGNVFSC SVMHEALHNH YTQKSLSLSP GK                    282

SEQ ID NO: 89          moltype = DNA  length = 4284
FEATURE                Location/Qualifiers
source                 1..4284
                       mol_type = other DNA
                       organism = synthetic construct
SEQUENCE: 89
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cggcacctct cgagcgcaaa tctagtgtcg  660
agtgcccacc gtgcccagca ccacctgtgg caggaccgtc agtcttcctc ttccccccaa  720
aacccaagga caccctcatg atctcccgga cccctgaggt cacgtgcgtg gtggtggacg  780
tgagccacga agaccccgag gtccagttca actggtacgt ggacggcgtg gaggtgcata  840
atgccaagac aaagccacgg gaggagcagt tcaacagcac gttccgtgtg gtcagcgtcc  900
tcaccgttgt gcaccaggac tggctgaacg gcaaggagta caagtgcaag gtctccaaca  960
aaggcctccc agcccccatc gagaaaacca tctccaaaac caaagggcag ccccgagaac  1020
cacaggtgta caccctgccc ccatcccggg aggagatgac caagaaccag gtcagcctga  1080
cctgcctggt caaaggcttc taccccagcg acatcgccgt ggagtgggag agcaatgggc  1140
agccggagaa caactacaag accacgcctc ccatgctgga ctccgacggc tccttcttcc  1200
tctacagcaa gctcaccgtg gacaagagca ggtggcagca ggggaacgtc ttctcatgct  1260
ccgtgatgca tgaggctctg cacaaccact acacgcagaa gagcctctcc ctgtctccgg  1320
gtgcacgtac gagcaccgag gagctgcggg tgcgcctcgc ctcccacctg cgcaagctgc  1380
gtaagcggct cctccgcgat gccgatgacc tgcagaagtg atatctcgag ctagctggcc  1440
agacatgata agatacattg atgagtttgg acaaaccaca actagaatgc agtgaaaaaa  1500
atgctttatt tgtgaaattt gtgatgctat tgctttattt gtaaccatta taagctgcaa  1560
taaacaagtt aacaacaaca attgcattca ttttatgttt caggttcagg gggaggtgtg  1620
ggaggttttt taaagcaagt aaaacctcta caaatgtggt atggaattaa ttctaaaata  1680
cagcatagca aaactttaac ctccaaatca agcctctact tgaatccttt tctgagggat  1740
gaataaggca taggcatcag ggctgttgc caatgtgcat tagctgtttg cagcctcacc  1800
ttctttcatg gagtttaaga tatagtgtat tttcccaagg tttgaactag ctcttcattt  1860
```

```
ctttatgttt taaatgcact gacctcccac attccctttt tagtaaaata ttcagaaata  1920
atttaaatac atcattgcaa tgaaaataaa tgttttttat taggcagaat ccagatgctc  1980
aaggcccttc ataatatccc ccagtttagt agttggactt agggaacaaa ggaaccttta  2040
atagaaattg gacagcaaga aagcgagctt ctagcttatc ctcagtcctg ctcctctgcc  2100
acaaagtgca cgcagttgcc ggccgggtcg cgcagggcga actcccgccc ccacggctgc  2160
tcgccgatct cggtcatggc cggcccggag gcgtcccgga agttcgtgga cacgacctcc  2220
gaccactcgg cgtacagctc gtccaggccg cgcacccaca cccaggccag ggtgttgtcc  2280
ggcaccacct ggtcctggac cgcgctgatg aacagggtca cgtcgtcccg gaccacaccg  2340
gcgaagtcgt cctccacgaa gtcccgggag aacccgagcc ggtcggtcca gaactcgacc  2400
gctccggcga cgtcgcgcgc ggtgagcacc ggaacggcac tggtcaactt ggccatgatg  2460
gctcctcctg tcaggagagg aaagagaaga aggttagtac aattgctata gtgagttgta  2520
ttatactatg cagatatact atgccaatga ttaattgtca aactagggct gcagggttca  2580
tagtgccact tttcctgcac tgccccatct cctgcccacc ctttcccagg catagacagt  2640
cagtgactta ccaaactcac aggagggaga aggcagaagc ttgagacaga cccgcgggac  2700
cgccgaactg cgaggggacg tggctagggc ggcttctttt atggtgcgcc ggccctcgga  2760
ggcagggcgc tcggggaggc ctagcggcca atctgcggtg gcaggaggcg gggccgaagg  2820
ccgtgcctga ccaatccgga gcacatagga gtctcagccc cccgccccaa agcaagggga  2880
agtcacgcgc ctgtagcgcc agcgtgttgt gaaatggggg cttggggggg ttggggccct  2940
gactagtcaa aacaaactcc cattgacgtc aatggggtgg agacttggaa atccccgtga  3000
gtcaaaccgc tatccacgcc cattgatgta ctgccaaaac cgcatcatca tggtaatagc  3060
gatgactaat acgtagatgt actgccaagt aggaaagtcc cataaggtca tgtactgggc  3120
ataatgccag gcgggccatt taccgtcatt gacgtcaata gggggcgtac ttggcatatg  3180
atacacttga tgtactgcca agtgggcagt ttaccgtaaa tactccaccc attgacgtca  3240
atggaaagtc cctattggcg ttactatggg aacatacgtc attattgacg tcaatgggcg  3300
ggggtcgttg ggcggtcagc caggcgggcc atttaccgta agttatgtaa cgcctgcagg  3360
ttaattaaga acatgtgagc aaaaggccag caaaaggcca ggaaccgtaa aaaggccgcg  3420
ttgctggcgt ttttccatag gctccgcccc cctgacgagc atcacaaaaa tcgacgctca  3480
agtcagaggt ggcgaaaccc gacaggacta taaagatacc aggcgtttcc ccctggaagc  3540
tccctcgtgc gctctcctgt tccgaccctg ccgcttaccg gatacctgtc cgcctttctc  3600
ccttcgggaa gcgtggcgct ttctcatagc tcacgctgta ggtatctcag ttcggtgtag  3660
gtcgttcgct ccaagctggg ctgtgtgcac gaaccccccg ttcagcccga ccgctgcgcc  3720
ttatccggta actatcgtct tgagtccaac ccggtaagac acgacttatc gccactggca  3780
gcagccactg gtaacaggat tagcagagcg aggtatgtag gcggtgctac agagttcttg  3840
aagtggtggc ctaactacgg ctacactaga agaacagtat ttggtatctg cgctctgctg  3900
aagccagtta ccttcggaaa aagagttggt agctcttgat ccggcaaaca aaccaccgct  3960
ggtagcggtg gtttttttgt ttgcaagcag cagattacgc gcagaaaaaa aggatctcaa  4020
gaagatcctt tgatcttttc tacggggtct gacgctcagt ggaacgaaaa ctcacgttaa  4080
gggattttgg tcatggctag ttaattaaca tttaaatcag cggccgcaat aaaatatctt  4140
tattttcatt acatctgtgt gttggttttt tgtgtgaatc gtaactaaca tacgctctcc  4200
atcaaaacaa aacgaaacaa aacaaactag caaaataggc tgtccccagt gcaagtgcag  4260
gtgccagaac atttctctat cgaa                                         4284
```

```
SEQ ID NO: 90          moltype = AA  length = 282
FEATURE                Location/Qualifiers
source                 1..282
                       mol_type = protein
                       organism = synthetic construct
SEQUENCE: 90
MYRMQLLSCI ALSLALVTNS APLERKSSVE CPPCPAPPVA GPSVFLFPPK PKDTLMISRT  60
PEVTCVVVDV SHEDPEVQFN WYVDGVEVHN AKTKPREEQF NSTFRVVSVL TVVHQDWLNG  120
KEYKCKVSNK GLPAPIEKTI SKTKGQPREP QVYTLPPSRE EMTKNQVSLT CLVKGFYPSD  180
IAVEWESNGQ PENNYKTTPP MLDSDGSFFL YSKLTVDKSR WQQGNVFSCS VMHEALHNHY  240
TQKSLSLSPG ARTSTEELRV RLASHLRKLR KRLLRDADDL QK                    282
```

```
SEQ ID NO: 91          moltype = DNA  length = 4284
FEATURE                Location/Qualifiers
source                 1..4284
                       mol_type = other DNA
                       organism = synthetic construct
SEQUENCE: 91
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gccttttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cggcacctct cgagcgcaaa tctagtgtcg  660
agtgcccacc gtgcccagca ccacctgtgg caggaccgtc agtcttcctc ttcccccccaa  720
aacccaagga caccctcatg atctcccgga cccctgaggt cacgtgcgtg gtggtggacg  780
tgagccacga agaccccgag gtccagttca actggtacgt ggacggcgtg gaggtgcata  840
atgccaagac aaagccacgg gaggagcagt tcaacagcac gttccgtgtg gtcagcgtcc  900
tcaccgttgt gcaccaggac tggctgaacg gcaaggagta caagtgcaag gtctccaaca  960
aaggcctccc agcccccatc gagaaaacca tctccaaaac caaagggcag ccccgagaac  1020
cacaggtgta caccctgccc ccatcccggg aggagatgac caagaaccag gtcagcctga  1080
cctgcctggt caaaggcttc taccccagcg acatcgccgt ggagtgggag agcaatgggc  1140
```

-continued

```
agccggagaa caactacaag accacgcctc ccatgctgga ctccgacggc tccttcttcc  1200
tctacagcaa gctcaccgtg gacaagagca ggtggcagca ggggaacgtc ttctcatgct  1260
ccgtgatgca tgaggctctg cacaaccact acacgcagaa gagcctctcc ctgtctccgg  1320
gtgcacgtac gagcaccgag gagctgcggg tgagcctcgc ctcccacctg cgcaagctgc  1380
gtaagcggct cctccgcgat gccgatgacc tgcagaagtg atatctcgag ctagctggcc  1440
agacatgata agatacattg atgagtttgg acaaaccaca actagaatgc agtgaaaaaa  1500
atgctttatt tgtgaaattt gtgatgctat tgctttattt gtaaccatta taagctgcaa  1560
taaacaagtt aacaacaaca attgcattca ttttatgttt caggttcagg gggaggtgtg  1620
ggaggttttt taaagcaagt aaaacctcta caaatgtggt atggaattaa ttctaaaata  1680
cagcatagca aaactttaac ctccaaatca agcctctact tgaatccttt tctgagggat  1740
gaataaggca taggcatcag gggctgttgc caatgtgcat tagctgtttg cagcctcacc  1800
ttctttcatg gagtttaaga tatagtgtat tttcccaagg tttgaactag ctcttcattt  1860
ctttatgttt taaatgcact gacctcccac attccctttt tagtaaaata ttcagaaata  1920
atttaaatac atcattgcaa tgaaaataaa tgttttttat taggcagaat ccagatgctc  1980
aaggcccttc ataatatccc ccagtttagt agttggactt agggaacaaa ggaaccttta  2040
atagaaattg gacagcaaga aagcgagctt ctagcttatc ctcagtcctg ctcctctgcc  2100
acaaagtgca cgcagttgcc ggccgggtcg cgcagggcga actcccgccc ccacggctgc  2160
tcgccgatct cggtcatggc cggcccggag gcgtcccgga agttcgtgga cacgacctcc  2220
gaccactcgg cgtacagctc gtccaggccg cgcacccaca cccaggccag ggtgttgtcc  2280
ggcaccacct ggtcctggac cgcgctgatg aacagggtca cgtcgtcccg gaccacaccg  2340
gcgaagtcgt cctccacgaa gtcccgggag aacccgagcc ggtcggtcca gaactcgacc  2400
gctccggcga cgtcgcgcgc ggtgagcacc ggaacggcac tggtcaactt ggccatgatg  2460
gctcctcctg tcaggagagg aaagagaaga aggttagtac aattgctata gtgagttgta  2520
ttatactatg cagatatact atgccaatga ttaattgtca aactagggct gcagggttca  2580
tagtgccact tttcctgcac tgccccatct cctgcccacc ctttcccagg catagacagt  2640
cagtgactta ccaaactcac aggagggaga aggcagaagc ttgagacaga cccgcgggac  2700
cgccgaactg cgaggggacg tggctagggc ggcttctttt atggtgcgcc ggccctcgga  2760
ggcagggcgc tcggggaggc ctagcggcca atctgcggtg gcaggaggcg gggccgaagg  2820
ccgtgcctga ccaatccgga gcacatagga gtctcagccc cccgccccaa agcaagggga  2880
agtcacgcgc ctgtagcgcc agcgtgttgt gaaatggggg cttgggggg ttggggccct  2940
gactagtcaa aacaaactcc cattgacgtc aatggggtgg agacttggaa atccccgtga  3000
gtcaaaccgc tatccacgcc cattgatgta ctgccaaaac cgcatcatca tggtaatagc  3060
gatgactaat acgtagatgt actgccaagt aggaaagtcc cataaggtca tgtactgggc  3120
ataatgccag gcgggccatt taccgtcatt gacgtcaata gggggcgtac ttggcatatg  3180
atacacttga tgtactgcca agtgggcagt ttaccgtaaa tactccaccc attgacgtca  3240
atggaaagtc cctattggcg ttactatggg aacatacgtc attattgacg tcaatgggcg  3300
ggggtcgttg ggcggtcagc caggcgggcc atttaccgta agttatgtaa cgcctgcagg  3360
ttaattaaga acatgtgagc aaaaggccag caaaaggcca ggaaccgtaa aaaggccgcg  3420
ttgctggcgt ttttccatag gctccgcccc cctgacgagc atcacaaaaa tcgacgctca  3480
agtcagaggt ggcgaaaccc gacaggacta taaagatacc aggcgtttcc ccctggaagc  3540
tccctcgtgc gctctcctgt tccgaccctg ccgcttaccg gatacctgtc cgcctttctc  3600
ccttcgggaa gcgtggcgct ttctcatagc tcacgctgta ggtatctcag ttcggtgtag  3660
gtcgttcgct ccaagctggg ctgtgtgcac gaaccccccg ttcagcccga ccgctgcgcc  3720
ttatccggta actatcgtct tgagtccaac ccggtaagac acgacttatc gccactggca  3780
gcagccactg gtaacaggat tagcagagcg aggtatgtag gcggtgctac agagttcttg  3840
aagtggtggc ctaactacgg ctacactaga agaacagtat ttggtatctg cgctctgctg  3900
aagccagtta ccttcggaaa aagagttggt agctcttgat ccggcaaaca aaccaccgct  3960
ggtagcggtg gtttttttgt ttgcaagcag cagattacgc gcagaaaaaa aggatctcaa  4020
gaagatcctt tgatcttttc tacggggtct gacgctcagt ggaacgaaaa ctcacgttaa  4080
gggattttgg tcatggctag ttaattaaca tttaaatcag cggccgcaat aaaatatctt  4140
tattttcatt acatctgtgt gttggttttt tgtgtgaatc gtaactaaca tacgctctcc  4200
atcaaaacaa aacgaaacaa aacaaactag caaaataggc tgtccccagt gcaagtgcag  4260
gtgccagaac atttctctat cgaa                                        4284

SEQ ID NO: 92          moltype = AA  length = 282
FEATURE                Location/Qualifiers
source                 1..282
                       mol_type = protein
                       organism = synthetic construct
SEQUENCE: 92
MYRMQLLSCI ALSLALVTNS APLERKSSVE CPPCPAPPVA GPSVFLFPPK PKDTLMISRT  60
PEVTCVVVDV SHEDPEVQFN WYVDGVEVHN AKTKPREEQF NSTFRVVSVL TVVHQDWLNG  120
KEYKCKVSNK GLPAPIEKTI SKTKGQPREP QVYTLPPSRE EMTKNQVSLT CLVKGFYPSD  180
IAVEWESNGQ PENNYKTTPP MLDSDGSFFL YSKLTVDKSR WQQGNVFSCS VMHEALHNHY  240
TQKSLSLSPG ARTSTEELRV SLASHLRKLR KRLLRDADDL QK                    282

SEQ ID NO: 93          moltype = DNA  length = 4278
FEATURE                Location/Qualifiers
source                 1..4278
                       mol_type = other DNA
                       organism = synthetic construct
SEQUENCE: 93
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
```

-continued

```
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cgataagcac cgaggagctg cgggtgcgcc  660
tcgcctccca cctgcgcaag ctgcgtaagc ggctcctccg cgatgccgat gacctgcaga  720
agatatcggc catggttaga tctgtggagt gcccaccttg cccagcacca cctgtggcag  780
gaccttcagt cttcctcttc cccccaaaac ccaaggacac cctgatgatc tccagaaccc  840
ctgaggtcac gtgcgtggtg gtggacgtga gccacgaaga ccccgaggtc cagttcaact  900
ggtacgtgga cggcatggag gtgcataatg ccaagacaaa gccacgggag gagcagttca  960
acagcacgtt ccgtgtggtc agcgtcctca ccgtcgtgca ccaggactgg ctgaacggca  1020
aggagtacaa gtgcaaggtc tccaacaaag gcctcccagc ccccatcgag aaaaccatct  1080
ccaaaaccaa agggcagccc cgagaaccac aggtgtacac cctgccccca tcccgggagg  1140
agatgaccaa gaaccaggtc agcctgacct gcctggtcaa aggcttctac cccagcgaca  1200
tcgccgtgga gtgggagagc aatgggcagc cggagaacaa ctacaagacc acacctccca  1260
tgctggactc cgacggctcc ttcttcctct acagcaagct caccgtggac aagagcaggt  1320
ggcagcaggg gaacgtcttc tcatgctccg tgatgcatga ggctctgcac aaccactaca  1380
cacagaagag cctctccctg tctccgggta aatgagtgcc acggctagct ggccagacat  1440
gataagatac attgatgagt ttggacaaac cacaactaga atgcagtgaa aaaaatgctt  1500
tatttgtgaa atttgtgatg ctattgcttt atttgtaacc attataagct gcaataaaca  1560
agttaacaac aacaattgca ttcattttat gtttcaggtt cagggggagg tgtgggaggt  1620
tttttaaagc aagtaaaacc tctacaaatg tggtatggaa ttaattctaa aatacagcat  1680
agcaaaactt taacctccaa atcaagcctc tacttgaatc cttttctgag ggatgaataa  1740
ggcataggca tcaggggctg ttgccaatgt gcattagctg tttgcagcct caccttcttt  1800
catggagttt aagatatagt gtattttccc aaggtttgaa ctagctcttc atttctttat  1860
gttttaaatg cactgacctc ccacattccc tttttagtaa aatattcaga aataatttaa  1920
atacatcatt gcaatgaaaa taaatgtttt ttattaggca gaatccagat gctcaaggcc  1980
cttcataata tcccccagtt tagtagttgg acttagggaa caaaggaacc tttaatagaa  2040
attggacagc aagaaagcga gcttctagct tatcctcagt cctgctcctc tgccacaaag  2100
tgcacgcagt tgccggccgg gtcgcgcagg gcgaactccc gcccccacgg ctgctcgccg  2160
atctcggtca tggccggccc ggaggcgtcc cggaagttcg tggacacgac ctccgaccac  2220
tcggcgtaca gctcgtccag gccgcgcacc cacacccagg ccagggtgtt gtccggcacc  2280
acctggtcct ggaccgcgct gatgaacagg gtcacgtcgt cccggaccac accggcgaag  2340
tcgtcctcca cgaagtcccg ggagaacccg agccggtcgg tccagaactc gaccgctccg  2400
gcgacgtcgc gcgcggtgag caccggaacg gcactggtca acttggccat gatggctcct  2460
cctgtcagga gaggaaagag aagaaggtta gtacaattgc tatagtgagt tgtattatac  2520
tatgcagata tactatgcca atgattaatt gtcaaactag ggctgcaggg ttcatagtgc  2580
cacttttcct gcactgcccc atctcctgcc caccctttcc caggcataga cagtcagtga  2640
cttaccaaac tcacaggagg gagaaggcag aagcttgaga cagacccgcg ggaccgccga  2700
actgcgaggg gacgtggcta gggcggcttc ttttatggtg cgccggccct cggaggcagg  2760
gcgctcgggg aggcctagcg gccaatctgc ggtggcagga ggcggggccg aaggccgtgc  2820
ctgaccaatc cggagcacat aggagtctca gcccccccgcc ccaaagcaag gggaagtcac  2880
gcgcctgtag cgccagcgtg ttgtgaaatg ggggcttggg ggggttgggg ccctgactag  2940
tcaaaacaaa ctcccattga cgtcaatggg gtggagactt ggaaatcccc gtgagtcaaa  3000
ccgctatcca cgcccattga tgtactgcca aaaccgcatc atcatggtaa tagcgatgac  3060
taatacgtag atgtactgcc aagtaggaaa gtcccataag gtcatgtact gggcataatg  3120
ccaggcgggc catttaccgt cattgacgtc aatagggggc gtacttggca tatgatacac  3180
ttgatgtact gccaagtggg cagtttaccg taaatactcc acccattgac gtcaatggaa  3240
agtccctatt ggcgttacta tgggaacata cgtcattatt gacgtcaatg ggcgggggtc  3300
gttgggcggt cagccaggcg ggccatttac cgtaagttat gtaacgcctg caggttaatt  3360
aagaacatgt gagcaaaagg ccagcaaaag gccaggaacc gtaaaaaggc cgcgttgctg  3420
gcgtttttcc ataggctccg cccccctgac gagcatcaca aaaatcgacg ctcaagtcag  3480
aggtggcgaa acccgacagg actataaaga taccaggcgt ttccccctgg aagctccctc  3540
gtgcgctctc ctgttccgac cctgccgctt accggatacc tgtccgcctt tctcccttcg  3600
ggaagcgtgg cgctttctca tagctcacgc tgtaggtatc tcagttcggt gtaggtcgtt  3660
cgctccaagc tgggctgtgt gcacgaaccc cccgttcagc ccgaccgctg cgccttatcc  3720
ggtaactatc gtcttgagtc caacccggta agacacgact tatcgccact ggcagcagcc  3780
actggtaaca ggattagcag agcgaggtat gtaggcggtg ctacagagtt cttgaagtgg  3840
tggcctaact acggctacac tagaagaaca gtatttggta tctgcgctct gctgaagcca  3900
gttaccttcg gaaaaagagt tggtagctct tgatccggca aacaaaccac cgctggtagc  3960
ggtggttttt ttgtttgcaa gcagcagatt acgcgcagaa aaaaaggatc tcaagaagat  4020
cctttgatct tttctacggg gtctgacgct cagtggaacg aaaactcacg ttaagggatt  4080
ttggtcatgg ctagttaatt aacatttaaa tcagcggccg caataaaata tctttatttt  4140
cattacatct gtgtgttggt tttttgtgtg aatcgtaact aacatacgct ctccatcaaa  4200
acaaaacgaa acaaaacaaa ctagcaaaat aggctgtccc cagtgcaagt gcaggtgcca  4260
gaacatttct ctatcgaa                                                4278

SEQ ID NO: 94          moltype = AA  length = 280
FEATURE                Location/Qualifiers
source                 1..280
                       mol_type = protein
                       organism = synthetic construct
SEQUENCE: 94
MYRMQLLSCI ALSLALVTNS ISTEELRVRL ASHLRKLRKR LLRDADDLQK ISAMVRSVEC  60
PPCPAPPVAG PSVFLFPPKP KDTLMISRTP EVTCVVVDVS HEDPEVQFNW YVDGMEVHNA  120
KTKPREEQFN STFRVVSVLT VVHQDWLNGK EYKCKVSNKG LPAPIEKTIS KTKGQPREPQ  180
VYTLPPSREE MTKNQVSLTC LVKGFYPSDI AVEWESNGQP ENNYKTTPPM LDSDGSFFLY  240
SKLTVDKSRW QQGNVFSCSV MHEALHNHYT QKSLSLSPGK                        280

SEQ ID NO: 95          moltype = DNA  length = 4278
```

```
FEATURE                Location/Qualifiers
source                 1..4278
                       mol_type = other DNA
                       organism = synthetic construct
SEQUENCE: 95
ggatctgcga tcgctccggt gcccgtcagt gggcagagcg cacatcgccc acagtccccg  60
agaagttggg gggaggggtc ggcaattgaa cgggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc ccgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctacctgaga tcaccggcga aggagggcca ccatgtacag gatgcaactc ctgtcttgca  600
ttgcactaag tcttgcactt gtcacgaatt cgataagcac cgaggagctg cgggtgagcc  660
tcgcctccca cctgcgcaag ctgcgtaagc ggctcctccg cgatgccgat gacctgcaga  720
agatatcggc catggttaga tctgtggagt gcccaccttg cccagcacca cctgtggcag  780
gaccttcagt cttcctcttc cccccaaaac ccaaggacac cctgatgatc tccagaaccc  840
ctgaggtcac gtgcgtggtg gtggacgtga gccacgaaga ccccgaggtc cagttcaact  900
ggtacgtgga cggcatggag gtgcataatg ccaagacaaa gccacgggag gagcagttca  960
acagcacgtt ccgtgtggtc agcgtcctca ccgtcgtgca ccaggactgg ctgaacggca  1020
aggagtacaa gtgcaaggtc tccaacaaag gcctcccagc ccccatcgag aaaaccatct  1080
ccaaaaccaa agggcagccc cgagaaccac aggtgtacac cctgccccca tcccgggagg  1140
agatgaccaa gaaccaggtc agcctgacct gcctggtcaa aggcttctac cccagcgaca  1200
tcgccgtgga gtgggagagc aatgggcagc cggagaacaa ctacaagacc acacctccca  1260
tgctggactc cgacggctcc ttcttcctct acagcaagct caccgtggac aagagcaggt  1320
ggcagcaggg gaacgtcttc tcatgctccg tgatgcatga ggctctgcac aaccactaca  1380
cacagaagag cctctccctg tctccgggta aatgagtgcc acggctagct ggccagacat  1440
gataagatac attgatgagt ttggacaaac cacaactaga atgcagtgaa aaaaatgctt  1500
tatttgtgaa atttgtgatg ctattgcttt atttgtaacc attataagct gcaataaaca  1560
agttaacaac aacaattgca ttcattttat gtttcaggtt cagggggagg tgtgggaggt  1620
tttttaaagc aagtaaaacc tctacaaatg tggtatggaa ttaattctaa aatacagcat  1680
agcaaaactt taacctccaa atcaagcctc tacttgaatc cttttctgag ggatgaataa  1740
ggcataggca tcaggggctg ttgccaatgt gcattagctg tttgcagcct caccttcttt  1800
catggagttt aagatatagt gtattttccc aaggtttgaa ctagctcttc atttctttat  1860
gttttaaatg cactgacctc ccacattccc tttttagtaa aatattcaga aataatttaa  1920
atacatcatt gcaatgaaaa taaatgtttt ttattaggca gaatccagat gctcaaggcc  1980
cttcataata tcccccagtt tagtagttgg acttagggaa caaaggaacc tttaatagaa  2040
attggacagc aagaaagcga gcttctagct tatcctcagt cctgctcctc tgccacaaag  2100
tgcacgcagt tgccggccgg gtcgcgcagg gcgaactccc gcccccacgg ctgctcgccg  2160
atctcggtca tggccggccc ggaggcgtcc cggaagttcg tggacacgac ctccgaccac  2220
tcggcgtaca gctcgtccag gccgcgcacc cacacccagg ccagggtgtt gtccggcacc  2280
acctggtcct ggaccgcgct gatgaacagg gtcacgtcgt cccggaccac accggcgaag  2340
tcgtcctcca cgaagtcccg ggagaacccg agccggtcgg tccagaactc gaccgctccg  2400
gcgacgtcgc gcgcggtgag caccggaacg gcactggtca acttggccat gatggctcct  2460
cctgtcagga gaggaaagag aagaaggtta gtacaattgc tatagtgagt tgtattatac  2520
tatgcagata tactatgcca atgattaatt gtcaaactag ggctgcaggg ttcatagtgc  2580
cacttttcct gcactgcccc atctcctgcc caccctttcc caggcataga cagtcagtga  2640
cttaccaaac tcacaggagg gagaaggcag aagcttgaga cagacccgcg ggaccgccga  2700
actgcgaggg gacgtggcta gggcggcttc ttttatggtg cgccggccct cggaggcagg  2760
gcgctcgggg aggcctagcg gccaatctgc ggtggcagga ggcggggccg aaggccgtgc  2820
ctgaccaatc cggagcacat aggagtctca gccccccgcc ccaaagcaag gggaagtcac  2880
gcgcctgtag cgccagcgtg ttgtgaaatg gggcttgggg ggggttgggg ccctgactag  2940
tcaaaacaaa ctcccattga cgtcaatggg gtggagactt ggaaatcccc gtgagtcaaa  3000
ccgctatcca cgcccattga tgtactgcca aaaccgcatc atcatggtaa tagcgatgac  3060
taatacgtag atgtactgcc aagtaggaaa gtcccataag gtcatgtact gggcataatg  3120
ccaggcgggc catttaccgt cattgacgtc aatagggggc gtacttggca tatgatacac  3180
ttgatgtact gccaagtggg cagtttaccg taaatactcc acccattgac gtcaatggaa  3240
agtccctatt ggcgttacta tgggaacata cgtcattatt gacgtcaatg ggcgggggtc  3300
gttgggcggt cagccaggcg ggccatttac cgtaagttat gtaacgcctg caggttaatt  3360
aagaacatgt gagcaaaagg ccagcaaaag gccaggaacc gtaaaaaggc cgcgttgctg  3420
gcgtttttcc ataggctccg cccccctgac gagcatcaca aaaatcgacg ctcaagtcag  3480
aggtggcgaa acccgacagg actataaaga taccaggcgt ttccccctgg aagctccctc  3540
gtgcgctctc ctgttccgac cctgccgctt accggatacc tgtccgcctt tctcccttcg  3600
ggaagcgtgg cgctttctca tagctcacgc tgtaggtatc tcagttcggt gtaggtcgtt  3660
cgctccaagc tgggctgtgt gcacgaaccc cccgttcagc ccgaccgctg cgccttatcc  3720
ggtaactatc gtcttgagtc caacccggta agacacgact tatcgccact ggcagcagcc  3780
actggtaaca ggattagcag agcgaggtat gtaggcggtg ctacagagtt cttgaagtgg  3840
tggcctaact acggctacac tagaagaaca gtatttggta tctgcgctct gctgaagcca  3900
gttaccttcg gaaaaagagt tggtagctct tgatccggca aacaaaccac cgctggtagc  3960
ggtggttttt ttgtttgcaa gcagcagatt acgcgcagaa aaaaaggatc tcaagaagat  4020
cctttgatct tttctacggg gtctgacgct cagtggaacg aaaactcacg ttaagggatt  4080
ttggtcatgg ctagttaatt aacatttaaa tcagcggccg caataaaata tctttatttt  4140
cattacatct gtgtgttggt tttttgtgtg aatcgtaact aacatacgct ctccatcaaa  4200
acaaaacgaa acaaaacaaa ctagcaaaat aggctgtccc cagtgcaagt gcaggtgcca  4260
gaacatttct ctatcgaa                                                 4278

SEQ ID NO: 96          moltype = AA  length = 280
```

```
FEATURE                Location/Qualifiers
source                 1..280
                       mol_type = protein
                       organism = synthetic construct
SEQUENCE: 96
MYRMQLLSCI ALSLALVTNS ISTEELRVSL ASHLRKLRKR LLRDADDLQK ISAMVRSVEC  60
PPCPAPPVAG PSVFLFPPKP KDTLMISRTP EVTCVVVDVS HEDPEVQFNW YVDGMEVHNA  120
KTKPREEQFN STFRVVSVLT VVHQDWLNGK EYKCKVSNKG LPAPIEKTIS KTKGQPREPQ  180
VYTLPPSREE MTKNQVSLTC LVKGFYPSDI AVEWESNGQP ENNYKTTPPM LDSDGSFFLY  240
SKLTVDKSRW QQGNVFSCSV MHEALHNHYT QKSLSLSPGK                        280

SEQ ID NO: 97          moltype = DNA  length = 6773
FEATURE                Location/Qualifiers
source                 1..6773
                       mol_type = other DNA
                       organism = synthetic construct
SEQUENCE: 97
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcagacaacg tgctgacaca gagccctgcc  840
agcctggctg tttctctggg acagagagcc accatcagct gcaaggccag ccagagcgtt  900
gactacgacg gcgacagcta catgaactgg tatcagcaga agcccggcca gccacctaag  960
gtgttcatct acgccgccag caacctggaa agcggcatcc ctgccagatt ttctggctct  1020
ggcagcggca ccgacttcac cctgaatatc catcctgtgg aagaagagga cgccgccacc  1080
tactactgcc agcagagcaa tgaggacccc tggacatttg gcggaggcac caagctggaa  1140
atcaagcgta cggtggctgc accatctgtc ttcatcttcc cgccatctga tgagcagttg  1200
aaatctggaa ctgcctctgt tgtgtgcctg ctgaataact tctatcccag agaggccaaa  1260
gtacagtgga aggtggataa cgccctccaa tcgggtaact cccaggagag tgtcacagag  1320
caggacagca aggacagcac ctacagcctc agcagcaccc tgacgctgag caaagcagac  1380
tacgagaaac acaaagtcta cgcctgcgaa gtcacccatc agggcctgag ctcgcccgtc  1440
acaaagagct tcaacagggg agagtgttag agggagctag cgtggcatct agacactctc  1500
gagaagggtt cgatccctac cggttagtaa tgagtttgat atctcgacaa tcaacctctg  1560
gattacaaaa tttgtgaaag attgactggt attcttaact atgttgctcc ttttacgcta  1620
tgtggatacg ctgctttaat gcctttgtat catgctattg cttcccgtat ggctttcatt  1680
ttctcctcct tgtataaatc ctggttgctg tctctttatg aggagttgtg gcccgttgtc  1740
aggcaacgtg gcgtggtgtg cactgtgttt gctgacgcaa cccccactgg ttggggcatt  1800
gccaccacct gtcagctcct ttccgggact ttcgctttcc ccctccctat tgccacggcg  1860
gaactcatcg ccgcctgcct tgcccgctgc tggacagggg ctcggctgtt gggcactgac  1920
aattccgtgg tgttgtcggg gaagctgacg tcctttccat ggctgctcgc ctgtgttgcc  1980
acctggattc tgcgcgggac gtccttctgc tacgtccctt cggccctcaa tccagcggac  2040
cttccttccc gcggcctgct gccggctctg cggcctcttc cgcgtcttcg ccttcgccct  2100
cagacgagtc ggatctccct ttgggccgcc tccccgcctg gaaacggggg aggctaactg  2160
aaacacggaa ggagacaata ccggaaggaa cccgcgctat gacggcaata aaaagacaga  2220
ataaaacgca cgggtgttgg gtcgtttgtt cataaacgcg gggttcggtc ccagggctgg  2280
cactctgtcg ataccccacc gagaccccat tggggccaat acgcccgcgt ttcttccttt  2340
tccccacccc accccccaag ttcgggtgaa ggcccagggc tcgcagccaa cgtcggggcg  2400
gcaggccctg ccatagcaga tctgcgcagc tggggctcta gggggtatcc ccacgcgccc  2460
tgtagcggcg cattaagcgc ggcgggtgtg gtggttacgc gcagcgtgac cgctacactt  2520
gccagcgccc tagcgcccgc tcctttcgct ttcttccctt cctttctcgc cacgttcgcc  2580
ggctttcccc gtcaagctct aaatcggggc atccctttag ggttccgatt tagtgcttta  2640
cggcacctcg accccaaaaa acttgattag ggtgatggtt cacgtagtgg gccatcgccc  2700
tgatagacgg tttttcgccc tttgacgttg gagtccacgt tctttaatag tggactcttg  2760
ttccaaactg gaacaacact caaccctatc tcggtctatt cttttgattt ataagggatt  2820
ttggggattt cggcctattg gttaaaaaat gagctgattt aacaaaaatt taacgcgaat  2880
taattctgtg gaatgtgtgt cagttagggt gtggaaagtc cccaggctcc ccagcaggca  2940
gaagtatgca aagcatgcat ctcaattagt cagcaaccag gtgtggaaag tccccaggct  3000
ccccagcagg cagaagtatg caaagcatgc atctcaatta gtcagcaacc atagtcccgc  3060
ccctaactcc gcccatcccg cccctaactc cgcccagttc cgcccattct ccgccccatg  3120
gctgactaat tttttttatt tatgcagagg ccgaggccgc ctctgcctct gagctattcc  3180
agaagtagtg aggaggcttt tttggaggcc taggcttttg caaaaagctc ccgggagctt  3240
gtatatccat tttcggatct gatcaagaga caggatgagg atcgtttcgc atgattgaac  3300
aagatggatt gcacgcaggt tctccggccg cttgggtgga gaggctattc ggctatgact  3360
gggcacaaca gacaatcggc tgctctgatg ccgccgtgtt ccggctgtca gcgcaggggc  3420
gcccggttct ttttgtcaag accgacctgt ccggtgccct gaatgaactg caggacgagg  3480
cagcgcggct atcgtggctg gccacgacgg gcgttccttg cgcagctgtg ctcgacgttg  3540
tcactgaagc gggaagggac tggctgctat tgggcgaagt gccggggcag gatctcctgt  3600
catctcacct tgctcctgcc gagaaagtat ccatcatggc tgatgcaatg cggcggctgc  3660
atacgcttga tccggctacc tgcccattcg accaccaagc gaaacatcgc atcgagcgag  3720
```

-continued

```
cacgtactcg gatggaagcc ggtcttgtcg atcaggatga tctggacgaa gagcatcagg  3780
ggctcgcgcc agccgaactg ttcgccaggc tcaaggcgcg catgcccgac ggcgaggatc  3840
tcgtcgtgac ccatggcgat gcctgcttgc cgaatatcat ggtggaaaat ggccgctttt  3900
ctggattcat cgactgtggc cggctgggtg tggcggaccg ctatcaggac atagcgttgg  3960
ctacccgtga tattgctgaa gagcttggcg gcgaatgggc tgaccgcttc ctcgtgcttt  4020
acggtatcgc cgctcccgat tcgcagcgca tcgccttcta tcgccttctt gacgagttct  4080
tctgagcggg actctggggt tcgcgaaatg accgaccaag cgacgcccaa cctgccatca  4140
cgagatttcg attccaccgc cgccttctat gaaaggttgg gcttcggaat cgttttccgg  4200
gacgccggct ggatgatcct ccagcgcggg gatctcatgc tggagttctt cgcccacccc  4260
aacttgttta ttgcagctta taatggttac aaataaagca atagcatcac aaatttcaca  4320
aataaagcat ttttttcact gcattctagt tgtggtttgt ccaaactcat caatgtatct  4380
tatcatgtct gtataccgtc gacctctagc tagagcttgg cgtaatcatg gtcatagctg  4440
tttcctgtgt gaaattgtta tccgctcaca attccacaca acatacgagc cggaagcata  4500
aagtgtaaag cctggggtgc ctaatgagtg agctaactca cattaattgc gttgcgctca  4560
ctgcccgctt tccagtcggg aaacctgtcg tgccagctgc attaatgaat cggccaacgc  4620
gcggggagag gcggtttgcg tattgggcgc tcttccgctt cctcgctcac tgactcgctg  4680
cgctcggtcg ttcggctgcg gcgagcggta tcagctcact caaaggcggt aatacggtta  4740
tccacagaat caggggataa cgcaggaaag aacatgtgag caaaaggcca gcaaaaggcc  4800
aggaaccgta aaaaggccgc gttgctggcg tttttccata ggctccgccc ccctgacgag  4860
catcacaaaa atcgacgctc aagtcagagg tggcgaaacc cgacaggact ataaagatac  4920
caggcgtttc cccctggaag ctccctcgtg cgctctcctg ttccgaccct gccgcttacc  4980
ggatacctgt ccgcctttct cccttcggga agcgtggcgc tttctcaatg ctcacgctgt  5040
aggtatctca gttcggtgta ggtcgttcgc tccaagctgg gctgtgtgca cgaacccccc  5100
gttcagcccg accgctgcgc cttatccggt aactatcgtc ttgagtccaa cccggtaaga  5160
cacgacttat cgccactggc agcagccact ggtaacagga ttagcagagc gaggtatgta  5220
ggcggtgcta cagagttctt gaagtggtgg cctaactacg gctacactag aaggacagta  5280
tttggtatct gcgctctgct gaagccagtt accttcggaa aaagagttgg tagctcttga  5340
tccggcaaac aaaccaccgc tggtagcggt ggtttttttg tttgcaagca gcagattacg  5400
cgcagaaaaa aaggatctca agaagatcct ttgatctttt ctacggggtc tgacgctcag  5460
tggaacgaaa actcacgtta agggattttg gtcatgagat tatcaaaaag gatcttcacc  5520
tagatccttt taaattaaaa atgaagtttt aaatcaatct aaagtatata tgagtaaact  5580
tggtctgaca gttaccaatg cttaatcagt gaggcaccta tctcagcgat ctgtctattt  5640
cgttcatcca tagttgcctg actccccgtc gtgtagataa ctacgatacg ggagggctta  5700
ccatctggcc ccagtgctgc aatgataccg cgagacccac gctcaccggc tccagattta  5760
tcagcaataa accagccagc cggaagggcc gagcgcagaa gtggtcctgc aactttatcc  5820
gcctccatcc agtctattaa ttgttgccgg gaagctagag taagtagttc gccagttaat  5880
agtttgcgca acgttgttgc cattgctaca ggcatcgtgg tgtcacgctc gtcgtttggt  5940
atggcttcat tcagctccgg ttcccaacga tcaaggcgag ttacatgatc ccccatgttg  6000
tgcaaaaaag cggttagctc cttcggtcct ccgatcgttg tcagaagtaa gttggccgca  6060
gtgttatcac tcatggttat ggcagcactg cataattctc ttactgtcat gccatccgta  6120
agatgctttt ctgtgactgg tgagtactca accaagtcat tctgagaata gtgtatgcgg  6180
cgaccgagtt gctcttgccc ggcgtcaata cgggataata ccgcgccaca tagcagaact  6240
ttaaaagtgc tcatcattgg aaaacgttct tcggggcgaa aactctcaag gatcttaccg  6300
ctgttgagat ccagttcgat gtaacccact cgtgcaccca actgatcttc agcatctttt  6360
actttcacca gcgtttctgg gtgagcaaaa acaggaaggc aaaatgccgc aaaaaaggga  6420
ataagggcga cacggaaatg ttgaatactc atactcttcc tttttcaata ttattgaagc  6480
atttatcagg gttattgtct catgagcgga tacatatttg aatgtattta gaaaaataaa  6540
caaatagggg ttccgcgcac atttccccga aaagtgccac ctgacgtcga cggatcggga  6600
gatctcccga tcccctatgg tcgactctca gtacaatctg ctctgatgcc gcatagttaa  6660
gccagtatct gctccctgct tgtgtgttgg aggtcgctga gtagtgcgcg agcaaaattt  6720
aagctacaac aaggcaaggc ttgaccgaca attgcatgaa gaatctgctt agg         6773

SEQ ID NO: 98          moltype = DNA  length = 7452
FEATURE                Location/Qualifiers
source                 1..7452
                       mol_type = other DNA
                       organism = synthetic construct
SEQUENCE: 98
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcggaagtga agctggtgga aagcggcgga  840
ggtgttgttc agcctggcgg atctctgaag ctgagctgtg ccgccagcgg cttcaccttt  900
agcagctaca caatgagctg ggtccgacag accccctgaga agagactgga atgggtcgcc  960
aagatccgga acggcggagg catcacctac tacctggata ccctgaaggg cagattcacc  1020
atcagccggg acaacgccaa gaacaccctg tacctgcaga tgagcagcct gaagtccgag  1080
gacaccgcca tctacttttg cgccagacac tactacggca gcgaggacta cttcgactat  1140
tggggccagg gcaccacact gaccgttagc tctgctagca ccaagggccc atcggtcttc  1200
cccctggcgc cctgctccag gagcacctcc gagagcacag cggccctggg ctgcctggtc  1260
```

-continued

```
aaggactact tccccgaacc ggtgacggtg tcgtggaact caggcgctct gaccagcggc  1320
gtgcacacct tcccagctgt cctacagtcc tcaggactct actccctcag cagcgtggtg  1380
accgtgccct ccagcaactt cggcacccag acctacacct gcaacgtaga tcacaagccc  1440
agcaacacca aggtggacaa gacagttgag cgcaaatgtt gtgtcgagtg cccaccgtgc  1500
ccagcaccac ctgtggcagg accgtcagtc ttcctcttcc ccccaaaacc caaggacacc  1560
ctcatgatct cccggacccc tgaggtcacg tgcgtggtgg tggacgtgag ccacgaagac  1620
cccgaggtcc agttcaactg gtacgtggac ggcgtggagg tgcataatgc caagacaaag  1680
ccacgggagg agcagttcaa cagcacgttc cgtgtggtca gcgtcctcac cgttgtgcac  1740
caggactggc tgaacggcaa ggagtacaag tgcaaggtct ccaacaaagg cctcccagcc  1800
cccatcgaga aaaccatctc caaaaccaaa gggcagcccc gagaaccaca ggtgtacacc  1860
ctgcccccat cccgggagga gatgaccaag aaccaggtca gcctgacctg cctggtcaaa  1920
ggcttctacc ccagcgacat cgccgtggag tgggagagca atgggcagcc ggagaacaac  1980
tacaagacca cgcctcccat gctggactcc gacggctcct tcttcctcta cagcaagctc  2040
accgtggaca agagcaggtg gcagcagggg aacgtcttct catgctccgt gatgcatgag  2100
gctctgcaca accactacac gcagaagagc ctctccctgt ctccgggtaa atgacctagc  2160
gtggcatcta gacactctcg agaagggttc gatccctacc ggttagtaat gagtttgata  2220
tctcgacaat caacctctgg attacaaaat ttgtgaaaga ttgactggta ttcttaacta  2280
tgttgctcct tttacgctat gtggatacgc tgctttaatg cctttgtatc atgctattgc  2340
ttcccgtatg gctttcattt tctcctcctt gtataaatcc tggttgctgt ctctttatga  2400
ggagttgtgg cccgttgtca ggcaacgtgg cgtggtgtgc actgtgtttg ctgacgcaac  2460
ccccactggt tggggcattg ccaccacctg tcagctcctt tccgggactt tcgctttccc  2520
cctccctatt gccacggcgg aactcatcgc cgcctgcctt gcccgctgct ggacaggggc  2580
tcggctgttg ggcactgaca attccgtggt gttgtcgggg aagctgacgt cctttccatg  2640
gctgctcgcc tgtgttgcca cctggattct gcgcgggacg tccttctgct acgtcccttc  2700
ggccctcaat ccagcggacc ttccttcccg cggcctgctg ccggctctgc ggcctcttcc  2760
gcgtcttcgc cttcgccctc agacgagtcg gatctccctt tgggccgcct ccccgcctgg  2820
aaacggggga ggctaactga aacacggaag gagacaatac cggaaggaac ccgcgctatg  2880
acggcaataa aaagacagaa taaaacgcac gggtgttggg tcgtttgttc ataaacgcgg  2940
ggttcggtcc cagggctggc actctgtcga taccccaccg agaccccatt ggggccaata  3000
cgcccgcgtt tcttcctttt ccccacccca ccccccaagt tcgggtgaag gcccagggct  3060
cgcagccaac gtcggggcgg caggccctgc catagcagat ctgcgcagct ggggctctag  3120
ggggtatccc cacgcgccct gtagcggcgc attaagcgcg gcgggtgtgg tggttacgcg  3180
cagcgtgacc gctacacttg ccagcgccct agcgcccgct cctttcgctt tcttcccttc  3240
ctttctcgcc acgttcgccg gctttccccg tcaagctcta aatcggggca tccctttagg  3300
gttccgattt agtgctttac ggcacctcga ccccaaaaaa cttgattagg gtgatggttc  3360
acgtagtggg ccatcgccct gatagacggt ttttcgccct ttgacgttgg agtccacgtt  3420
ctttaatagt ggactcttgt tccaaactgg aacaacactc aaccctatct cggtctattc  3480
ttttgattta taagggattt tggggatttc ggcctattgg ttaaaaaatg agctgattta  3540
acaaaaattt aacgcgaatt aattctgtgg aatgtgtgtc agttagggtg tggaaagtcc  3600
ccaggctccc cagcaggcag aagtatgcaa agcatgcatc tcaattagtc agcaaccagg  3660
tgtggaaagt ccccaggctc cccagcaggc agaagtatgc aaagcatgca tctcaattag  3720
tcagcaacca tagtcccgcc cctaactccg cccatcccgc ccctaactcc gcccagttcc  3780
gcccattctc cgccccatgg ctgactaatt ttttttattt atgcagaggc cgaggccgcc  3840
tctgcctctg agctattcca gaagtagtga ggaggctttt ttggaggcct aggcttttgc  3900
aaaaagctcc cgggagcttg tatatccatt ttcggatctg atcaagagac aggatgagga  3960
tcgtttcgca tgattgaaca agatggattg cacgcaggtt ctccggccgc ttgggtggag  4020
aggctattcg gctatgactg ggcacaacag acaatcggct gctctgatgc cgccgtgttc  4080
cggctgtcag cgcaggggcg cccggttctt tttgtcaaga ccgacctgtc cggtgccctg  4140
aatgaactgc aggacgaggc agcgcggcta tcgtggctgg ccacgacggg cgttccttgc  4200
gcagctgtgc tcgacgttgt cactgaagcg ggaagggact ggctgctatt gggcgaagtg  4260
ccggggcagg atctcctgtc atctcacctt gctcctgccg agaaagtatc catcatggct  4320
gatgcaatgc ggcggctgca tacgcttgat ccggctacct gcccattcga ccaccaagcg  4380
aaacatcgca tcgagcgagc acgtactcgg atggaagccg gtcttgtcga tcaggatgat  4440
ctggacgaag agcatcaggg gctcgcgcca gccgaactgt tcgccaggct caaggcgcgc  4500
atgcccgacg gcgaggatct cgtcgtgacc catggcgatg cctgcttgcc gaatatcatg  4560
gtggaaaatg gccgcttttc tggattcatc gactgtggcc ggctgggtgt ggcggaccgc  4620
tatcaggaca tagcgttggc tacccgtgat attgctgaag agcttggcgg cgaatgggct  4680
gaccgcttcc tcgtgcttta cggtatcgcc gctcccgatt cgcagcgcat cgccttctat  4740
cgccttcttg acgagttctt ctgagcggga ctctggggtt cgcgaaatga ccgaccaagc  4800
gacgcccaac ctgccatcac gagatttcga ttccaccgcc gccttctatg aaaggttggg  4860
cttcggaatc gttttccggg acgccggctg gatgatcctc cagcgcgggg atctcatgct  4920
ggagttcttc gcccacccca acttgtttat tgcagcttat aatggttaca aataaagcaa  4980
tagcatcaca aatttcacaa ataaagcatt tttttcactg cattctagtt gtggtttgtc  5040
caaactcatc aatgtatctt atcatgtctg tataccgtcg acctctagct agagcttggc  5100
gtaatcatgg tcatagctgt ttcctgtgtg aaattgttat ccgctcacaa ttccacacaa  5160
catacgagcc ggaagcataa agtgtaaagc ctggggtgcc taatgagtga gctaactcac  5220
attaattgcg ttgcgctcac tgcccgcttt ccagtcggga aacctgtcgt gccagctgca  5280
ttaatgaatc ggccaacgcg cggggagagg cggtttgcgt attgggcgct cttccgcttc  5340
ctcgctcact gactcgctgc gctcggtcgt tcggctgcgg cgagcggtat cagctcactc  5400
aaaggcggta atacggttat ccacagaatc aggggataac gcaggaaaga acatgtgagc  5460
aaaaggccag caaaaggcca ggaaccgtaa aaaggccgcg ttgctggcgt ttttccatag  5520
gctccgcccc cctgacgagc atcacaaaaa tcgacgctca agtcagaggt ggcgaaaccc  5580
gacaggacta taaagatacc aggcgtttcc ccctggaagc tccctcgtgc gctctcctgt  5640
tccgaccctg ccgcttaccg gatacctgtc cgcctttctc ccttcgggaa gcgtggcgct  5700
ttctcaatgc tcacgctgta ggtatctcag ttcggtgtag gtcgttcgct ccaagctggg  5760
ctgtgtgcac gaaccccccg ttcagcccga ccgctgcgcc ttatccggta actatcgtct  5820
tgagtccaac ccggtaagac acgacttatc gccactggca gcagccactg gtaacaggat  5880
tagcagagcg aggtatgtag gcggtgctac agagttcttg aagtggtggc ctaactacgg  5940
ctacactaga aggacagtat ttggtatctg cgctctgctg aagccagtta ccttcggaaa  6000
```

-continued

```
aagagttggt agctcttgat ccggcaaaca aaccaccgct ggtagcggtg gtttttttgt  6060
ttgcaagcag cagattacgc gcagaaaaaa aggatctcaa gaagatcctt tgatcttttc  6120
tacggggtct gacgctcagt ggaacgaaaa ctcacgttaa gggattttgg tcatgagatt  6180
atcaaaaagg atcttcacct agatcctttt aaattaaaaa tgaagtttta aatcaatcta  6240
aagtatatat gagtaaactt ggtctgacag ttaccaatgc ttaatcagtg aggcacctat  6300
ctcagcgatc tgtctatttc gttcatccat agttgcctga ctccccgtcg tgtagataac  6360
tacgatacgg gagggcttac catctggccc cagtgctgca atgataccgc gagacccacg  6420
ctcaccggct ccagatttat cagcaataaa ccagccagcc ggaagggccg agcgcagaag  6480
tggtcctgca actttatccg cctccatcca gtctattaat tgttgccggg aagctagagt  6540
aagtagttcg ccagttaata gtttgcgcaa cgttgttgcc attgctacag gcatcgtggt  6600
gtcacgctcg tcgtttggta tggcttcatt cagctccggt tcccaacgat caaggcgagt  6660
tacatgatcc cccatgttgt gcaaaaaagc ggttagctcc ttcggtcctc cgatcgttgt  6720
cagaagtaag ttggccgcag tgttatcact catggttatg gcagcactgc ataattctct  6780
tactgtcatg ccatccgtaa gatgcttttc tgtgactggt gagtactcaa ccaagtcatt  6840
ctgagaatag tgtatgcggc gaccgagttg ctcttgcccg gcgtcaatac gggataatac  6900
cgcgccacat agcagaactt taaaagtgct catcattgga aaacgttctt cggggcgaaa  6960
actctcaagg atcttaccgc tgttgagatc cagttcgatg taacccactc gtgcacccaa  7020
ctgatcttca gcatctttta ctttcaccag cgtttctggg tgagcaaaaa caggaaggca  7080
aaatgccgca aaaaagggaa taagggcgac acggaaatgt tgaatactca tactcttcct  7140
ttttcaatat tattgaagca tttatcaggg ttattgtctc atgagcggat acatatttga  7200
atgtatttag aaaaataaac aaataggggt tccgcgcaca tttccccgaa aagtgccacc  7260
tgacgtcgac ggatcgggag atctcccgat cccctatggt cgactctcag tacaatctgc  7320
tctgatgccg catagttaag ccagtatctg ctccctgctt gtgtgttgga ggtcgctgag  7380
tagtgcgcga gcaaaattta agctacaaca aggcaaggct tgaccgacaa ttgcatgaag  7440
aatctgctta gg                                                     7452

SEQ ID NO: 99          moltype = DNA  length = 6773
FEATURE                Location/Qualifiers
source                 1..6773
                       mol_type = other DNA
                       organism = synthetic construct
SEQUENCE: 99
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcagacatcg tgctgacaca gagccctgcc  840
agcctggctg tttctctggg acagagagcc accatcagct gcaaggccag ccagagcgtt  900
gactacgacg gcgagaacta catgaactgg tatcagcaga agcccggaca gagccccaag  960
ctgctgatct acgtggccag caatctggaa agcggcatcc ccgccagatt ttctggcagc  1020
ggaagcggca ccgacttcac cctgaatatc catcctgtgg aagaagagga cgccgccacc  1080
tactactgcc agcagtccaa tctggacccc tggacatttg gcggaggcac caagctggaa  1140
atcaagcgta cggtggctgc accatctgtc ttcatcttcc cgccatctga tgagcagttg  1200
aaatctggaa ctgcctctgt tgtgtgcctg ctgaataact tctatcccag agaggccaaa  1260
gtacagtgga aggtggataa cgccctccaa tcgggtaact cccaggagag tgtcacagag  1320
caggacagca aggacagcac ctacagcctc agcagcaccc tgacgctgag caaagcagac  1380
tacgagaaac acaaagtcta cgcctgcgaa gtcacccatc agggcctgag ctcgcccgtc  1440
acaaagagct tcaacagggg agagtgttag agggagctag cgtggcatct agacactctc  1500
gagaagggtt cgatccctac cggttagtaa tgagtttgat atctcgacaa tcaacctctg  1560
gattacaaaa tttgtgaaag attgactggt attcttaact atgttgctcc ttttacgcta  1620
tgtggatacg ctgctttaat gcctttgtat catgctattg cttcccgtat ggctttcatt  1680
ttctcctcct tgtataaatc ctggttgctg tctctttatg aggagttgtg gcccgttgtc  1740
aggcaacgtg gcgtggtgtg cactgtgttt gctgacgcaa cccccactgg ttggggcatt  1800
gccaccacct gtcagctcct ttccgggact ttcgctttcc ccctccctat tgccacggcg  1860
gaactcatcg ccgcctgcct tgcccgctgc tggacagggg ctcggctgtt gggcactgac  1920
aattccgtgg tgttgtcggg gaagctgacg tcctttccat ggctgctcgc ctgtgttgcc  1980
acctggattc tgcgcgggac gtccttctgc tacgtccctt cggccctcaa tccagcggac  2040
cttccttccc gcggcctgct gccggctctg cggcctcttc cgcgtcttcg ccttcgccct  2100
cagacgagtc ggatctccct ttgggccgcc tccccgcctg gaaacggggg aggctaactg  2160
aaacacggaa ggagacaata ccggaaggaa cccgcgctat gacggcaata aaaagacaga  2220
ataaaacgca cgggtgttgg gtcgtttgtt cataaacgcg gggttcggtc ccagggctgg  2280
cactctgtcg ataccccacc gagaccccat tggggccaat acgcccgcgt ttcttccttt  2340
tccccacccc accccccaag ttcgggtgaa ggcccagggc tcgcagccaa cgtcggggcg  2400
gcaggccctg ccatagcaga tctgcgcagc tggggctcta gggggtatcc ccacgcgccc  2460
tgtagcggcg cattaagcgc ggcgggtgtg gtggttacgc gcagcgtgac cgctacactt  2520
gccagcgccc tagcgcccgc tcctttcgct ttcttccctt cctttctcgc cacgttcgcc  2580
ggctttcccc gtcaagctct aaatcggggc atccctttag ggttccgatt tagtgcttta  2640
cggcacctcg accccaaaaa acttgattag ggtgatggtt cacgtagtgg gccatcgccc  2700
tgatagacgg tttttcgccc tttgacgttg gagtccacgt tctttaatag tggactcttg  2760
ttccaaactg gaacaacact caaccctatc tcggtctatt cttttgattt ataagggatt  2820
```

```
ttggggattt cggcctattg gttaaaaaat gagctgattt aacaaaaatt taacgcgaat  2880
taattctgtg gaatgtgtgt cagttagggt gtggaaagtc cccaggctcc ccagcaggca  2940
gaagtatgca aagcatgcat ctcaattagt cagcaaccag gtgtggaaag tccccaggct  3000
ccccagcagg cagaagtatg caaagcatgc atctcaatta gtcagcaacc atagtcccgc  3060
ccctaactcc gcccatcccg cccctaactc cgcccagttc cgcccattct ccgccccatg  3120
gctgactaat tttttttatt tatgcagagg ccgaggccgc ctctgcctct gagctattcc  3180
agaagtagtg aggaggcttt tttggaggcc taggcttttg caaaaagctc ccgggagctt  3240
gtatatccat tttcggatct gatcaagaga caggatgagg atcgtttcgc atgattgaac  3300
aagatggatt gcacgcaggt tctccggccg cttgggtgga gaggctattc ggctatgact  3360
gggcacaaca gacaatcggc tgctctgatg ccgccgtgtt ccggctgtca gcgcaggggc  3420
gcccggttct ttttgtcaag accgacctgt ccggtgccct gaatgaactg caggacgagg  3480
cagcgcggct atcgtggctg gccacgacgg gcgttccttg cgcagctgtg ctcgacgttg  3540
tcactgaagc gggaagggac tggctgctat tgggcgaagt gccggggcag gatctcctgt  3600
catctcacct tgctcctgcc gagaaagtat ccatcatggc tgatgcaatg cggcggctgc  3660
atacgcttga tccggctacc tgcccattcg accaccaagc gaaacatcgc atcgagcgag  3720
cacgtactcg gatggaagcc ggtcttgtcg atcaggatga tctggacgaa gagcatcagg  3780
ggctcgcgcc agccgaactg ttcgccaggc tcaaggcgcg catgcccgac ggcgaggatc  3840
tcgtcgtgac ccatggcgat gcctgcttgc cgaatatcat ggtggaaaat ggccgctttt  3900
ctggattcat cgactgtggc cggctgggtg tggcggaccg ctatcaggac atagcgttgg  3960
ctacccgtga tattgctgaa gagcttggcg gcgaatgggc tgaccgcttc ctcgtgcttt  4020
acggtatcgc cgctcccgat tcgcagcgca tcgccttcta tcgccttctt gacgagttct  4080
tctgagcggg actctggggt tcgcgaaatg accgaccaag cgacgcccaa cctgccatca  4140
cgagatttcg attccaccgc cgccttctat gaaaggttgg gcttcggaat cgttttccgg  4200
gacgccggct ggatgatcct ccagcgcggg gatctcatgc tggagttctt cgcccacccc  4260
aacttgttta ttgcagctta taatggttac aaataaagca atagcatcac aaatttcaca  4320
aataaagcat ttttttcact gcattctagt tgtggtttgt ccaaactcat caatgtatct  4380
tatcatgtct gtataccgtc gacctctagc tagagcttgg cgtaatcatg gtcatagctg  4440
tttcctgtgt gaaattgtta tccgctcaca attccacaca acatacgagc cggaagcata  4500
aagtgtaaag cctggggtgc ctaatgagtg agctaactca cattaattgc gttgcgctca  4560
ctgcccgctt tccagtcggg aaacctgtcg tgccagctgc attaatgaat cggccaacgc  4620
gcggggagag gcggtttgcg tattgggcgc tcttccgctt cctcgctcac tgactcgctg  4680
cgctcggtcg ttcggctgcg gcgagcggta tcagctcact caaaggcggt aatacggtta  4740
tccacagaat caggggataa cgcaggaaag aacatgtgag caaaaggcca gcaaaaggcc  4800
aggaaccgta aaaaggccgc gttgctggcg tttttccata ggctccgccc ccctgacgag  4860
catcacaaaa atcgacgctc aagtcagagg tggcgaaacc cgacaggact ataaagatac  4920
caggcgtttc cccctggaag ctccctcgtg cgctctcctg ttccgaccct gccgcttacc  4980
ggatacctgt ccgcctttct cccttcggga agcgtggcgc tttctcaatg ctcacgctgt  5040
aggtatctca gttcggtgta ggtcgttcgc tccaagctgg gctgtgtgca cgaacccccc  5100
gttcagcccg accgctgcgc cttatccggt aactatcgtc ttgagtccaa cccggtaaga  5160
cacgacttat cgccactggc agcagccact ggtaacagga ttagcagagc gaggtatgta  5220
ggcggtgcta cagagttctt gaagtggtgg cctaactacg gctacactag aaggacagta  5280
tttggtatct gcgctctgct gaagccagtt accttcggaa aaagagttgg tagctcttga  5340
tccggcaaac aaaccaccgc tggtagcggt ggtttttttg tttgcaagca gcagattacg  5400
cgcagaaaaa aaggatctca agaagatcct ttgatctttt ctacggggtc tgacgctcag  5460
tggaacgaaa actcacgtta agggattttg gtcatgagat tatcaaaaag gatcttcacc  5520
tagatccttt taaattaaaa atgaagtttt aaatcaatct aaagtatata tgagtaaact  5580
tggtctgaca gttaccaatg cttaatcagt gaggcaccta tctcagcgat ctgtctattt  5640
cgttcatcca tagttgcctg actccccgtc gtgtagataa ctacgatacg ggagggctta  5700
ccatctggcc ccagtgctgc aatgataccg cgagacccac gctcaccggc tccagattta  5760
tcagcaataa accagccagc cggaagggcc gagcgcagaa gtggtcctgc aactttatcc  5820
gcctccatcc agtctattaa ttgttgccgg gaagctagag taagtagttc gccagttaat  5880
agtttgcgca acgttgttgc cattgctaca ggcatcgtgg tgtcacgctc gtcgtttggt  5940
atggcttcat tcagctccgg ttcccaacga tcaaggcgag ttacatgatc ccccatgttg  6000
tgcaaaaaag cggttagctc cttcggtcct ccgatcgttg tcagaagtaa gttggccgca  6060
gtgttatcac tcatggttat ggcagcactg cataattctc ttactgtcat gccatccgta  6120
agatgctttt ctgtgactgg tgagtactca accaagtcat tctgagaata gtgtatgcgg  6180
cgaccgagtt gctcttgccc ggcgtcaata cgggataata ccgcgccaca tagcagaact  6240
ttaaaagtgc tcatcattgg aaaacgttct tcggggcgaa aactctcaag gatcttaccg  6300
ctgttgagat ccagttcgat gtaacccact cgtgcaccca actgatcttc agcatctttt  6360
actttcacca gcgtttctgg gtgagcaaaa acaggaaggc aaaatgccgc aaaaaaggga  6420
ataagggcga cacggaaatg ttgaatactc atactcttcc tttttcaata ttattgaagc  6480
atttatcagg gttattgtct catgagcgga tacatatttg aatgtattta gaaaaataaa  6540
caaatagggg ttccgcgcac atttccccga aaagtgccac ctgacgtcga cggatcggga  6600
gatctcccga tcccctatgg tcgactctca gtacaatctg ctctgatgcc gcatagttaa  6660
gccagtatct gctccctgct tgtgtgttgg aggtcgctga gtagtgcgcg agcaaaattt  6720
aagctacaac aaggcaaggc ttgaccgaca attgcatgaa gaatctgctt agg         6773
```

```
SEQ ID NO: 100         moltype = DNA  length = 7446
FEATURE                Location/Qualifiers
source                 1..7446
                       mol_type = other DNA
                       organism = synthetic construct
SEQUENCE: 100
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
```

-continued

```
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcggaggtcc agctgcagca gtctggcgcc  840
gaacttgtta gacctggcgc tctggtcaag ctgagctgta aagccagcgg cttcaacatc  900
aaggactacc atctgcactg ggtcaagcag aggcctgagc agggactcga gtggatcggc  960
tggatcgacc ccgagaacgg caacgtgatc tacgacccca agttccaggg caaagccacc  1020
atgaccgtgg tcaccagcag caacacagcc tacctgcagc tgagaagcct gaccagcgaa  1080
gataccgccg tgtacttctg caccagaggc acagccagag ccagcttcga ttattggggc  1140
cagggcacca gcctgaccgt ttcttctgct agcaccaagg gcccatcggt cttccccctg  1200
gcgccctgct ccaggagcac ctccgagagc acagcggccc tgggctgcct ggtcaaggac  1260
tacttccccg aaccggtgac ggtgtcgtgg aactcaggcg ctctgaccag cggcgtgcac  1320
accttcccag ctgtcctaca gtcctcagga ctctactccc tcagcagcgt ggtgaccgtg  1380
ccctccagca acttcggcac ccagacctac acctgcaacg tagatcacaa gcccagcaac  1440
accaaggtgg acaagacagt tgagcgcaaa tgttgtgtcg agtgcccacc gtgcccagca  1500
ccacctgtgg caggaccgtc agtcttcctc ttccccccaa aacccaagga caccctcatg  1560
atctcccgga cccctgaggt cacgtgcgtg gtggtggacg tgagccacga agaccccgag  1620
gtccagttca actggtacgt ggacggcgtg gaggtgcata atgccaagac aaagccacgg  1680
gaggagcagt tcaacagcac gttccgtgtg gtcagcgtcc tcaccgttgt gcaccaggac  1740
tggctgaacg gcaaggagta caagtgcaag gtctccaaca aaggcctccc agcccccatc  1800
gagaaaacca tctccaaaac caaagggcag ccccgagaac cacaggtgta caccctgccc  1860
ccatcccggg aggagatgac caagaaccag gtcagcctga cctgcctggt caaaggcttc  1920
taccccagcg acatcgccgt ggagtgggag agcaatgggc agccggagaa caactacaag  1980
accacgcctc ccatgctgga ctccgacggc tccttcttcc tctacagcaa gctcaccgtg  2040
gacaagagca ggtggcagca ggggaacgtc ttctcatgct ccgtgatgca tgaggctctg  2100
cacaaccact acacgcagaa gagcctctcc ctgtctccgg gtaaatgacc tagcgtggca  2160
tctagacact ctcgagaagg gttcgatccc taccggttag taatgagttt gatatctcga  2220
caatcaacct ctggattaca aaatttgtga aagattgact ggtattctta actatgttgc  2280
tccttttacg ctatgtggat acgctgcttt aatgcctttg tatcatgcta ttgcttcccg  2340
tatggctttc attttctcct ccttgtataa atcctggttg ctgtctcttt atgaggagtt  2400
gtggcccgtt gtcaggcaac gtggcgtggt gtgcactgtg tttgctgacg caacccccac  2460
tggttggggc attgccacca cctgtcagct cctttccggg actttcgctt tccccctccc  2520
tattgccacg gcggaactca tcgccgcctg ccttgcccgc tgctggacag gggctcggct  2580
gttgggcact gacaattccg tggtgttgtc ggggaagctg acgtcctttc catggctgct  2640
cgcctgtgtt gccacctgga ttctgcgcgg gacgtccttc tgctacgtcc cttcggccct  2700
caatccagcg gaccttcctt cccgcggcct gctgccggct ctgcggcctc ttccgcgtct  2760
tcgccttcgc cctcagacga gtcggatctc cctttgggcc gcctccccgc ctggaaacgg  2820
gggaggctaa ctgaaacacg gaaggagaca ataccggaag gaacccgcgc tatgacggca  2880
ataaaaagac agaataaaac gcacgggtgt tgggtcgttt gttcataaac gcggggttcg  2940
gtcccagggc tggcactctg tcgatacccc accgagaccc cattggggcc aatacgcccg  3000
cgtttcttcc ttttccccac cccacccccc aagttcgggt gaaggcccag ggctcgcagc  3060
caacgtcggg gcggcaggcc ctgccatagc agatctgcgc agctggggct ctagggggta  3120
tccccacgcg ccctgtagcg gcgcattaag cgcggcgggt gtggtggtta cgcgcagcgt  3180
gaccgctaca cttgccagcg ccctagcgcc cgctcctttc gctttcttcc cttcctttct  3240
cgccacgttc gccggctttc cccgtcaagc tctaaatcgg ggcatccctt tagggttccg  3300
atttagtgct ttacggcacc tcgaccccaa aaaacttgat tagggtgatg gttcacgtag  3360
tgggccatcg ccctgataga cggtttttcg ccctttgacg ttggagtcca cgttctttaa  3420
tagtggactc ttgttccaaa ctggaacaac actcaaccct atctcggtct attcttttga  3480
tttataaggg attttgggga tttcggccta ttggttaaaa aatgagctga tttaacaaaa  3540
atttaacgcg aattaattct gtggaatgtg tgtcagttag ggtgtggaaa gtccccaggc  3600
tccccagcag gcagaagtat gcaaagcatg catctcaatt agtcagcaac caggtgtgga  3660
aagtccccag gctccccagc aggcagaagt atgcaaagca tgcatctcaa ttagtcagca  3720
accatagtcc cgcccctaac tccgcccatc ccgcccctaa ctccgcccag ttccgcccat  3780
tctccgcccc atggctgact aattttttttt atttatgcag aggccgaggc cgcctctgcc  3840
tctgagctat tccagaagta gtgaggaggc ttttttggag gcctaggctt ttgcaaaaag  3900
ctcccgggag cttgtatatc cattttcgga tctgatcaag agacaggatg aggatcgttt  3960
cgcatgattg aacaagatgg attgcacgca ggttctccgg ccgcttgggt ggagaggcta  4020
ttcggctatg actgggcaca acagacaatc ggctgctctg atgccgccgt gttccggctg  4080
tcagcgcagg ggcgcccggt tctttttgtc aagaccgacc tgtccggtgc cctgaatgaa  4140
ctgcaggacg aggcagcgcg gctatcgtgg ctggccacga cgggcgttcc ttgcgcagct  4200
gtgctcgacg ttgtcactga agcgggaagg gactggctgc tattgggcga agtgccgggg  4260
caggatctcc tgtcatctca ccttgctcct gccgagaaag tatccatcat ggctgatgca  4320
atgcggcggc tgcatacgct tgatccggct acctgcccat tcgaccacca agcgaaacat  4380
cgcatcgagc gagcacgtac tcggatggaa gccggtcttg tcgatcagga tgatctggac  4440
gaagagcatc aggggctcgc gccagccgaa ctgttcgcca ggctcaaggc gcgcatgccc  4500
gacggcgagg atctcgtcgt gacccatggc gatgcctgct tgccgaatat catggtggaa  4560
aatggccgct tttctggatt catcgactgt ggccggctgg gtgtggcgga ccgctatcag  4620
gacatagcgt tggctacccg tgatattgct gaagagcttg gcggcgaatg ggctgaccgc  4680
ttcctcgtgc tttacggtat cgccgctccc gattcgcagc gcatcgcctt ctatcgcctt  4740
cttgacgagt tcttctgagc gggactctgg ggttcgcgaa atgaccgacc aagcgacgcc  4800
caacctgcca tcacgagatt tcgattccac cgccgccttc tatgaaaggt tgggcttcgg  4860
aatcgttttc cgggacgccg gctggatgat cctccagcgc ggggatctca tgctggagtt  4920
cttcgcccac cccaacttgt ttattgcagc ttataatggt tacaaataaa gcaatagcat  4980
cacaaatttc acaaataaag cattttttttc actgcattct agttgtggtt tgtccaaact  5040
catcaatgta tcttatcatg tctgtatacc gtcgacctct agctagagct tggcgtaatc  5100
```

-continued

```
atggtcatag ctgtttcctg tgtgaaattg ttatccgctc acaattccac acaacatacg  5160
agccggaagc ataaagtgta aagcctgggg tgcctaatga gtgagctaac tcacattaat  5220
tgcgttgcgc tcactgcccg ctttccagtc gggaaacctg tcgtgccagc tgcattaatg  5280
aatcggccaa cgcgcgggga gaggcggttt gcgtattggg cgctcttccg cttcctcgct  5340
cactgactcg ctgcgctcgg tcgttcggct gcggcgagcg gtatcagctc actcaaaggc  5400
ggtaatacgg ttatccacag aatcagggga taacgcagga aagaacatgt gagcaaaagg  5460
ccagcaaaag gccaggaacc gtaaaaaggc cgcgttgctg gcgtttttcc ataggctccg  5520
cccccctgac gagcatcaca aaaatcgacg ctcaagtcag aggtggcgaa acccgacagg  5580
actataaaga taccaggcgt ttccccctgg aagctccctc gtgcgctctc ctgttccgac  5640
cctgccgctt accggatacc tgtccgcctt tctcccttcg ggaagcgtgg cgctttctca  5700
atgctcacgc tgtaggtatc tcagttcggt gtaggtcgtt cgctccaagc tgggctgtgt  5760
gcacgaaccc cccgttcagc ccgaccgctg cgccttatcc ggtaactatc gtcttgagtc  5820
caacccggta agacacgact tatcgccact ggcagcagcc actggtaaca ggattagcag  5880
agcgaggtat gtaggcggtg ctacagagtt cttgaagtgg tggcctaact acggctacac  5940
tagaaggaca gtatttggta tctgcgctct gctgaagcca gttaccttcg gaaaaagagt  6000
tggtagctct tgatccggca aacaaaccac cgctggtagc ggtggttttt ttgtttgcaa  6060
gcagcagatt acgcgcagaa aaaaaggatc tcaagaagat cctttgatct tttctacggg  6120
gtctgacgct cagtggaacg aaaactcacg ttaagggatt ttggtcatga gattatcaaa  6180
aaggatcttc acctagatcc ttttaaatta aaaatgaagt tttaaatcaa tctaaagtat  6240
atatgagtaa acttggtctg acagttacca atgcttaatc agtgaggcac ctatctcagc  6300
gatctgtcta tttcgttcat ccatagttgc ctgactcccc gtcgtgtaga taactacgat  6360
acgggagggc ttaccatctg gccccagtgc tgcaatgata ccgcgagacc cacgctcacc  6420
ggctccagat ttatcagcaa taaaccagcc agccggaagg gccgagcgca gaagtggtcc  6480
tgcaacttta tccgcctcca tccagtctat taattgttgc cgggaagcta gagtaagtag  6540
ttcgccagtt aatagtttgc gcaacgttgt tgccattgct acaggcatcg tggtgtcacg  6600
ctcgtcgttt ggtatggctt cattcagctc cggttcccaa cgatcaaggc gagttacatg  6660
atcccccatg ttgtgcaaaa aagcggttag ctccttcggt cctccgatcg ttgtcagaag  6720
taagttggcc gcagtgttat cactcatggt tatggcagca ctgcataatt ctcttactgt  6780
catgccatcc gtaagatgct tttctgtgac tggtgagtac tcaaccaagt cattctgaga  6840
atagtgtatg cggcgaccga gttgctcttg cccggcgtca atacgggata ataccgcgcc  6900
acatagcaga actttaaaag tgctcatcat tggaaaacgt tcttcggggc gaaaactctc  6960
aaggatctta ccgctgttga gatccagttc gatgtaaccc actcgtgcac ccaactgatc  7020
ttcagcatct tttactttca ccagcgtttc tgggtgagca aaaacaggaa ggcaaaatgc  7080
cgcaaaaaag ggaataaggg cgacacggaa atgttgaata ctcatactct tcctttttca  7140
atattattga agcatttatc agggttattg tctcatgagc ggatacatat ttgaatgtat  7200
ttagaaaaat aaacaaatag gggttccgcg cacatttccc cgaaaagtgc cacctgacgt  7260
cgacggatcg ggagatctcc cgatccccta tggtcgactc tcagtacaat ctgctctgat  7320
gccgcatagt taagccagta tctgctccct gcttgtgtgt tggaggtcgc tgagtagtgc  7380
gcgagcaaaa tttaagctac aacaaggcaa ggcttgaccg acaattgcat gaagaatctg  7440
cttagg                                                             7446

SEQ ID NO: 101          moltype = DNA  length = 6773
FEATURE                 Location/Qualifiers
source                  1..6773
                        mol_type = other DNA
                        organism = synthetic construct
SEQUENCE: 101
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcagacatcg tgctgacaca gagccctgcc  840
agcctggctg tttctctggg acagagagcc accatcagct gcaaggccag ccagagcgtt  900
gactacgacg gcgacagcta catgaactgg tatcagcaga agtccggcca gcctcctaag  960
ctgctgatct acgccgccag caatctggaa agcggcatcc ctgccagatt ttccggctct  1020
ggcagcggca ccgacttcac cctgaatatc catcctgtgg aagaagagga cgccgccacc  1080
tactactgcc agcagagcaa tgtggacccc tggacatttg gcggaggcac caagctggaa  1140
atcaagcgta cggtggctgc accatctgtc ttcatcttcc cgccatctga tgagcagttg  1200
aaatctggaa ctgcctctgt tgtgtgcctg ctgaataact tctatcccag agaggccaaa  1260
gtacagtgga aggtggataa cgccctccaa tcgggtaact cccaggagag tgtcacagag  1320
caggacagca aggacagcac ctacagcctc agcagcaccc tgacgctgag caaagcagac  1380
tacgagaaac acaaagtcta cgcctgcgaa gtcacccatc agggcctgag ctcgcccgtc  1440
acaaagagct tcaacagggg agagtgttag agggagctag cgtggcatct agacactctc  1500
gagaagggtt cgatccctac cggttagtaa tgagtttgat atctcgacaa tcaacctctg  1560
gattacaaaa tttgtgaaag attgactggt attcttaact atgttgctcc ttttacgcta  1620
tgtggatacg ctgctttaat gcctttgtat catgctattg cttcccgtat ggctttcatt  1680
ttctcctcct tgtataaatc ctggttgctg tctctttatg aggagttgtg gcccgttgtc  1740
aggcaacgtg gcgtggtgtg cactgtgttt gctgacgcaa cccccactgg ttggggcatt  1800
gccaccacct gtcagctcct ttccgggact ttcgctttcc ccctccctat tgccacggcg  1860
gaactcatcg ccgcctgcct tgcccgctgc tggacagggg ctcggctgtt gggcactgac  1920
```

-continued

```
aattccgtgg tgttgtcggg gaagctgacg tcctttccat ggctgctcgc ctgtgttgcc  1980
acctggattc tgcgcgggac gtccttctgc tacgtccctt cggccctcaa tccagcggac  2040
cttccttccc gcggcctgct gccggctctg cggcctcttc cgcgtcttcg ccttcgccct  2100
cagacgagtc ggatctccct ttgggccgcc tccccgcctg gaaacggggg aggctaactg  2160
aaacacggaa ggagacaata ccggaaggaa cccgcgctat gacggcaata aaaagacaga  2220
ataaaacgca cgggtgttgg gtcgtttgtt cataaacgcg gggttcggtc ccagggctgg  2280
cactctgtcg ataccccacc gagaccccat tggggccaat acgcccgcgt ttcttccttt  2340
tccccacccc accccccaag ttcgggtgaa ggcccagggc tcgcagccaa cgtcggggcg  2400
gcaggccctg ccatagcaga tctgcgcagc tggggctcta gggggtatcc ccacgcgccc  2460
tgtagcggcg cattaagcgc ggcgggtgtg gtggttacgc gcagcgtgac cgctacactt  2520
gccagcgccc tagcgcccgc tcctttcgct ttcttccctt cctttctcgc cacgttcgcc  2580
ggctttcccc gtcaagctct aaatcggggc atccctttag ggttccgatt tagtgcttta  2640
cggcacctcg accccaaaaa acttgattag ggtgatggtt cacgtagtgg gccatcgccc  2700
tgatagacgg tttttcgccc tttgacgttg gagtccacgt tctttaatag tggactcttg  2760
ttccaaactg gaacaacact caaccctatc tcggtctatt cttttgattt ataagggatt  2820
ttggggattt cggcctattg gttaaaaaat gagctgattt aacaaaaatt taacgcgaat  2880
taattctgtg gaatgtgtgt cagttagggt gtggaaagtc cccaggctcc ccagcaggca  2940
gaagtatgca aagcatgcat ctcaattagt cagcaaccag gtgtggaaag tccccaggct  3000
ccccagcagg cagaagtatg caaagcatgc atctcaatta gtcagcaacc atagtcccgc  3060
ccctaactcc gcccatcccg cccctaactc cgcccagttc cgcccattct ccgccccatg  3120
gctgactaat tttttttatt tatgcagagg ccgaggccgc ctctgcctct gagctattcc  3180
agaagtagtg aggaggcttt tttggaggcc taggcttttg caaaaagctc ccgggagctt  3240
gtatatccat tttcggatct gatcaagaga caggatgagg atcgtttcgc atgattgaac  3300
aagatggatt gcacgcaggt tctccggccg cttgggtgga gaggctattc ggctatgact  3360
gggcacaaca gacaatcggc tgctctgatg ccgccgtgtt ccggctgtca gcgcaggggc  3420
gcccggttct ttttgtcaag accgacctgt ccggtgccct gaatgaactg caggacgagg  3480
cagcgcggct atcgtggctg gccacgacgg gcgttccttg cgcagctgtg ctcgacgttg  3540
tcactgaagc gggaagggac tggctgctat tgggcgaagt gccggggcag gatctcctgt  3600
catctcacct tgctcctgcc gagaaagtat ccatcatggc tgatgcaatg cggcggctgc  3660
atacgcttga tccggctacc tgcccattcg accaccaagc gaaacatcgc atcgagcgag  3720
cacgtactcg gatggaagcc ggtcttgtcg atcaggatga tctggacgaa gagcatcagg  3780
ggctcgcgcc agccgaactg ttcgccaggc tcaaggcgcg catgcccgac ggcgaggatc  3840
tcgtcgtgac ccatggcgat gcctgcttgc cgaatatcat ggtggaaaat ggccgctttt  3900
ctggattcat cgactgtggc cggctgggtg tggcggaccg ctatcaggac atagcgttgg  3960
ctacccgtga tattgctgaa gagcttggcg gcgaatgggc tgaccgcttc ctcgtgcttt  4020
acggtatcgc cgctcccgat tcgcagcgca tcgccttcta tcgccttctt gacgagttct  4080
tctgagcggg actctggggt tcgcgaaatg accgaccaag cgacgcccaa cctgccatca  4140
cgagatttcg attccaccgc cgccttctat gaaaggttgg gcttcggaat cgttttccgg  4200
gacgccggct ggatgatcct ccagcgcggg gatctcatgc tggagttctt cgcccacccc  4260
aacttgttta ttgcagctta taatggttac aaataaagca atagcatcac aaatttcaca  4320
aataaagcat ttttttcact gcattctagt tgtggtttgt ccaaactcat caatgtatct  4380
tatcatgtct gtataccgtc gacctctagc tagagcttgg cgtaatcatg gtcatagctg  4440
tttcctgtgt gaaattgtta tccgctcaca attccacaca acatacgagc cggaagcata  4500
aagtgtaaag cctggggtgc ctaatgagtg agctaactca cattaattgc gttgcgctca  4560
ctgcccgctt tccagtcggg aaacctgtcg tgccagctgc attaatgaat cggccaacgc  4620
gcggggagag gcggtttgcg tattgggcgc tcttccgctt cctcgctcac tgactcgctg  4680
cgctcggtcg ttcggctgcg gcgagcggta tcagctcact caaaggcggt aatacggtta  4740
tccacagaat caggggataa cgcaggaaag aacatgtgag caaaaggcca gcaaaaggcc  4800
aggaaccgta aaaaggccgc gttgctggcg tttttccata ggctccgccc ccctgacgag  4860
catcacaaaa atcgacgctc aagtcagagg tggcgaaacc cgacaggact ataaagatac  4920
caggcgtttc cccctggaag ctccctcgtg cgctctcctg ttccgaccct gccgcttacc  4980
ggatacctgt ccgcctttct cccttcggga agcgtggcgc tttctcaatg ctcacgctgt  5040
aggtatctca gttcggtgta ggtcgttcgc tccaagctgg gctgtgtgca cgaacccccc  5100
gttcagcccg accgctgcgc cttatccggt aactatcgtc ttgagtccaa cccggtaaga  5160
cacgacttat cgccactggc agcagccact ggtaacagga ttagcagagc gaggtatgta  5220
ggcggtgcta cagagttctt gaagtggtgg cctaactacg gctacactag aaggacagta  5280
tttggtatct gcgctctgct gaagccagtt accttcggaa aaagagttgg tagctcttga  5340
tccggcaaac aaaccaccgc tggtagcggt ggtttttttg tttgcaagca gcagattacg  5400
cgcagaaaaa aaggatctca agaagatcct ttgatctttt ctacggggtc tgacgctcag  5460
tggaacgaaa actcacgtta agggattttg gtcatgagat tatcaaaaag gatcttcacc  5520
tagatccttt taaattaaaa atgaagtttt aaatcaatct aaagtatata tgagtaaact  5580
tggtctgaca gttaccaatg cttaatcagt gaggcaccta tctcagcgat ctgtctattt  5640
cgttcatcca tagttgcctg actccccgtc gtgtagataa ctacgatacg ggagggctta  5700
ccatctggcc ccagtgctgc aatgataccg cgagacccac gctcaccggc tccagattta  5760
tcagcaataa accagccagc cggaagggcc gagcgcagaa gtggtcctgc aactttatcc  5820
gcctccatcc agtctattaa ttgttgccgg gaagctagag taagtagttc gccagttaat  5880
agtttgcgca acgttgttgc cattgctaca ggcatcgtgg tgtcacgctc gtcgtttggt  5940
atggcttcat tcagctccgg ttcccaacga tcaaggcgag ttacatgatc ccccatgttg  6000
tgcaaaaaag cggttagctc cttcggtcct ccgatcgttg tcagaagtaa gttggccgca  6060
gtgttatcac tcatggttat ggcagcactg cataattctc ttactgtcat gccatccgta  6120
agatgctttt ctgtgactgg tgagtactca accaagtcat tctgagaata gtgtatgcgg  6180
cgaccgagtt gctcttgccc ggcgtcaata cgggataata ccgcgccaca tagcagaact  6240
ttaaaagtgc tcatcattgg aaaacgttct tcggggcgaa aactctcaag gatcttaccg  6300
ctgttgagat ccagttcgat gtaacccact cgtgcaccca actgatcttc agcatctttt  6360
actttcacca gcgtttctgg gtgagcaaaa acaggaaggc aaaatgccgc aaaaaaggga  6420
ataagggcga cacggaaatg ttgaatactc atactcttcc tttttcaata ttattgaagc  6480
atttatcagg gttattgtct catgagcgga tacatatttg aatgtattta gaaaaataaa  6540
caaatagggg ttccgcgcac atttccccga aaagtgccac ctgacgtcga cggatcggga  6600
gatctcccga tcccctatgg tcgactctca gtacaatctg ctctgatgcc gcatagttaa  6660
```

```
gccagtatct gctccctgct tgtgtgttgg aggtcgctga gtagtgcgcg agcaaaattt  6720
aagctacaac aaggcaaggc ttgaccgaca attgcatgaa gaatctgctt agg         6773

SEQ ID NO: 102          moltype = DNA  length = 7449
FEATURE                 Location/Qualifiers
source                  1..7449
                        mol_type = other DNA
                        organism = synthetic construct
SEQUENCE: 102
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcggaggtcc agctgcagca gtctggcgcc  840
gaacttgtta gacctggcgc tctggtcaag ctgagctgta aagccagcgg cttcaacatc  900
aaggactacc acatgcactg ggtcaaagag cggcctgagc agggactcga gtggatcgga  960
tggatcgacc ccgagaacgg caacactatg tacgacccca agttccaggg caaagccagc  1020
atcaccgccg acacctctag caacacagcc tacctgcagc tgagcagcct gacctctgaa  1080
gataccgccg tgtactactg cgtgcgggga acagccagag ccagctttga ttattggggc  1140
cagggcacca cactgaccgt gtcatctgct agcaccaagg gcccatcggt cttccccctg  1200
gcgccctgct ccaggagcac ctccgagagc acagccgccc tgggctgcct ggtcaaggac  1260
tacttccccg aaccggtgac ggtgtcgtgg aactcaggcg ccctgaccag cggcgtgcac  1320
accttcccgg ctgtcctaca gtcctcagga ctctactccc tcagcagcgt ggtgaccgtg  1380
ccctccagca gcttgggcac gaagacctac acctgcaacg tagatcacaa gcccagcaac  1440
accaaggtgg acaagagagt tgagtccaaa tatggtcccc catgcccatc atgcccagca  1500
cctgagttcc tggggggacc atcagtcttc ctgttccccc caaaacccaa ggacactctc  1560
atgatctccc ggacccctga ggtcacgtgc gtggtggtgg acgtgagcca ggaagacccc  1620
gaggtccagt tcaactggta cgtggatggc gtggaggtgc ataatgccaa gacaaagccg  1680
cgggaggagc agttcaacag cacgtaccgt gtggtcagcg tcctcaccgt cctgcaccag  1740
gactggctga acggcaagga gtacaagtgc aaggtctcca acaaaggcct cccgtcctcc  1800
atcgagaaaa ccatctccaa agccaaaggg cagccccgag agccacaggt gtacaccctg  1860
cccccatccc aggaggagat gaccaagaac caggtcagcc tgacctgcct ggtcaaaggc  1920
ttctacccca gcgacatcgc cgtggagtgg gagagcaatg ggcagccgga gaacaactac  1980
aagaccacgc ctcccgtgct ggactccgac ggctccttct tcctctacag caggctaacc  2040
gtggacaaga gcaggtggca ggaggggaat gtcttctcat gctccgtgat gcatgaggct  2100
ctgcacaacc actacacaca gaagagcctc tccctgtctc tgggtaaata acctagcgtg  2160
gcatctagac actctcgaga agggttcgat ccctaccggt tagtaatgag tttgatatct  2220
cgacaatcaa cctctggatt acaaaatttg tgaaagattg actggtattc ttaactatgt  2280
tgctcctttt acgctatgtg gatacgctgc tttaatgcct ttgtatcatg ctattgcttc  2340
ccgtatggct ttcattttct cctccttgta taaatcctgg ttgctgtctc tttatgagga  2400
gttgtggccc gttgtcaggc aacgtggcgt ggtgtgcact gtgtttgctg acgcaacccc  2460
cactggttgg ggcattgcca ccacctgtca gctcctttcc gggactttcg ctttccccct  2520
ccctattgcc acggcggaac tcatcgccgc ctgccttgcc cgctgctgga caggggctcg  2580
gctgttgggc actgacaatt ccgtggtgtt gtcggggaag ctgacgtcct ttccatggct  2640
gctcgcctgt gttgccacct ggattctgcg cgggacgtcc ttctgctacg tcccttcggc  2700
cctcaatcca gcggaccttc cttcccgcgg cctgctgccg gctctgcggc ctcttccgcg  2760
tcttcgcctt cgccctcaga cgagtcggat ctccctttgg gccgcctccc cgcctggaaa  2820
cgggggaggc taactgaaac acggaaggag acaataccgg aaggaacccg cgctatgacg  2880
gcaataaaaa gacagaataa aacgcacggg tgttgggtcg tttgttcata aacgcggggt  2940
tcggtcccag ggctggcact ctgtcgatac cccaccgaga ccccattggg gccaatacgc  3000
ccgcgtttct tccttttccc caccccaccc cccaagttcg ggtgaaggcc cagggctcgc  3060
agccaacgtc ggggcggcag gccctgccat agcagatctg cgcagctggg gctctagggg  3120
gtatccccac gcgccctgta gcggcgcatt aagcgcggcg ggtgtggtgg ttacgcgcag  3180
cgtgaccgct acacttgcca gcgccctagc gcccgctcct ttcgctttct tcccttcctt  3240
tctcgccacg ttcgccggct ttccccgtca agctctaaat cggggcatcc ctttagggtt  3300
ccgatttagt gctttacggc acctcgaccc caaaaaactt gattagggtg atggttcacg  3360
tagtgggcca tcgccctgat agacggtttt tcgccctttg acgttggagt ccacgttctt  3420
taatagtgga ctcttgttcc aaactggaac aacactcaac cctatctcgg tctattcttt  3480
tgatttataa gggattttgg ggatttcggc ctattggtta aaaaatgagc tgatttaaca  3540
aaaatttaac gcgaattaat tctgtggaat gtgtgtcagt tagggtgtgg aaagtcccca  3600
ggctccccag caggcagaag tatgcaaagc atgcatctca attagtcagc aaccaggtgt  3660
ggaaagtccc caggctcccc agcaggcaga agtatgcaaa gcatgcatct caattagtca  3720
gcaaccatag tcccgcccct aactccgccc atcccgcccc taactccgcc cagttccgcc  3780
cattctccgc cccatggctg actaattttt tttatttatg cagaggccga ggccgcctct  3840
gcctctgagc tattccagaa gtagtgagga ggcttttttg gaggcctagg cttttgcaaa  3900
aagctcccgg gagcttgtat atccattttc ggatctgatc aagagacagg atgaggatcg  3960
tttcgcatga ttgaacaaga tggattgcac gcaggttctc cggccgcttg ggtggagagg  4020
ctattcggct atgactgggc acaacagaca atcggctgct ctgatgccgc cgtgttccgg  4080
ctgtcagcgc aggggcgccc ggttcttttt gtcaagaccg acctgtccgg tgccctgaat  4140
gaactgcagg acgaggcagc gcggctatcg tggctggcca cgacgggcgt tccttgcgca  4200
```

```
gctgtgctcg acgttgtcac tgaagcggga agggactggc tgctattggg cgaagtgccg  4260
gggcaggatc tcctgtcatc tcaccttgct cctgccgaga aagtatccat catggctgat  4320
gcaatgcggc ggctgcatac gcttgatccg gctacctgcc cattcgacca ccaagcgaaa  4380
catcgcatcg agcgagcacg tactcggatg gaagccggtc ttgtcgatca ggatgatctg  4440
gacgaagagc atcaggggct cgcgccagcc gaactgttcg ccaggctcaa ggcgcgcatg  4500
cccgacggcg aggatctcgt cgtgacccat ggcgatgcct gcttgccgaa tatcatggtg  4560
gaaaatggcc gcttttctgg attcatcgac tgtggccggc tgggtgtggc ggaccgctat  4620
caggacatag cgttggctac ccgtgatatt gctgaagagc ttggcggcga atgggctgac  4680
cgcttcctcg tgctttacgg tatcgccgct cccgattcgc agcgcatcgc cttctatcgc  4740
cttcttgacg agttcttctg agcgggactc tggggttcgc gaaatgaccg accaagcgac  4800
gcccaacctg ccatcacgag atttcgattc caccgccgcc ttctatgaaa ggttgggctt  4860
cggaatcgtt ttccgggacg ccggctggat gatcctccag cgcggggatc tcatgctgga  4920
gttcttcgcc caccccaact tgtttattgc agcttataat ggttacaaat aaagcaatag  4980
catcacaaat ttcacaaata aagcattttt ttcactgcat tctagttgtg gtttgtccaa  5040
actcatcaat gtatcttatc atgtctgtat accgtcgacc tctagctaga gcttggcgta  5100
atcatggtca tagctgtttc ctgtgtgaaa ttgttatccg ctcacaattc cacacaacat  5160
acgagccgga agcataaagt gtaaagcctg gggtgcctaa tgagtgagct aactcacatt  5220
aattgcgttg cgctcactgc ccgctttcca gtcgggaaac ctgtcgtgcc agctgcatta  5280
atgaatcggc caacgcgcgg ggagaggcgg tttgcgtatt gggcgctctt ccgcttcctc  5340
gctcactgac tcgctgcgct cggtcgttcg gctgcggcga gcggtatcag ctcactcaaa  5400
ggcggtaata cggttatcca cagaatcagg ggataacgca ggaaagaaca tgtgagcaaa  5460
aggccagcaa aaggccagga accgtaaaaa ggccgcgttg ctggcgtttt tccataggct  5520
ccgcccccct gacgagcatc acaaaaatcg acgctcaagt cagaggtggc gaaacccgac  5580
aggactataa agataccagg cgtttccccc tggaagctcc ctcgtgcgct ctcctgttcc  5640
gaccctgccg cttaccggat acctgtccgc ctttctccct tcgggaagcg tggcgctttc  5700
tcaatgctca cgctgtaggt atctcagttc ggtgtaggtc gttcgctcca agctgggctg  5760
tgtgcacgaa ccccccgttc agcccgaccg ctgcgcctta tccggtaact atcgtcttga  5820
gtccaacccg gtaagacacg acttatcgcc actggcagca gccactggta acaggattag  5880
cagagcgagg tatgtaggcg gtgctacaga gttcttgaag tggtggccta actacggcta  5940
cactagaagg acagtatttg gtatctgcgc tctgctgaag ccagttacct tcggaaaaag  6000
agttggtagc tcttgatccg gcaaacaaac caccgctggt agcggtggtt tttttgtttg  6060
caagcagcag attacgcgca gaaaaaaagg atctcaagaa gatcctttga tcttttctac  6120
ggggtctgac gctcagtgga acgaaaactc acgttaaggg attttggtca tgagattatc  6180
aaaaaggatc ttcacctaga tccttttaaa ttaaaaatga agttttaaat caatctaaag  6240
tatatatgag taaacttggt ctgacagtta ccaatgctta atcagtgagg cacctatctc  6300
agcgatctgt ctatttcgtt catccatagt tgcctgactc cccgtcgtgt agataactac  6360
gatacgggag ggcttaccat ctggccccag tgctgcaatg ataccgcgag acccacgctc  6420
accggctcca gatttatcag caataaacca gccagccgga agggccgagc gcagaagtgg  6480
tcctgcaact ttatccgcct ccatccagtc tattaattgt tgccgggaag ctagagtaag  6540
tagttcgcca gttaatagtt tgcgcaacgt tgttgccatt gctacaggca tcgtggtgtc  6600
acgctcgtcg tttggtatgg cttcattcag ctccggttcc caacgatcaa ggcgagttac  6660
atgatccccc atgttgtgca aaaaagcggt tagctccttc ggtcctccga tcgttgtcag  6720
aagtaagttg gccgcagtgt tatcactcat ggttatggca gcactgcata attctcttac  6780
tgtcatgcca tccgtaagat gcttttctgt gactggtgag tactcaacca agtcattctg  6840
agaatagtgt atgcggcgac cgagttgctc ttgcccggcg tcaatacggg ataataccgc  6900
gccacatagc agaactttaa aagtgctcat cattggaaaa cgttcttcgg ggcgaaaact  6960
ctcaaggatc ttaccgctgt tgagatccag ttcgatgtaa cccactcgtg cacccaactg  7020
atcttcagca tcttttactt tcaccagcgt ttctgggtga gcaaaaacag gaaggcaaaa  7080
tgccgcaaaa aagggaataa gggcgacacg gaaatgttga atactcatac tcttcctttt  7140
tcaatattat tgaagcattt atcagggtta ttgtctcatg agcggataca tatttgaatg  7200
tatttagaaa aataaacaaa taggggttcc gcgcacattt ccccgaaaag tgccacctga  7260
cgtcgacgga tcgggagatc tcccgatccc ctatggtcga ctctcagtac aatctgctct  7320
gatgccgcat agttaagcca gtatctgctc cctgcttgtg tgttggaggt cgctgagtag  7380
tgcgcgagca aaatttaagc tacaacaagg caaggcttga ccgacaattg catgaagaat  7440
ctgcttagg                                                          7449

SEQ ID NO: 103          moltype = DNA  length = 6773
FEATURE                 Location/Qualifiers
source                  1..6773
                        mol_type = other DNA
                        organism = synthetic construct
SEQUENCE: 103
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcagacatcg tgctgacaca gagccctgcc  840
agcctggctg tttctctggg acagagagcc accatcagct gcaaggccag ccagagcgtt  900
gactacgacg gcgacaccta catgaactgg tatcagcaga agcccggcca gccacctaag  960
ctgctgatct acacagccag caacctggaa agcggcatcc ccgccagatt ttctggcagc  1020
```

-continued

```
ggaagcggca ccgacttcac cctgaatatc catcctgtgg aagaggtgga cgccgccacc  1080
tactactgcc agcagagcaa tgaggacccc tggacatttg gcggaggcac caagctggaa  1140
atcaagcgta cggtggctgc accatctgtc ttcatcttcc cgccatctga tgagcagttg  1200
aaatctggaa ctgcctctgt tgtgtgcctg ctgaataact tctatcccag agaggccaaa  1260
gtacagtgga aggtggataa cgccctccaa tcgggtaact cccaggagag tgtcacagag  1320
caggacagca aggacagcac ctacagcctc agcagcaccc tgacgctgag caaagcagac  1380
tacgagaaac acaaagtcta cgcctgcgaa gtcacccatc agggcctgag ctcgcccgtc  1440
acaaagagct tcaacagggg agagtgttag agggagctag cgtggcatct agacactctc  1500
gagaagggtt cgatccctac cggttagtaa tgagtttgat atctcgacaa tcaacctctg  1560
gattacaaaa tttgtgaaag attgactggt attcttaact atgttgctcc ttttacgcta  1620
tgtggatacg ctgctttaat gcctttgtat catgctattg cttcccgtat ggctttcatt  1680
ttctcctcct tgtataaatc ctggttgctg tctctttatg aggagttgtg gcccgttgtc  1740
aggcaacgtg gcgtggtgtg cactgtgttt gctgacgcaa cccccactgg ttggggcatt  1800
gccaccacct gtcagctcct ttccgggact ttcgctttcc ccctccctat tgccacggcg  1860
gaactcatcg ccgcctgcct tgcccgctgc tggacagggg ctcggctgtt gggcactgac  1920
aattccgtgg tgttgtcggg gaagctgacg tcctttccat ggctgctcgc ctgtgttgcc  1980
acctggattc tgcgcgggac gtccttctgc tacgtccctt cggccctcaa tccagcggac  2040
cttccttccc gcggcctgct gccggctctg cggcctcttc cgcgtcttcg ccttcgccct  2100
cagacgagtc ggatctccct ttgggccgcc tccccgcctg gaaacggggg aggctaactg  2160
aaacacggaa ggagacaata ccggaaggaa cccgcgctat gacggcaata aaaagacaga  2220
ataaaacgca cgggtgttgg gtcgtttgtt cataaacgcg gggttcggtc ccagggctgg  2280
cactctgtcg ataccccacc gagaccccat tggggccaat acgcccgcgt ttcttccttt  2340
tccccacccc accccccaag ttcgggtgaa ggcccagggc tcgcagccaa cgtcggggcg  2400
gcaggccctg ccatagcaga tctgcgcagc tggggctcta ggggtatcc ccacgcgccc  2460
tgtagcggcg cattaagcgc ggcgggtgtg gtggttacgc gcagcgtgac cgctacactt  2520
gccagcgccc tagcgcccgc tcctttcgct ttcttccctt cctttctcgc cacgttcgcc  2580
ggctttcccc gtcaagctct aaatcggggc atccctttag ggttccgatt tagtgcttta  2640
cggcacctcg accccaaaaa acttgattag ggtgatggtt cacgtagtgg gccatcgccc  2700
tgatagacgg tttttcgccc tttgacgttg gagtccacgt tctttaatag tggactcttg  2760
ttccaaactg gaacaacact caaccctatc tcggtctatt cttttgattt ataagggatt  2820
ttggggattt cggcctattg gttaaaaaat gagctgattt aacaaaaatt taacgcgaat  2880
taattctgtg gaatgtgtgt cagttagggt gtggaaagtc cccaggctcc ccagcaggca  2940
gaagtatgca aagcatgcat ctcaattagt cagcaaccag gtgtggaaag tccccaggct  3000
ccccagcagg cagaagtatg caaagcatgc atctcaatta gtcagcaacc atagtcccgc  3060
ccctaactcc gcccatcccg cccctaactc cgcccagttc cgcccattct ccgccccatg  3120
gctgactaat tttttttatt tatgcagagg ccgaggccgc ctctgcctct gagctattcc  3180
agaagtagtg aggaggcttt tttggaggcc taggcttttg caaaaagctc ccgggagctt  3240
gtatatccat tttcggatct gatcaagaga caggatgagg atcgtttcgc atgattgaac  3300
aagatggatt gcacgcaggt tctccggccg cttgggtgga gaggctattc ggctatgact  3360
gggcacaaca gacaatcggc tgctctgatg ccgccgtgtt ccggctgtca gcgcaggggc  3420
gcccggttct ttttgtcaag accgacctgt ccggtgccct gaatgaactg caggacgagg  3480
cagcgcggct atcgtggctg gccacgacgg gcgttccttg cgcagctgtg ctcgacgttg  3540
tcactgaagc gggaagggac tggctgctat tgggcgaagt gccggggcag gatctcctgt  3600
catctcacct tgctcctgcc gagaaagtat ccatcatggc tgatgcaatg cggcggctgc  3660
atacgcttga tccggctacc tgcccattcg accaccaagc gaaacatcgc atcgagcgag  3720
cacgtactcg gatggaagcc ggtcttgtcg atcaggatga tctggacgaa gagcatcagg  3780
ggctcgcgcc agccgaactg ttcgccaggc tcaaggcgcg catgcccgac ggcgaggatc  3840
tcgtcgtgac ccatggcgat gcctgcttgc cgaatatcat ggtggaaaat ggccgctttt  3900
ctggattcat cgactgtggc cggctgggtg tggcggaccg ctatcaggac atagcgttgg  3960
ctacccgtga tattgctgaa gagcttggcg gcgaatgggc tgaccgcttc ctcgtgcttt  4020
acggtatcgc cgctcccgat tcgcagcgca tcgccttcta tcgccttctt gacgagttct  4080
tctgagcggg actctggggt tcgcgaaatg accgaccaag cgacgcccaa cctgccatca  4140
cgagatttcg attccaccgc cgccttctat gaaaggttgg gcttcggaat cgttttccgg  4200
gacgccggct ggatgatcct ccagcgcggg gatctcatgc tggagttctt cgcccacccc  4260
aacttgttta ttgcagctta taatggttac aaataaagca atagcatcac aaatttcaca  4320
aataaagcat ttttttcact gcattctagt tgtggtttgt ccaaactcat caatgtatct  4380
tatcatgtct gtataccgtc gacctctagc tagagcttgg cgtaatcatg gtcatagctg  4440
tttcctgtgt gaaattgtta tccgctcaca attccacaca acatacgagc cggaagcata  4500
aagtgtaaag cctggggtgc ctaatgagtg agctaactca cattaattgc gttgcgctca  4560
ctgcccgctt tccagtcggg aaacctgtcg tgccagctgc attaatgaat cggccaacgc  4620
gcggggagag gcggtttgcg tattgggcgc tcttccgctt cctcgctcac tgactcgctg  4680
cgctcggtcg ttcggctgcg gcgagcggta tcagctcact caaaggcggt aatacggtta  4740
tccacagaat caggggataa cgcaggaaag aacatgtgag caaaaggcca gcaaaaggcc  4800
aggaaccgta aaaaggccgc gttgctggcg tttttccata ggctccgccc ccctgacgag  4860
catcacaaaa atcgacgctc aagtcagagg tggcgaaacc cgacaggact ataaagatac  4920
caggcgtttc cccctggaag ctccctcgtg cgctctcctg ttccgaccct gccgcttacc  4980
ggatacctgt ccgcctttct cccttcggga agcgtggcgc tttctcaatg ctcacgctgt  5040
aggtatctca gttcggtgta ggtcgttcgc tccaagctgg gctgtgtgca cgaacccccc  5100
gttcagcccg accgctgcgc cttatccggt aactatcgtc ttgagtccaa cccggtaaga  5160
cacgacttat cgccactggc agcagccact ggtaacagga ttagcagagc gaggtatgta  5220
ggcggtgcta cagagttctt gaagtggtgg cctaactacg gctacactag aaggacagta  5280
tttggtatct gcgctctgct gaagccagtt accttcggaa aaagagttgg tagctcttga  5340
tccggcaaac aaaccaccgc tggtagcggt ggtttttttg tttgcaagca gcagattacg  5400
cgcagaaaaa aaggatctca agaagatcct ttgatctttt ctacggggtc tgacgctcag  5460
tggaacgaaa actcacgtta agggattttg gtcatgagat tatcaaaaag gatcttcacc  5520
tagatccttt taaattaaaa atgaagtttt aaatcaatct aaagtatata tgagtaaact  5580
tggtctgaca gttaccaatg cttaatcagt gaggcaccta tctcagcgat ctgtctattt  5640
cgttcatcca tagttgcctg actccccgtc gtgtagataa ctacgatacg ggagggctta  5700
ccatctggcc ccagtgctgc aatgataccg cgagacccac gctcaccggc tccagattta  5760
```

-continued

```
tcagcaataa accagccagc cggaagggcc gagcgcagaa gtggtcctgc aactttatcc  5820
gcctccatcc agtctattaa ttgttgccgg gaagctagag taagtagttc gccagttaat  5880
agtttgcgca acgttgttgc cattgctaca ggcatcgtgg tgtcacgctc gtcgtttggt  5940
atggcttcat tcagctccgg ttcccaacga tcaaggcgag ttacatgatc ccccatgttg  6000
tgcaaaaaag cggttagctc cttcggtcct ccgatcgttg tcagaagtaa gttggccgca  6060
gtgttatcac tcatggttat ggcagcactg cataattctc ttactgtcat gccatccgta  6120
agatgctttt ctgtgactgg tgagtactca accaagtcat tctgagaata gtgtatgcgg  6180
cgaccgagtt gctcttgccc ggcgtcaata cgggataata ccgcgccaca tagcagaact  6240
ttaaaagtgc tcatcattgg aaaacgttct tcggggcgaa aactctcaag gatcttaccg  6300
ctgttgagat ccagttcgat gtaacccact cgtgcaccca actgatcttc agcatctttt  6360
actttcacca gcgtttctgg gtgagcaaaa acaggaaggc aaaatgccgc aaaaaaggga  6420
ataagggcga cacggaaatg ttgaatactc atactcttcc tttttcaata ttattgaagc  6480
atttatcagg gttattgtct catgagcgga tacatatttg aatgtattta gaaaaataaa  6540
caaatagggg ttccgcgcac atttccccga aaagtgccac ctgacgtcga cggatcggga  6600
gatctcccga tcccctatgg tcgactctca gtacaatctg ctctgatgcc gcatagttaa  6660
gccagtatct gctccctgct tgtgtgttgg aggtcgctga gtagtgcgcg agcaaaattt  6720
aagctacaac aaggcaaggc ttgaccgaca attgcatgaa gaatctgctt agg         6773

SEQ ID NO: 104         moltype = DNA  length = 7449
FEATURE                Location/Qualifiers
source                 1..7449
                       mol_type = other DNA
                       organism = synthetic construct
SEQUENCE: 104
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcggaggtcc agctgcagca gtctggcgcc  840
gaacttgtta gacctggcgc tctggtcaag tggtcctgta aagccagcgg cttcaacatc  900
aaggactacc acatccactg ggtcaagcag aggcctgagc agggcctcga ttggatcggc  960
tggatcgacc ccgagatcga caagaccctg tacgacccca agttccaggg caaagccaga  1020
atcaccgccg acaccagcag caacacagcc tacctgcaac tgagcagcct gaccagcgaa  1080
gataccgccg tgtactactg cgccagagga acagccagag ccagcttcga ttattggggc  1140
cagggcacca cactgaccgt gtcatctgct agcaccaagg gcccatcggt cttccccctg  1200
gcgccctgct ccaggagcac ctccgagagc acagccgccc tgggctgcct ggtcaaggac  1260
tacttccccg aaccggtgac ggtgtcgtgg aactcaggcg ccctgaccag cggcgtgcac  1320
accttcccgg ctgtcctaca gtcctcagga ctctactccc tcagcagcgt ggtgaccgtg  1380
ccctccagca gcttgggcac gaagacctac acctgcaacg tagatcacaa gcccagcaac  1440
accaaggtgg acaagagagt tgagtccaaa tatggtcccc catgcccatc atgcccagca  1500
cctgagttcc tggggggacc atcagtcttc ctgttccccc caaaacccaa ggacactctc  1560
atgatctccc ggacccctga ggtcacgtgc gtggtggtgg acgtgagcca ggaagacccc  1620
gaggtccagt tcaactggta cgtggatggc gtggaggtgc ataatgccaa gacaaagccg  1680
cgggaggagc agttcaacag cacgtaccgt gtggtcagcg tcctcaccgt cctgcaccag  1740
gactggctga acggcaagga gtacaagtgc aaggtctcca acaaaggcct cccgtcctcc  1800
atcgagaaaa ccatctccaa agccaaaggg cagccccgag agccacaggt gtacaccctg  1860
cccccatccc aggaggagat gaccaagaac caggtcagcc tgacctgcct ggtcaaaggc  1920
ttctacccca gcgacatcgc cgtggagtgg gagagcaatg ggcagccgga gaacaactac  1980
aagaccacgc ctcccgtgct ggactccgac ggctccttct tcctctacag caggctaacc  2040
gtggacaaga gcaggtggca ggaggggaat gtcttctcat gctccgtgat gcatgaggct  2100
ctgcacaacc actacacaca gaagagcctc tccctgtctc tgggtaaata acctagcgtg  2160
gcatctagac actctcgaga agggttcgat ccctaccggt tagtaatgag tttgatatct  2220
cgacaatcaa cctctggatt acaaaatttg tgaaagattg actggtattc ttaactatgt  2280
tgctcctttt acgctatgtg gatacgctgc tttaatgcct ttgtatcatg ctattgcttc  2340
ccgtatggct ttcattttct cctccttgta taaatcctgg ttgctgtctc tttatgagga  2400
gttgtggccc gttgtcaggc aacgtggcgt ggtgtgcact gtgtttgctg acgcaacccc  2460
cactggttgg ggcattgcca ccacctgtca gctcctttcc gggactttcg ctttccccct  2520
ccctattgcc acggcggaac tcatcgccgc ctgccttgcc cgctgctgga caggggctcg  2580
gctgttgggc actgacaatt ccgtggtgtt gtcggggaag ctgacgtcct ttccatggct  2640
gctcgcctgt gttgccacct ggattctgcg cgggacgtcc ttctgctacg tcccttcggc  2700
cctcaatcca gcggaccttc cttcccgcgg cctgctgccg gctctgcggc ctcttccgcg  2760
tcttcgcctt cgccctcaga cgagtcggat ctccctttgg gccgcctccc cgcctggaaa  2820
cgggggaggc taactgaaac acggaaggag acaataccgg aaggaacccg cgctatgacg  2880
gcaataaaaa gacagaataa aacgcacggg tgttgggtcg tttgttcata aacgcggggt  2940
tcggtcccag ggctggcact ctgtcgatac cccaccgaga ccccattggg gccaatacgc  3000
ccgcgtttct tccttttccc caccccaccc cccaagttcg ggtgaaggcc cagggctcgc  3060
agccaacgtc ggggcggcag gccctgccat agcagatctg cgcagctggg gctctagggg  3120
gtatccccac gcgccctgta gcggcgcatt aagcgcggcg ggtgtggtgg ttacgcgcag  3180
cgtgaccgct acacttgcca gcgccctagc gcccgctcct ttcgctttct tcccttcctt  3240
tctcgccacg ttcgccggct ttccccgtca agctctaaat cggggcatcc ctttagggtt  3300
```

-continued

```
ccgatttagt gctttacggc acctcgaccc caaaaaactt gattagggtg atggttcacg  3360
tagtgggcca tcgccctgat agacggtttt tcgccctttg acgttggagt ccacgttctt  3420
taatagtgga ctcttgttcc aaactggaac aacactcaac cctatctcgg tctattcttt  3480
tgatttataa gggattttgg ggatttcggc ctattggtta aaaaatgagc tgatttaaca  3540
aaaatttaac gcgaattaat tctgtggaat gtgtgtcagt tagggtgtgg aaagtcccca  3600
ggctccccag caggcagaag tatgcaaagc atgcatctca attagtcagc aaccaggtgt  3660
ggaaagtccc caggctcccc agcaggcaga agtatgcaaa gcatgcatct caattagtca  3720
gcaaccatag tcccgcccct aactccgccc atcccgcccc taactccgcc cagttccgcc  3780
cattctccgc cccatggctg actaattttt tttatttatg cagaggccga ggccgcctct  3840
gcctctgagc tattccagaa gtagtgagga ggcttttttg gaggcctagg cttttgcaaa  3900
aagctcccgg gagcttgtat atccattttc ggatctgatc aagagacagg atgaggatcg  3960
tttcgcatga ttgaacaaga tggattgcac gcaggttctc cggccgcttg ggtggagagg  4020
ctattcggct atgactgggc acaacagaca atcggctgct ctgatgccgc cgtgttccgg  4080
ctgtcagcgc aggggcgccc ggttcttttt gtcaagaccg acctgtccgg tgccctgaat  4140
gaactgcagg acgaggcagc gcggctatcg tggctggcca cgacgggcgt tccttgcgca  4200
gctgtgctcg acgttgtcac tgaagcggga agggactggc tgctattggg cgaagtgccg  4260
gggcaggatc tcctgtcatc tcaccttgct cctgccgaga aagtatccat catggctgat  4320
gcaatgcggc ggctgcatac gcttgatccg gctacctgcc cattcgacca ccaagcgaaa  4380
catcgcatcg agcgagcacg tactcggatg gaagccggtc ttgtcgatca ggatgatctg  4440
gacgaagagc atcaggggct cgcgccagcc gaactgttcg ccaggctcaa ggcgcgcatg  4500
cccgacggcg aggatctcgt cgtgacccat ggcgatgcct gcttgccgaa tatcatggtg  4560
gaaaatggcc gcttttctgg attcatcgac tgtggccggc tgggtgtggc ggaccgctat  4620
caggacatag cgttggctac ccgtgatatt gctgaagagc ttggcggcga atgggctgac  4680
cgcttcctcg tgctttacgg tatcgccgct cccgattcgc agcgcatcgc cttctatcgc  4740
cttcttgacg agttcttctg agcgggactc tggggttcgc gaaatgaccg accaagcgac  4800
gcccaacctg ccatcacgag atttcgattc caccgccgcc ttctatgaaa ggttgggctt  4860
cggaatcgtt ttccgggacg ccggctggat gatcctccag cgcggggatc tcatgctgga  4920
gttcttcgcc caccccaact tgtttattgc agcttataat ggttacaaat aaagcaatag  4980
catcacaaat ttcacaaata aagcattttt ttcactgcat tctagttgtg gtttgtccaa  5040
actcatcaat gtatcttatc atgtctgtat accgtcgacc tctagctaga gcttggcgta  5100
atcatggtca tagctgtttc ctgtgtgaaa ttgttatccg ctcacaattc cacacaacat  5160
acgagccgga agcataaagt gtaaagcctg gggtgcctaa tgagtgagct aactcacatt  5220
aattgcgttg cgctcactgc ccgctttcca gtcgggaaac ctgtcgtgcc agctgcatta  5280
atgaatcggc caacgcgcgg ggagaggcgg tttgcgtatt gggcgctctt ccgcttcctc  5340
gctcactgac tcgctgcgct cggtcgttcg gctgcggcga gcggtatcag ctcactcaaa  5400
ggcggtaata cggttatcca cagaatcagg ggataacgca ggaaagaaca tgtgagcaaa  5460
aggccagcaa aaggccagga accgtaaaaa ggccgcgttg ctggcgtttt tccataggct  5520
ccgcccccct gacgagcatc acaaaaatcg acgctcaagt cagaggtggc gaaacccgac  5580
aggactataa agataccagg cgtttccccc tggaagctcc ctcgtgcgct ctcctgttcc  5640
gaccctgccg cttaccggat acctgtccgc ctttctccct tcgggaagcg tggcgctttc  5700
tcaatgctca cgctgtaggt atctcagttc ggtgtaggtc gttcgctcca agctgggctg  5760
tgtgcacgaa ccccccgttc agcccgaccg ctgcgcctta tccggtaact atcgtcttga  5820
gtccaacccg gtaagacacg acttatcgcc actggcagca gccactggta acaggattag  5880
cagagcgagg tatgtaggcg gtgctacaga gttcttgaag tggtggccta actacggcta  5940
cactagaagg acagtatttg gtatctgcgc tctgctgaag ccagttacct tcggaaaaag  6000
agttggtagc tcttgatccg gcaaacaaac caccgctggt agcggtggtt tttttgtttg  6060
caagcagcag attacgcgca gaaaaaaagg atctcaagaa gatcctttga tcttttctac  6120
ggggtctgac gctcagtgga acgaaaactc acgttaaggg attttggtca tgagattatc  6180
aaaaaggatc ttcacctaga tccttttaaa ttaaaaatga agttttaaat caatctaaag  6240
tatatatgag taaacttggt ctgacagtta ccaatgctta atcagtgagg cacctatctc  6300
agcgatctgt ctatttcgtt catccatagt tgcctgactc cccgtcgtgt agataactac  6360
gatacgggag ggcttaccat ctggccccag tgctgcaatg ataccgcgag acccacgctc  6420
accggctcca gatttatcag caataaacca gccagccgga agggccgagc gcagaagtgg  6480
tcctgcaact ttatccgcct ccatccagtc tattaattgt tgccgggaag ctagagtaag  6540
tagttcgcca gttaatagtt tgcgcaacgt tgttgccatt gctacaggca tcgtggtgtc  6600
acgctcgtcg tttggtatgg cttcattcag ctccggttcc caacgatcaa ggcgagttac  6660
atgatccccc atgttgtgca aaaaagcggt tagctccttc ggtcctccga tcgttgtcag  6720
aagtaagttg gccgcagtgt tatcactcat ggttatggca gcactgcata attctcttac  6780
tgtcatgcca tccgtaagat gcttttctgt gactggtgag tactcaacca agtcattctg  6840
agaatagtgt atgcggcgac cgagttgctc ttgcccggcg tcaatacggg ataataccgc  6900
gccacatagc agaactttaa aagtgctcat cattggaaaa cgttcttcgg ggcgaaaact  6960
ctcaaggatc ttaccgctgt tgagatccag ttcgatgtaa cccactcgtg cacccaactg  7020
atcttcagca tcttttactt tcaccagcgt ttctgggtga gcaaaaacag gaaggcaaaa  7080
tgccgcaaaa aagggaataa gggcgacacg gaaatgttga atactcatac tcttcctttt  7140
tcaatattat tgaagcattt atcagggtta ttgtctcatg agcggataca tatttgaatg  7200
tatttagaaa aataaacaaa taggggttcc gcgcacattt ccccgaaaag tgccacctga  7260
cgtcgacgga tcgggagatc tcccgatccc ctatggtcga ctctcagtac aatctgctct  7320
gatgccgcat agttaagcca gtatctgctc cctgcttgtg tgttggaggt cgctgagtag  7380
tgcgcgagca aaatttaagc tacaacaagg caaggcttga ccgacaattg catgaagaat  7440
ctgcttagg                                                          7449
```

```
SEQ ID NO: 105          moltype = DNA  length = 6773
FEATURE                 Location/Qualifiers
source                  1..6773
                        mol_type = other DNA
                        organism = synthetic construct
SEQUENCE: 105
gttaggcgtt ttgcgctgct tcgcgatgta cgggccagat atacgcgttg acattgatta  60
ttgactagtt attaatagta atcaattacg gggtcattag ttcatagccc atatatggag  120
```

-continued

```
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcagacaacg tgctgacaca gagccctgcc  840
agcctggctg tttctctggg acagagagcc accatcagct gcaaggccag ccagagcgtt  900
gactacgacg gcgacagcta catgaactgg tatcagcaga agcccggcca gccacctaag  960
gtgttcatct acgccgccag caacctggaa agcggcatcc ctgccagatt ttctggctct  1020
ggcagcggca ccaacttcac cctgaacatt caccccgtgg aagaagagga cgccgccacc  1080
tactactgcc agcagagcaa tgaggacccc tggacatttg gcggaggcac caagctggaa  1140
atcaagcgta cggtggctgc accatctgtc ttcatcttcc cgccatctga tgagcagttg  1200
aaatctggaa ctgcctctgt tgtgtgcctg ctgaataact tctatcccag agaggccaaa  1260
gtacagtgga aggtggataa cgccctccaa tcgggtaact cccaggagag tgtcacagag  1320
caggacagca aggacagcac ctacagcctc agcagcaccc tgacgctgag caaagcagac  1380
tacgagaaac acaaagtcta cgcctgcgaa gtcacccatc agggcctgag ctcgcccgtc  1440
acaaagagct tcaacagggg agagtgttag agggagctag cgtggcatct agacactctc  1500
gagaagggtt cgatccctac cggttagtaa tgagtttgat atctcgacaa tcaacctctg  1560
gattacaaaa tttgtgaaag attgactggt attcttaact atgttgctcc ttttacgcta  1620
tgtggatacg ctgctttaat gcctttgtat catgctattg cttcccgtat ggctttcatt  1680
ttctcctcct tgtataaatc ctggttgctg tctctttatg aggagttgtg gcccgttgtc  1740
aggcaacgtg gcgtggtgtg cactgtgttt gctgacgcaa cccccactgg ttggggcatt  1800
gccaccacct gtcagctcct ttccgggact ttcgctttcc ccctccctat tgccacggcg  1860
gaactcatcg ccgcctgcct tgcccgctgc tggacagggg ctcggctgtt gggcactgac  1920
aattccgtgg tgttgtcggg gaagctgacg tcctttccat ggctgctcgc ctgtgttgcc  1980
acctggattc tgcgcgggac gtccttctgc tacgtccctt cggccctcaa tccagcggac  2040
cttccttccc gcggcctgct gccggctctg cggcctcttc cgcgtcttcg ccttcgccct  2100
cagacgagtc ggatctccct ttgggccgcc tccccgcctg gaaacggggg aggctaactg  2160
aaacacggaa ggagacaata ccggaaggaa cccgcgctat gacggcaata aaaagacaga  2220
ataaaacgca cgggtgttgg gtcgtttgtt cataaacgcg gggttcggtc ccagggctgg  2280
cactctgtcg ataccccacc gagaccccat tggggccaat acgcccgcgt ttcttccttt  2340
tccccacccc accccccaag ttcgggtgaa ggcccagggc tcgcagccaa cgtcggggcg  2400
gcaggccctg ccatagcaga tctgcgcagc tggggctcta ggggtatcc ccacgcgccc  2460
tgtagcggcg cattaagcgc ggcgggtgtg gtggttacgc gcagcgtgac cgctacactt  2520
gccagcgccc tagcgcccgc tcctttcgct ttcttccctt cctttctcgc cacgttcgcc  2580
ggctttcccc gtcaagctct aaatcggggc atccctttag ggttccgatt tagtgcttta  2640
cggcacctcg accccaaaaa acttgattag ggtgatggtt cacgtagtgg gccatcgccc  2700
tgatagacgg tttttcgccc tttgacgttg gagtccacgt tctttaatag tggactcttg  2760
ttccaaactg gaacaacact caaccctatc tcggtctatt cttttgattt ataagggatt  2820
ttggggattt cggcctattg gttaaaaaat gagctgattt aacaaaaatt taacgcgaat  2880
taattctgtg gaatgtgtgt cagttagggt gtggaaagtc cccaggctcc ccagcaggca  2940
gaagtatgca aagcatgcat ctcaattagt cagcaaccag gtgtggaaag tccccaggct  3000
ccccagcagg cagaagtatg caaagcatgc atctcaatta gtcagcaacc atagtcccgc  3060
ccctaactcc gcccatcccg cccctaactc cgcccagttc cgcccattct ccgccccatg  3120
gctgactaat tttttttatt tatgcagagg ccgaggccgc ctctgcctct gagctattcc  3180
agaagtagtg aggaggcttt tttggaggcc taggcttttg caaaaagctc ccgggagctt  3240
gtatatccat tttcggatct gatcaagaga caggatgagg atcgtttcgc atgattgaac  3300
aagatggatt gcacgcaggt tctccggccg cttgggtgga gaggctattc ggctatgact  3360
gggcacaaca gacaatcggc tgctctgatg ccgccgtgtt ccggctgtca gcgcaggggc  3420
gcccggttct ttttgtcaag accgacctgt ccggtgccct gaatgaactg caggacgagg  3480
cagcgcggct atcgtggctg gccacgacgg gcgttccttg cgcagctgtg ctcgacgttg  3540
tcactgaagc gggaagggac tggctgctat tgggcgaagt gccggggcag gatctcctgt  3600
catctcacct tgctcctgcc gagaaagtat ccatcatggc tgatgcaatg cggcggctgc  3660
atacgcttga tccggctacc tgcccattcg accaccaagc gaaacatcgc atcgagcgag  3720
cacgtactcg gatggaagcc ggtcttgtcg atcaggatga tctggacgaa gagcatcagg  3780
ggctcgcgcc agccgaactg ttcgccaggc tcaaggcgcg catgcccgac ggcgaggatc  3840
tcgtcgtgac ccatggcgat gcctgcttgc cgaatatcat ggtggaaaat ggccgctttt  3900
ctggattcat cgactgtggc cggctgggtg tggcggaccg ctatcaggac atagcgttgg  3960
ctacccgtga tattgctgaa gagcttggcg gcgaatgggc tgaccgcttc ctcgtgcttt  4020
acggtatcgc cgctcccgat tcgcagcgca tcgccttcta tcgccttctt gacgagttct  4080
tctgagcggg actctggggt tcgcgaaatg accgaccaag cgacgcccaa cctgccatca  4140
cgagatttcg attccaccgc cgccttctat gaaaggttgg gcttcggaat cgttttccgg  4200
gacgccggct ggatgatcct ccagcgcggg gatctcatgc tggagttctt cgcccacccc  4260
aacttgttta ttgcagctta taatggttac aaataaagca atagcatcac aaatttcaca  4320
aataaagcat ttttttcact gcattctagt tgtggtttgt ccaaactcat caatgtatct  4380
tatcatgtct gtataccgtc gacctctagc tagagcttgg cgtaatcatg gtcatagctg  4440
tttcctgtgt gaaattgtta tccgctcaca attccacaca acatacgagc cggaagcata  4500
aagtgtaaag cctggggtgc ctaatgagtg agctaactca cattaattgc gttgcgctca  4560
ctgcccgctt tccagtcggg aaacctgtcg tgccagctgc attaatgaat cggccaacgc  4620
gcggggagag gcggtttgcg tattgggcgc tcttccgctt cctcgctcac tgactcgctg  4680
cgctcggtcg ttcggctgcg gcgagcggta tcagctcact caaaggcggt aatacggtta  4740
tccacagaat caggggataa cgcaggaaag aacatgtgag caaaaggcca gcaaaaggcc  4800
aggaaccgta aaaggccgc gttgctggcg tttttccata ggctccgccc ccctgacgag  4860
```

-continued

```
catcacaaaa atcgacgctc aagtcagagg tggcgaaacc cgacaggact ataaagatac  4920
caggcgtttc cccctggaag ctccctcgtg cgctctcctg ttccgaccct gccgcttacc  4980
ggatacctgt ccgcctttct cccttcggga agcgtggcgc tttctcaatg ctcacgctgt  5040
aggtatctca gttcggtgta ggtcgttcgc tccaagctgg gctgtgtgca cgaacccccc  5100
gttcagcccg accgctgcgc cttatccggt aactatcgtc ttgagtccaa cccggtaaga  5160
cacgacttat cgccactggc agcagccact ggtaacagga ttagcagagc gaggtatgta  5220
ggcggtgcta cagagttctt gaagtggtgg cctaactacg gctacactag aaggacagta  5280
tttggtatct gcgctctgct gaagccagtt accttcggaa aaagagttgg tagctcttga  5340
tccggcaaac aaaccaccgc tggtagcggt ggtttttttg tttgcaagca gcagattacg  5400
cgcagaaaaa aaggatctca agaagatcct ttgatctttt ctacggggtc tgacgctcag  5460
tggaacgaaa actcacgtta agggattttg gtcatgagat tatcaaaaag gatcttcacc  5520
tagatccttt taaattaaaa atgaagtttt aaatcaatct aaagtatata tgagtaaact  5580
tggtctgaca gttaccaatg cttaatcagt gaggcaccta tctcagcgat ctgtctattt  5640
cgttcatcca tagttgcctg actccccgtc gtgtagataa ctacgatacg ggagggctta  5700
ccatctggcc ccagtgctgc aatgataccg cgagacccac gctcaccggc tccagattta  5760
tcagcaataa accagccagc cggaagggcc gagcgcagaa gtggtcctgc aactttatcc  5820
gcctccatcc agtctattaa ttgttgccgg gaagctagag taagtagttc gccagttaat  5880
agtttgcgca acgttgttgc cattgctaca ggcatcgtgg tgtcacgctc gtcgtttggt  5940
atggcttcat tcagctccgg ttcccaacga tcaaggcgag ttacatgatc ccccatgttg  6000
tgcaaaaaag cggttagctc cttcggtcct ccgatcgttg tcagaagtaa gttggccgca  6060
gtgttatcac tcatggttat ggcagcactg cataattctc ttactgtcat gccatccgta  6120
agatgctttt ctgtgactgg tgagtactca accaagtcat tctgagaata gtgtatgcgg  6180
cgaccgagtt gctcttgccc ggcgtcaata cgggataata ccgcgccaca tagcagaact  6240
ttaaaagtgc tcatcattgg aaaacgttct tcggggcgaa aactctcaag gatcttaccg  6300
ctgttgagat ccagttcgat gtaacccact cgtgcaccca actgatcttc agcatctttt  6360
actttcacca gcgtttctgg gtgagcaaaa acaggaaggc aaaatgccgc aaaaaaggga  6420
ataagggcga cacggaaatg ttgaatactc atactcttcc tttttcaata ttattgaagc  6480
atttatcagg gttattgtct catgagcgga tacatatttg aatgtattta gaaaaataaa  6540
caaatagggg ttccgcgcac atttccccga aaagtgccac ctgacgtcga cggatcggga  6600
gatctcccga tcccctatgg tcgactctca gtacaatctg ctctgatgcc gcatagttaa  6660
gccagtatct gctccctgct tgtgtgttgg aggtcgctga gtagtgcgcg agcaaaattt  6720
aagctacaac aaggcaaggc ttgaccgaca attgcatgaa gaatctgctt agg         6773

SEQ ID NO: 106         moltype = DNA  length = 7452
FEATURE                Location/Qualifiers
source                 1..7452
                       mol_type = other DNA
                       organism = synthetic construct
SEQUENCE: 106
gttaggcgtt ttgcgctgct tcgcgatgta cgggccagat atacgcgttg acattgatta  60
ttgactagtt attaatagta atcaattacg gggtcattag ttcatagccc atatatggag  120
ttccgcgtta cataacttac ggtaaatggc ccgcctggct gaccgcccaa cgacccccgc  180
ccattgacgt caataatgac gtatgttccc atagtaacgc caatagggac tttccattga  240
cgtcaatggg tggagtattt acggtaaact gcccacttgg cagtacatca agtgtatcat  300
atgccaagta cgccccctat tgacgtcaat gacggtaaat ggcccgcctg gcattatgcc  360
cagtacatga ccttatggga ctttcctact tggcagtaca tctacgtatt agtcatcgct  420
attaccatgg tgatgcggtt ttggcagtac atcaatgggc gtggatagcg gtttgactca  480
cggggatttc caagtctcca ccccattgac gtcaatggga gtttgttttg gcaccaaaat  540
caacgggact ttccaaaatg tcgtaacaac tccgccccat tgacgcaaat gggcggtagg  600
cgtgtacggt gggaggtcta tataagcaga gctcgtttag tgaaccgtca gatcgcctgg  660
agacgccatc cacgctgttt tgacctccat agaagacacc gggaccgatc cagcctccgg  720
actctagagg atcgaaccct taagcttgcc accatgtaca ggatgcaact cctgtcttgc  780
attgcactaa gtcttgcact tgtcacgaat tcggaagtga agctggtgga aagcggcgga  840
ggactggttc aacctggcgg atctctgaag ctgagctgtg ccgccagcgg cttcaccttc  900
agcagataca caatgagctg ggtccgacag acccctgaga agagactgga atgggtcgcc  960
aagatcagaa acgtcggcgg catcacctac tatcccgaca ccgtgaaggg cagattcacc  1020
atctccagag acaacgccaa gaacaccctg tacctgcaga tgagcagcct gaagtccgag  1080
gacaccgcca tgtactactg cgccagacac tactacggca gcgaggacta cttcgactat  1140
tggggccagg gcaccacact gaccgttagc tctgctagca ccaagggccc atcggtcttc  1200
cccctggcgc cctgctccag gagcacctcc gagagcacag cggccctggg ctgcctggtc  1260
aaggactact tccccgaacc ggtgacggtg tcgtggaact caggcgctct gaccagcggc  1320
gtgcacacct tcccagctgt cctacagtcc tcaggactct actccctcag cagcgtggtg  1380
accgtgccct ccagcaactt cggcacccag acctacacct gcaacgtaga tcacaagccc  1440
agcaacacca aggtggacaa gacagttgag cgcaaatgtt gtgtcgagtg cccaccgtgc  1500
ccagcaccac ctgtggcagg accgtcagtc ttcctcttcc ccccaaaacc caaggacacc  1560
ctcatgatct cccggacccc tgaggtcacg tgcgtggtgg tggacgtgag ccacgaagac  1620
cccgaggtcc agttcaactg gtacgtggac ggcgtggagg tgcataatgc caagacaaag  1680
ccacgggagg agcagttcaa cagcacgttc cgtgtggtca gcgtcctcac cgttgtgcac  1740
caggactggc tgaacggcaa ggagtacaag tgcaaggtct ccaacaaagg cctcccagcc  1800
cccatcgaga aaaccatctc caaaaccaaa gggcagcccc gagaaccaca ggtgtacacc  1860
ctgcccccat cccgggagga gatgaccaag aaccaggtca gcctgacctg cctggtcaaa  1920
ggcttctacc ccagcgacat cgccgtggag tgggagagca atgggcagcc ggagaacaac  1980
tacaagacca cgcctcccat gctggactcc gacggctcct tcttcctcta cagcaagctc  2040
accgtggaca agagcaggtg gcagcagggg aacgtcttct catgctccgt gatgcatgag  2100
gctctgcaca accactacac gcagaagagc ctctccctgt ctccgggtaa atgacctagc  2160
gtggcatcta gacactctcg agaagggttc gatccctacc ggttagtaat gagtttgata  2220
tctcgacaat caacctctgg attacaaaat ttgtgaaaga ttgactggta ttcttaacta  2280
tgttgctcct tttacgctat gtggatacgc tgctttaatg cctttgtatc atgctattgc  2340
ttcccgtatg gctttcattt tctcctcctt gtataaatcc tggttgctgt ctctttatga  2400
```

-continued ggagttgtgg cccgttgtca ggcaacgtgg cgtggtgtgc actgtgtttg ctgacgcaac 2460
ccccactggt tggggcattg ccaccacctg tcagctcctt tccgggactt tcgctttccc 2520
cctccctatt gccacggcgg aactcatcgc cgcctgcctt gcccgctgct ggacaggggc 2580
tcggctgttg ggcactgaca attccgtggt gttgtcgggg aagctgacgt cctttccatg 2640
gctgctcgcc tgtgttgcca cctggattct gcgcgggacg tccttctgct acgtcccttc 2700
ggccctcaat ccagcggacc ttccttcccg cggcctgctg ccggctctgc ggcctcttcc 2760
gcgtcttcgc cttcgccctc agacgagtcg gatctccctt tgggccgcct ccccgcctgg 2820
aaacggggga ggctaactga aacacggaag gagacaatac cggaaggaac ccgcgctatg 2880
acggcaataa aaagacagaa taaaacgcac gggtgttggg tcgtttgttc ataaacgcgg 2940
ggttcggtcc cagggctggc actctgtcga taccccaccg agaccccatt ggggccaata 3000
cgcccgcgtt tcttcctttt ccccacccca ccccccaagt tcgggtgaag gcccagggct 3060
cgcagccaac gtcggggcgg caggccctgc catagcagat ctgcgcagct ggggctctag 3120
ggggtatccc cacgcgccct gtagcggcgc attaagcgcg gcgggtgtgg tggttacgcg 3180
cagcgtgacc gctacacttg ccagcgccct agcgcccgct cctttcgctt tcttcccttc 3240
ctttctcgcc acgttcgccg gctttccccg tcaagctcta aatcggggca tccctttagg 3300
gttccgattt agtgctttac ggcacctcga ccccaaaaaa cttgattagg gtgatggttc 3360
acgtagtggg ccatcgccct gatagacggt ttttcgccct ttgacgttgg agtccacgtt 3420
ctttaatagt ggactcttgt tccaaactgg aacaacactc aaccctatct cggtctattc 3480
ttttgattta taagggattt tggggatttc ggcctattgg ttaaaaaatg agctgattta 3540
acaaaaattt aacgcgaatt aattctgtgg aatgtgtgtc agttagggtg tggaaagtcc 3600
ccaggctccc cagcaggcag aagtatgcaa agcatgcatc tcaattagtc agcaaccagg 3660
tgtggaaagt ccccaggctc cccagcaggc agaagtatgc aaagcatgca tctcaattag 3720
tcagcaacca tagtcccgcc cctaactccg cccatcccgc ccctaactcc gcccagttcc 3780
gcccattctc cgccccatgg ctgactaatt ttttttattt atgcagaggc cgaggccgcc 3840
tctgcctctg agctattcca gaagtagtga ggaggctttt ttggaggcct aggcttttgc 3900
aaaaagctcc cgggagcttg tatatccatt ttcggatctg atcaagagac aggatgagga 3960
tcgtttcgca tgattgaaca agatggattg cacgcaggtt ctccggccgc ttgggtggag 4020
aggctattcg gctatgactg ggcacaacag acaatcggct gctctgatgc cgccgtgttc 4080
cggctgtcag cgcaggggcg cccggttctt tttgtcaaga ccgacctgtc cggtgccctg 4140
aatgaactgc aggacgaggc agcgcggcta tcgtggctgg ccacgacggg cgttccttgc 4200
gcagctgtgc tcgacgttgt cactgaagcg ggaagggact ggctgctatt gggcgaagtg 4260
ccggggcagg atctcctgtc atctcacctt gctcctgccg agaaagtatc catcatggct 4320
gatgcaatgc ggcggctgca tacgcttgat ccggctacct gcccattcga ccaccaagcg 4380
aaacatcgca tcgagcgagc acgtactcgg atggaagccg gtcttgtcga tcaggatgat 4440
ctggacgaag agcatcaggg gctcgcgcca gccgaactgt tcgccaggct caaggcgcgc 4500
atgcccgacg gcgaggatct cgtcgtgacc catggcgatg cctgcttgcc gaatatcatg 4560
gtggaaaatg gccgcttttc tggattcatc gactgtggcc ggctgggtgt ggcggaccgc 4620
tatcaggaca tagcgttggc tacccgtgat attgctgaag agcttggcgg cgaatgggct 4680
gaccgcttcc tcgtgcttta cggtatcgcc gctcccgatt cgcagcgcat cgccttctat 4740
cgccttcttg acgagttctt ctgagcggga ctctggggtt cgcgaaatga ccgaccaagc 4800
gacgcccaac ctgccatcac gagatttcga ttccaccgcc gccttctatg aaaggttggg 4860
cttcggaatc gttttccggg acgccggctg gatgatcctc cagcgcgggg atctcatgct 4920
ggagttcttc gcccacccca acttgtttat tgcagcttat aatggttaca aataaagcaa 4980
tagcatcaca aatttcacaa ataaagcatt tttttcactg cattctagtt gtggtttgtc 5040
caaactcatc aatgtatctt atcatgtctg tataccgtcg acctctagct agagcttggc 5100
gtaatcatgg tcatagctgt ttcctgtgtg aaattgttat ccgctcacaa ttccacacaa 5160
catacgagcc ggaagcataa agtgtaaagc ctggggtgcc taatgagtga gctaactcac 5220
attaattgcg ttgcgctcac tgcccgcttt ccagtcggga aacctgtcgt gccagctgca 5280
ttaatgaatc ggccaacgcg cggggagagg cggtttgcgt attgggcgct cttccgcttc 5340
ctcgctcact gactcgctgc gctcggtcgt tcggctgcgg cgagcggtat cagctcactc 5400
aaaggcggta atacggttat ccacagaatc aggggataac gcaggaaaga acatgtgagc 5460
aaaaggccag caaaaggcca ggaaccgtaa aaaggccgcg ttgctggcgt ttttccatag 5520
gctccgcccc cctgacgagc atcacaaaaa tcgacgctca agtcagaggt ggcgaaaccc 5580
gacaggacta taaagatacc aggcgtttcc ccctggaagc tccctcgtgc gctctcctgt 5640
tccgaccctg ccgcttaccg gatacctgtc cgcctttctc ccttcgggaa gcgtggcgct 5700
ttctcaatgc tcacgctgta ggtatctcag ttcggtgtag gtcgttcgct ccaagctggg 5760
ctgtgtgcac gaaccccccg ttcagcccga ccgctgcgcc ttatccggta actatcgtct 5820
tgagtccaac ccggtaagac acgacttatc gccactggca gcagccactg gtaacaggat 5880
tagcagagcg aggtatgtag gcggtgctac agagttcttg aagtggtggc ctaactacgg 5940
ctacactaga aggacagtat ttggtatctg cgctctgctg aagccagtta ccttcggaaa 6000
aagagttggt agctcttgat ccggcaaaca aaccaccgct ggtagcggtg gtttttttgt 6060
ttgcaagcag cagattacgc gcagaaaaaa aggatctcaa gaagatcctt tgatcttttc 6120
tacggggtct gacgctcagt ggaacgaaaa ctcacgttaa gggattttgg tcatgagatt 6180
atcaaaaagg atcttcacct agatcctttt aaattaaaaa tgaagtttta aatcaatcta 6240
aagtatatat gagtaaactt ggtctgacag ttaccaatgc ttaatcagtg aggcacctat 6300
ctcagcgatc tgtctatttc gttcatccat agttgcctga ctccccgtcg tgtagataac 6360
tacgatacgg gagggcttac catctggccc cagtgctgca atgataccgc gagacccacg 6420
ctcaccggct ccagatttat cagcaataaa ccagccagcc ggaagggccg agcgcagaag 6480
tggtcctgca actttatccg cctccatcca gtctattaat tgttgccggg aagctagagt 6540
aagtagttcg ccagttaata gtttgcgcaa cgttgttgcc attgctacag gcatcgtggt 6600
gtcacgctcg tcgtttggta tggcttcatt cagctccggt tcccaacgat caaggcgagt 6660
tacatgatcc cccatgttgt gcaaaaaagc ggttagctcc ttcggtcctc cgatcgttgt 6720
cagaagtaag ttggccgcag tgttatcact catggttatg gcagcactgc ataattctct 6780
tactgtcatg ccatccgtaa gatgcttttc tgtgactggt gagtactcaa ccaagtcatt 6840
ctgagaatag tgtatgcggc gaccgagttg ctcttgcccg gcgtcaatac gggataatac 6900
cgcgccacat agcagaactt taaaagtgct catcattgga aaacgttctt cggggcgaaa 6960
actctcaagg atcttaccgc tgttgagatc cagttcgatg taacccactc gtgcacccaa 7020
ctgatcttca gcatctttta ctttcaccag cgtttctggg tgagcaaaaa caggaaggca 7080
aaatgccgca aaaaagggaa taagggcgac acggaaatgt tgaatactca tactcttcct 7140

```
ttttcaatat tattgaagca tttatcaggg ttattgtctc atgagcggat acatatttga  7200
atgtatttag aaaaataaac aaataggggt tccgcgcaca tttccccgaa aagtgccacc  7260
tgacgtcgac ggatcgggag atctcccgat cccctatggt cgactctcag tacaatctgc  7320
tctgatgccg catagttaag ccagtatctg ctccctgctt gtgtgttgga ggtcgctgag  7380
tagtgcgcga gcaaaattta agctacaaca aggcaaggct tgaccgacaa ttgcatgaag  7440
aatctgctta gg                                                      7452

SEQ ID NO: 107         moltype = DNA  length = 15
FEATURE                Location/Qualifiers
source                 1..15
                       mol_type = other DNA
                       organism = synthetic construct
SEQUENCE: 107
atggaggacg tgtgc                                                   15

SEQ ID NO: 108         moltype = DNA  length = 15
FEATURE                Location/Qualifiers
source                 1..15
                       mol_type = other DNA
                       organism = synthetic construct
SEQUENCE: 108
atggaggacg tgtgc                                                   15

SEQ ID NO: 109         moltype = DNA  length = 15
FEATURE                Location/Qualifiers
source                 1..15
                       mol_type = other DNA
                       organism = synthetic construct
SEQUENCE: 109
atggaggacg tgtgc                                                   15

SEQ ID NO: 110         moltype = DNA  length = 15
FEATURE                Location/Qualifiers
source                 1..15
                       mol_type = other DNA
                       organism = synthetic construct
SEQUENCE: 110
gagctgcggg tgcgc                                                   15

SEQ ID NO: 111         moltype = DNA  length = 15
FEATURE                Location/Qualifiers
source                 1..15
                       mol_type = other DNA
                       organism = synthetic construct
SEQUENCE: 111
gagctgcggg tgagc                                                   15

SEQ ID NO: 112         moltype = DNA  length = 15
FEATURE                Location/Qualifiers
source                 1..15
                       mol_type = other DNA
                       organism = synthetic construct
SEQUENCE: 112
gagctgcggg tgagc                                                   15

SEQ ID NO: 113         moltype = DNA  length = 15
FEATURE                Location/Qualifiers
source                 1..15
                       mol_type = other DNA
                       organism = synthetic construct
SEQUENCE: 113
gacctgcaga agcgc                                                   15

SEQ ID NO: 114         moltype = DNA  length = 15
FEATURE                Location/Qualifiers
source                 1..15
                       mol_type = other DNA
                       organism = synthetic construct
SEQUENCE: 114
gacctgcaga agcgc                                                   15

SEQ ID NO: 115         moltype = DNA  length = 15
FEATURE                Location/Qualifiers
source                 1..15
                       mol_type = other DNA
                       organism = synthetic construct
SEQUENCE: 115
gacctgcana agcgc                                                   15
```

-continued

```
SEQ ID NO: 116          moltype = AA  length = 17
FEATURE                 Location/Qualifiers
source                  1..17
                        mol_type = protein
                        organism = synthetic construct
VARIANT                 5
                        note = G or V
VARIANT                 12
                        note = L or P
VARIANT                 15
                        note = V or L
SEQUENCE: 116
KIRNXGGITY YXDTXKG                                                   17

SEQ ID NO: 117          moltype = AA  length = 15
FEATURE                 Location/Qualifiers
source                  1..15
                        mol_type = protein
                        organism = synthetic construct
VARIANT                 11
                        note = D or E
VARIANT                 12
                        note = T, N or S
SEQUENCE: 117
KASQSVDYDG XXYMN                                                     15
```

ANTI-APOLIPOPROTEIN E (APOE) ANTIBODIES AND POLYNUCLEOTIDES THEREOF

CLAIM OF PRIORITY

This application is a continuation of U.S. patent application Ser. No. 17/614,008, filed Nov. 24, 2021, which claims the benefit of U.S. Provisional Application No. 62/853,676, filed May 28, 2019, and U.S. Provisional Application No. 62/873,019, filed Jul. 11, 2019. The entire contents of the foregoing are incorporated by reference herein.

FEDERALLY SPONSORED RESEARCH OR DEVELOPMENT

This invention was made under government support under AG054671, AG031581, AG019610, NS100121, NS110048, and OD019833 awarded by the National Institutes of Health. The government has certain rights in the invention.

SEQUENCE LISTING

This application contains a Sequence Listing that has been submitted electronically as an XML file named "29539-0386002_UPDATEDSL ST26.XML." The XML file, created on Sep. 17, 2024, is 219,081 bytes in size. The material in the XML file is hereby incorporated by reference in its entirety.

TECHNICAL FIELD

Described herein are methods and compositions for preventing or treating cognitive decline associated with dementia and/or mild cognitive impairment by modulating the heparan sulfate proteoglycans (HSPG)/glycosaminoglycan (GAG) heparin-binding affinity of Apolipoprotein E (ApoE).

BACKGROUND

Alzheimer's disease (AD) is a chronic neurodegenerative disease that usually starts slowly and gradually worsens over time. It is the cause of 60-70% of cases of dementia. The disease process is associated with plaques and neurofibrillary tangles in the brain. There are presently no treatments to stop or reverse its progression, though some may temporarily improve symptoms. The accumulation, aggregation and deposition of amyloid-β (AB) peptides in the brain are central to the pathogenesis of Alzheimer's disease (AD). Growing evidence has demonstrated that ApoE strongly influences AD pathogenesis by controlling Aβ aggregation and metabolism (Fu et al., Mol Neurodegener 11:37, 2016). APOE impacts amyloid production, aggregation, and clearance, is a component of amyloid plaques, and exacerbates tau-mediated neurodegeneration. ApoE is 299 amino acids long and is polymorphic with three major alleles (epsilon 2, epsilon 3, and epsilon 4) which differ from each other by only one or two amino acids at positions 112 and 158: ApoE2 (cys112, cys158), ApoE3 (cys112, arg158), and ApoE4 (arg112, arg158). Accordingly, there is a need of therapeutics targeting and modulating the function of ApoE proteins for treating or preventing AD and cognitive decline associated with dementia or mild cognitive impairment.

SUMMARY

In one aspect, this disclosure features an isolated monoclonal antibody that specifically binds to one or more (e.g. 1, 2, 3 or 4) HSPG-binding sites or one or more (e.g. 1, 2, 3, or 4) sites of allosteric modulation of HSPG binding of a wild type or mutant Apolipoprotein E (ApoE). In some embodiments, the antibody binds to a polypeptide having an amino acid sequence at least 95% (e.g. 96%, 97%, 98%, 99% or 100%) identical to TEELRVRLASHLRK (SEQ ID NO:3). In some embodiments, the antibody binds to a polypeptide having an amino acid sequence at least 95% (e.g. 96%, 97%, 98%, 99% or 100%) identical to TEELRVSLASHLRK (SEQ ID NO:2). In some embodiments, the antibody binds to one or more (e.g. 1, 2, 3 or 4) HSPG-binding sites of a wild type or mutant ApoE2, ApoE3, or ApoE4.

In some embodiments, the antibody competes with and/or binds the same epitope as a reference anti-ApoE antibody comprising a heavy chain variable region (VH) and a light chain variable region (VL), wherein the VH and VL of the reference antibody comprise: (i) the amino acid sequence set forth in SEQ ID NO: 13 and the amino acid sequence set forth in SEQ ID NO:12, respectively; (ii) the amino acid sequence set forth in SEQ ID NO:23 and the amino acid sequence set forth in SEQ ID NO: 22, respectively; (iii) the amino acid sequence set forth in SEQ ID NO:33 and the amino acid sequence set forth in SEQ ID NO:32, respectively; or (iv) the amino acid sequence set forth in SEQ ID NO:43 and the amino acid sequence set forth in SEQ ID NO: 42, respectively. In some embodiments of any of the antibodies described herein, the antibody competes with and/or binds the same epitope as a reference anti-ApoE antibody comprising a heavy chain and a light chain, wherein the heavy chain and light chain of the reference antibody comprise the amino acid sequence set forth in SEQ ID NO: 53 and the amino acid sequence set forth in SEQ ID NO: 52.

In another aspect, provided herein are anti-ApoE antibodies comprising a VH comprising VHCDR1, VHCDR2, and VHCDR3, and a VL comprising VLCDR1, VLCDR2, and VLCDR3, wherein VHCDR1, VHCDR2, VHCDR3, VLCDR1, VLCDR2, and VLCDR3 comprise: (i) SEQ ID Nos: 7, 8, 9, 4, 5, 6, respectively; (ii) SEQ ID Nos: 17, 18, 19, 14, 15, 16, respectively; (iii) SEQ ID Nos: 27, 28, 29, 24, 25, 26, respectively; (iv) SEQ ID Nos: 37, 38, 39, 34, 35, 36, respectively; or (v) SEQ ID Nos: 47, 48, 49, 44, 45, 46, respectively. In some embodiments of any of the antibodies described herein, (i) the VH and the VL comprise an amino acid sequence that is at least 75%, 80%, 85%, 90%, 95%, or 100% identical to the amino acid sequences set forth in SEQ ID NOs: 13 and 12, respectively; (ii) the VH and the VL comprise an amino acid sequence that is at least 75%, 80%, 85%, 90%, 95%, or 100% identical to the amino acid sequences set forth in SEQ ID NOs: 23 and 22, respectively; (iii) the VH and the VL comprise an amino acid sequence that is at least 75%, 80%, 85%, 90%, 95%, or 100% identical to the amino acid sequences set forth in SEQ ID NOs: 33 and 32, respectively; or (iv) the VH and the VL comprise an amino acid sequence that is at least 75%, 80%, 85%, 90%, 95%, or 100% identical to the amino acid sequences set forth in SEQ ID NOs: 43 and 42, respectively. In some embodiments of any of the antibodies described herein, the antibody comprises a heavy chain and a light chain comprising an amino acid sequence that is at least 70%, 75%, 80%, 85%, 90%, 95%, or 100% identical to the amino acid sequence set forth in SEQ ID Nos: 53 and 52, respectively. In some embodiments, the antibody includes a mouse IgG1, IgG2a, IgG2b, IgG2c, or IgG3 heavy chain constant region. In some embodiments, the antibody includes a human IgG1, IgG2, IgG3, or IgG4 heavy chain constant region. In some embodiments, the antibody includes a human kappa or human lambda light chain constant region. In some embodiments, the antibody is a whole antibody, a single domain antibody, a humanized antibody, a chimeric antibody, a bispecific antibody, a Fv, a scFv, an sc(Fv)2, a diabody, an Fab, or an F(ab')2. In some embodiments, the antibody further includes a half-life extending moiety. In some embodiments, the antibody further includes a blood-brain barrier penetrating moiety. In some embodiments, the antibody further includes a detectable label. In some embodiments, provided herein are pharmaceutical compositions comprising any of the antibodies described herein. In some embodiments, provided herein are polynucleotide or polynucleotides encoding any of the antibodies described herein. In some embodiments, provided herein are vector or vectors comprising the polynucleotide or polynucleotides described herein. In some embodiments provided herein are host cells comprising the polynucleotide or polynucleotides described herein, or the vector or vectors described herein. In another aspect, provided herein are methods of making an anti-ApoE antibody, the methods include: (a) culturing any of the host cells described herein under conditions that permit expression of the antibody; and (b) isolating the antibody. In some embodiments, the methods further include formulating the antibody as a sterile formulation suitable for administration to a human.

In another aspect, provided herein is an Fc-fusion protein that includes: a HSPG-binding domain of a wild type ApoE or mutant ApoE comprising an amino acid sequence at least 95% identical to an amino acid sequence selected from the group consisting of STEELRVRLASHLRKLRKRLLRDADDLQK (SEQ ID NO:57), STEELRVSLASHLRKLRKRLLRDADDLQK (SEQ ID NO:58), RLVQYRGEVQAMLGQSTEELRVRLASHLRKL (SEQ ID NO:59), and RLVQYRGEVQAMLGQSTEELRVSLASHLRKL (SEQ ID NO:60). In some embodiments, the Fc-fusion protein includes an Fc region of a human antibody. In some embodiments, the human antibody is selected from the group consisting of a human IgG1, IgG2, IgG3 and IgG4 molecule. In some embodiments, provided herein are pharmaceutical compositions comprising any of the Fc-fusion proteins described herein. In some embodiments, provided herein are polynucleotide or polynucleotides encoding the Fc-fusion proteins described herein. In some embodiments, provided herein are vector or vectors comprising any of the polynucleotide or polynucleotides described herein. In some embodiments, provided herein are host cells comprising the polynucleotide or polynucleotides described herein, or the vector or vectors described herein.

In another aspect, provided herein are pharmaceutical composition for eliciting an immune response that include: (i) a HSPG-binding domain of a wild type ApoE or mutant ApoE comprising an amino acid sequence at least 95% identical to an amino acid sequence selected from the group consisting of STEELRVRLASHLRKLRKRLLRDADDLQK (SEQ ID NO:57), STEELRVSLASHLRKLRKRLLRDADDLQK (SEQ ID NO:58), RLVQYRGEVQAMLGQSTEELRVRLASHLRKL (SEQ ID NO:59), and RLVQYRGEVQAMLGQSTEELRVSLASHLRKL (SEQ ID NO:60); and (ii) a pharmaceutically acceptable adjuvant.

In another aspect, provided herein is a pharmaceutical composition comprising a human cell expressing any of the antibodies described herein or any of the Fc-fusion proteins described herein.

In another aspect, provided herein is a method of improving, slowing down, delaying the onset of, preventing or reversing cognitive decline associated with dementia and/or mild cognitive impairment and/or neurodegeneration in a human subject in need thereof, comprising administering to the human subject a therapeutically effective amount of any of the antibody, the Fc-fusion protein, or the pharmaceutical compositions described herein.

In another aspect, provided herein is a method of improving, slowing down, delaying the onset, preventing or reversing cognitive decline associated with dementia and/or mild cognitive impairment and/or neurodegeneration in a human subject in need thereof, the method comprising administering to said subject: (i) a viral vector comprising a nucleotide sequence encoding a gRNA molecule comprising a targeting domain complementary with a target domain from the APOE gene; (ii) a viral vector comprising a nucleotide sequence encoding a Cas9 molecule; and (iii) a viral vector comprising a template nucleic acid, wherein the template nucleic acid comprises an Adenine to replace the Cytosine at position 19: g.45412013C>A in the APOE gene, wherein said administration results in the generation of one or more ApoE R136S alleles in one or more cells of said subject. In some embodiments, the targeting domain of the gRNA molecule includes a sequence that is the same as, or differs by no more than 3 nucleotides from, a sequence from Table 7.

As used herein, "prevent" means to reduce risk of developing the disorder.

In some embodiments, the human subject is diagnosed with or is at risk for developing Alzheimer's disease. In some embodiments, the human subject carries one or more copies of the APOE4 allele. In some embodiments, the human subject carries one or more mutations in at least one gene selected from the group consisting of: APP, PSEN1, and PSEN2. In some embodiments, the human subject carries one or more mutations in additional genes that cause autosomal-dominant Alzheimer's disease (e.g. those described in Bateman et al., Alzheimer's Research & Therapy 3 (1): 1, 2011). In some embodiments, the human subject carries all or a portion of a third copy of chromosome 21. In some embodiments, the human subject is diagnosed with Alzheimer's disease by established biomarkers, such as those obtained via brain imaging, or blood or CSF samples. In some embodiments, the human subject is over the age of 50 (e.g. over the age of 55, 60, 65, 70, 75, 80, 85, 90, or 95).

In some embodiments, the human subject is diagnosed with or is at risk of developing a disorder selected from the group consisting of: vascular cognitive impairment, vascular dementia, cerebral autosomal dominant arteriopathy with subcortical infarcts and leukoencephalopathy (CADASIL), cerebral autosomal recessive arteriopathy with subcortical infarcts and leukoencephalopathy (CARASIL), Lewy body dementia, frontotemporal dementia, amyotrophic lateral sclerosis, multiple sclerosis, Parkinson's disease, Huntington's disease, neurodegenerative diseases, cerebrovascular diseases, brain injury, chronic traumatic encephalopathy, tauopathies, amyloidopathies, synucleinopathies, Creutzfeldt-Jakob disease, retinal degeneration, glaucoma, retinal injury, optic nerve degeneration, and aging.

In yet another aspect, provided herein is a method of identifying a human subject less susceptible to developing an early onset neurodegenerative disease, comprising: obtaining a biological sample from the subject; detecting the presence of at least one mutant allele of APOE3, or the presence of a mutant ApoE3 gene product, in the biological sample; and identifying a subject as being less susceptible to developing an early onset neurodegenerative disease, based on the presence of a mutant ApoE3 allele or gene product in the biological sample. In some embodiments, the biological sample is blood, cerebrospinal fluid, saliva, urine, tears, vitreous humor, aqueous humor, or a tissue specimen. In some embodiments, the neurodegenerative disease is Alzheimer's disease, Parkinson's disease, Huntington's disease, amyotrophic lateral sclerosis, retinal degeneration, or glaucoma. In some embodiments, the retinal degeneration is age-related macular degeneration. In some embodiments, the detecting comprises determining the sequence of an APOE3 allele in the subject. In some embodiments, the detecting comprises determining the presence or absence of an APOE3 sequence that encodes an ApoE3 protein with a mutation at R136 as compared to a wild type ApoE3 protein. In some embodiments, the mutation at R136 is R136S, R136H, or R136C. In some embodiments of any of the methods of identifying a human subject less susceptible to developing an early onset neurodegenerative disease described herein, the methods further include selecting a subject for inclusion in a clinical trial, and optionally administering an experimental treatment, or excluding the subject from the clinical trial, if the subject does not have a mutant APOE3 allele. In some embodiments of any of the methods of identifying a human subject less susceptible to developing an early onset neurodegenerative disease described herein, the methods further include selecting a subject for inclusion in a clinical trial, and optionally administering an experimental treatment, or excluding the subject from the clinical trial, if the subject has a mutant APOE3 allele.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 13A shows the amount of ApoE3 in various fractions in the absence of the ApoE3 antibody. FIG. 13B shows the amount of ApoE3 in various fractions in the presence of the ApoE3 antibody.

FIG. 17A shows a model of the wild type ApoE fragment containing amino acids 129-157 interacting with heparin. FIG. 17B shows a model of the fragment of ApoE R136S that contains amino acids 129-157 interacting with heparin. FIG. 17C shows a model of the wild type ApoE fragment containing amino acids 114-144 interacting with heparin. FIG. 17D shows a model of the fragment of ApoE R136S that contains amino acids 114-144 interacting with heparin.

FIG. 42A shows an exemplary experimental outline for an intraocular model of inducible APOE-dependent Tau hyperphosphorylation. FIG. 42B shows PHF tau in control retina injected with PBS. FIG. 42C shows retina injected with recombinant human APOE3.

DETAILED DESCRIPTION

Figure 1:
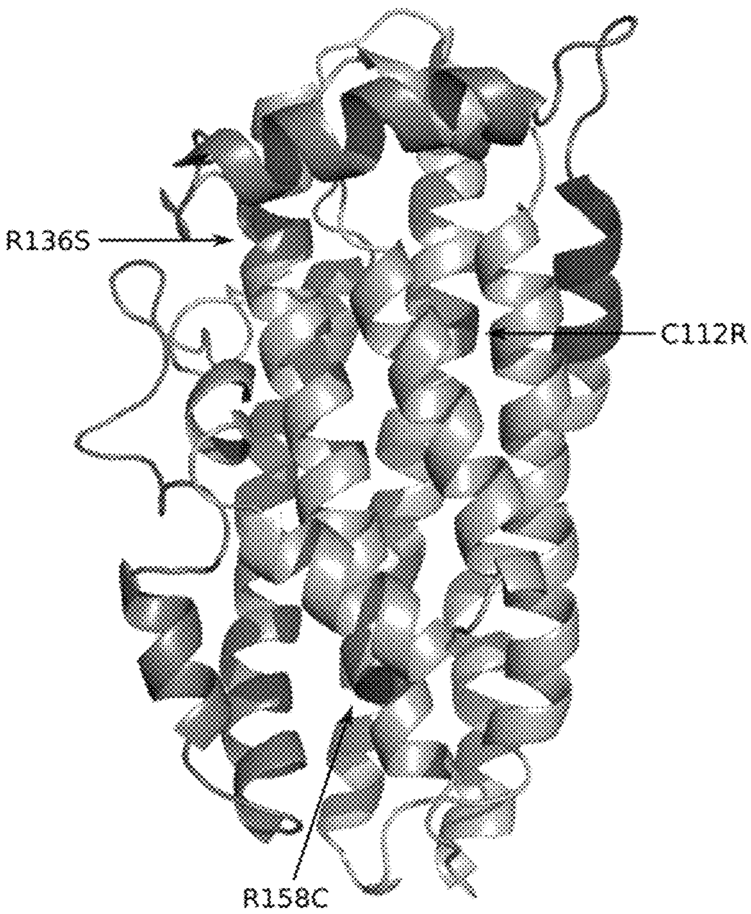
FIG. 1 shows a model of the structure of the wild-type APOE3 protein. N-terminal (residues 1-191) and C-terminal (residues 201-299) domains are shown. The amino acid positions for APOE4 (C112R), APOE3ch (R136S) and APOE2 (R158C) variants are shown.

The present disclosure uncovers that homozygosity for APOE3ch (having two copies of the APOE3 Christchurch (R136S) mutation) is associated with a profound resistance to the clinical onset of Alzheimer's disease, and that the R136S mutation significantly diminishes the ability of ApoE to bind heparan sulfate proteoglycans (HSPG)/heparin. Accordingly, the present disclosure is related to antibodies that bind to wild type ApoE and/or ApoE isoform(s) containing the R136S mutation (e.g. antibodies that block the interaction and/or reduces binding between ApoE and HSPG/GAG/heparin). Fusion proteins containing peptide fragments (e.g. HSPG/GAG/heparin-binding domain) of wild type and mutant ApoE containing the R136S mutation are also contemplated. These proteins may be administered via human cells expressing such compositions. The present disclosure is further related to small molecules that block the interaction between ApoE and HSPG/heparin, and methods of screening for small molecules of the same. Also provided are compositions and methods of editing the ApoE locus with a genome editing system. The antibodies, fusion proteins, small molecules, and genome editing systems described herein are useful in the treatment or prevention of cognitive decline associated with dementia and/or mild cognitive impairment (MCI) and/or neurodegeneration, e.g. Alzheimer's disease, vascular dementia, Lewy body dementia, frontotemporal dementia, Parkinson's disease, or Huntington's disease. The antibodies, fusion proteins, small molecules, and genome editing systems described herein are also useful in the treatment or prevention of neurodegenerative diseases, cerebrovascular conditions, brain injuries, retinal degeneration, optic nerve degeneration, or retinal injury.

Apolipoprotein E (ApoE)

Apolipoprotein E variants are the major genetic modifier of AD contributing to the susceptibility to late-onset AD. APOE4 allele leads to a change of cysteine to arginine at position 112 and is associated with a 5 fold increase in AD risk in single allele carriers, reaching a 20 fold increase in homozygote carriers. APOE2 leads to an amino acid change of arginine to cysteine at position 158 and is protective for AD whereas the APOE3 allele is thought to be neutral (Corder et al., Nat Genet (7) 180-184, 1994; Hauser et al., Cure Alzheimer Res (10); 808-817, 2013). APOE impacts amyloid production, aggregation, and clearance, is a component of amyloid plaques, and exacerbates tau-mediated neurodegeneration. APOE alleles also regulate lipid metabolism and cardiovascular risk. About 5-10% of APOE2 homozygote individuals develop hyperlipoproteinemia type III (HLP III), whereas other APOE rare variants are linked to autosomal dominant HLP III. HLP III is characterized by increased plasma cholesterol and triglycerides levels and by the presence of tuberous or striated palmar xanthomas. The mechanisms by which APOE alleles modify AD risk and cause HLP III are not completely understood. Salient APOE properties impacted by specific mutations include differences in 1) binding affinities to lipids and the LDL receptor; 2) nature of interdomain interactions between its N-terminus (amino acids 1 to 199) and C-terminus domains (216 to 299); and, 3) ability to form homo-oligomers mediated by the C-terminus domain (Frieden et al., PNAS (109): 8913-8918, 2012; Georgiadou et al., PLOS One (6) e27037, 2011; Lalazar et al., J Biol Chem (263) 3542-3545, 1988).

Heparan sulfate (HS) is a linear polysaccharide found in all animal tissues, which occurs as a proteoglycan (HSPG) in which two or three HS chains are attached in close proximity to cell surface or extracellular matrix proteins. HSPG moieties are present in hundreds of proteins located in the plasma membrane and in the extracellular matrix. Protein-protein interactions mediated via HSPG play a critical role in a multitude of processes relevant to Alzheimer's pathology including amyloid and tau pathology. Heparan sulfate is a member of the glycosaminoglycan family of carbohydrates and is very closely related in structure to heparin. Both consist of a variably sulfated repeating disaccharide unit. Heparan sulfate binds with a large number of extracellular proteins. These are often collectively called the "heparin interactome" or "heparin-binding proteins", because they are isolated by affinity chromatography on the related polysaccharide heparin.

An exemplary amino acid sequence of the human ApoE3 protein (Uniprot Accession No. P02649) is shown below:

(SEQ ID NO: 1)

KVEQAVETEPEPELRQQTEWQSGQRWELALGRFWDYLRWVQTLSEQVQEE

LLSSQVTQELRALMDETMKELKAYKSELEEQLTPVAEETRARLSKELQAA

QARLGADMEDVCGRLVQYRGEVQAMLGQSTEELRVRLASHLRKLRKRLLR

DADDLQKRLAVYQAGAREGAERGLSAIRERLGPLVEQGRVRAATVGSLAG

QPLQERAQAWGERLRARMEEMGSRTRDRLDEVKEQVAEVRAKLEEQAQQI

RLQAEAFQARLKSWEEPLVEDMQRQWAGLVEKVQAAVGTSAAPVPSDNH

At least two HSPG/heparin-binding domains have been identified in human ApoE, one located in the N-terminal domain and one in the C-terminal domain (Weisgraber et al. J Biol Chem, 261 (5): 2068-76, 1986; Saito et al., J Biol Chem, 278 (17): 14782-7, 2003). The HSPG/heparin-binding domain near arginine 136 (R136) (the N-terminal HSPG/heparin-binding domain) is functional in the full-length lipidated and delipidated ApoE, while the HSPG/heparin-binding domain in the C-terminal domain is functional only in the absence of the N-terminal domain and in delipidated ApoE. The N-terminal HSPG/heparin-binding domain is well-characterized, and comprises the amino acid residues 142 to 147 of SEQ ID NO: 1 (bolded). The C-terminal HSPG/heparin-binding domain is less well-characterized, and comprises the lysine (K) at position 233 and other charged amino acids in the vicinity including amino acid residues 211 to 218 and 243 to 272 of SEQ ID NO: 1. The present inventors show that the arginine at position 136 of ApoE plays a critical role in heparin binding of ApoE. Without wishing to be bound by theory, a potential mechanism is the allosteric modulation of heparin binding mediated by the arginine at position 136. Allosteric modulation as used herein is related to the modulation of ligand binding through the binding of allosteric modulators at one or more sites of allosteric modulation, which may be different from the binding site(s) of the ligand. In some embodiments, the one or more sites of allosteric modulation for ApoE and HSPG/heparin binding comprise the arginine at position 136 of ApoE as shown in SEQ ID NO: 1. "HSPG/heparin-binding domain(s)", "HSPG/heparin-binding site(s)", "HSPG-binding domain(s)", and "HSPG-binding site(s)" are used interchangeably herein.

Anti-ApoE Antibodies

Provided are anti-ApoE antibodies that bind to a wild type or a mutant ApoE protein (e.g., a human ApoE protein). In some instances, the antibodies described herein bind to a wild type ApoE protein (e.g. ApoE2, ApoE3 or ApoE4), but not to a mutant ApoE protein (e.g. ApoEch). In some instances, the antibodies described herein bind to a mutant ApoE protein (e.g. ApoEch), but not to a wild type ApoE protein (e.g. ApoE2, ApoE3 or ApoE4). In some instances, the antibodies described herein bind to both a mutant ApoE protein (e.g. ApoEch), and a wild type ApoE protein (e.g. ApoE2, ApoE3 or ApoE4).

In some instances, the antibodies provided herein block the interaction between a wild type ApoE protein (e.g. ApoE2, ApoE3 or ApoE4) and HSPG. The antibodies provided herein may reduce or modulate the binding affinity of an ApoE protein (e.g. ApoE2, ApoE3 or ApoE4) to HSPG. In some instances, the antibodies provided herein bind to the HSPG-binding domain of a wild type ApoE protein. In some instances, the antibodies provided herein bind to one or more sites of allosteric modulation of HSPG/ApoE binding (e.g., amino acid position 136 of ApoE). In some instances, the antibodies described herein reduces fibril formation and/or amyloid oligomerization.

In some instances, the antibodies provided herein bind to an amino acid sequence in a wild type or mutant ApoE that comprises or consists of TEELRVSLASHLRK (SEQ ID NO:2). In some instances, the antibodies provided herein bind to an amino acid sequence in a wild type or mutant ApoE that comprises or consists of TEELRVRLASHLRK (SEQ ID NO:3). In some instances, the amino acid sequence TEELRVSLASHLRK (SEQ ID NO:2) comprises or consists of an epitope for the antibodies provided herein. In some instances, the amino acid sequence TEELRVRLASHLRK (SEQ ID NO:3) comprises or consists of an epitope for the antibodies provided herein. Variants of these sequences can also be used, e.g., those that are at least 80%, 85%, 90%, or 95% identical to these sequences.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 70% (e.g., at least 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the Needleman and Wunsch ((1970) J. Mol. Biol. 48:444-453) algorithm, which has been incorporated into the GAP program in the GCG software package (available at gcg.com), using either a Blossum 62 matrix, a PAM250 matrix, a NWSgapdna.CMP matrix. In some embodiments, the percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

Usage of the term "antibody" in this disclosure is meant to cover a whole antibody (as opposed to a minibody, or antibody fragment), a bispecific antibody, a tertravalent antibody, a multispecific antibody, a minibody, and antibody fragments. In some instances, the anti-ApoE antibody of this disclosure is a whole antibody. In some instances, the anti-ApoE antibody of this disclosure is a chimeric, human, or humanized antibody. In certain instances, the heavy chain constant region of the anti-ApoE antibody is a human IgG1, human IgG2, human IgG3, or human IgG4 constant region.

binding to heparin; and (iii) reduces Paired Helical Filament (PHF) Tau formation in retinal cells.

Any of the anti-ApoE antibodies described herein are useful for treating or preventing disorders associated with dementia or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury.

Exemplary Antibody 1H4-2

Antibody 1H4-2 was generated by immunizing with APOE: KLH-CTEELRVRLASHLRK-CONH2 (SEQ ID NO: 54). The amino acid sequences of the complementarity determining regions (CDRs) and the heavy chain variable region and light chain variable regions of 1H4-2 are provided below.

| Variable region | Chain type | CDR-1 | CDR-2 | CDR-3 |
|---|---|---|---|---|
| 1H4-2 VL | Light chain | KASQSVDYDGDSYMN (SEQ ID NO: 4) | AASNLES (SEQ ID NO: 5) | QQSNEDPWT (SEQ ID NO: 6) |
| 1H4-2 VH | Heavy chain | SYTMS (SEQ ID NO: 7) | KIRNGGGITYYLDTLKG (SEQ ID NO: 8) | HYYGSEDYFDY (SEQ ID NO: 9) |

In certain instances, the light constant region is a human kappa constant region. In other instances, the light constant region is a human lambda constant region. In some instances, the antibodies of this disclosure are designed to have low effector functionality (e.g., by Fc modifications such as N297Q, T299A, etc. See, also, Wang, X., Mathieu, M. & Brezski, R. J. *Protein Cell* (2018) 9:63. doi.org/10.1007/s13238-017-0473-8 (incorporated by reference herein)). In some cases, the Fc moiety of the antibody is a hIgG1 Fc, a hIgG2 Fc, a hIgG3 Fc, a hIgG4 Fc, a hIgG1agly Fc, a hIgG2 SAA Fc, a hIgG4 (S228P) Fc, or a hIgG4 (S228P)/G1 agly Fc (in this format—that minimizes effector function—the CH1 and CH2 domains are IgG4 with a 'fixed' hinge (S228P) and is aglycosylated. The CH3 domain is hIgG1, or a hIgG4 (S228P) agly Fc). In one case, the antibody has one of the following three scaffolds with reduced effector function: hIgG1 agly (N297Q); hIgG2 SAA (see, Vafa et al. *Methods,* 65 (1): 114-26 (2014); and hIgG4P/G1 agly (see, US 2012/0100140 A1).

In some embodiments, an antibody or ApoE-binding fragment thereof described herein demonstrates the binding characteristics and/or biological properties as outlined for the antibodies 1H4-2, 7C11-1, 19G10-2, 23B2 (1343), 2H79-1, 30E1-2, 16H8, 25F1-2, and 29G10-1 illustrated in the Examples section below.

In some embodiments, the present disclosure provides an antibody that binds to wild type human ApoE or a portion thereof and has one or more of the following properties: (i) binds with high affinity of KD≤20 nM to wild type human ApoE; (ii) competes with wild type human ApoE for binding to heparin; and (iii) reduces Paired Helical Filament (PHF) Tau formation in retinal cells.

In some embodiments, the present disclosure provides an antibody that binds to a mutant human ApoE (e.g., those having a mutation at amino acid position 136 of the human ApoE, such as ApoEch) or a portion thereof and has one or more of the following properties: (i) binds with high affinity of KD≤20 nM to mutant human ApoE (e.g., mutation at amino acid position 136 of the human ApoE, such as ApoEch); (ii) competes with wild type human ApoE for Variable Light Chain:

Nucleotide sequence:
Signal sequence-FR1-CDR1-FR2-CDR2-FR3 -CDR3-FR4
(SEQ ID NO: 10)

ATGGAGACAGACACAATCCTGCTATGGGTGCTGCTGCTCTGGGTTCCAGG

CTCCACTGGTGACAATGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAAGTCTTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGA

GGATCCGTGGACGTTCGGTGGAGGCACCAAGCTGGAAATCAAA

Amino acid sequence:
Signal peptide-FR1-CDR1-FR2-CDR2-FR3-CDR3-FR4
(SEQ ID NO: 12)

METDTILLWVLLLWVPGSTGDNVLTQSPASLAVSLGQRATISCKASQSVD

YDGDSYMNWYQQKPGQPPKVFIYAASNLESGIPARFSGSGSGTDFTLNIH

PVEEEDAATYYCQQSNEDPWTFGGGTKLEIK

Variable Heavy Chain:

Nucleotide sequence
Signal sequence-FR1-CDR1-FR2-CDR2-FR3-CDR3-FR4
(SEQ ID NO: 11)

ATGAATTTCGGGCTCAGCTTGATTTTCCTTGTCCTTGTTTTAAAAGGTGT

CCTGTGTGAAGTGAAGCTGGTGGAATCTGGGGGAGGTGTGGTGCAGCCTG

GAGGGTCCCTGAAACTCTCCTGTGCAGCCTCTGGATTCACTTTCAGTAGC

TATACCATGTCTTGGGTTCGTCAGACTCCAGAGAAGAGGCTGGAGTGGGT

CGCAAAAATTCGTAATGGTGGTGGTATCACCTACTATTTAGACACTTTAA

AGGGCCGATTCACCATCTCCAGAGACAACGCCAAGAACACCCTATACCTG

-continued

CAAATGAGCAGTCTGAAGTCTGAAGACACGGCCATTTATTTCTGTGCAAG

ACATTACTACGGTAGCGAGGACTACTTTGACTACTGGGGCCAAGGCACCA

CTCTCACAGTCTCCTCA

Amino acid sequence:
Signal peptide-FR1-CDR1-FR2-CDR2-FR3-CDR3-FR4
(SEQ ID NO: 13)

MNFGLSLIFLVLVLKGVLCEVKLVESGGGVVQPGGSLKLSCAASGFTFSS

YTMSWVRQTPEKRLEWVAKIRNGGGITYYLDTLKGRFTISRDNAKNTLYL

QMSSLKSEDTAIYFCARHYYGSEDYFDYWGQGTTLTVSS

In some instances, the anti-ApoE antibody comprises a VH comprising the three VH CDRs and a VL comprising the three VL CDRs of antibody 1H4-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 7, a VHCDR2 comprising the amino acid sequence set forth in SEQ ID NO: 8, and a VHCDR3 comprising the amino acid sequence set forth in SEQ ID NO: 9; and (ii) a VL comprising a VLCDR1 comprising the amino acid sequence set forth in SEQ ID NO: 4, a VLCDR2 comprising the amino acid sequence set forth in SEQ ID NO: 5, and a VLCDR3 comprising the amino acid sequence set forth in SEQ ID NO: 6.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 13. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 12. In one instance, the anti-ApoE antibody comprises a VH that is at least 85% identical to the amino acid sequence set forth in SEQ ID NO: 13 and a VL that is at least 85% identical to the amino acid sequence set forth in SEQ ID NO: 12. In another instance, the anti-ApoE antibody comprises a VH that is at least 90% identical to the amino acid sequence set forth in SEQ ID NO: 13 and a VL that is at least 90% identical to the amino acid sequence set forth in SEQ ID NO: 12. In yet another instance, the anti-ApoE antibody comprises a VH that is identical to the amino acid sequence set forth in SEQ ID NO: 13 and a VL that is identical to the amino acid sequence set forth in SEQ ID NO: 12.

In certain instances, an antibody of this disclosure that binds to ApoE is one that competes with or binds to the same epitope as a reference antibody with a VH having the amino acid sequence set forth in SEQ ID NO: 13 and a VL having the amino acid sequence set forth in SEQ ID NO: 12.

Exemplary Antibody 7C11-1

Antibody 7C11-1 generated by immunizing with APOE: KLH-CTEELRVRLASHLRK-CONH2 (SEQ ID NO: 54). The amino acid sequences of the complementarity determining regions (CDRs) and the heavy chain variable region and light chain variable regions of 7C11-1 are provided below.

| Variable region | Chain type | CDR-1 | CDR-2 | CDR-3 |
|---|---|---|---|---|
| 7C11-1 VL | Light chain | KASQSVDYDGDSYMN (SEQ ID NO: 14) | AASNLES (SEQ ID NO: 15) | QQSNEDPWT (SEQ ID NO: 16) |
| 7C11-1 VH | Heavy chain | RYTMS (SEQ ID NO: 17) | KIRNVGGITYYPD TVKG (SEQ ID NO: 18) | HYYGSEDYFDY (SEQ ID NO: 19) |

Variable Heavy Chain:

Nucleotide sequence
Signal sequence-FR1-CDR1-FR2-CDR2-FR3-CDR3-FR4
(SEQ ID NO: 20)

ATGAATTTCGGGCTCAGCGTGATTTTCCTTGTCCTTGTTTTAAAAGGTGT

CCTGTGTGAAGTGAAGCTGGTGGAGTCTGGGGGAGGTTTAGTGCAGCCTG

GAGGGTCCCTGAAACTCTCCTGTGCAGCCTCTGGATTCACTTTCAGTAGG

TATACCATGTCTTGGGTTCGGCAGACTCCAGAGAAGAGGCTGGAGTGGGT

CGCAAAAATTCGTAATGTTGGTGGTATCACCTACTATCCAGACACTGTAA

AGGGCCGATTCACCATCTCCAGAGACAACGCCAAGAACACCCTTTACCTG

CAAATGAGCAGTCTGAAGTCTGAAGACACGGCCATGTATTACTGTGCAAG

ACATTATTACGGTAGCGAGGACTACTTTGACTACTGGGGCCAAGGCACCA

CTCTCACAGTCTCCTCA

Amino acid sequence:
Signal peptide-FR1-CDR1-FR2-CDR2-FR3-CDR3-FR4
(SEQ ID NO: 22)

MNFGLSVIFLVLVLKGVLCEVKLVESGGGLVQPGGSLKLSCAASGFTFSR

YTMSWVRQTPEKRLEWVAKIRNVGGITYYPDTVKGRFTISRDNAKNTLYL

QMSSLKSEDTAMYYCARHYYGSEDYFDYWGQGTTLTVSS

Variable Light Chain:

Nucleotide sequence:
Signal sequence-FR1-CDR1-FR2-CDR2-FR3-CDR3-FR4
(SEQ ID NO: 21)

ATGGAGACAGACACAATCCTGCTATGGGTGCTGCTGCTCTGGGTTCCAGG

CTCCACTGGTGACAATGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAAGTCTTCATCTATGCTGCATCCAATCTAGAATCTGGGATCCCAG

CCAGGTTTAGTGGCAGTGGGTCTGGGACAAACTTCACCCTCAACATCCAT

CCTGTGGAGGAGGAGGATGCTGCAACCTATTACTGTCAGCAAAGTAATGA

GGATCCGTGGACGTTCGGTGGA GGCACCAAGCTGGAAATCAAA

-continued

Amino acid sequence:
Signal sequence-FR1-CDR1-FR2-CDR2-FR3-CDR3-FR4
(SEQ ID NO: 23)

METDTILLWVLLLWVPGSTGDNVLTQSPASLAVSLGQRATISCKASQSVD

YDGDSYMNWYQQKPGQPPKVFIYAASNLESGIPARFSGSGSGTNFTLNIH

PVEEEDAATYYCQQSNEDPWTFGG GTKLEIK

In some instances, the anti-ApoE antibody comprises a VH comprising the three VH CDRs and a VL comprising the three VL CDRs of antibody 7C11-1. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 17, a VHCDR2 comprising the amino acid sequence set forth in SEQ ID NO: 18, and a VHCDR3 comprising the amino acid sequence set forth in SEQ ID NO: 19; and (ii) a VL comprising a VLCDR1 comprising the amino acid sequence set forth in SEQ ID NO: 14, a VLCDR2 comprising the amino acid sequence set forth in SEQ ID NO: 15, and a VLCDR3 comprising the amino acid sequence set forth in SEQ ID NO: 16.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 22. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 23. In one instance, the anti-ApoE antibody comprises a VH that is at least 85% identical to the amino acid sequence set forth in SEQ ID NO: 22 and a VL that is at least 85% identical to the amino acid sequence set forth in SEQ ID NO: 23. In another instance, the anti-ApoE antibody comprises a VH that is at least 90% identical to the amino acid sequence set forth in SEQ ID NO: 22 and a VL that is at least 90% identical to the amino acid sequence set forth in SEQ ID NO: 23. In yet another instance, the anti-ApoE antibody comprises a VH that is identical to the amino acid sequence set forth in SEQ ID NO: 22 and a VL that is identical to the amino acid sequence set forth in SEQ ID NO: 23.

In certain instances, an antibody of this disclosure that binds to ApoE is one that competes with or binds to the same epitope as a reference antibody with a VH having the amino acid sequence set forth in SEQ ID NO: 22 and a VL having the amino acid sequence set forth in SEQ ID NO: 23.

Exemplary Antibody 19G10-2

Antibody 19G10-2 generated by immunizing with KLH-CTEELRVSLASHLRK-CONH2 (SEQ ID NO: 55). The amino acid sequences of the complementarity determining regions (CDRs) and the heavy chain variable region and light chain variable regions of 19G10-2 are provided below.

| Variable region | Chain type | CDR-1 | CDR-2 | CDR-3 |
|---|---|---|---|---|
| 19G10-2 VL | Light chain | KASQSVDYDGDSYMN (SEQ ID NO: 24) | AASNLES (SEQ ID NO: 25) | QQSNVDPWT (SEQ ID NO: 26) |
| 19G10-2 VH | Heavy chain | DYHMH (SEQ ID NO: 27) | WIDPENGNTMYD PKFQG (SEQ ID NO: 28) | GTARASFDY (SEQ ID NO: 29) |

Variable Light Chain:

Nucleotide sequence:
Signal sequence-FR1-CDR1-FR2-CDR2-FR3-CDR3-FR4
(SEQ ID NO: 30)

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAATTGGTACCAACAGAAATCAGGACAGCC

ACCCAAACTCCTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTAATGT

GGATCCGTGGACGTTCGGTGGAGGCACCAAGCTGGAAATCAAA

Amino acid sequence:
Signal sequence-FR1-CDR1-FR2-CDR2-FR3-CDR3-FR4
(SEQ ID NO: 32)

METDTILLWVLLLWVPGSTGDIVLTQSPASLAVSLGQRATISCKASQSVD

YDGDSYMNWYQQKSGQPPKLLIYAASNLESGIPARFSGSGSGTDFTLNIH

PVEEEDAATYYCQQSNVDPWTFGGGTKLEIK

Variable Heavy Chain Analysis:

Nucleotide sequence
Signal sequence-FR1-CDR1-FR2-CDR2-FR3-CDR3-FR4
(SEQ ID NO: 31)

ATGAAATGCAGCTGGGTCATCTTCTTCCTGATGGCAGTGGTTACAGGGGT

CAATTCAGAGGTTCAGCTGCAGCAGTCTGGGGCTGAGCTTGTGAGGCCAG

GGGCCTTAGTCAAGTTGTCCTGCAAAGCTTCTGGCTTCAACATTAAAGAC

TACCATATGCACTGGGTGAAGGAGAGGCCTGAACAGGGCCTGGAGTGGAT

TGGATGGATTGATCCTGAGAATGGTAATACTATGTATGACCCGAAGTTCC

AGGGCAAGGCCAGTATAACAGCAGACACATCCTCCAACACAGCCTACCTG

CAGCTCAGCAGCCTGACATCTGAGGACACTGCCGTCTATTACTGTGTTAG

GGGGACAGCTCGGGCTTCCTTTGACTACTGGGGCCAAGGCACCACTCTCA

CAGTCTCCTCA

-continued

Amino acid sequence:
Signal sequence-FR1-CDR1-FR2-CDR2-FR3-CDR3-FR4
(SEQ ID NO: 33)

MKCSWVIFFLMAVVTGVNSEVQLQQSGAELVRPGALVKLSCKASGFNIKD

YHMHWVKERPEQGLEWIGWIDPENGNTMYDPKFQGKASITADTSSNTAYL

QLSSLTSEDTAVYYCVRGTARASFDYWGQGTTLTVSS

In some instances, the anti-ApoE antibody comprises a VH comprising the three VH CDRs and a VL comprising the three VL CDRs of antibody 19G10-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 27, a VHCDR2 comprising the amino acid sequence set forth in SEQ ID NO: 28, and a VHCDR3 comprising the amino acid sequence set forth in SEQ ID NO: 29; and (ii) a VL comprising a VLCDR1 comprising the amino acid sequence set forth in SEQ ID NO: 24, a VLCDR2 comprising the amino acid sequence set forth in SEQ ID NO: 25, and a VLCDR3 comprising the amino acid sequence set forth in SEQ ID NO: 26.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 33. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 32. In one instance, the anti-ApoE antibody comprises a VH that is at least 85% identical to the amino acid sequence set forth in SEQ ID NO: 33 and a VL that is at least 85% identical to the amino acid sequence set forth in SEQ ID NO: 32. In another instance, the anti-ApoE antibody comprises a VH that is at least 90% identical to the amino acid sequence set forth in SEQ ID NO: 33 and a VL that is at least 90% identical to the amino acid sequence set forth in SEQ ID NO: 32. In yet another instance, the anti-ApoE antibody comprises a VH that is identical to the amino acid sequence set forth in SEQ ID NO: 33 and a VL that is identical to the amino acid sequence set forth in SEQ ID NO: 32.

In certain instances, an antibody of this disclosure that binds to ApoE is one that competes with or binds to the same epitope as a reference antibody with a VH having the amino acid sequence set forth in SEQ ID NO: 33 and a VL having the amino acid sequence set forth in SEQ ID NO: 32.

Exemplary Antibody 25F1-2

Antibody 25F1-2 was generated by immunizing with KLH-CTEELRVSLASHLRK-CONH2 (SEQ ID NO: 55). The amino acid sequences of the complementarity determining regions (CDRs) and the heavy chain variable region and light chain variable regions of 25F1-2 are provided below.

| Variable region | Chain type | CDR-1 | CDR-2 | CDR-3 |
|---|---|---|---|---|
| 25F1-2 VL | Light chain | KASQSVDYDGDTYMN (SEQ ID NO: 34) | TASNLES (SEQ ID NO: 35) | QQSNEDPWT (SEQ ID NO: 36) |
| 25F1-2 VH | Heavy chain | DYHIH (SEQ ID NO: 37) | WIDPEIDKTLYDP KFQG (SEQ ID NO: 38) | GTARASFDY (SEQ ID NO: 39) |

Variable Light Chain Analysis:

Nucleotide sequence:
Signal sequence-FR1-CDR1-FR2-CDR2-FR3-CDR3-FR4
(SEQ ID NO: 40)

ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATACTTATATGAACTGGTACCAACAGAAACCAGGACAGCC

ACCCAAACTCCTCATCTATACTGCATCCAATCTAGAATCTGGGATCCCAG

CCAGGTTTAGTGGCAGTGGGTCTGGGACAGACTTCACCCTCAACATCCAT

CCTGTGGAGGAGGTGGATGCTGCAACCTATTACTGTCAGCAAAGTAATGA

GGATCCATGGACGTTCGGTGGAGGCACCAAGCTGG AAATCAAA

Amino acid sequence:
Signal sequence-FR1-CDR1-FR2-CDR2-FR3-CDR3-FR4
(SEQ ID NO: 42)

METDTILLWVLLLWVPGSTGDIVLTQSPASLAVSLGQRATISCKASQSVD

YDGDTYMNWYQQKPGQPPKLLIYTASNLESGIPARFSGSGSGTDFTLNIH

PVEEVDAATYYCQQSNEDPWTFGGGTKLEIK

Variable Heavy Chain Analysis:

Nucleotide sequence
Signal sequence-FR1-CDR1-FR2-CDR2-FR3-CDR3-FR4
(SEQ ID NO: 41)

ATGAAATGCAGCTGGGTCATCTTCTTCCTGATGGCAGTGGTTACAGGGGT

CAATTCAGAGGTTCAGCTGCAGCAGTCTGGGGCTGAGCTTGTGAGGCCAG

GGGCCTTAGTCAAGTGGTCCTGCAAAGCTTCTGGCTTCAACATTAAAGAC

TACCATATACACTGGGTGAAACAGAGGCCTGAACAGGGCCTGGACTGGAT

TGGATGGATTGATCCTGAGATTGATAAAACTCTATATGACCCGAAGTTTC

AGGGCAAGGCCAGAATAACAGCAGACACATCCTCCAATACAGCCTACCTG

CAGCTCAGCAGCCTGACATCTGAAGACACTGCCGTCTATTACTGTGCCAG

GGGGACAGCTCGGGCTTCCTTTGACTACTGGGGCCAAGGCACCACTCTCA

CAGTCTCCTCA

Amino acid sequence:
Signal sequence-FR1-CDR1-FR2-CDR2-FR3-CDR3-FR4
(SEQ ID NO: 43)

MKCSWVIFFLMAVVTGVNSEVQLQQSGAELVRPGALVKWSCKASGFNIKD

YHIHWVKQRPEQGLDWIGWIDPEIDKTLYDPKFQGKARITADTSSNTAYL

QLSSLTSEDTAVYYCARGTARASFDYWGQGTTLTVSS

In some instances, the anti-ApoE antibody comprises a VH comprising the three VH CDRs and a VL comprising the three VL CDRs of antibody 25F1-2. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 37, a VHCDR2 comprising the amino acid sequence set forth in SEQ ID NO: 38, and a VHCDR3 comprising the amino acid sequence set forth in SEQ ID NO: 39; and (ii) a VL comprising a VLCDR1 comprising the amino acid sequence set forth in SEQ ID NO: 34, a VLCDR2 comprising the amino acid sequence set forth in SEQ ID NO: 35, and a VLCDR3 comprising the amino acid sequence set forth in SEQ ID NO: 36.

In some instances, the anti-ApoE antibody comprises a VH that is at least 75%, 80%, 85%, 90%, 91%, 92%, 93%, 94%, 95%, 96%, 97%, 98%, or 99% identical to the amino acid sequence set forth in SEQ ID NO: 43. In some instances, the anti-ApoE antibody comprises a VL that is at least 75%, 80%, 85%, 90%, 91%, 92%, 93%, 94%, 95%, 96%, 97%, 98%, or 99% identical to the amino acid sequence set forth in SEQ ID NO: 42. In one instance, the anti-ApoE antibody comprises a VH that is at least 85% identical to the amino acid sequence set forth in SEQ ID NO: 43 and a VL that is at least 85% identical to the amino acid sequence set forth in SEQ ID NO: 42. In another instance, the anti-ApoE antibody comprises a VH that is at least 90% identical to the amino acid sequence set forth in SEQ ID NO: 43 and a VL that is at least 90% identical to the amino acid sequence set forth in SEQ ID NO: 42. In yet another instance, the anti-ApoE antibody comprises a VH that is identical to the amino acid sequence set forth in SEQ ID NO: 43 and a VL that is identical to the amino acid sequence set forth in SEQ ID NO: 42.

In certain instances, an antibody of this disclosure that binds to ApoE is one that competes with or binds to the same epitope as a reference antibody with a VH having the amino acid sequence set forth in SEQ ID NO: 43 and a VL having the amino acid sequence set forth in SEQ ID NO: 42.

Exemplary Antibody 1343Ab

Antibody 1343ab was generated by immunizing with KLH-CTEELRVSLASHLRK-CONH2 (SEQ ID NO: 55). The amino acid sequences of the complementarity determining regions (CDRs) and the full length heavy and light chains are provided below.

| Variable region | Chain type | CDR-1 | CDR-2 | CDR-3 |
|---|---|---|---|---|
| 1343 VL | Light chain | KASQSVDYDGEN YMN (SEQ ID NO: 44) | VASNLES (SEQ ID NO: 45) | QQSNLDPWT (SEQ ID NO: 46) |
| 1343 VH | Heavy chain | GFNIKDY (SEQ ID NO: 47) | DPENGN (SEQ ID NO: 48) | GTARASFDY (SEQ ID NO: 49) |

Full Length Heavy Chain (SEQ ID NO: 53)

EVQLQQSGAELVRPGALVKLSCKASGFNIKDYHLHWVKQRPEQGLE

WIGWIDPENGNVIYDPKFQGKATMTVVTSSNTAYLQLRSLTSEDTA

VYFCTRGTARASFDYWGQGTSLTVSSAKTTPPSVYPLAPGSAAQTN

SMVTLGCLVKGYFPEPVTVTWNSGSLSSGVHTFPAVLQSDLYTLSS

SVTVPSSTWPSETVTCNVAHPASSTKVDKKIVPRDCGCKPCICTVP

EVSSVFIFPPKPKDVLTITLTPKVTCVVVDISKDDPEVQFSWFVDD

VEVHTAQTQPREEQFNSTFRSVSELPIMHQDWLNGKEFKCRVNSAA

FPAPIEKTISKTKGRPKAPQVYTIPPPKEQMAKDKVSLTCMITDFF

PEDITVEWQWNGQPAENYKNTQPIMDTDGSYFVYSKLNVQKSNWEA

GNTFTCSVLHEGLHNHHTEKSLSHSPGK

Full Length Light Chain

```
                                              (SEQ ID NO: 52)
DIVLTQSPASLAVSLGQRATISCKASQSVDYDGENYMNWYQQKPGQS

PKLLIYVASNLESGIPARFSGSGSGDFTLNIHPVETEEDAATYYCQQ

SNLDPWTFGGGTKLEIKRADAAPTVSIFPPSSEQLTSGGASVVCFLN

NFYPKDINVKWKIDGSERQNGVLNSWTDQDSKDSTYSMSSTLTLTKD

EYERHNSYTCEATHKTSTSPIVKSFNRNEC
```

N-linked glycosylation was detected on heavy chain constant region N at 292. Loss of C-terminal lysine observed on heavy chain.

In some instances, the anti-ApoE antibody comprises a VH comprising the three VH CDRs and a VL comprising the three VL CDRs of antibody 1343ab. The six CDRs can be based on any definition known in the art such as, but not limited to, Kabat, Chothia, enhanced Chothia, contact, IMGT, or Honegger definitions. These CDRs can be determined, e.g., by using the AbYsis database (bioinf.org.uk/abysis/sequence_input/key_annotation/key_annotation.cgi).

In one instance, an anti-ApoE antibody of this disclosure comprises (i) a VH comprising a VHCDR1 comprising the amino acid sequence set forth in SEQ ID NO: 47, a VHCDR2 comprising the amino acid sequence set forth in SEQ ID NO: 48, and a VHCDR3 comprising the amino acid sequence set forth in SEQ ID NO: 49; and (ii) a VL comprising a VLCDR1 comprising the amino acid sequence set forth in SEQ ID NO: 44, a VLCDR2 comprising the amino acid sequence set forth in SEQ ID NO: 45, and a VLCDR3 comprising the amino acid sequence set forth in SEQ ID NO: 46.

In some instances, the anti-ApoE antibody comprises a heavy chain that is at least 70%, 71%, 72%, 73%, 74%, 75%, 80%, 85%, 90%, 91%, 92%, 93%, 94%, 95%, 96%, 97%, 98%, or 99% identical to the amino acid sequence set forth in SEQ ID NO: 53. In some instances, the anti-ApoE antibody comprises a light chain that is at least 70%, 71%, 72%, 73%, 74%, 75%, 80%, 85%, 90%, 91%, 92%, 93%, 94%, 95%, 96%, 97%, 98%, or 99% identical to the amino acid sequence set forth in SEQ ID NO: 52. In one instance, the anti-ApoE antibody comprises a heavy chain that is at least 80% identical to the amino acid sequence set forth in SEQ ID NO: 53 and a light chain that is at least 80% identical to the amino acid sequence set forth in SEQ ID NO: 52. In another instance, the anti-ApoE antibody comprises a heavy chain that is at least 85% identical to the amino acid sequence set forth in SEQ ID NO: 53 and a light chain that is at least 85% identical to the amino acid sequence set forth in SEQ ID NO: 52. In yet another instance, the anti-ApoE antibody comprises a heavy chain that is identical to the amino acid sequence set forth in SEQ ID NO: 53 and a light chain that is identical to the amino acid sequence set forth in SEQ ID NO: 52.

In certain instances, an antibody of this disclosure that binds to ApoE is one that competes with or binds to the same epitope as a reference antibody with a heavy chain having the amino acid sequence set forth in SEQ ID NO: 53 and a light chain having the amino acid sequence set forth in SEQ ID NO: 52.

Chimeric, human, or humanized antibodies having the CDR sequences of any of the above antibodies can be generated based on methods described herein.

Antibody Fragments

Antibody fragments (e.g., Fab, Fab', F(ab')2, Facb, and Fv) can be prepared by proteolytic digestion of intact antibodies. For example, antibody fragments can be obtained by treating the whole antibody with an enzyme such as papain, pepsin, or plasmin. Papain digestion of whole antibodies produces F(ab) 2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J. Immunol.,* 152:2968-2976 (1994); Better, M. and Horwitz, A. H., *Methods in Enzymology,* 178:476-496 (1989); Pluckthun, A. and Skerra, *A., Methods in Enzymology,* 178:476-496 (1989); Lamoyi, E., *Methods in Enzymology,* 121:652-663 (1989); Rousseaux, J. et al., *Methods in Enzymology*, (1989) 121:663-669 (1989); and Bird, R. E. et al., *TIBTECH,* 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab) 2 fragments (Carter et al., *Bio/Technology,* 10:163-167 (1992)). According to another approach, F(ab')2 fragments can be isolated directly from recombinant host cell culture. Fab and F(ab') 2 fragment with increased in vivo half-life comprising a salvage receptor binding epitope residues are described in U.S. Pat. No. 5,869,046.

Conjugated Antibodies

The antibodies disclosed herein can be conjugated antibodies that are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. 90Y, 1311), fluorescent substances, luminescent substances, haptens, enzymes, metal chelates, and drugs.

In some embodiments, the antibodies described herein are modified with a moiety that improves its stabilization and/or retention in circulation, e.g., in blood, serum, or other tissues, including the brain, e.g., by at least 1.5, 2, 5, 10, 15, 20, 25, 30, 40, or 50-fold. For example, the antibodies described herein can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the antibodies described herein can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides. In some embodiments, the antibodies described herein are modified with a moiety that improves its penetration of the blood-brain barrier (such as those described in Pardridge, J Cereb Blood Flow Metab 32 (11): 1959-1972, 2012). Exemplary blood-brain barrier penetrating moieties include, but are not limited to, glucose transporter type 1 (GLUT1), cationic amino-acid transporter type 1 (CAT1), monocarboxylic acid transporter type 1 (MCT1), concentrative nucleoside transporter type 2 (CNT2), active efflux transporter (AET) (e.g., p-glycoprotein, and those described in Pardridge, J Cereb Blood Flow Metab 32 (11): 1959-1972, 2012), Additional blood-brain barrier penetrating moieties are known in the art.

The above-described conjugated antibodies can be prepared by performing chemical modifications on the antibodies or the lower molecular weight forms thereof described herein. Methods for modifying antibodies are well known in the art (e.g., U.S. Pat. Nos. 5,057,313 and 5,156,840).

The anti-ApoE antibodies can be in the form of full length (or whole) antibodies, or in the form of low molecular weight forms (e.g., biologically active antibody fragments or minibodies) of the anti-ApoE antibodies, e.g., Fab, Fab', $F(ab')_2$, Fv, Fd, dAb, scFv, and sc(Fv)2. Other anti-ApoE antibodies encompassed by this disclosure include single domain antibody (sdAb) containing a single variable chain such as, VH or VL, or a biologically active fragment thereof. See, e.g., Moller et al., *J. Biol. Chem.,* 285 (49): 38348-38361 (2010); Harmsen et al., *Appl. Microbiol. Biotechnol.,* 77 (1): 13-22 (2007); U.S. 2005/0079574 and Davies et al. (1996) *Protein Eng.,* 9 (6): 531-7. Like a whole antibody, a sdAb is able to bind selectively to a specific antigen (e.g., ApoE2, ApoE3, ApoE4, or ApoEch). With a molecular weight of only 12-15 kDa, sdAbs are much smaller than common antibodies and even smaller than Fab fragments and single-chain variable fragments.

In certain embodiments, an anti-ApoE antibody or antigen-binding fragment thereof or low molecular weight antibodies thereof specifically binds to the HSPG/heparin-binding domain of ApoE and reduces the severity of symptoms when administered to human patients having one or more of, or animal models of: dementia and/or mild cognitive impairment (MCI) (e.g. those associated with Alzheimer's disease, vascular dementia, Lewy body dementia, frontotemporal dementia, Parkinson's disease, Huntington's disease, or neurodegeneration). In certain embodiments, an anti-ApoE antibody or antigen-binding fragment thereof or low molecular weight antibodies thereof specifically binds to the HSPG/heparin-binding domain of ApoE and reduces the severity of symptoms when administered to human patients having one or more of, or animal models of: neurodegenerative diseases, cerebrovascular diseases (e.g. stroke, carotid stenosis, vertebral stenosis, or aneurysms), brain injuries (e.g. traumatic brain injury, acquired brain injury), retinal degeneration, glaucoma, or retinal injury. These features of an anti-ApoE antibody or low molecular weight antibodies thereof can be measured according to methods known in the art.

Nucleic Acids, Vector, Host Cells

This disclosure also features nucleic acids encoding the antibodies disclosed herein. Provided herein are nucleic acids encoding the VH CDR1, VH CDR2, and VH CDR3 of the anti-ApoE antibodies described herein. Also provided are nucleic acids encoding the VL CDR1, VL CDR2, and VL CDR3 of the anti-ApoE antibodies described herein. Provided herein are nucleic acids encoding the VH CDR1, VH CDR2, VH CDR3, VL CDR1, VL CDR2, and VL CDR3 of the anti-ApoE antibodies described herein. Also provided are nucleic acids encoding the heavy chain variable region (VH) of the anti-ApoE antibodies described herein, and/or nucleic acids encoding the light chain variable region (VL) of the anti-ApoE antibodies described herein. In certain instances, provided herein are nucleic acids encoding the VH and/or VL of the anti-ApoE antibodies described herein, linked to human heavy and/or human light chain constant regions, respectively. Also provided herein are nucleic acids encoding both VH and VL of the anti-ApoE antibodies described herein. In some instances, the nucleic acids described herein include a nucleic acid encoding the Fc region of a human antibody (e.g., human IgG1, IgG2, IgG3, or IgG4). In certain instances, the nucleic acids include a nucleic acid encoding the Fc region of a human antibody that has been modified to reduce or eliminate effector function (e.g., a N297Q or T299A substitution in a human IgG1 Fc region (numbering according to EU numbering)). In some cases, the nucleic acids include a nucleic acid encoding an Fc moiety that is a hIgG1 Fc, a hIgG2 Fc, a hIgG3 Fc, a hIgG4 Fc, a hIgG1agly Fc, a hIgG2 SAA Fc, a hIgG4 (S228P) Fc, or a hIgG4 (S228P)/Gl agly Fc.

Also disclosed herein are vectors (e.g. expression vectors) containing any of the nucleic acids described above.

Furthermore, this disclosure relates to host cells (e.g. bacterial cells, yeast cells, insect cells, or mammalian cells) containing the vector(s) or the nucleic acid(s) described above.

Methods of Obtaining Anti-ApoE Antibodies

Also provided herein are methods for making anti-ApoE antibodies useful in the present methods. General methods for making antibodies, e.g., monospecific, polyclonal, or monoclonal antibodies, are known in the art. For monoclonal antibodies, the process involves obtaining antibody-secreting immune cells (lymphocytes) from the spleen of a mammal (e.g., mouse) that has been previously immunized with the antigen of interest (e.g., a peptide antigen as described herein) either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975).

Mammalian lymphocytes can be immunized by in vivo immunization of the animal (e.g., a mouse) with a peptide antigen, e.g., a peptide antigen that is at least 80%, 85%, 90%, or 95% identical to KLH-CTEELRVRLASHLRK-$CONH_2$ (SEQ ID NO: 54) or KLH-CTEELRVSLASHLRK-$CONH_2$ (SEQ ID NO:55), optionally with one or more substitutions or deletions, e.g., of up to 20% of the residues. For example, the methods can include immunizing the animal with a peptide comprising a sequence that is at least 80% identical to at least 10 consecutive amino acids from: the heparin-binding domain of APOE, e.g., a peptide comprising TEELRVRLASHLRK (SEQ ID NO: 3) or TEELRVSLASHLRK (SEQ ID NO: 2). Such immunizations are repeated as necessary at intervals of up to several weeks to obtain a sufficient titer of antibodies. Following the last antigen boost, the animals are sacrificed, and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. Typically, such antibodies can be raised by administering the protein or polypeptide of the present invention subcutaneously to New Zealand white rabbits that have first been bled to obtain pre-immune serum. The antigens can be injected, e.g., at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/Kg IV. This and other procedures for raising polyclonal antibodies are disclosed in E. Harlow, et. al., editors, Antibodies: A Laboratory Manual (1988).

The method described herein comprises any one of the step(s) of producing a chimeric antibody, humanized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody described herein may exist in a variety of forms besides complete antibodies; including, for example, Fv, Fab and F(ab) 2, as well as in single chains; see e.g. international application WO88/09344.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology.

In the known hybridoma process (Kohler et al., Nature 256 (1975), 495) the relatively short-lived, or mortal, lymphocytes from a mammal, e.g., B cells derived from a murine subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific immunoglobulins that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibodies, such as those described above, can be made, for example, by preparing and expressing synthetic genes that encode the recited amino acid sequences. Methods of generating variants (e.g., comprising amino acid substitutions) of any of the anti-ApoE antibodies are well known in the art. These methods include, but are not limited to, preparation by site-directed (or oligonucleotide-mediated) mutagenesis, PCR mutagenesis, and cassette mutagenesis of a prepared DNA molecule encoding the antibody or any portion thereof (e.g., a framework region, a CDR, a constant region). Site-directed mutagenesis is well known in the art (see, e.g., Carter et al., *Nucl. Acids Res.,* 13:4431-4443 (1985) and Kunkel et al., *Proc. Natl. Acad. Sci. USA,* 82:488 (1987)). PCR mutagenesis is also suitable for making amino acid sequence variants of the starting polypeptide. See Higuchi, in *PCR Protocols*, pp. 177-183 (Academic Press, 1990); and Vallette et al., *Nucl. Acids Res.* 17:723-733 (1989). Another method for preparing sequence variants, cassette mutagenesis, is based on the technique described by Wells et al., *Gene,* 34:315-323 (1985).

Antibodies can be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS, Hela). In addition, antibodies (e.g., scFv's) can be expressed in a yeast cell such as *Pichia* (see, e.g., Powers et al., *J Immunol Methods.* 251:123-35 (2001)), Hanseula, or *Saccharomyces*. To produce the antibody or antigen binding fragments thereof of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., *Science,* 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.,* 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature,* 277:108 (1979)), MMLV-LTR promoter, EF1α promoter (Mizushima et al., *Nucleic Acids Res.,* 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Characterization of the Antibodies

The ApoE-binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

Methods for using SPR are described, for example, in U.S. Pat. No. 5,641,640; Raether (1988) *Surface Plasmons Springer Verlag*; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Information from SPR can be used to provide an accurate and quantitative measure of the equilibrium dissociation constant ($K_d$), and kinetic parameters, including Kon and $K_{off}$, for the binding of a biomolecule to a target.

Epitopes can also be directly mapped by assessing the ability of different antibodies to compete with each other for binding to wild type ApoE or mutant ApoE (e.g. ApoEch) using BIACORE chromatographic techniques (Pharmacia BIAtechnology Handbook, "Epitope Mapping", Section 6.3.2, (May 1994); see also Johne et al. (1993) *J. Immunol. Methods,* 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in *Antibodies: A Laboratory Manual*, ed. by Harlow and Lane, Cold Spring Harbor press (1988)).

Mutant ApoE Proteins, Peptides and Fusion Proteins Thereof

The present disclosure provides mutant ApoE proteins or fragments thereof containing amino acid substitutions at one or more positions in the HSPG-binding domain as compared to a wild type ApoE protein. In some embodiments, the mutant ApoE protein or fragments thereof includes an amino acid other than Arginine at position 136. In some embodiments, the mutant ApoE protein or fragments thereof contains Serine, Histidine, or Cysteine at position 136. Also provided are nucleic acid (e.g., DNA or RNA) sequences encoding the mutant ApoE proteins or fragments thereof, and vectors containing the nucleic acid sequences. The mutant ApoE proteins or fragments thereof, nucleic acids encoding such proteins or fragments, and vectors containing the nucleic acid sequences are useful for treating or preventing disorders associated with dementia or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury.

In some embodiments, the mutant ApoE protein is an ApoEch protein (e.g. ApoE2ch, ApoE3ch, or ApoE4ch protein). Fragments of the ApoEch protein that includes the amino acid position 136 are also contemplated here. Exemplary sequence of a full-length ApoE3ch protein is shown below. The mutation from arginine to serine is bolded and double underlined.

```
                                            (SEQ ID NO: 45)
MKVLWAALLVTFLAGCQAKVEQAVETEPEPELRQQTEWQSGQRWELALG

RFWDYLRWVQTLSEQVQEELLSSQVTQELRALMDETMKELKAYKSELEE

QLTPVAEETRARLSKELQAAQARLGADMEDVCGRLVQYRGEVQAMLGQS

TEELRVSLASHLRKLRKRLLRDADDLQKRLAVYQAGAREGAERGLSAIR

ERLGPLVEQGRVRAATVGSLAGQPLQERAQAWGERLRARMEEMGSRTRD

RLDEVKEQVAEVRAKLEEQAQQIRLQAEAFQARLKSWFEPLVEDMQRQW

AGLVEKVQAAVGTSAAPVPSDNH
```

In some embodiments, the methods disclosed herein allows the mutant ApoE protein or fragments thereof to cross the blood-brain barrier. The mutant ApoE protein or fragments thereof may be delivered using nanocarriers, including but not limited to, polymeric nanoparticles, lipid based nanoparticles, liposome, micelle, dendrimer, a human cell expressing the protein, and nanotube (See, Dominguez et al. J Nanosci nanotechnol. 14 (1): 766-79, 2014). In some embodiments, the mutant ApoE protein or fragments thereof is delivered intranasally, via intracarotid or transmucosal delivery (e.g. intracarotid infusion of hypertonic solutions (arabinose or mannitol); see, Sanchez-Covarrubias et al., Curr Pharm Des. 20 (10): 1422-49, 2014 and Miyake et al., World J Otorhinolaryngol Head Neck Surg. 1 (1): 11-16, 2015), or via the use of chlorotoxin (See, McCall et al., Tissue Barriers 2 (4): e944449, 2014). Hypothermia techniques, receptor-mediated transport, cell-penetrating peptides, and cell-mediated delivery can also be used to facilitate the ApoE3ch protein to cross the blood brain barrier (See, Pandey et al., Tissue Barriers 4 (1): e1129476, 2016). For example, immunocytes and stem cells (e.g., neural stem cells, induced pluripotent cells, and mesenchymal stem cells) can be used to carry therapeutic payloads across the BBB. Nanoparticle-loaded mesenchymal stem cells can be used for this purpose (See e.g., Roger et al. Biomaterials 31:8393-401, 2010). Genetically modified stem cells (e.g. genetically modified mesenchymal stem cells) can also be used (See e.g., Ebrahimi and Lalvand Hygeia. J. D. Med. vol. 5 (1): 90-104, 2013). Chemical drug delivery systems (CDDS), such as those described in He et al., Cells, 7 (4): 24, 2018, can also be used. Additional methods of transporting proteins across the blood-brain barrier are known in the art.

Nucleic acids (e.g., DNA or mRNA) encoding the mutant ApoE protein (e.g., any of the mutant ApoE proteins described herein, e.g. ApoEch) or fragments thereof are contemplated herein. In some embodiments, mRNA encoding the ApoEch protein may be modified to increase stability (such as those described in Zangi et al., Nat Biotechnol. 31 (10): 898-907, 2013 and developed by Moderna, Inc.; and those described in Alberer et al., Lancet 390 (10101): 1511-1520, 2017 and developed by Curevac and BioNTech).

Viral vectors containing DNA sequences encoding the mutant ApoE or fragments thereof are contemplated herein. An exemplary cDNA sequence encoding the full-length ApoE3ch protein (including the signal peptide region) is shown below. The mutation from Cytosine to Adenine is bolded and double underlined.

```
                                            (SEQ ID NO: 56)
ATGAAGGTTCTGTGGGCTGCGTTGCTGGTCACATTCCTGGCAGGATGCCA

GGCCAAGGTGGAGCAAGCGGTGGAGACAGAGCCGGAGCCCGAGCTGCGCC

AGCAGACCGAGTGGCAGAGCGGCCAGCGCTGGGAACTGGCACTGGGTCGC

TTTTGGGATTACCTGCGCTGGGTGCAGACACTGTCTGAGCAGGTGCAGGA

GGAGCTGCTCAGCTCCCAGGTCACCCAGGAACTGAGGGCGCTGATGGACG

AGACCATGAAGGAGTTGAAGGCCTACAAATCGGAACTGGAGGAACAACTG

ACCCCGGTGGCGGAGGAGACGCGGGCACGGCTGTCCAAGGAGCTGCAGGC

GGCGCAGGCCCGGCTGGGCGCGGACATGGAGGACGTGTGCGGCCGCCTGG

TGCAGTACCGCGGCGAGGTGCAGGCCATGCTCGGCCAGAGCACCGAGGAG

CTGCGGGTGAGCCTCGCCTCCCACCTGCGCAAGCTGCGTAAGCGGCTCCT

CCGCGATGCCGATGACCTGCAGAAGCGCCTGGCAGTGTACCAGGCCGGGG
```

-continued

```
CCCGCGAGGGCGCCGAGCGCGGCCTCAGCGCCATCCGCGAGCGCCTGGGG

CCCCTGGTGGAACAGGGCCGCGTGCGGGCCGCCACTGTGGGCTCCCTGGC

CGGCCAGCCGCTACAGGAGCGGGCCCAGGCCTGGGGCGAGCGGCTGCGCG

CGCGGATGGAGGAGATGGGCAGCCGGACCCGCGACCGCCTGGACGAGGTG

AAGGAGCAGGTGGCGGAGGTGCGCGCCAAGCTGGAGGAGCAGGCCCAGCA

GATACGCCTGCAGGCCGAGGCCTTCCAGGCCCGCCTCAAGAGCTGGTTCG

AGCCCCTGGTGGAAGACATGCAGCGCCAGTGGGCCGGGCTGGTGGAGAAG

GTGCAGGCTGCCGTGGGCACCAGCGCCGCCCCTGTGCCCAGCGACAATCA

CTGA
```

Suitable vectors are known in the art. In some embodiments, the viral vector is an AAV vector (such as those described in Rosenberg et al., Hum Gene Ther Clin Dev 29 (1): 24-47, 2018). cDNA sequences encoding an ApoE protein containing a mutation at the R136 position other than R136S are also included. In some embodiments, the mutation is R136H or R136C.

Peptides and Fusion Proteins

In some embodiments, provided herein are peptides that comprise or consist of the HSPG/heparin-binding domain of a wild type or mutant ApoE (e.g., any of the mutant ApoE proteins described herein). In some instances, the amino acid sequence of the peptides provided herein comprise or consist of the sequences selected from the group consisting of STEELRVRLASHLRKLRKRLLRDADDLQK (SEQ ID NO:57), STEELRVSLASHLRKLRKRLLRDADDLQK (SEQ ID NO:58), RLVQYRGEVQAMLGQSTEELRVR-LASHLRKL (SEQ ID NO:59), and RLVQYR-GEVQAMLGQSTEELRVSLASHLRKL (SEQ ID NO:60). Variants having at least 80%, 85%, 90%, 95%, 96%, 97%, 98%, 99% or greater sequence identity with these sequences can also be used. Also disclosed are fusion proteins comprising the peptides provided above. In some embodiments, the fusion proteins further include an Fc region of a human antibody (e.g., human IgG1, IgG2, IgG3, or IgG4). In some instances, the fusion protein comprises an Fc region of a human antibody at the C-terminal of the HSPG/heparin-binding domain of a wild type or mutant ApoE. In some instances, the fusion protein comprises an Fc region of a human antibody at the N-terminal of the HSPG/heparin-binding domain of a wild type or mutant ApoE.

In some instances, the peptides and fusion proteins provided herein competes with a wild type ApoE protein for binding to HSPG/heparin. In some instances, the peptides and fusion proteins provided herein reduce or modulate the binding between a wild type ApoE protein and HSPG/heparin. In certain embodiments, the peptides and fusion proteins provided herein inhibits and/or reduces HSPG/heparin-binding of a wild type ApoE protein, and reduces the severity of symptoms when administered to human patients having one or more of, or animal models of: disorders associated with dementia or mild cognitive impairment (MCI) (e.g. Alzheimer's disease, vascular dementia, Lewy body dementia, frontotemporal dementia, Parkinson's disease, Huntington's disease), neurodegenerative diseases, cerebrovascular diseases, brain injury, retinal degeneration, or retinal injury. These features of the peptides and fusion proteins provided herein can be measured according to methods known in the art.

Also provided herein are anti-ApoE vaccines, which can be used to elicit a protective immune response against ApoE. In some embodiments, the anti-ApoE vaccines include one or more of the ApoE peptides provided herein (e.g., and a pharmaceutically acceptable adjuvant. Pharmaceutically acceptable adjuvants are known in the art.

Pharmaceutical Compositions and Methods of Administration

The methods described herein include the use of pharmaceutical compositions comprising any of the antibodies, peptides or fusion proteins described herein as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intracranial, intranasal, intra-carotid, intravenous, intradermal, subcutaneous, oral (e.g., inhalation), and transmucosal.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal. For transmucosal administration, penetrants appropriate to the barrier to be permeated are used in the formulation. Such penetrants are generally known in the art, and include, for example, detergents, bile salts, and fusidic acid derivatives. Transmucosal administration can be accomplished through the use of nasal sprays or suppositories or injection.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

CRISPR/Cas9-Mediated Gene Editing of APOE

Included herein are methods for treating or preventing disorders associated with dementia and/or mild cognitive impairment (MCI) (e.g. Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury, by editing the APOE gene using a genome editing system. Generally, the methods include administering a therapeutically effective amount of a genome editing system as described herein, to a subject who is in need of, or who has been determined to be in need of, such treatment. The term "genome editing system" refers to any system having RNA-guided DNA editing activity. Genome editing systems of the present disclosure include at least two components adapted from naturally occurring CRISPR systems: a gRNA and an RNA-guided nuclease. These two components form a complex that is capable of associating with a specific nucleic acid sequence in a cell and editing the DNA in or around that nucleic acid sequence, for example by making one or more of a single-strand break (an SSB or nick), a double-strand break (a DSB) and/or a base substitution. See, e.g., WO2018/026976 for a full description of genome editing systems. In certain aspects, the present disclosure provides AAV vectors encoding CRISPR/Cas9 genome editing systems, and on the use of such vectors to treat or prevent disorders as described herein.

RNA-Guided Nucleases/Cas9

Various RNA-guided nucleases can be used in the present methods, e.g., as described in WO 2018/026976. In some embodiments, the RNA-guided nuclease used in the present methods and compositions is a *S. aureus* Cas9 or a *S. pyogenes* cas9. Exemplary Cas9 proteins of the disclosure may be isolated or derived from any species, including, but not limited to, a bacteria or an archaea. In some embodiments of this disclosure a Cas9 sequence is modified to include two nuclear localization sequences (NLSs) (e.g., PKKKRKV (SEQ ID NO:61) at the C- and N-termini of the Cas9 protein, and a mini-polyadenylation signal (or Poly-A sequence). An exemplary NLS is SV40 large T antigen NLS (PKKKRRV (SEQ ID NO:62)) and nucleoplasmin NLS (KRPAATKKAGQAKKKK (SEQ ID NO:63)). Other NLSs are known in the art; see, e.g., Cokol et al., EMBO Rep. 2000 Nov. 15; 1 (5): 411-415; Freitas and Cunha, Curr Genomics. 2009 December; 10 (8): 550-557. An exemplary polyadenylation signal is TAGCAATAAAGGATCGTTTATTTTCATTGGAAGCGTGTGTTGGTTTTTTGATCAGGCGCG (SEQ ID NO:64). In some embodiments, the RNA-guided nuclease is a nuclease-dead Cas protein (e.g., dCas9).

Guide RNAs

Provided herein are guide RNAs (gRNAs) designed to target one or more sites in the HSPG binding domain of a wile type ApoE. In some embodiments, the gRNAs are designed to introduce a mutation in the wild type ApoE that results in a mutation at amino acid position 136. In some embodiments, the guide RNAs provided herein are designed to introduce an R136S mutation in a wild type APOE gene (e.g. APOE2, APOE3, or APOE4), where exemplary guide RNAs can be found in Table 7. In some embodiments, also provided are templates for repairing the double stranded break and introducing an R136S mutation. An exemplary template sequence is as follows:

(SEQ ID NO: 65)
CGCCTGGTGCAGTACCGCGGCGAGGTGCAGGCCATGCTCGGCCAGAGCAC aGAGGAGCT*c*CGcGTGaGtCTCGCaagtCCACCTGCGCAAGCTGCGTAAG

CGGCTCCTCCGCGATGCCGATGACCTGC where silent mutations to abolish PAM motifs are double underlined, the codon corresponding to the R136S mutation is bolded, and silent mutation to generate SacI site for cleaving PCR products from clones that received the template is italicized.

In some embodiments, the guide RNAs provided herein are designed to target exon 3 (amino acids 1-61) of a wild type APOE gene, or of a variant present in a subject (the methods can thus include determining the sequence of the APOE gene in a subject, and using that sequence to determine the sequence of a suitable guideRNA for targeting exon 3 in that subject). In some embodiments, a double stranded break repair through non-homologous end joining (NHEJ) results in short insertions or deletions leading to ApoE knockout. Exemplary guide RNA sequences for ApoE knockout are shown in Table 8.

Base Editing

In some embodiments, the APOE gene is edited using the base editing technique (e.g. those described in Rees and Liu, Nature Reviews Genetics 19, 770-788, 2018; Komor et al., Nature 533, 420-424). In some embodiments, guide RNAs are designed to introduce an R136H mutation in a wild type APOE gene (e.g. APOE2, APOE3, or APOE4) using base editing, where exemplary guide RNAs can be found in Table 6. Base editors that convert C/G to A/T and adenine base editors that convert A/T to G/C can be used to introduce point mutations. Exemplary base editors include those described in Komor et al., Nature 533, 420-424 and Gaudelli et al., Nature 551, 464-471).

AAV Delivery Systems

The methods include delivery of a CRISPR/Cas9 genome editing system, including a Cas9 nuclease and one or two guide RNAs, to a subject in need thereof. The delivery methods can include, e.g., viral delivery, e.g., preferably using an adeno-associated virus (AAV) vector that comprises sequences encoding the Cas9 and guide RNA(s). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro and Immunol. 158:97-129 (1992)). AAV vectors efficiently transduce various cell types and can produce long-term expression of transgenes in vivo. AAV vectors have been extensively used for gene augmentation or replacement and have shown therapeutic efficacy in a range of animal models as well as in the clinic; see, e.g., Mingozzi and High, Nature Reviews Genetics 12, 341-355 (2011); Deyle and Russell, Curr Opin Mol Ther. 2009 August; 11 (4): 442-447; Asokan et al., Mol Ther. 2012 April; 20 (4): 699-708. AAV vectors containing as little as 300 base pairs of AAV can be packaged and can produce recombinant protein expression. For example, AAV2, AAV5, AAV2/5, AAV2/8 and AAV2/7 vectors have been used to introduce DNA into photoreceptor cells (see, e.g., Pang et al., Vision Research 2008, 48 (3): 377-385; Khani et al., Invest Ophthalmol Vis Sci. 2007 September; 48 (9): 3954-61; Allocca et al., J. Virol. 2007 81 (20): 11372-11380). In some embodiments, the AAV vector can include (or include a sequence encoding) an AAV capsid polypeptide described in PCT/US2014/060163; for example, a virus particle comprising an AAV capsid polypeptide having an amino acid sequence selected from the group consisting of SEQ ID NOs: 1, 3, 5, 7, 9, 11, 13, 15, and 17 of PCT/US2014/060163, and a Cas9 sequence and guide RNA sequence as described herein. In some embodiments, the AAV capsid polypeptide is an Anc80 polypeptide, e.g., Anc80L27; Anc80L59; Anc80L60; Anc80L62; Anc80L65; Anc80L33; Anc80L36; or Anc80L44. In some embodiments, the AAV incorporates inverted terminal repeats (ITRs) derived from the AAV2 serotype. Exemplary left and right ITRs are presented in Table 6 of WO 2018/026976. It should be noted, however, that numerous modified versions of the AAV2 ITRs are used in the field, and the ITR sequences shown below are exemplary and are not intended to be limiting. Modifications of these sequences are known in the art, or will be evident to skilled artisans, and are thus included in the scope of this disclosure.

Cas9 expression is driven by a promoter known in the art. In some embodiments, expression is driven by one of three promoters: cytomegalovirus (CMV), elongation factor-1 (EFS), or human g-protein receptor coupled kinase-1 (hGRKI), which is specifically expressed in retinal photoreceptor cells. Nucleotide sequences for each of these promoters are provided in Table 5 of WO 2018/026976. Modifications of these sequences may be possible or desirable in certain applications, and such modifications are within the scope of this disclosure.

Expression of the gRNAs in the AAV vector is driven by a promoter known in the art. In some embodiments, a polymerase III promoter, such as a human U6 promoter. An exemplary U6 promoter sequence is presented below:

(SEQ ID NO: 66)
AAGGTCGGGCAGGAAGAGGGCCTATTTCCCATGATTCCTTCATATTTGCA

TATACGATACAAGGCTGTTAGAGAGATAATTAGAATTAATTTGACTGTAA

ACACAAAGATATTAGTACAAAATACGTGACGTAGAAAGTAATAATTTCTT

GGGTAGTTTGCAGTTTTAAAATTATGTTTTAAAATGGACTATCATATGCT

TACCGTAACTTGAAAGTATTTCGATTTCTTGGCTTTATATATCTTGTGGA

AAGGACGAAACACC.

In some embodiments, the nucleic acid or AAV vector shares at least 80%, 85%, 90%, 95%, 96%, 97%, 98%, 99% or greater sequence identity with one of the nucleic acids or AAV vectors recited above.

The AAV genomes described above can be packaged into AAV capsids (for example, AAV5 capsids), which capsids can be included in compositions (such as pharmaceutical compositions) and/or administered to subjects. An exemplary pharmaceutical composition comprising an AAV capsid according to this disclosure can include a pharmaceutically acceptable carrier such as balanced saline solution (BSS) and one or more surfactants (e.g., Tween 20) and/or a thermosensitive or reverse-thermosensitive polymer (e.g., pluronic). Other pharmaceutical formulation elements known in the art may also be suitable for use in the compositions described here.

Compositions comprising AAV vectors according to this disclosure can be administered to subjects by any suitable means, including without limitation injection (e.g., intracranial injection) and intranasal delivery. The concentration of AAV vector within the composition is selected to ensure, among other things, that a sufficient AAV dose is administered to the brain of the subject, taking account of dead volume within the injection apparatus and the relatively limited volume that can be safely administered. Suitable doses may include, for example, $1\times10^{11}$ viral genomes (vg)/mL, $2\times10^{11}$ viral genomes (vg)/mL, $3\times10^{11}$ viral genomes (vg)/mL, $4\times10^{11}$ viral genomes (vg)/mL, $5\times10^{11}$ viral genomes (vg)/mL, $6\times10^{11}$ viral genomes (vg)/mL, $7\times10^{11}$ viral genomes (vg)/mL, $8\times10^{11}$ viral genomes (vg)/mL, $9\times10^{11}$ viral genomes (vg)/mL, $1\times10^{12}$ vg/mL, $2\times10^{12}$ viral genomes (vg)/mL, $3\times10^{12}$ viral genomes (vg)/mL, $4\times10^{12}$ viral genomes (vg)/mL, $5\times10^{12}$ viral genomes (vg)/mL, $6\times10^{12}$ viral genomes (vg)/mL, $7\times10^{12}$ viral genomes (vg)/mL, $8\times10^{12}$ viral genomes (vg)/mL, $9\times10^{12}$ viral genomes (vg)/mL, $1\times10^{13}$ vg/mL, $2\times10^{13}$ viral genomes (vg)/mL, $3\times10^{13}$ viral genomes (vg)/mL, $4\times10^{13}$ viral genomes (vg)/mL, $5\times10^{13}$ viral genomes (vg)/mL, $6\times10^{13}$ viral genomes (vg)/mL, $7\times10^{13}$ viral genomes (vg)/mL, $8\times10^{13}$ viral genomes (vg)/mL, or $9\times10^{13}$ viral genomes (vg)/mL. Any suitable volume of the composition may be delivered to the subretinal or cochlear space. In some instances, the volume is selected to form a bleb in the subretinal space, for example 1 microliter, 10 microliters, 50 microliters, 100 microliters, 150 microliters, 200 microliters, 250 microliters, 300 microliters, etc.

Explants are particularly useful for studying the expression of gRNAs and/or Cas9 following viral transduction, and for studying genome editing over comparatively short intervals. These models also permit higher throughput than may be possible in animal models, and can be predictive of expression and genome editing in animal models and subjects. Small (mouse, rat) and large animal models (such as rabbit, pig, nonhuman primate) can be used for pharmacological and/or toxicological studies and for testing the systems, nucleotides, vectors and compositions of this disclosure under conditions and at volumes that approximate those that will be used in clinic. Because model systems are selected to recapitulate relevant aspects of human anatomy and/or physiology, the data obtained in these systems will generally (though not necessarily) be predictive of the behavior of AAV vectors and compositions according to this disclosure in human and animal subjects.

Methods of Screening (Test Compounds)

Included herein are methods for screening test compounds, e.g., polypeptides, polynucleotides, inorganic or organic large or small molecule test compounds, to identify agents useful in the treatment or prevention of disorders associated with dementia and/or mild cognitive impairment (e.g., Alzheimer's disease, vascular dementia, Lewy body dementia, frontotemporal dementia, Parkinson's disease, or Huntington's disease), neurodegenerative diseases, cerebrovascular diseases, brain injury, retinal degeneration, or retinal injury. In some embodiments, the test compounds modulate the HSPG/heparin-binding properties of an ApoE protein (e.g. a wild type ApoE protein). In some embodiments, the test compounds reduce the HSPG/heparin-binding properties of an ApoE protein (e.g. a wild type ApoE protein).

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a sample containing one or more ApoE protein (s), and one or more effects of the test compound (e.g. HSPG/heparin binding affinity of the ApoE protein(s)) is evaluated. The ability of test compounds to modify the HSPG/heparin binding affinity of the ApoE protein(s) can be evaluated, e.g. using heparin sepharose columns, or antibodies that specifically recognize the HSPG-binding domain of ApoE as described herein. In some embodiments, methods for screening test compounds as described herein include evaluating the ability of a test compound to modify (e.g. inhibit or reduce) binding of antibodies as described herein that bind to one or more HSPG-binding sites or one or more sites of allosteric modulation of HSPG binding of a wild type or mutant ApoE. In some embodiments, a test compound competes with the antibodies as described herein for ApoE binding.

In some embodiments, the test sample is, or is derived from (e.g., a sample taken from) an in vivo model of a disorder as described herein. For example, an animal model, e.g., a rodent such as a rat, can be used.

A test compound that has been screened by a method described herein and determined to reduce or modify ApoE and HSPG/heparin binding, can be considered a candidate compound. A candidate compound that has been screened, e.g., in an in vivo model of a disorder, e.g., dementia and/or mild cognitive impairment (such as those associated with Alzheimer's disease, vascular dementia, Lewy body dementia, frontotemporal dementia, Parkinson's disease or Huntington's disease), neurodegenerative diseases, cerebrovascular diseases, brain injury, retinal degeneration, or retinal injury, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that have a desirable effect on the disorder) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating, preventing, or delaying of development or progression of disorders associated with dementia and/or mild cognitive impairment, as described herein, e.g., Alzheimer's disease, vascular dementia, Lewy body dementia, frontotemporal dementia, Parkinson's disease or Huntington's disease, and useful in treating, preventing, or delaying of development or progression of neurodegenerative diseases, cerebrovascular diseases, brain injury, retinal degeneration, or retinal injury. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with any of the disorders as described herein. The animal can be monitored for a change in the disorder, e.g., for an improvement in a parameter of the disorder, e.g., a parameter related to clinical outcome.

Methods of Treatment

The methods described herein include methods for the treatment, prevention, or delay of development or progression of disorders associated with dementia and/or mild cognitive impairments, neurodegenerative diseases, cerebrovascular diseases, brain injury, retinal degeneration, or retinal injury. In some embodiments, the disorder associated with dementia and/or mild cognitive impairments is Alzheimer's disease, vascular dementia, Lewy body dementia, frontotemporal dementia, Parkinson's disease, or Huntington's disease. Additional non-limiting examples of neurodegenerative diseases include prion disease, motor neuron disease, and amyotrophic lateral sclerosis (ALS). Non-limiting examples of cerebrovascular diseases include stroke, carotid stenosis, vertebral stenosis, and aneurysms. Non-limiting examples of brain injuries include traumatic brain injury and acquired brain injury. Retinal degeneration such as glaucoma, age-related macular degeneration, may involve amyloid-beta and neurofibrillary tangle toxicity, establishing a link between retinal degeneration and neurodegeneration (e.g., Alzheimer's disease) (See, e.g. Mckinnon, Frontiers in Bioscience 8, s1140-1156, 2003; Johnson et al. PNAS 99 (18) 11830-11835, 2002; and Sivak, Investigative Ophthalmology & Visual Science, 54 (1) 871-880, 2013). Accordingly, treatments for neurodegeneration can be used to treat retinal or optic nerve degeneration.

The methods include administering a therapeutically effective amount of any of the antibodies, peptides, fusion proteins, or genome editing system as described herein, to a subject who is in need of, or who has been determined to be in need of, such treatment.

The methods described herein are also useful for subjects at risk for developing any of the disorders described herein. Subjects at risk for developing Alzheimer's disease may include those that are homozygous or heterozygous for the APOE4 allele, carriers of autosomal dominant Alzheimer's disease-causing mutations (e.g. mutations in the amyloid beta precursor (APP) gene, PSEN1 gene, or PSEN2 gene), trisomy 21 (e.g. subjects whose cognitive impairment is developmental only). Subjects at risk for developing Alzheimer's disease may also include those that have polygenic risk scores associated with increased risk of developing the disease, and those with brain imaging or other biomarker (e.g. biomarker in the body fluids) evidence of Alzheimer's disease. The methods for preventing or delaying the development of disorders described herein may also be useful for subjects that are not at risk for developing the above disorders, such as any subjects over the age of 50 (e.g. over the age of 55, 60, 65, 70, 75, 80, 85, 90, or 95).

As used in this context, to "treat" means to ameliorate at least one symptom of the disorder associated with the disorders as described herein. Often, Alzheimer's disease results in fibril formation, amyloid aggregation, and reduced cognitive performance; thus, a treatment can result in a reduction in fibril formation and/or amyloid aggregation in the brain, reduced tau formation of tangles, improved brain metabolism, improved neurocognitive functions and/or cognitive performance.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1: Identification of the APOE3 Christchurch R136S Mutation in a PSEN1 Mutation Carrier Materials and Methods:

Clinical assessments: Institutional review boards from the University of Antioquia, Massachusetts General Hospital, and the Schepens Eye Research Institute of Massachusetts Eye and Ear approved this study. Like all of the research participants, the proband case provided her written informed consent. Clinical ratings and neuropsychological tests were performed as noted in Table 1. PSEN1 E280A genotyping was conducted as previously described.[1]

All clinical measures were undertaken at the University of Antioquia (Medellín, Colombia) and were conducted in Spanish by physicians and psychologists trained in assessment. Neurocognitive testing included a comprehensive multi-domain assessment. Some of the test administered were the Spanish versions of the Mini-Mental State Examination (MMSE), the Clinical Dementia Rating (CDR), and the Consortium to Establish a Registry for Alzheimer's disease battery, which have been adapted to this Colombian population.[2] Additional testing consisted of the Yesavage Geriatric Depression Scale[3] and the Functional Assessment Staging test[4], which were done within six months of brain imaging.

A detailed ophthalmic evaluation was performed. It included visual acuity assessment, slit-lamp and indirect ophthalmoscopy examination. Ultra-widefield fundus and fundus autofluorescence images using Optos Panoramic 200Tx imaging system (Optos PLC, Dunfermline, Scotland, UK) were obtained.

Additionally, Spectralis SD-OCT (Heidelberg Engineering, Heidelberg, Germany) and OCT angiography with Cirrus HD-OCT with AngioPlex (Carl Zeiss Meditec, Dublin, CA) were also done.

Additional studies were conducted after the PSEN1 E280A mutation carrier was discovered to have two copies of the APOE3ch variant. A fasting serum lipid panel was performed to explore the possibility of hyperliproteinemia type III, a condition found in 5-10% of persons homozygous for the relatively AD protective APOE2 allele and in most but not all APOE3ch carriers.[5]

Finally, an analysis of data from clinically and neuropathologically verified AD cases and controls from the AD Genetics Consortium was used to clarify whether homozygosity for the APOE2 allele was associated with an exceptionally low risk of late-onset AD dementia.

Whole exome sequencing: Whole-exome capture and sequencing were performed using Illumina chemistry for variant discovery; rare variants with less than 1% frequency in genes previously associated with AD were considered in the search for candidate risk modifiers. Specifically, rare DNA variants (minor allele frequency <1%) within exonic regions and splice-site junctions (5 bp into introns) of genes were identified using bioinformatics tools. Whole exome libraries were constructed and sequenced on an Illumina HiSeq 4000 sequencer with the use of 151 bp paired-end reads. Library construction was performed using a previously described protocol 6 modified as follows. Genomic DNA input was reduced from 3 μg to 50 ng in 10 μL of solution and enzymatically sheared. Dual-indexed Illumina paired end adapters were replaced with palindromic forked adapters with unique 8 base index sequences embedded within the adapter and added to each end for adapter ligation. In-solution hybrid selection was performed using the Illumina Rapid Capture Exome enrichment kit with 38 Mb target territory (29 Mb baited). The targeted region included 98.3% of the intervals in the Refseq exome database. Dual-indexed libraries were pooled into groups of up to 96 samples prior to hybridization. The enriched library pools were quantified via PicoGreen after elution from streptavadin beads and then normalized. For cluster amplification and sequencing, the libraries prepared using forked, indexed adapters were quantified using quantitative PCR (KAPA biosystems), normalized to 2 nM using Hamilton Starlet Liquid Handling system, and pooled with equal volume using the Hamilton Starlet Liquid Handling system. Pools were then denatured in 0.1 N NaOH. Denatured samples were diluted into strip tubes using the Hamilton Starlet Liquid Handling system. Cluster amplification of the templates was performed according to the manufacturer's protocol (Illumina) using the Illumina cBot. Flowcells were sequenced on HiSeq 4000 Sequencing-by-Synthesis Kits, then analyzed using RTA2.7.3.

Exome sequencing data was processed and analyzed with the bioinformatics pipeline of the Center's Clinical Exome Sequencing of the Center for Personalized Medicine (CPM) Clinical Genomics Laboratory and the Translational Genomics Research Institute. Briefly, Edico Genome's Dragen Genome Pipeline with default parameters was used to perform sequence alignment and variant calling. The open source software samtools and bcftools (samtools.github.io/) were used along with a set of custom scripts to perform coverage determination and initial variant filtering based on ExAC (Exome Aggregation Consortium, exac. broadinstitute.org/) allele frequencies.[7] Sequence alignment was done against the Human hs37d5 decoy genome.[8] To identify the potential modifier variants, a primary gene list of 15 genes was generated based on two HPO terms: HP: 0002511, Alzheimer disease; HP: 0003584, Late onset. These genes were AAGAB, ABCC8, AKT2, APOE, APP, BEANI, GATAI, GCK, HMGAI, HNFIB, HNF4A, LDB3, PAX4, PSEN1, and PSEN2.[9] Rare DNA variants (minor allele frequency <1%) within exonic regions and splice-site junctions (5 bp into introns) of these genes were further annotated and analyzed using a commercial tool (Cartagenia v5.0). Sequence alterations were reported according to the Human Genome Variation Society (HGVS v2.0) nomenclature guidelines.

Whole genome sequencing: Whole-genome sequencing (WGS) and a Genomizer analysis (v 10.1.0) were used to conduct a comprehensive and unbiased ranking of other potential genetic risk modifiers, including those associated with a lower risk of Alzheimer's dementia, helping to exclude other potentially protective genetic factors.[10] For processing the WGS data, the same dragen pipeline described above was used. The data was aligned to the GRCh37 decoy genome (hs37d5). Variants that were called at a depth of <10× were filtered out and then were annotated using Ensembl's Variant Effect Predictor (VEP) tool. The version of VEP using was v93. The filtered and annotated set of variants was then compiled for Genomizer analysis.

APOE structure display: Image was obtained and modified from the RCSB PDB (rcsb.org) of PDB 2L7B a previously published structure[11] using NGL Viewer[12].

APOE Genotyping by Sanger sequencing: Reaction mixture for the amplification process was performed in a 50 μL volume that included the following components: 1×PfuUltra II Hostart Master Mix, 1 μL of each primer (10 μmol/L) (Forward primer: 5'-AGCCCTTCTCCCCGCCTCCCACTGT-3' (SEQ ID NO: 67) and Reverse primer: 5'-CTCCGCCACCTGCTCCTTCACCTCG-3' (SEQ ID NO: 68)), 5% DMSO and 1 μL of genomic DNA (100 ng/μL).[13] PCR cycling was run with initial denaturation at 95° C. for 2 min followed by 35 cycles with denaturation at 95° C. for 20 seconds, annealing at 60° C. for 30 seconds, extension at 72° C. for 40 seconds, and a final extension at 72° C. for 5 min. PCR products were purified using QIAquick Gel Extraction kit from Qiagen and sequenced by MGH CCIB DNA core using the 3730xl sequencer from Applied Biosystems.

MRI and PET imaging: Pittsburgh Compound B (PiB), flortaucipir (FTP) positron emission tomography (PET) and structural magnetic resonance imaging (MRI) measurements were acquired at Massachusetts General Hospital and analyzed at Massachusetts General Hospital and Banner Alzheimer's Institute as previously described.[14] Fluorodeoxyglucose PET images were acquired at the University of Antioquia, Colombia, and analyzed as previously described[15]. Imaging data from the case were compared to those from younger PSEN1 E280A mutation carriers who developed MCI at the kindred's expected age at clinical onset, and from mutation carriers who were cognitively unimpaired.

MRI was performed on a 3T Tim Trio (Siemens) and included a magnetization-prepared rapid gradient-echo (MPRAGE) processed with Freesurfer (FS) to identify grey white and pial surfaces to permit regions of interest (ROI) parcellation as follows: cerebellar grey, hippocampus, and the following Braak Stage related cortices: entorhinal, parahippocampal, inferior temporal, fusiform, posterior cingulate, as described previously[16]-19

18F-Flortaucipir (FTP) was prepared at MGH with a radiochemical yield of 14±3% and specific activity of 216±60 GBq/umol at the end of synthesis (60 min), and validated for human use (Shoup et al., 2013). 11C-Pittsburgh Compound B was prepared and PET images were acquired as previously described.[16] All PET images were acquired using a Siemens/CTI (Knoxville, TN) ECAT HR+scanner (3D mode; 63 image planes; 15.2 cm axial field of view; 5.6 mm transaxial resolution and 2.4 mm slice interval. 11C PiB PET was acquired with a 8.5 to 15 mCi bolus injection followed immediately by a 60-minute dynamic acquisition in 69 frames (12×15 seconds, 57×60 seconds)). 18F FTP was acquired from 80-100 minutes after a 9.0 to 11.0 mCi bolus injection in 4×5-minute frames. PET images were reconstructed and attenuation-corrected, and each frame was evaluated to verify adequate count statistics and absence of head motion.

18F FTP specific binding was expressed in FS ROIs as the standardized uptake value ratio (SUVR) to cerebellum, similar to a previous report 19, using the FS cerebellar grey ROI as reference. For voxelwise analyses, each subject's MPRAGE was registered to the template MR in SPM8 (SPM), and the spatially transformed SUVR PET data was smoothed with a 8 mm Gaussian kernel to account for individual anatomic differences[20]. To account for possible 18F FTP off-target binding in choroid plexus, which may confound hippocampal signal, we used a linear regression to regress the choroid plexus, as previously reported 21.

11C PiB PET data were expressed as the distribution volume ratio (DVR) with cerebellar grey as reference tissue; regional time-activity curves were used to compute regional DVRs for each ROI using the Logan graphical method applied to data from 40 to 60 minutes after injection[16,22]. 11C PiB retention was assessed using a large cortical ROI aggregate that included frontal, lateral temporal and retrosplenial cortices (FLR) as described previously[23,24]

18F-fludeoxyglucose PET was performed on a 64-section PET/computed tomography imaging system (Biograph mCT; Siemens) using intravenous administration of 5 mCi (185 million Bq) of 18F-fludeoxyglucose after a 30-minute radiotracer uptake period when resting in a darkened room, followed by a 30-minute dynamic emission scan (six 5-minute frames). Images were reconstructed with computed tomographic attenuation correction. Precuneus to whole-brain cerebral metabolic rate for glucose (CMRgl) ratios were characterized from a bilateral region of interest (ROI) in each participant's 18F-fludeoxyglucose PET image using an automated brain mapping algorithm (SPM8; fil.ion.ucl.ac.uk/spm/software/spm8). Hippocampal to total intracranial volume ratios were characterized from bilateral ROIs in each participant's T1-weighted MR image using FreeSurfer (surfer.nmr.mgh.harvard.edu). All images were visually inspected to verify ROI characterization.

Amyloid aggregation studies: Human ApoE3 protein fragments (including the carboxyl-terminus domain plus a histidine tag) with and without the Christchurch variant were synthesized in bacteria, purified (Innovagen), and used to assess the differential effects of these proteins on $A\beta_{42}$ aggregation in vitro using Thioflavin T (SensoLyteR ThT β-Amyloid (1-42) Aggregation kit, cat. #AS-72214). For this assay, 55 μM of $A\beta_{42}$ was added to solutions of either 10 μM Wild Type apoE3 protein or Mutant 136 Arg→Ser ApoE3 protein in a transparent, no-binding 96-well plate. Samples were then mixed with 2 mM Thioflavin T dye and fluorescence was read at Ex/Em=440/484 at intermittent time intervals over 2 hours. The plate was kept at 37° C. with 15 seconds shaking between reads.

Full-length ApoE3 proteins with and without the Christchurch mutation were also expressed in Flp-In™ T-REX™ 293 (Thermo Fisher Scientific) mammalian cells via transient transfection to confirm the impact of these proteins on $A\beta_{42}$ aggregation using a previously published split-luciferase complementation assay.[26] The latter analysis were conducted using the human APOE3 expression from Addgene (Plasmid #8708627) as the WT or APOE3 with the Christchurch variant introduced via site-directed mutagenesis. Reagents for luciferase assay were purchased from Promega.

Results

About 1,200 Colombian Presenilin 1 (PSEN1) E280A mutation carriers and 4,600 non-carriers were identified, who together compose the world's largest known kindred with autosomal dominant Alzheimer's disease (ADAD).[28,29] The mutation carriers usually develop mild cognitive impairment (MCI) and dementia at the respective median ages of 44 (95% CI, 43-45) and 49 (95% CI, 49-50) years.[30,31] Studying autosomal dominant AD (ADAD) mutation carriers who remain cognitively unimpaired until older ages could help in the discovery of risk-reducing gene variants.[32] Characterizing AD biomarkers in these individuals could help inform the potentially targetable mechanisms by which these genes exert their relative protective effects. We identified a PSEN1 E280A mutation carrier who did not develop MCI until her seventies, nearly three decades after the median age at onset.

This study was conducted with the participant's written informed consent following Institutional Review Board guidelines (her exact age and other identifying information are omitted to protect her anonymity and confidentiality). The participant was confirmed to carry the amyloid-$\beta_{42}$ ($A\beta_{42}$)-overproducing PSEN1 E280A mutation, confirmed by report of family informants to be cognitively unimpaired until her seventies, and subsequently met criteria for MCI[33] during a 24-month period of annual assessments. She remained fully independent for basic and instrumental activities of daily living, without evident signs of worsening of her abilities to perform these activities. At intake assessment, her memory deficits were limited to recent events and her neurological exams were normal. Her age and education-adjusted neuropsychological test scores indicated a preferential impairment in recall memory, relatively preserved recognition memory, initial learning, naming, visuospatial abilities and verbal fluency skills, and relatively stable cognitive performance during the 24-month assessment period (Table 1).

TABLE 1

Cognitive Test Scores and Percentiles

| Cognitive Tests | Raw Scores (Percentiles**) | | | Mean (SD)** |
|---|---|---|---|---|
| MMSE/30* | 18 ($1^{st}$) | 16 (<$1^{st}$) | 19 ($4^{th}$) | 22 (1.7) |
| Naming/15 | 9 ($7^{th}$) | 9 ($7^{th}$) | 8 ($3^{rd}$) | 12.03 (2.1) |
| CERAD Word List Learning/30 | 10 ($5^{th}$) | 6 (<$1^{st}$) | 8 ($1^{st}$) | 15.64 (3.44) |
| CERAD Word List Delayed Recall/10 | 0 (<$1^{st}$) | 0 (<$1^{st}$) | 0 (<$1^{st}$) | 5.77 (1.98) |
| CERAD Word List Recognition/10 | 9 ($27^{th}$) | 8 ($5^{th}$) | 7 ($1^{st}$) | 9.58 (0.98) |
| CERAD Praxis-Copy/11 | 8 ($18^{th}$) | 9 ($39^{th}$) | 6 ($1^{st}$) | 9.42 (1.57) |
| CERAD Praxis-Recall/11 | 0 (<$1^{st}$) | 2 ($3^{rd}$) | 0 (<$1^{st}$) | 7.52 (2.84) |
| Semantic Fluency (Animals) | 12 ($13^{th}$) | 12 ($13^{th}$) | 12 ($13^{th}$) | 16.97 (4.3) |
| Phonemic Fluency ("F" Words) | 10 ($13^{th}$) | 11 ($14^{th}$) | 10 ($13^{th}$) | 23.75 (11.89) |
| Raven's Matrices Test, Form A/12 | 7 ($27^{th}$) | 7 ($27^{th}$) | 8 ($47^{th}$) | 8.21 (2.13) |
| GDS/15 | 9 | 2 | 9 | |
| EDG/7 | 3 | 3 | 4 | |

MMSE: Mini-Mental State Examination

CERAD: Consortium to Establish a Registry for Alzheimer's Disease Test Battery.

GDS: Geriatric Depression Scale

EDG: Global Deterioration Scale

*MMSE subtests that require reading and writing skills were not administered due to her limited literacy skills. Her maximum possible score was 23 (instead of 30).

**Percentiles were calculated using norms for this Colombian population.

Percentiles between 25 and 75 place her performance in the average range for her age and education.

Percentiles between 9 and 25 classify her performance as below average.

Percentiles between 2 and 8 classify her performance as low.

Percentiles below 1 classify her performance as extremely low.

#Brain imaging described in this report was acquired three months after the initial cognitive testing.

Whole exome sequencing corroborated her PSEN1 E280A mutation and discovered that she also had two copies of the rare APOE3 Christchurch R136S (APOEch) mutation. Sanger sequencing confirmed the latter finding. Whole genome sequencing and a Genomizer analysis were used to comprehensibly identify and rank all potentially significant rare and common variants.[34] Using this approach, the PSEN1 E280A mutation was confirmed to be the participant's primary risk factor and APOE3ch homozygosity was confirmed to be her primary resistance factor.

APOE, the major susceptibility gene for late-onset AD, has three common alleles (APOE2, 3, and 4). Compared to the most common APOE3/3 genotype, APOE2 is associated with a lower AD risk and older age at dementia onset,[35] and each additional copy of APOE4 is associated with a higher risk and younger age at onset.[36,37] The APOEch variant, an arginine-to-serine substitution at amino acid 136 (136Arg→Ser), corresponding to codon 154,[38] can reside on any of the common APOE alleles,[39] including this participant's two APOE3 alleles. FIG. 1 shows a model of the structure of the wild type ApoE3 protein. N-terminal (residues 1-191) and C-terminal (residues 201-299) domains are highlighted. The amino acid positions for APOE4 (C112R), APOE3ch (R136S) and APOE2 (R158C) variants are shown.

The APOE3ch variant was absent from AlzAD or ExAC databases reporting on about 180,000 exomes. The R136S was previously identified in APOE2 individuals with HLP III but its potential effect in the progression of AD has not been previously reported.[40] We sequenced DNA samples from two other PSEN1 E280A carriers with delayed age-at-onset (age at onset 62 and 70 years) via whole genome sequencing. None of these individuals had the APOE3 R136S variant nor APOE2; the latter was previously shown to delay disease onset in this kindred.[41]

Figure 2:
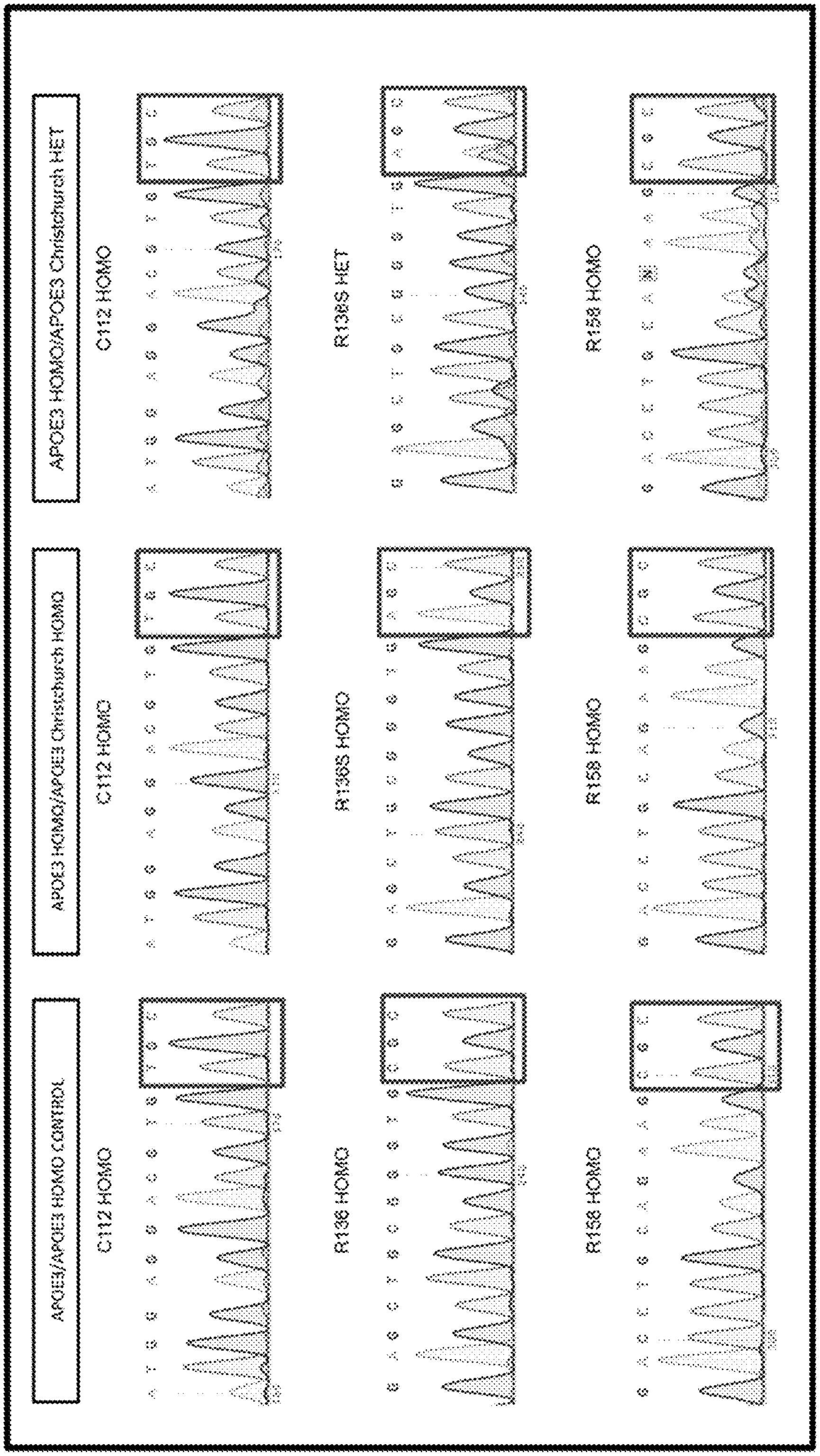
FIG. 2 shows representative Sanger sequencing results of APOE from control, proband and descendant's samples.
Figure 3:
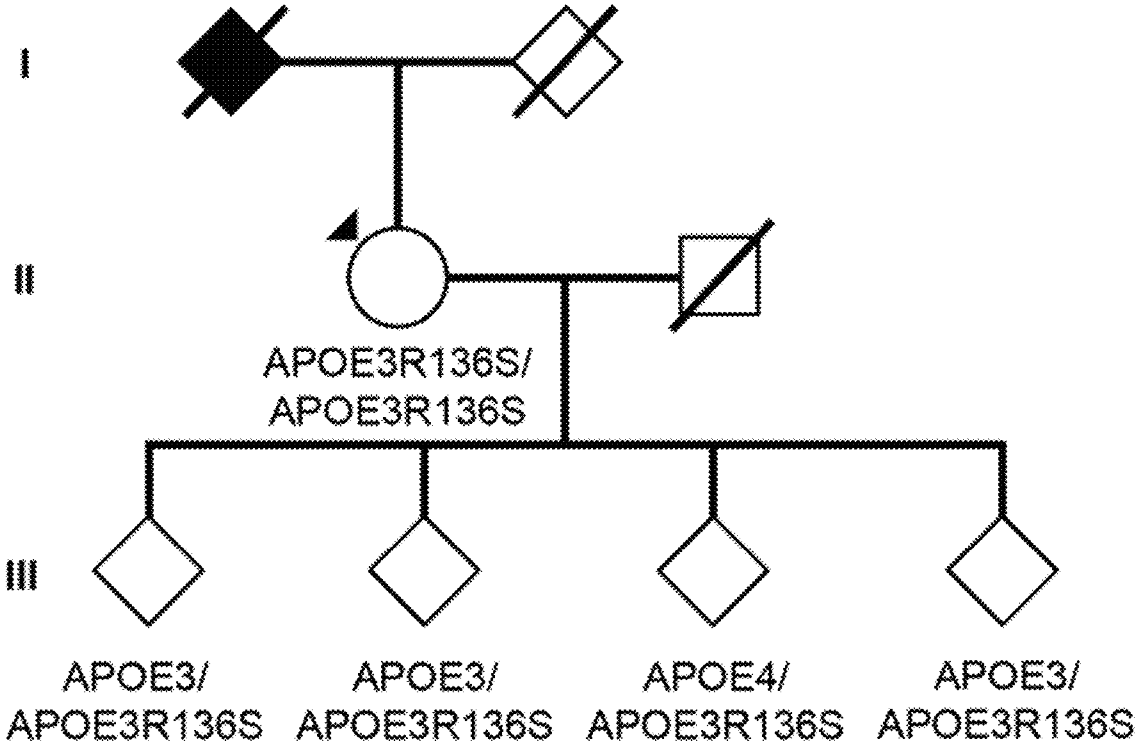
FIG. 3 depicts the subject's genealogy, with circles representing females, squares representing males, diamonds representing individuals whose gender has been masked for privacy, arrowhead depicts proband individual with MCI, and shading indicates individual with history of dementia. Deceased individuals are marked with a crossed bar. The individual APOE and PSEN1 genotypes are indicated as appropriate to preserve anonymity.

To confirm a potential association between the APOE3 R136S mutation and delayed age at onset of AD, we conducted whole genome sequencing, neurological, and neuropsychological testing in the four descendants of the proband case, which were all older than fifty years, and expected to carry the APOE3 R136S. FIG. 2 shows representative Sanger sequencing results of APOE from control, proband and descendant's samples. Upper row: C112 homozygous sequences are shown in all cases. Middle row: R136 homozygous sequence is shown in left panel from a control individual. Middle panel shows homozygous change resulting in R136S mutation. Right panel shows a R136S heterozygous mutation example of a descendant of the proband. Low row: R158 homozygous sequences are shown in all cases. FIG. 3 shows the proband's genealogy, with circles representing females, squares representing males, diamonds representing individuals whose gender has been masked for privacy, arrowhead depicts proband individual with MCI, and shading indicates individual with history of dementia. Deceased individuals are marked with a crossed bar. The individual APOE and PSEN1 genotypes are indicated as appropriate to preserve anonymity. Although other unknown genetic or epigenetic factors may have contributed to late age at onset of cognitive impairment in these two related PSEN1 E280A carriers, we suggest that the APOE3 R136S variant modifies the AD phenotype by buffering the effects of amyloid-β accumulation in the brain and subsequently delaying the emergence of tau pathology, neurodegeneration (i.e. brain atrophy), and symptoms onset.

Carriers of APOEch and other rare mutations in APOE's low density lipoprotein receptor (LDLR) binding region commonly have hyperlipoproteinemia type III (HLP-III), similar to that observed in 5-10% of APOE2 homozygotes.[43,44] The participant in this report was confirmed to have HLP-III, including APOEch and elevated triglyceride and total cholesterol levels (See, Table 2).

TABLE 2

Dyslipidemia workup

| Test Lipid panel | Subject | Normal range* |
|---|---|---|
| Triglycerides (mg/dl) | 691.88 | <250 |
| Total Cholesterol (mg/dl) | 511.76 | 150-199 |
| VLDL-C (mg/dl) | (—) | <30 |
| LDL-C (mg/dl) | (—) | ≤130 |
| Direct LDL-C (mg/dl) | 147 | ≤130 |
| HDL-C (mg/dl) | 55.74 | ≥40 |
| Cholesterol/HDL ratio | 9.18 | <5 |
| Apolipoprotein A-I (mg/dl) | 177 | F: 98-210 |
| Apolipoprotein B (mg/dl) | 217 | F: 44-148 |

TABLE 2-continued

| Dyslipidemia workup | | |
|---|---|---|
| Test<br>Lipid panel | Subject | Normal range* |
| Apo B/Apo-I ratio | 1.23 | F: 0.35-1.15 |
| Lipoprotein A (mg/dl) | 86.6 | ≤30 |

HDL-C: High-density lipoprotein cholesterol,
VLDL-C: Very low-density lipoprotein cholesterol,
LDL-C: Low-density lipoprotein cholesterol.
*Normal range according to Merck Manual and Laboratory values.

Detailed laboratory workup showed abnormal lipid profile in our proband individual and three of the four descendants carrying the APOE3 R136S (Table 3). These four subjects had high level of total cholesterol and triglycerides. Very low-density lipoprotein (VLDL) and low-density lipoprotein (LDL) were higher in two of the descendants and not measurable in the proband individual and one of the descendants, which had triglyceride levels higher 400 mg/dL (the threshold for accuracy of the indirect method of lipid profiling) (Table 3). Further analyses using direct enzymatic tests showed higher than normal LDL in these two individuals. One of the descendants had a lipid profile within normal limits despite carrying the APOE3 R136S and the APOE4. Incomplete penetrance of HLP III has been previously reported for APOE2 and for R136S mutation carriers.[45] We ruled out secondary causes of lipid disorders as diabetes, obesity, alcoholism, renal disorders or thyroid diseases in these subjects. None of the mutation carrier individuals had xanthomas, which are diagnostic of HLP III, or cardiovascular diseases. The combination of the abnormal lipid profile and APOE3 R136S mutation in these subjects is consistent with a diagnosis of familial HLP III.

TABLE 3

| Dementia and dyslipidemia workup in study population | | | | | | |
|---|---|---|---|---|---|---|
| | Patient No. (Sex-Age) | | | | | |
| Test | 1 (F-75) | 2 (F-51) | 3 (F-53) | 4 (M-49) | 5 (M-54) | Normal range* |
| CBC | | | | | | |
| RBC count (×$10^6$ $mm^3$) | 4.7 | 4.73 | 4.47 | 5.26 | 5.37 | 4.2-5.9 |
| Hemoglobin (g/dl) | 13 | 14.1 | 12.9 | 15.1 | 15.1 | M: 14-17 F: 12-16 |
| Hematocrit (%) | 38.5 | 42.3 | 39.2 | 46.3 | 45.7 | M: 41-51 F: 36-47 |
| MCV (fL) | 81.9 | 89.4 | 87.8 | 88.1 | 85 | 80-100 |
| MCH (pg) | 27.6 | 29.8 | 28.8 | 28.6 | 28.1 | 28-32 |
| MCHC (g/dl) | 33.7 | 33.4 | 32.8 | 32.5 | 33 | 32-36 |
| RDW (%) | 13.7 | 12.5 | 13 | 13.3 | 13.5 | 11.5-14.5 |
| WBC count (×$10^3$ $mm^3$) | 5.51 | 10.45 | 9.61 | 12.78 | 20.18 | 4.5-11 |
| Platelets (×$10^3$ $mm^3$) | 264 | 289 | 334 | 256 | 295 | 150-350 |
| MPV (fL) | 7 | 8.2 | 8.8 | 8.3 | 7.8 | 6.5-13.5 |
| ESR (mm/h) | 30 | 20 | 51 | 18 | 2 | M: 0-15 F: 0-20 |
| BMP | | | | | | |
| Glucose (mg/dl) | 107.1 | 128.28 | 107.82 | 112.15 | 131.19 | 70-105 |
| BUN (mg/dl) | 11.98 | 13.03 | 9.71 | 15.65 | 14.39 | 8-20 |
| Creatinine (mg/dl) | 0.57 | 0.59 | 0.67 | 1.04 | 0.95 | 0.7-1.3 |
| Sodium (mmol/l) | 139.3 | 141.4 | 140 | 137.3 | 136.6 | 136-145 |
| Potassium (mmol/l) | 3.79 | 4.03 | 4.92 | 4.76 | 4.29 | 3.5-5 |
| Chloride (mmol/l) | 102 | 106.5 | 108.3 | 106.6 | 107.1 | 98-106 |
| LPP | | | | | | |
| Total Cholesterol (mg/dl) | 511.76 | 192.6 | 434.25 | 336.21 | 323.2 | 150-199 |
| HDL-C (mg/dl) | 55.74 | 60.52 | 60.56 | 53.76 | 33.78 | ≥40 |
| Cholesterol/HDL ratio | 9.18 | 3.18 | 7.17 | 6.25 | 9.57 | <5 |
| Triglycerides (mg/dl) | 691.88 | 50.32 | 321.3 | 282.49 | 437.92 | <250 |
| VLDL-C (mg/dl) | (—) | 10.06 | 64.26 | 56.5 | (—) | <30 |
| LDL-C (mg/dl) | (—) | 122.02 | 309.43 | 225.95 | (—) | ≤130 |
| Additional tests | | | | | | |
| Apolipoprotein A-I (mg/dl) | 177 | 106 | 150 | 126 | 133 | M: 88-180 F: 98-210 |
| Apolipoprotein B (mg/dl) | 217 | 75 | 179 | 173 | 160 | M: 55-151 F: 44-148 |
| Apo B/Apo-I ratio | 1.23 | 0.71 | 1.19 | 1.37 | 1.2 | M: 0.45-1.25 F: 0.35-1.15 |
| Hemolytic Complement 50% (U/ml) | 50.8 | 58 | 58.6 | 56.1 | 68.8 | 31.6-57.6 |
| Plasmatic homocysteine (μmol/l) | 9.54 | 6.47 | 7.48 | 15.34 | 13.55 | M: 4-16 F: 3-14 |
| Lipoprotein A (mg/dl) | 86.6 | 6 | 86.1 | 6.5 | 62 | ≤30 |
| Serum complement C3 (mg/dl) | 130.1 | 1202.6 | 1314.5 | 1281.9 | 1292.6 | 55-120 |
| Serum complement C4 (mg/dl) | 20.6 | 177.9 | 131.7 | 146.5 | 245.5 | 20-59 |
| Complement Clq (mg/dl) | 24 | 23 | 28 | 28 | 33 | 10-25 |
| Free thyroxine (ng/dl) | 1.38 | 1.13 | 1.12 | 1.26 | 1.09 | 0.9-2.4 |
| TSH (μIU/ml) | 4.5 | 0.78 | 4.08 | 3.56 | 3.72 | 0.50-5.0 |
| Vitamin B12 (pg/ml) | 517 | 382 | 294 | 263 | 352 | 200-800 |
| Folate (ng/ml) | 16.14 | 7.52 | 8.38 | 2.14 | 6.6 | 2.5-20 |

Figure 4B:
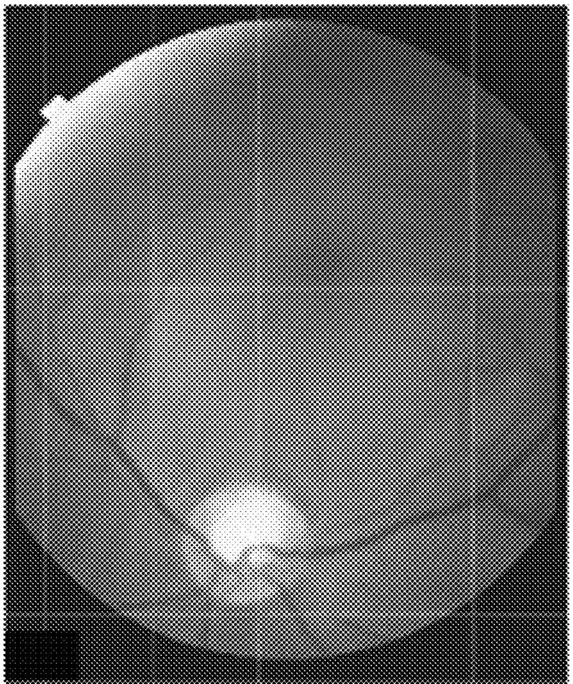
FIGS. 4A and 4B are fundus photographs of the right and left eyes, respectively.
Figure 4A:
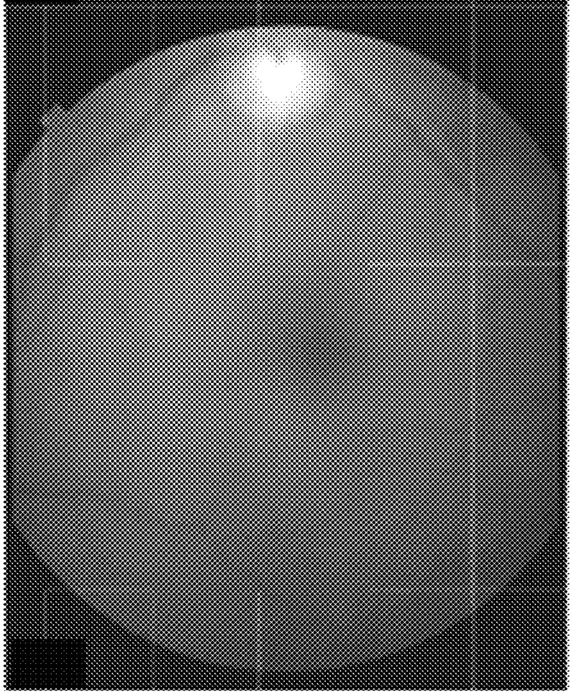
Figure 4C:
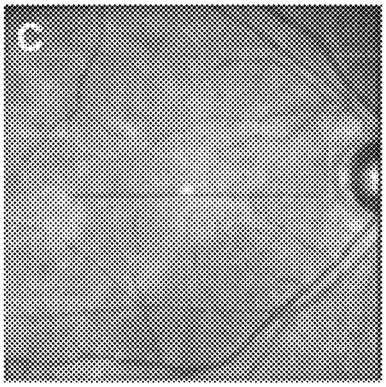
FIG. 4C shows an infrared image of the right eye that depicts the cross section of the retina (line) seen in FIG. 4D.
Figure 4D:
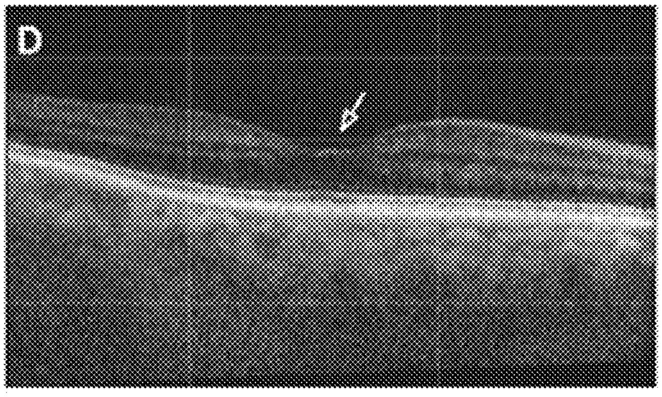
FIG. 4D shows results of optical coherence tomography (OCT) of the right eye.
Figure 4E:
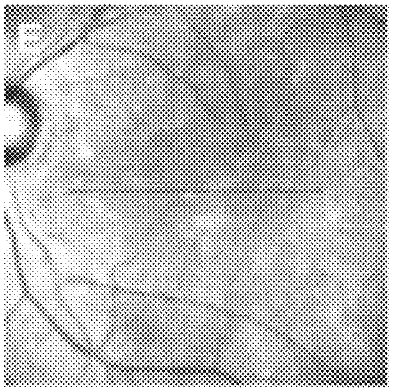
FIG. 4E shows an infrared image of the left eye.
Figure 4F:
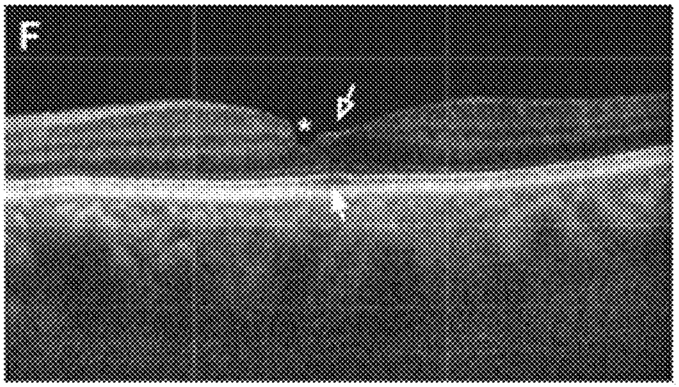
FIG. 4F shows results of OCT imaging of the left eye.

A detailed ophthalmic evaluation of the PSEN1 E280A mutation carrier with two APOE3ch alleles was performed. This carrier had a vision of 20/70 in the right eye and 20/40 in the left eye. The anterior segment exam was notable for a posterior chamber intraocular lens in the right eye with a dense posterior capsular opacification. Anterior segment of the left eye was notable for a nuclear sclerotic cataract (FIGS. 4A and 4B). The posterior segment examination of both eyes was normal, with a clear vitreous cavity, normal appearing optic nerve, macula, and peripheral retina. Further testing via optical coherence tomography (OCT) of the right eye was normal except for a small area of hyper-reflectivity overlying the fovea (FIG. 4D). FIG. 4C shows an infrared image of the right eye that depicts the cross section of the retina (line) seen in FIG. 4D. Further, OCT imaging of the left eye revealed a degenerative lamellar hole (denoted by the * in FIG. 4F) with a small defect in the external limiting membrane and ellipsoid layer (arrow in FIG. 4F).

While several mechanisms have been proposed to account for the impact of APOE variants on AD risk, most studies have focused on their differential effects (APOE2<3<4) on $A\beta_{42}$ aggregation and plaque burden.[47] In the present study, neuroimaging measurements were used to clarify whether the participant's resistance to the clinical onset of AD was associated with a) relatively little Aβ plaque burden despite more than seventy years of $A\beta_{42}$ overproduction or with b) relatively high Aβ plaque burden but limited downstream measurements of paired helical filament (PHF) tau (neurofibrillary tangle burden) and neurodegeneration.

Figure 5:
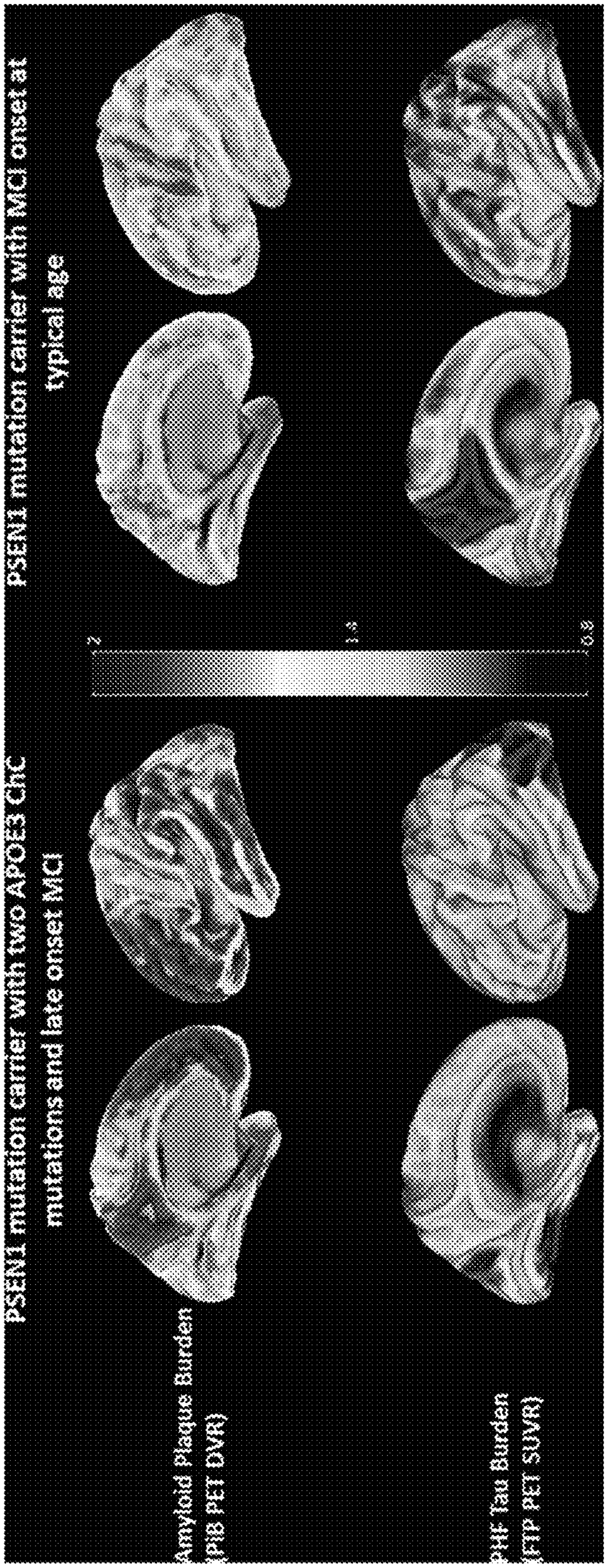
FIG. 5 shows brain imaging results showing the amyloid plaque burden and PHF Tau burden in the brains of the PSEN1 mutation carrier with late onset MCI (mild cognitive impairment) and a PSEN1 mutation carrier with MCI onset at a typical age for this mutation (44 years).

The participant's neuroimaging findings are shown in FIG. 5. The positron emission tomography (PET) images are superimposed onto the medial and lateral surfaces of the left hemisphere. The top row shows PET measurements of amyloid plaque burden (PiB DVRs). The bottom row shows PET measurements of paired helical filament (PHF) tau (i.e., neurofibrillary tangle) burden. The person with late-onset of MCI is in her seventies, and the person with the typical age at MCI onset is 44 years old.

As shown in FIG. 5, the person with late onset of MCI had unusually high PET measurements of Aβ plaque burden, as indicated by a higher mean cortical-to-cerebellar Pittsburgh Compound B (PiB) distribution volume ratio (DVR=1.96) than in PSEN1 E280A carriers who developed MCI in their forties (DVRs of 1.49-1.60). Despite her high Aβ plaque burden, the magnitude and/or spatial extent of her PHF tau burden and neurodegeneration were relatively limited: Her flortaucipir (tau) PET measurements were restricted to medial temporal and less commonly affected occipital regions with relative sparing of other regions that are characteristically affected in the clinical stages of AD (FIG. 5). Her fluorodeoxyglucose PET measurements of the cerebral metabolic rate for glucose were preserved in brain regions that are known to be preferentially affected by AD, including higher precuneus-to-whole brain measurements than in PSEN1 E280A mutation carriers who developed MCI at younger ages and many younger, cognitively unimpaired mutation carriers.

Figure 6:
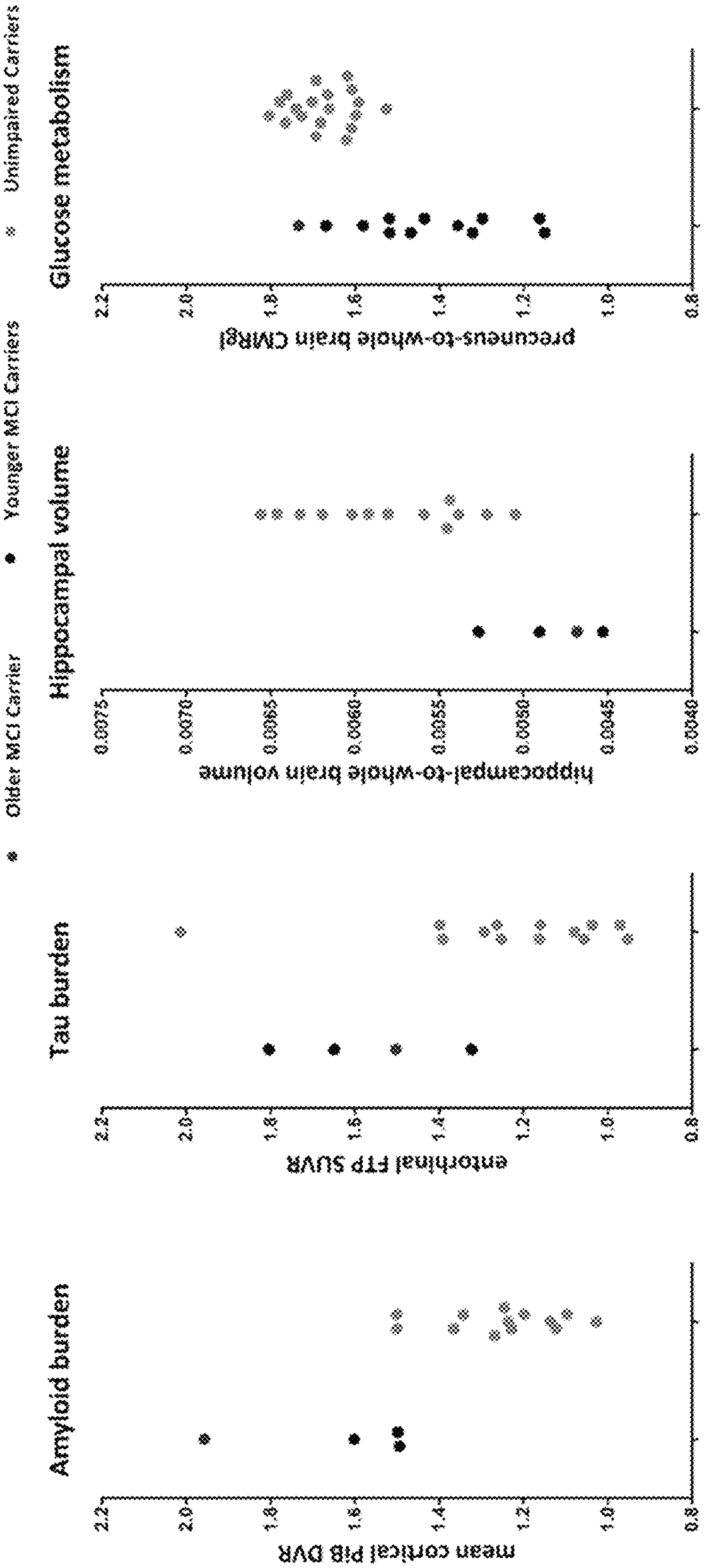
FIG. 6 shows measurements of amyloid burden, tau burden, hippocampal volume, and the levels of glucose metabolism in PSEN1 E280A mutation carriers. Red dots represent the measurements for the carrier with two APOE3ch alleles and an exceptionally late onset of MCI. Black dots represent PSEN1 E280A mutation carriers with MCI at the kindred's typical, younger age at MCI onset. Gray dots represent PSEN1 E280A mutation carriers who have not yet developed MCI.

FIG. 6 shows measurements of mean cortical amyloid plaque burden, entorhinal cortex PHF tau burden, hippocampal volume, and precuneus glucose metabolism. These measurements were based on brain imaging results obtain from the PSEN1 E280A mutation carrier with two APOE3ch alleles and exceptionally late-onset of MCI (red dots), PSEN1 E280A mutation carriers with MCI at the kindred's typical, younger age at MCI onset (black dots), and PSEN1 E280A mutation carriers who have not yet developed MCI (gray dots). Amyloid plaque burden is expressed as mean cortical-to-cerebellar distribution volume ratios (DVRs). Paired helical filament (PHF) tau burden is expressed as entorhinal cortex-to-cerebellar flortaucipir (FTP) standard uptake value ratios (SUVRs). Hippocampal volumes, which may be reduced by hippocampal atrophy, are expressed as hippocampal-to-whole brain volume ratios. Cerebral glucose metabolism, which is reduced in AD-affected brain regions with synaptic dysfunction and loss, is reflected as precuneus-to-whole brain cerebral metabolic rate for glucose (CMRgl) ratios. As shown FIG. 6, while the PSEN1 E280A mutation carrier with two APOE3ch alleles had by far the highest amyloid plaque burden, she did not have comparably severe PHF tau burden or hippocampal atrophy, and she had no evidence of precuneus glucose hypometabolism. Her MRI-based hippocampal-to-whole brain volume, a hippocampal atrophy measurement that can be affected by AD and/or normal aging, was within the range of mutation carriers who developed MCI in their forties. Without wishing to be bound by theory, these results suggest that this APOE3ch homozygote's resistance to the clinical onset of AD is mediated through a mechanism that limits tau pathology and neurodegeneration even in the face of high Aβ plaque burden.

Figure 7:
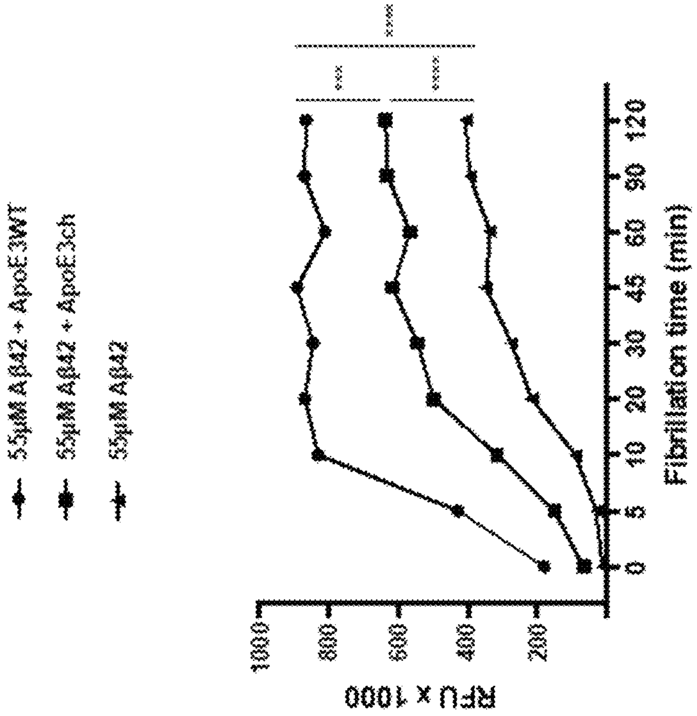
FIG. 7 shows the rate of $A\beta_{42}$ fibril formation in the presence of APOE3 wild-type, APOE3ch, or in the absence of APOE as detected by Thioflavin T fluorescence. Changes in relative fluorescence units (RFU) were plotted for time in minutes (min). (*$P<0.001$, **$P<0.0001$)

To study functional consequences of the APOE3ch variant, $A\beta_{42}$ aggregation in vitro in the presence of the bacteria-derived wild type human ApoE3 protein, presence of the mutant ApoE3ch protein, or in the absence of any ApoE protein were compared. The rate of $A\beta_{42}$ fibril formation was detected by Thioflavin T fluorescence. $A\beta_{42}$ aggregation was highest in the presence of wild type human ApoE3 protein (C-terminus domain), lower in the presence of human ApoE3ch (similar to that observed in the presence of ApoE2[48]), and lowest in the absence of any ApoE (FIG. 7).

Figure 8:
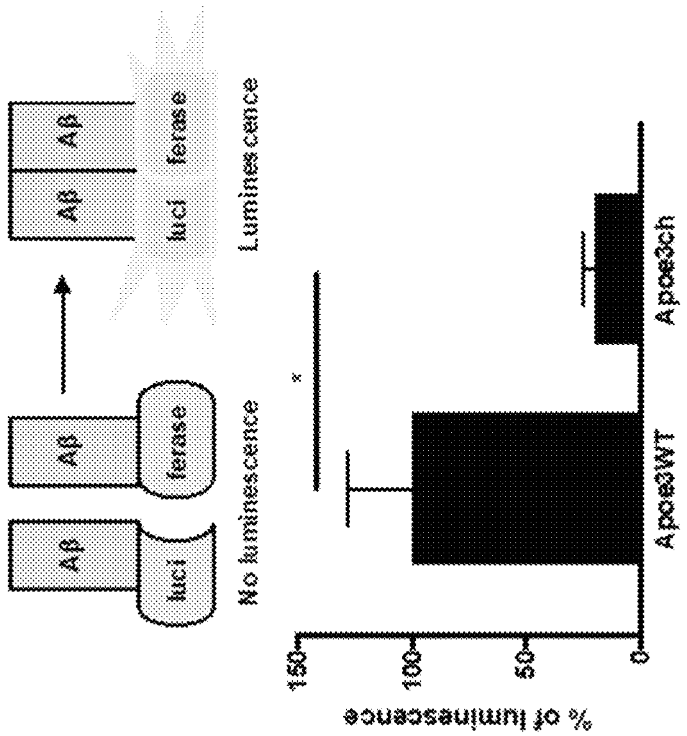
FIG. 8 shows schematic of the split-luciferase complementation triggered by amyloid oligomerization (top) and percentage of luminescence obtained by split-luciferase complementation assay after 24 hours in culture medium from 293T cells transfected with ApoE3ch or ApoE3 wild type.

This finding was confirmed using a sensitive split-luciferase complementation assay in which luciferase signal is reconstituted once amyloid forms oligomers,[48] some of the most toxic amyloid species.[49] Full-length ApoE3ch expression in mammalian cells triggered significantly less oligomerization of $A\beta_{42}$ compared to wild type ApoE3, as luciferase luminescence by oligomer formation was significantly reduced in ApoE3ch compared to wild type ApoE3 (FIG. 8). These results provide validation of the genetic analysis and suggest that the protective effects of the ApoEch protein may result, at least in part, from its limited ability to promote $A\beta_{42}$ aggregation. It remains possible that the research participant may have had even greater AB plaque deposition had she survived to her seventies without the APOEch/3ch genotype and that the ApoE3ch protein altered the morphology of AB aggregates in ways that limited downstream neuroinflammation, tau pathology, neurodegeneration and cognitive decline.

A small percentage of Colombian kindred members were found to carry one copy of the APOE3ch mutation,[50] including four PSEN1 E280A mutation carriers who progressed to MCI at the median age of 45. For this reason, it was postulated that APOE3ch homozygosity may be required to dramatically lower the risk and postpone the clinical onset of autosomal dominant AD. Because the sample size was small, it remains possible that APOEch heterozygote individuals may have partial protection against autosomal dominant AD-related cognitive decline and substantial protection against sporadic late onset AD and/or neurodegeneration.

These results suggest that APOE variants differ in the extent of their pathogenic functions (APOEch and APOE2<3<4) and APOE3ch/3ch and APOE2/2 are associated with greatest functional loss. Interventions that safely and sufficiently edit APOE, lower its expression, or inhibit its pathogenic functions could have a profound impact on the treatment and prevention of AD. Interestingly, suppression of APOE expression in brain using an anti-sense oligonucleotide in Aβ-overproducing mice led to altered Aβ plaque morphology and fewer dystrophic neurites.[51] This approach may be feasible because absence of APOE expression was tolerated in a middle-aged man who was homozygous for a frame-shift variant[52] and availability of statins to treat HPL-III support the potential tolerability of ApoE-lowering treatments. See, e.g. Reiman et al. Nat Commun 1191): 667, 2020.

Without wishing to be bound by theory, these results further suggest that homozygosity for APOE3ch—and APOE2—is associated with a profound resistance to the clinical onset of AD; that these genotypes exert their beneficial effects by directly or indirectly limiting downstream tau pathology and neurodegeneration; and that these effects are not based solely on the magnitude of Aβ plaque burden despite relative reductions in ApoE-mediated Aβ aggregation. These findings have implications for APOE's roles in the understanding, treatment, and prevention of AD, and may galvanize interest in developing APOE-modifying genetic and drug therapies for this disorder.

Example 2: Heparin Binding Properties of the APOE3ch Mutant Protein

Materials and Methods

Heparin column protocol: The heparin binding affinity of ApoE2, ApoE3, ApoE3ch and ApoE4 protein isoforms were compared using 1 ml Heparin Columns (Bio Vision-6554-1). The columns were acclimatized to room temperature for 1 hour prior to use. The columns were washed with 5 mL of 20 mM TRIS-HCL (pH7.5). 1 mL sample containing 50 μg/mL of APOE recombinant protein in 20 mM TRIS-HCL (pH7.5) was then recycled through the column 5 times. The column was then washed through 5 times with 20 mM TRIS-HCL (pH7.5). An increasing NaCl gradient (0.025-1M) in 20 mM TRIS-HCL was passed through the column and 1 mL fractions were collected and subsequently prepared for western blotting.

Western blotting: Western Blotting confirmed the elution of ApoE isoforms within fractions collected from the heparin binding columns. Fractions were diluted in 10 μl RIPA buffer (Cell Signaling Technology), 4 μl DTT (1M) and 10 μl Laemmli buffer to a final volume of 40 μl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals), and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences). Individual gels were stitched together to generate FIG. 10.

Heparin plate ELISA protocol: An ELISA was carried out using heparin microplates (Bioworld; 50-197-531). These were blocked for one hour using sample preparation reagent (DY008). Heparin plates were incubated with 0.1 μg/well of each of the recombinant ApoE protein isoforms (ApoE2, ApoE3, ApoE3ch and ApoE4) for 2 hours, the plate was then washed five times in PBS containing a gradient of NaCl (0-0.5M) and then washed three times in the Wash Buffer (DY008). Anti-His tag antibody was incubated overnight at 1:10,000 (Novus biologicals; NBP2-61482). The plate was then washed five times to ensure removal of unbound primary antibody, incubated with donkey anti-rabbit-HRP (1:10000) for 45 minutes, and then washed five times to ensure removal of secondary antibody. Sulfuric acid from the ELISA reagent kit (DY008) was warmed to 37° C. prior to addition of 100 μl of tetramethylbenzidine (Millipore) initiating the detection phase of the reaction. After a 5-mins incubation, sulfuric acid was added to terminate the reaction. The plate was then read using a SPECTRAmax plus 384 (Molecular Devices). The wavelength of the read was 450 nm. For calculating the amount of antigen present in the samples, a standard curve was plotted using Prism 6 (GraphPad Software) based on the serial diluted recombinant Notch3 protein.

Results

Figure 9:
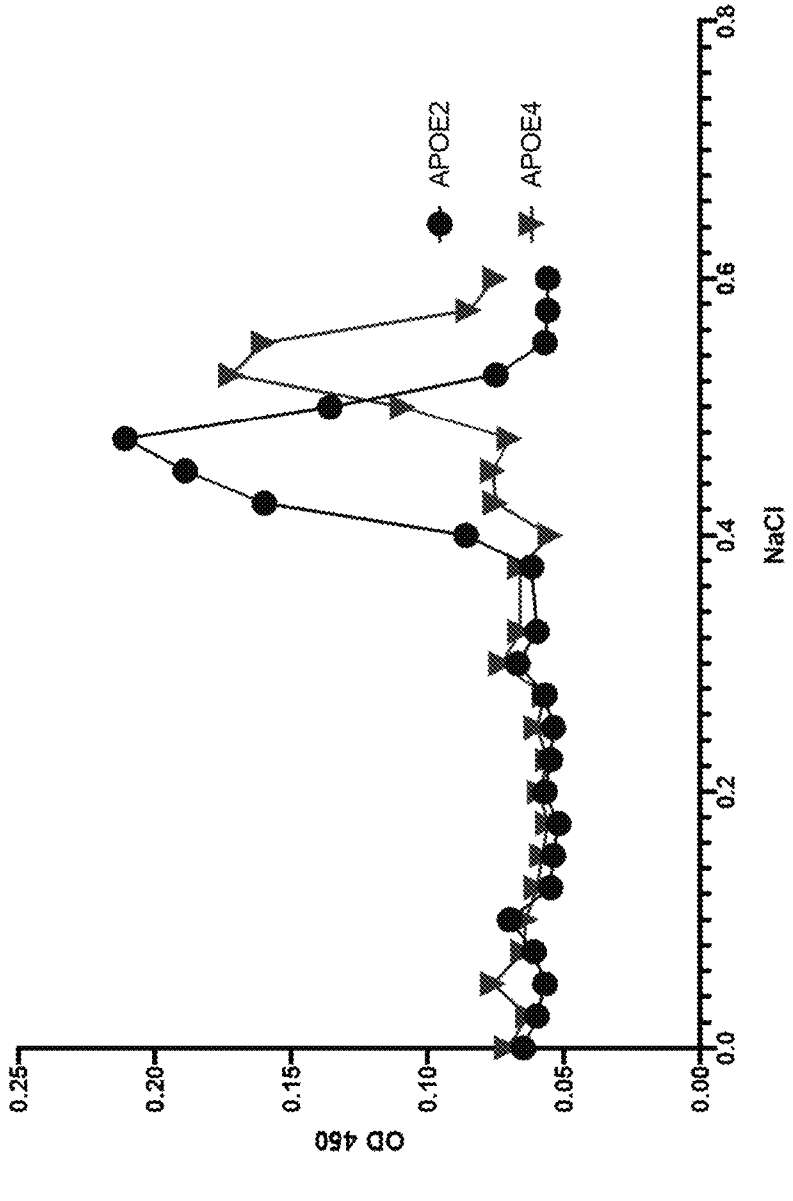
FIG. 9 shows ELISA results of APOE2 and APOE4 heparin-binding affinity.
Figure 10:
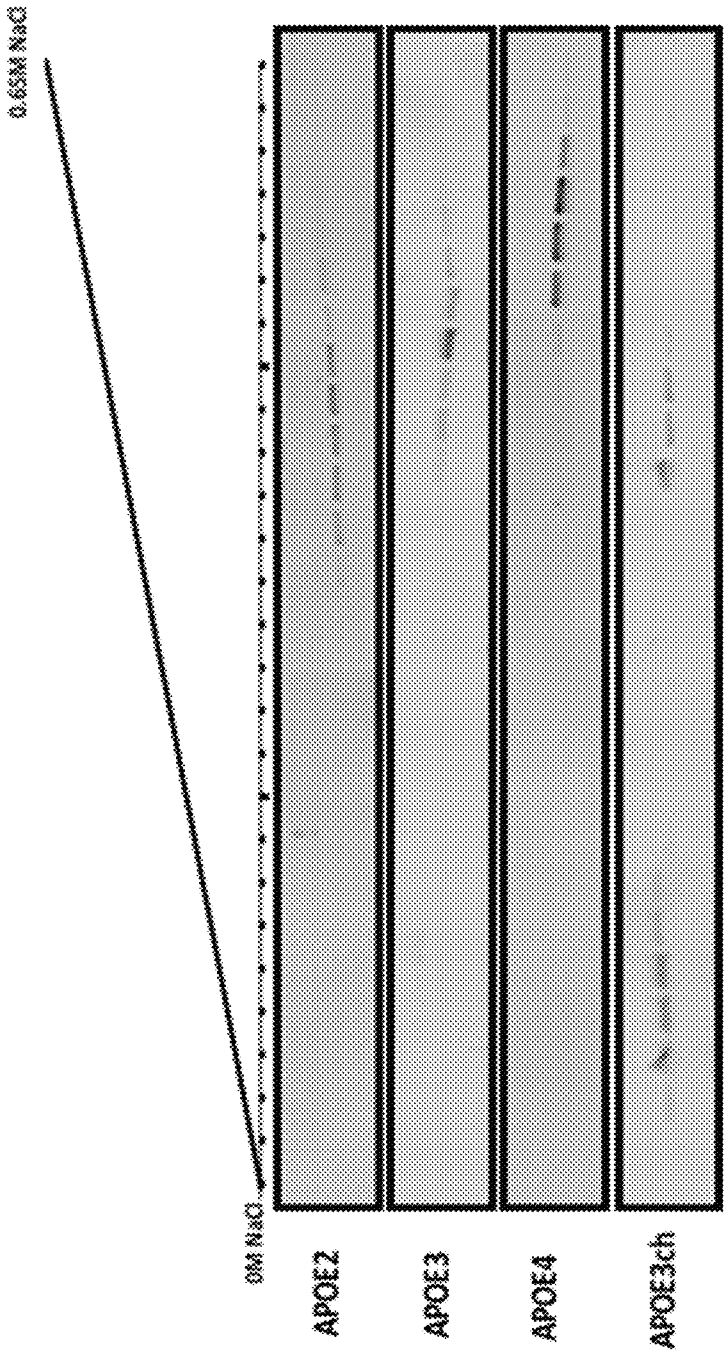
FIG. 10 shows western blot analysis of the heparin-binding affinity of ApoE2, ApoE3, ApoE4 and ApoE3ch.
Figure 11A:
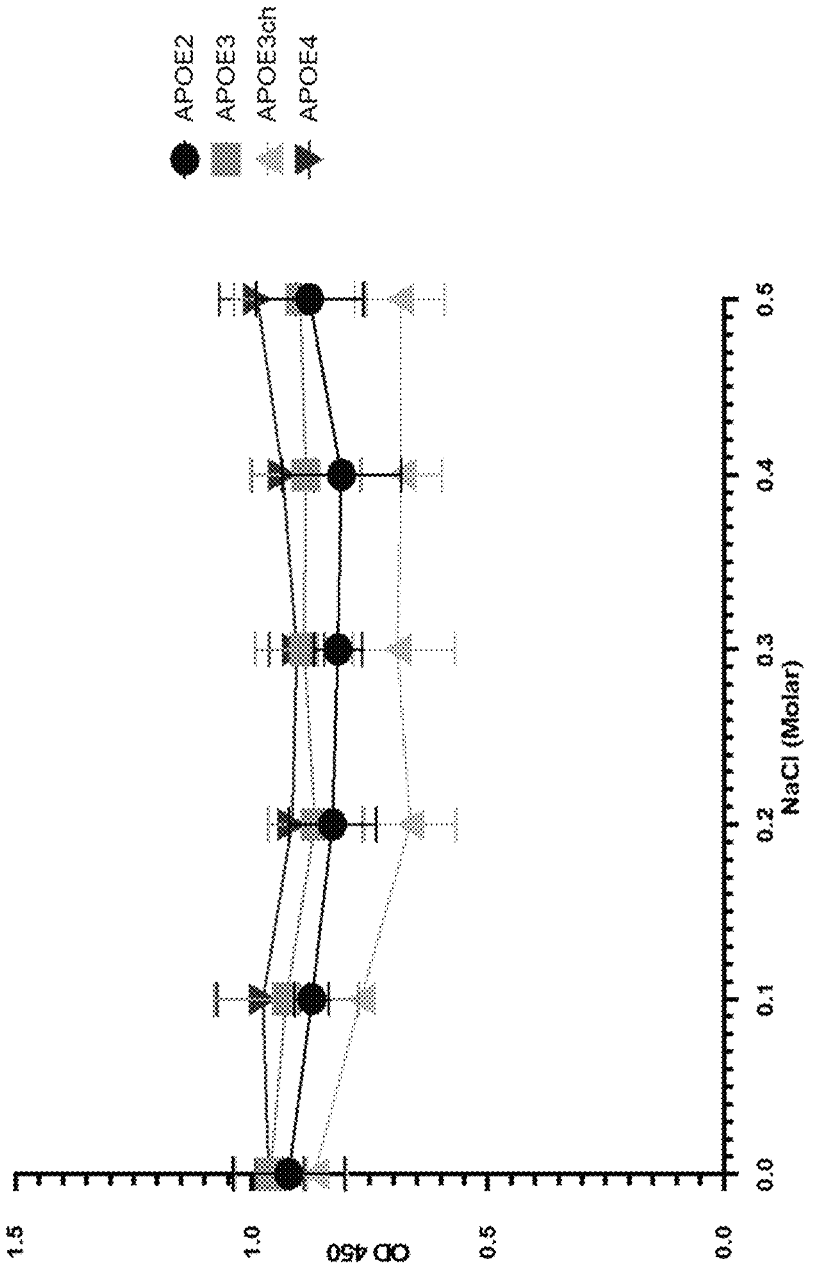
FIGS. 11A and 11B show ELISA results of the heparin-binding affinity of ApoE2, ApoE3, ApoE4 and ApoE3ch.
Figure 11B:
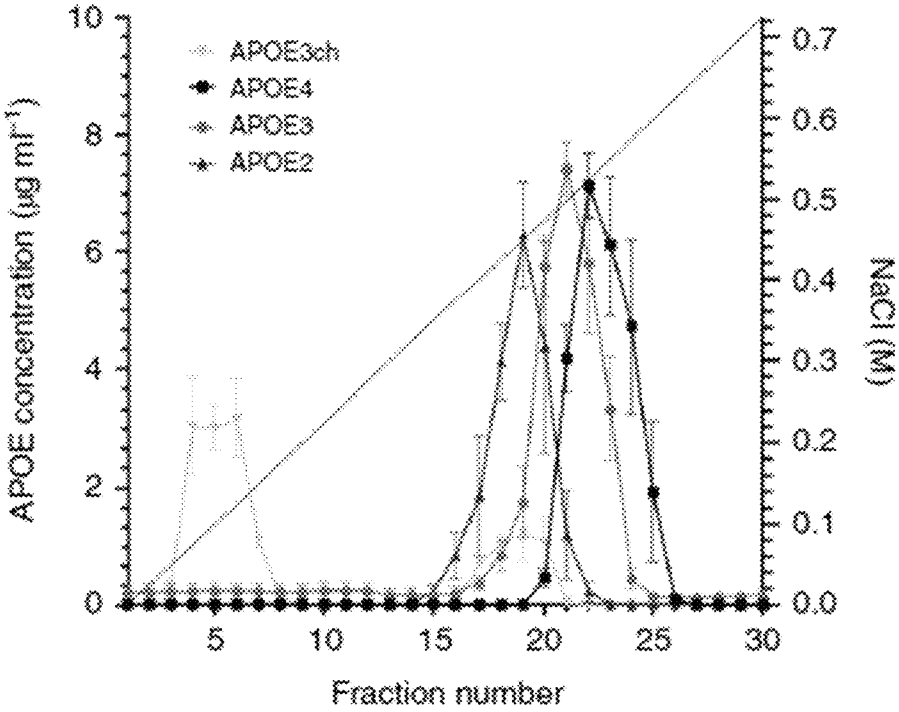

Heparin sulfate proteoglycans (HSPG) moieties are a type of glycosaminoglycans present in hundreds of proteins located in the plasma membrane and in the extracellular matrix. Protein-protein interactions mediated via HSPG play a critical role in a multitude of processes relevant to Alzheimer's pathology including amyloid and tau pathology and neurodegeneration. The ability of various ApoE isoforms, including ApoEch, to bind to heparin, a glycosaminoglycan commonly used to model HSPG-protein interactions, was investigated. Briefly, fractions containing ApoE isoforms ApoE2 and ApoE4 eluted from heparin columns under an increasing NaCl gradient (0-0.65M) were analyzed using ELISA. As shown in FIG. 9, the ApoE variant associated with higher risk of Alzheimer's disease, ApoE4, has higher affinity for heparin compared to the variant ApoE2, which is known to be protective. Next, fractions that contain His-tagged ApoE2, ApoE3, ApoE4 and ApoE3ch which were eluted from heparin columns under an increasing NaCl gradient (0-0.65M) were analyzed using western blot. As shown in FIG. 10, ApoE3ch had impaired heparin binding, which is much lower than that of ApoE2. The affinity of the ApoE isoforms for heparin were also analyzed using the heparin plate ELISA protocol as described in Materials and Methods. As shown in FIGS. 11A-11B, ApoE3ch showed remarkably low level of heparin binding, as ApoE3ch was released from the heparin column at much lower concentrations of NaCl compared to those required for ApoE4 release.

Example 3: Generation of Antibodies Against Wild Type ApoE and ApoEch Mutant Protein Materials and Methods Antibody competition assay: Antibodies were incubated with an ApoE3 recombinant protein (50 ug/ml in 20 mM Tris-HCL) at a 1:10 ratio and incubated for 3 hours at room temperature. A negative control containing the media only, and a positive control containing the recombinant protein ApoE3 only were used. The antibody/ApoE3 recombinant protein solution and controls were passed through heparin columns and exposed to an increasing NaCl gradient (as described in Example 2 above). Fractions were collected and assessed by ELISA and western blotting.

BCA Assay: Fractions collected from the heparin columns were first screened using the bicinchoninic acid assay (BCA assay) (Pierce BCA Protein Assay Kit). The assay was preformed using 200 μl of Reagent A and B Mix and 25 μl of each fraction. The 96 well plate was incubated for 30 minutes at 37° C., and read at 562 nm. The plate was read using Synery 2 microplate reader (BioTek Instrument. Inc) and the Gen5 version1.11 software).

Western Blotting: Western Blotting confirmed the elution of ApoE3 recombinant protein within fractions collected from the heparin binding columns. Fractions were diluted in 10 µl using RIPA buffer (Cell Signaling Technology), 10× (DTT 1M) and 4× Laemmli buffer for a final volume of 40 µl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals) and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences).

ELISA: Antibodies designed against the heparin-binding domain of ApoE were tested for their affinity to ApoE3 and ApoEch mutant recombinant proteins using ELISA. The Ni-NTA HisSorb Plates (Qiagen) were washed 3 times with wash buffer 1 (DY008). The ApoE recombinant proteins were suspended in buffer (DY008) to give a final concentration of 0.5 ug/ml. The plates were incubated with 200 µl of ApoE recombinant proteins for 2 hours, and washed 5 times with 1× wash buffer (DY008). The plates were then incubated with antibodies at a serial dilution of from 1:1,000 to 1:32,000 for overnight at 4° C. The plate was then washed 5 times in 1× wash buffer (DY008), and incubated with anti-mouse HRP (Abcam; ab97046, 1:10,000) for 45 minutes, followed by 5 washes in 1× wash buffer to ensure complete removal of unbound secondary antibody. The sulfuric acid from the ELISA reagent kit (DY008) was warmed to 37° C. 100 µl of tetramethylbenzidine (Millipore) was added to initiate the detection phase of the reaction. After a 5-min incubation, sulfuric acid was added to terminate the reaction. The plate was then read using Synery 2 microplate reader (BioTek Instrument. Inc) and the Gen5 version1.11 software).

Results

Figure 12A:
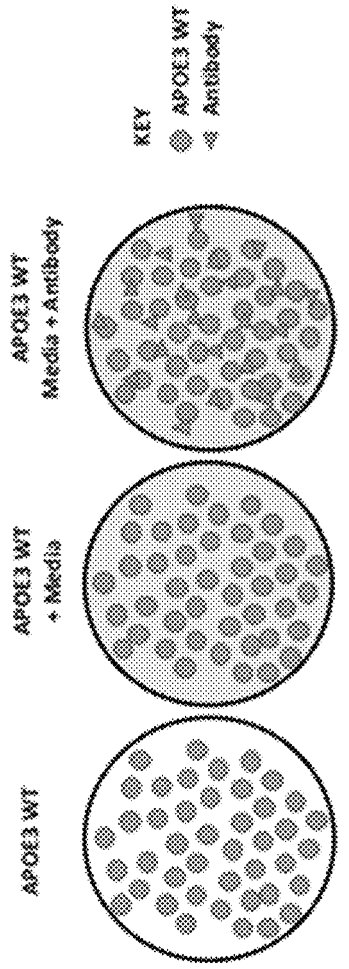
FIG. 12A is a schematic showing the experimental setup for testing the specificity of the monoclonal ApoE3 antibody in blocking ApoE3/heparin binding.
Figure 12B:
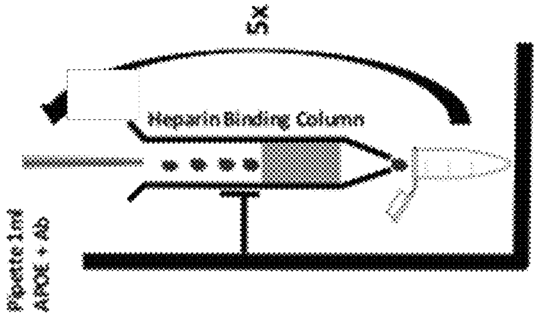
FIGS. 12B and 12C are schematics showing the process of passing the ApoE3 protein pre-incubated with the monoclonal antibody through a heparin binding column followed by washing and eluting.
Figure 12C:
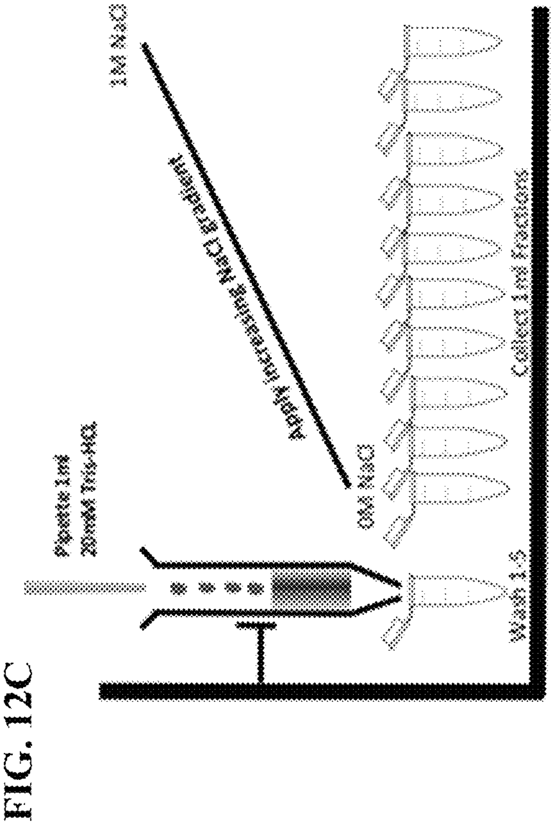

A monoclonal antibody against amino acids 130 to 143 of ApoE was generated and tested for its effect on the binding between full-length ApoE3 protein and heparin. Briefly, full-length wild type ApoE3 protein or those pre-incubated with the monoclonal antibody was passed through a heparin column and recycled five times to ensure maximal ApoE3 binding. The column was then washed five times with 20 mM Tris-HCl (pH=7.5) and exposed to an increasing gradient of NaCl (0 to 1M) in 20 mM Tris-HCl (pH=7.5). The elution from the Tris-HCl washes and from various NaCl concentrations were collected (FIGS. 12A-12C).

Figure 13B:
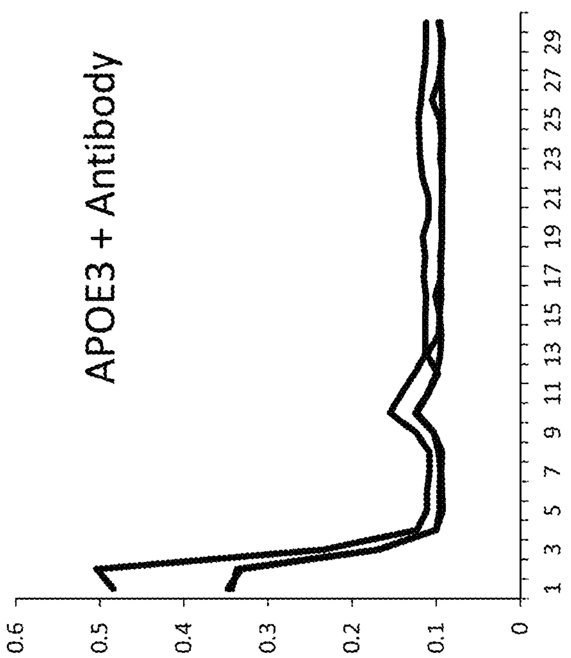
FIGS. 13A-13B show results from BCA assays performed on various fractions from the heparin binding column.
Figure 13A:
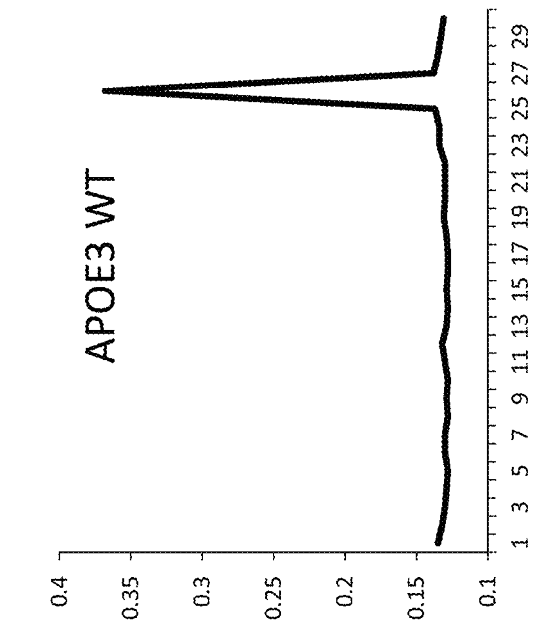
Figure 14:
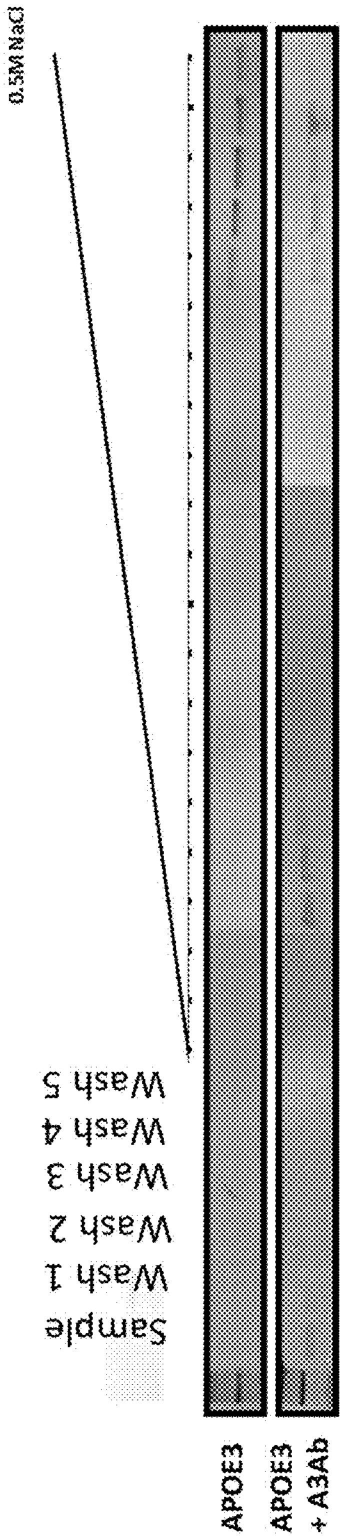
FIG. 14 shows western blot results showing the amount of ApoE3 in various fractions with or without pre-incubation with the monoclonal ApoE3 antibody.

The fractions collected from the column were first screened by the bicinchoninic acid (BCA) assay. As shown in FIG. 13A, protein signal was detected for wild type ApoE3 in fractions to the right of the curve, indicating strong binding of ApoE3 to heparin. In contrast, strong signal was observed in early fractions with low ionic strength when ApoE3 was pre-incubated with the monoclonal antibody (FIG. 13B). To verify the results, western blotting was used to analyze the column washes and NaCl gradient fractions collected from the heparin column. As shown in FIG. 14, pre-incubation of wild type ApoE3 with the monoclonal antibody (A3Ab) (this antibody was named 1343 in Arboleda-Velasquez et al., Nature Medicine, 25, pages 1680-1683 (2019)) reduced its ability to bind to heparin, to a level similar to that of an ApoE3ch mutant protein. Individual gels were stitched together to generate FIG. 14. These results suggest that an antibody may be used to modify the binding properties of ApoE to heparin, thereby preventing or treating Alzheimer's disease or related dementias or neurodegeneration.

Figure 15A:
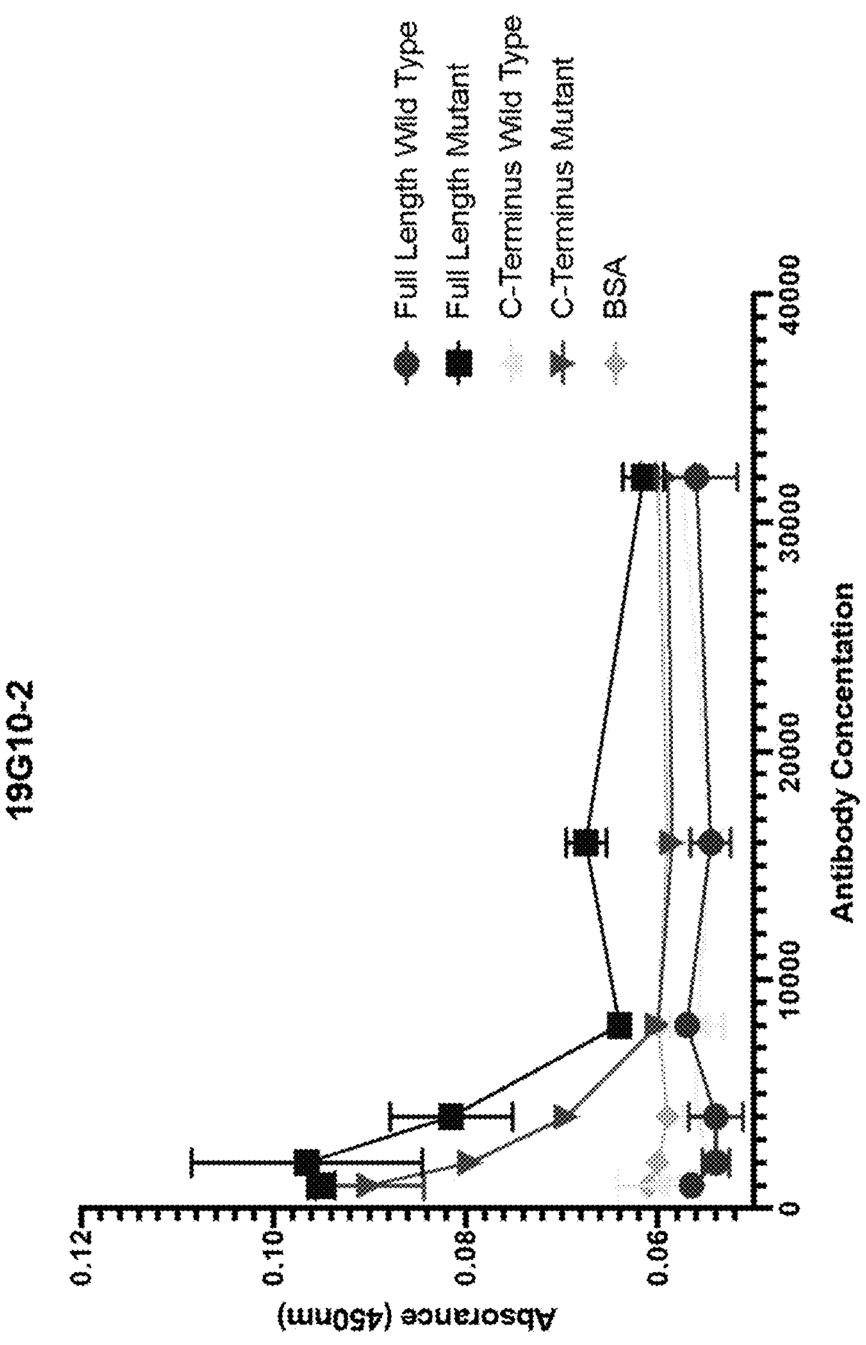
FIGS. 15A-15G show ELISA analysis of the 19G10-2, 23B2, 2H79-1, 30E1-2, 16H8, 25F1-2, and 29G10-1 antibody, respectively.
Figure 15B:
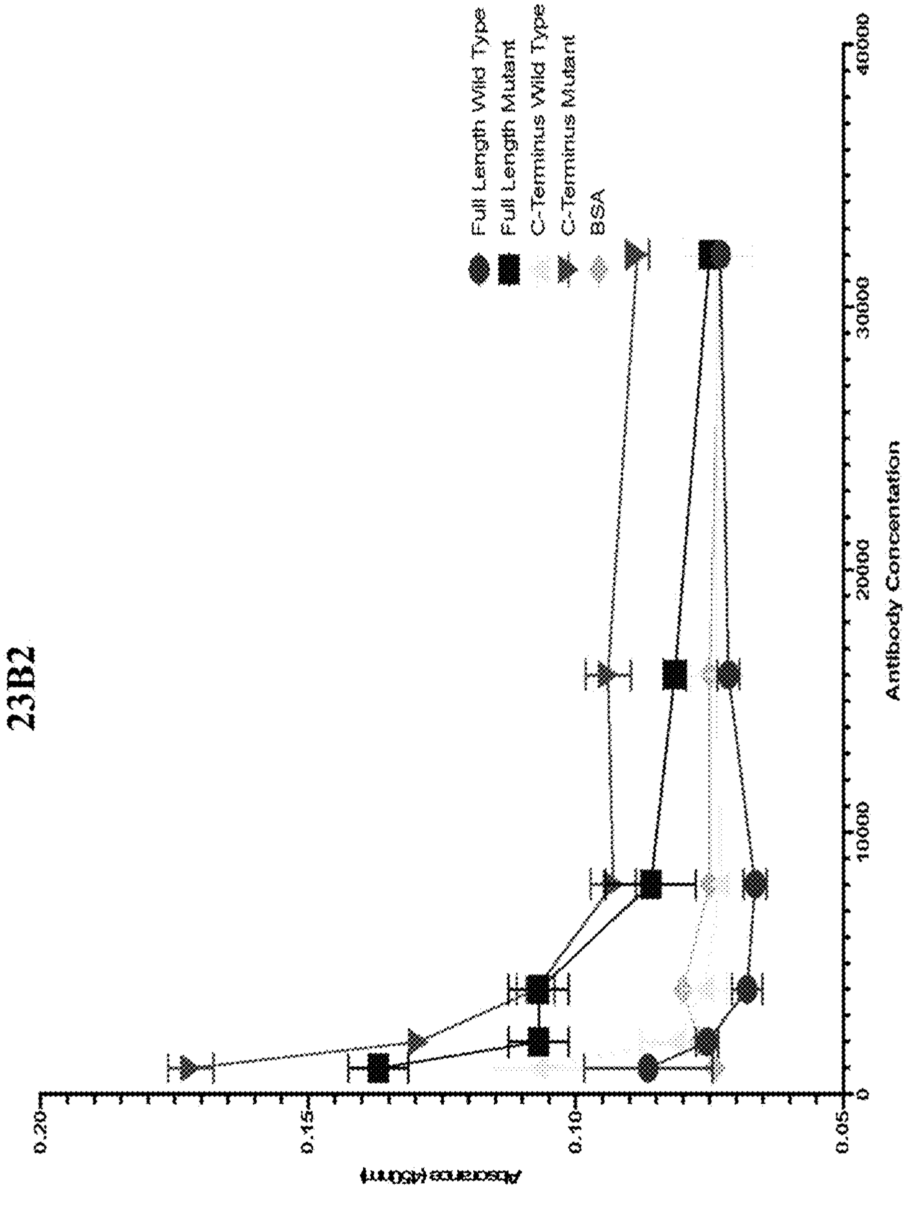
Figure 15C:
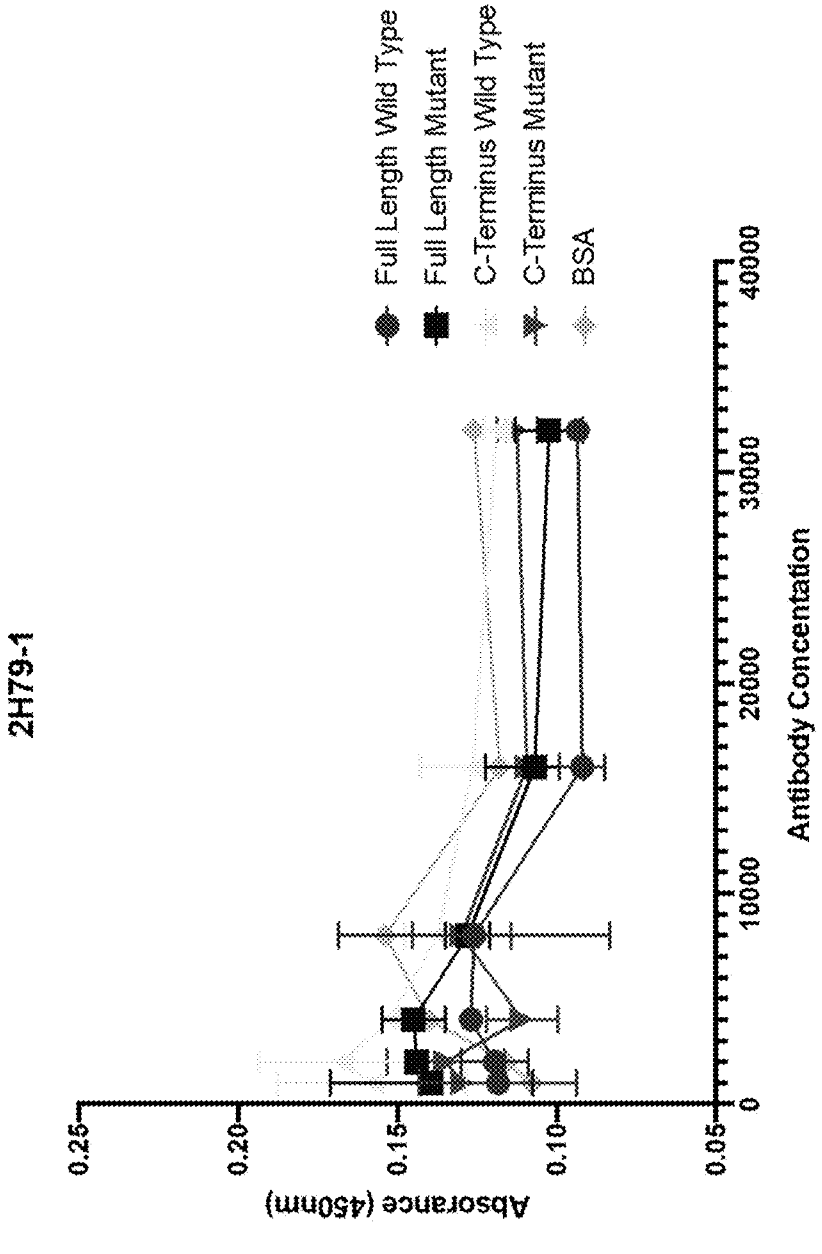
Figure 15D:
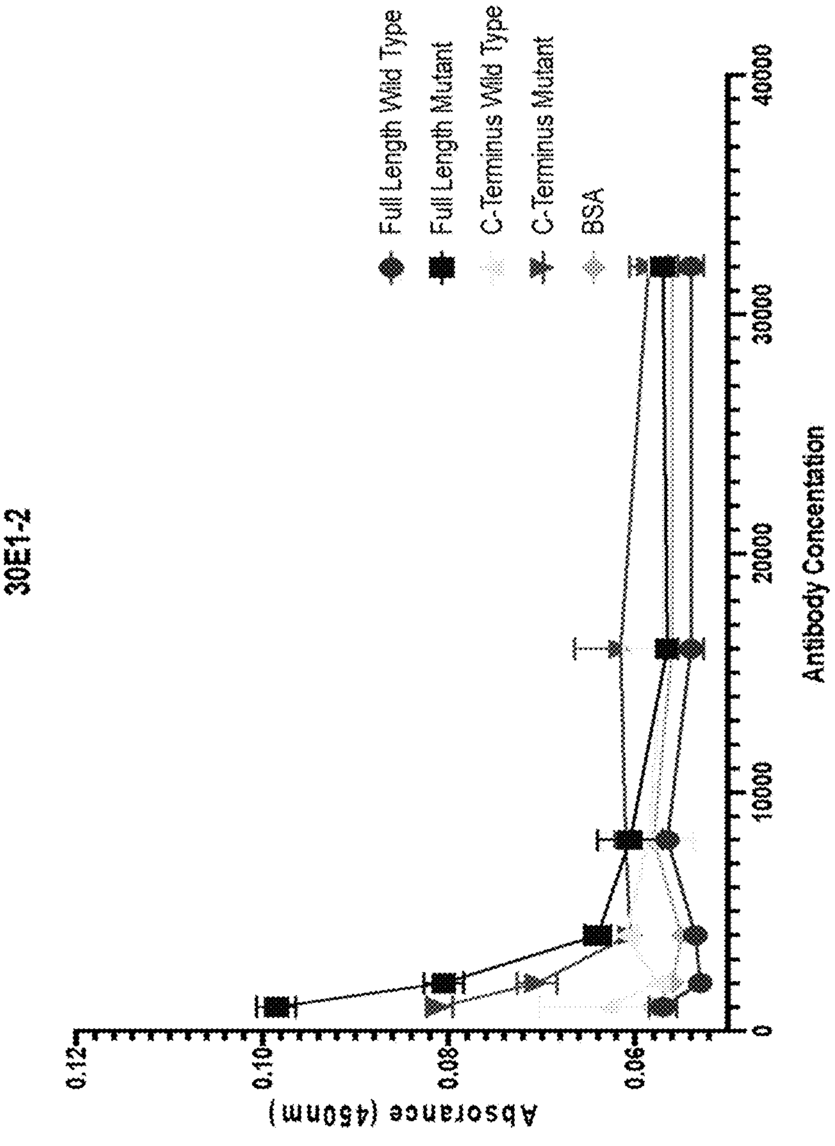
Figure 15E:
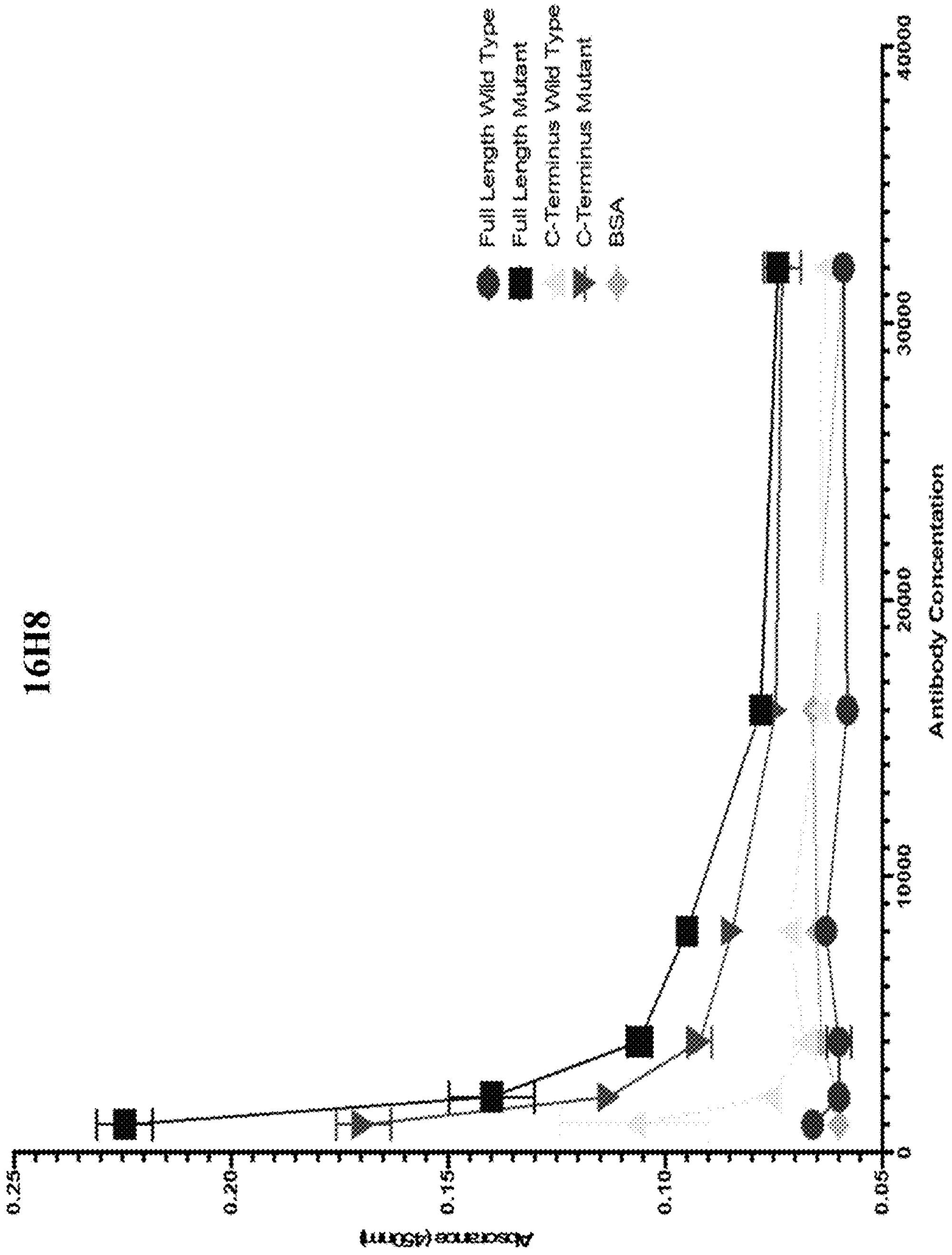
Figure 15F:
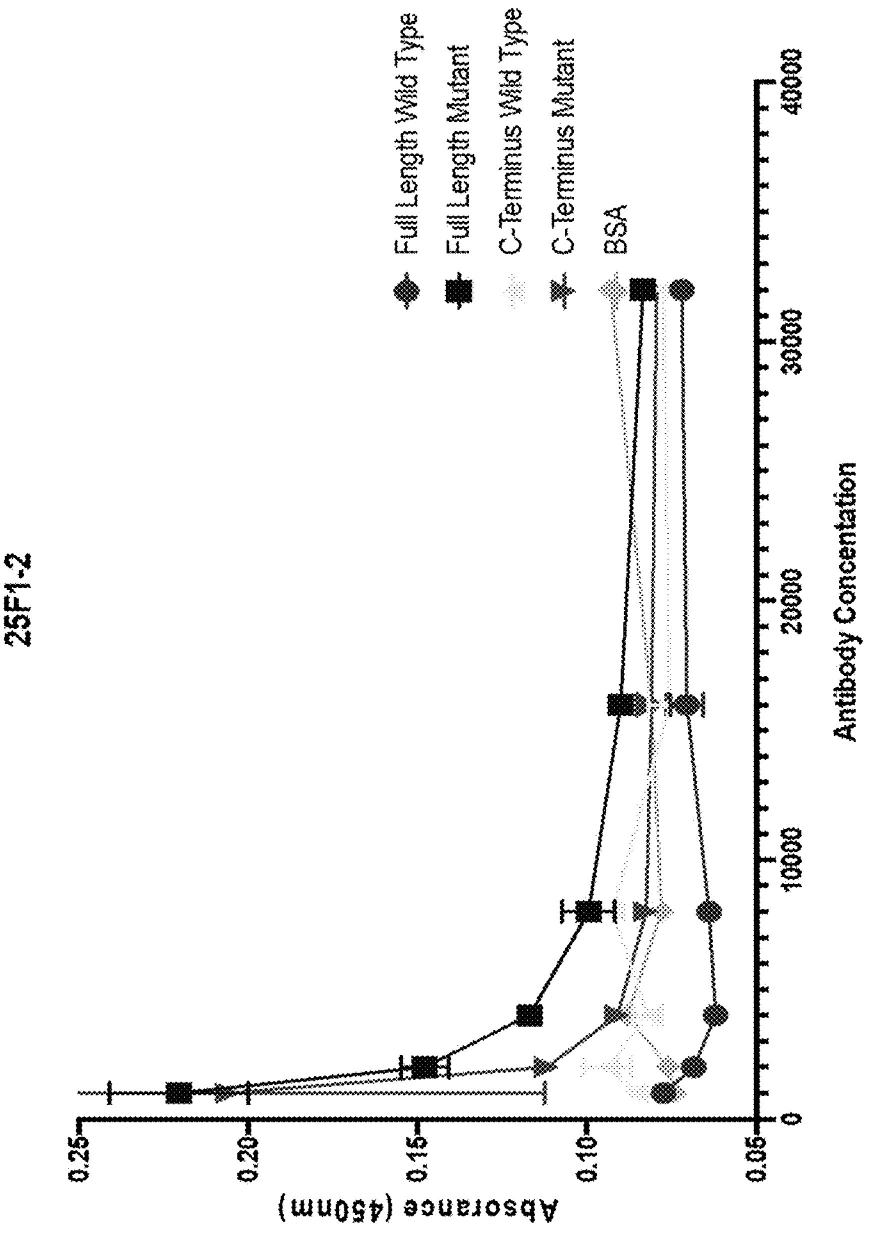
Figure 15G:
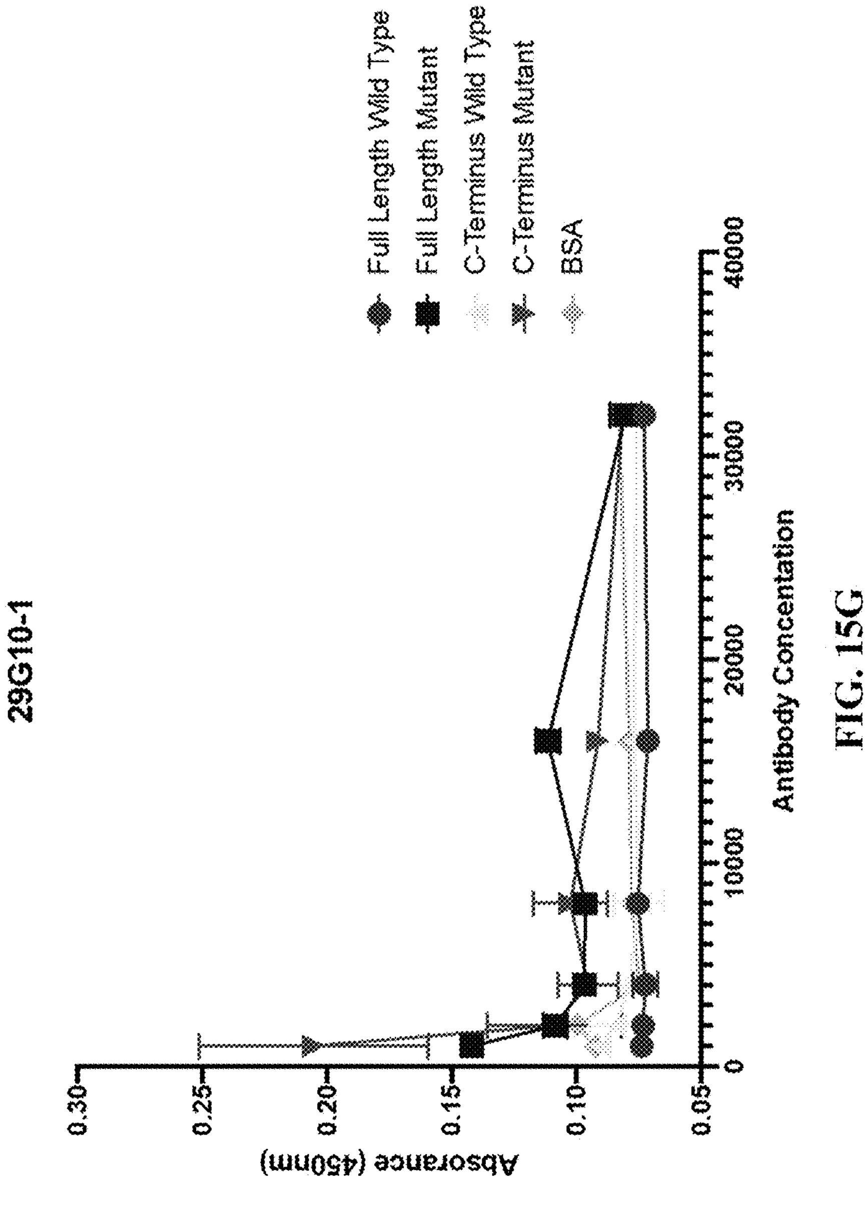

To generate monoclonal antibodies against the heparin-binding domain of ApoE, mice were immunized using the wild type ApoE peptide: KLH-CTEELRVRLASHLRK-$CONH_2$ (SEQ ID NO:54), and the ApoEch peptide: KLH-CTEELRVSLASHLRK-$CONH_2$ (SEQ ID NO:55). A cysteine residue was added at the N-terminus to facilitate conjugation of the peptides. Cell fusions were obtained from positive clones and cell supernatants tested for activity against the wild type and mutant peptides and proteins. Seven antibodies generated were analyzed by ELISA as examples, as described in the materials and methods section. The 19G10-2 antibody serum displayed specificity towards both the full-length and C-terminal of the APOE3ch mutant protein and some interaction with the wild type APOE3 protein (FIG. 15A). The 23B2 antibody displayed reactivity to both the wild type ApoE3 and ApoE3ch mutant C-terminal and full-length recombinant proteins (FIG. 15B). The 2H79-1 antibody displayed non-specific binding to bovine serum albumin (BSA) and showed no affinity for either wild type ApoE3 or ApoE3ch mutant (FIG. 15C). Both the 30E1-2 and 16H8 antibodies showed reactivity to the full-length and C-terminal ApoE3ch mutant proteins and the C-terminal form of wild type ApoE3, but did not react with the full-length wild type APOE3 protein (FIGS. 15D and 15E). The 25F1-2 antibody serum showed high affinity for the full-length and C-terminal ApoE3ch mutant proteins, and appeared to have variable binding to the C-terminus of the wild type ApoE3 protein and some interaction with the full-length wild type ApoE3 protein (FIG. 15F). The 29G10-2 antibody showed high affinity for both the full-length and C-terminal of the ApoE3ch mutant proteins, and also showed reactivity to the C-terminal wild type ApoE3 and BSA. Lastly, the 29G10-2 antibody did not interact with the full-length wild type ApoE3 protein (FIG. 15G).

The variable heavy chain (VH), variable light chain (VL) and complementarity determining region (CDR) sequences of 25F1-2 and 19G10-2 are described herein.

Further, the following parental clones with specificity for wild type ApoE were generated, and the specificity for the wild type ApoE peptide (WT peptide), the wild type ApoE protein (WT protein), the mutant ApoE peptide (ApoEch; Mut peptide) and the mutant ApoE3ch protein (Mut protein) were tested as shown in Table 6. The values indicate levels of absorbance as detected by ELISA. The bolded clones showed specificity for the wild type ApoE peptide (KLH-CTEELRVRLASHLRK-$CONH_2$ (SEQ ID NO:54) and the wild type ApoE protein).

TABLE 6

| | WT peptide | WT protein | Mut peptide | Mut protein |
|---|---|---|---|---|
| 1D5 | 1.742 | 1.086 | 0.060 | 0.062 |
| 1H4 | 2.578 | 2.113 | 0.070 | 0.056 |
| 3A6 | 2.412 | 0.733 | 0.059 | 0.056 |
| 7C3 | 1.698 | 1.245 | 0.064 | 0.051 |
| 7C4 | 2.097 | 0.586 | 0.057 | 0.056 |
| 7C11 | 1.282 | 0.689 | 0.058 | 0.055 |
| 16G6 | 0.739 | 0.449 | 0.076 | 0.067 |
| Pos. ctrl | 1.980 | 1.171 | 0.254 | 0.144 |
| Neg. ctrl | 0.068 | 0.051 | 0.056 | 0.048 |

Example 4: Generation of Fusion Proteins Containing the Heparin-Binding Domain of APOE Materials and Methods Peptide Competition Assay: Wild type ApoE3 and ApoE3ch mutant peptides (50 ug/ml) were incubated with ApoE3 recombinant protein (50 ug/ml prepared in 20 mM Tris-HCL) for 3 hours at room temperature. The peptide/ApoE3 recombinant protein solution were then passed through heparin columns and exposed to an increasing NaCl gradient (as described in Example 2 and 3 above). Fractions were collected and assessed by western blotting.

Western Blotting: Western blotting confirmed the elution of ApoE3 within fractions collected from the heparin binding columns. Fractions were diluted in 10 μl RIPA buffer (Cell Signaling Technology), 10× (DTT 1M) and 4× Laemmli buffer to a final volume of 40 μl. Samples were separated on a 4-20% Mini-PROTEAN® TGX™ Precast Protein Gels (Bio-Rad), transferred to nitrocellulose membranes (VWR; 27376-991), blocked with Odyssey Blocking Buffer (LI-COR Biosciences, Lincoln, NE), and probed with mouse anti-his tag (Novus biologicals) and IRDye 800CW donkey anti-rabbit (LI-COR Biosciences) antibodies. Immunoreactive bands were visualized using the Odyssey Infrared Imaging System and visualized on the Image Studio version 2.1 (LI-COR Biosciences).

Results

Figure 16:
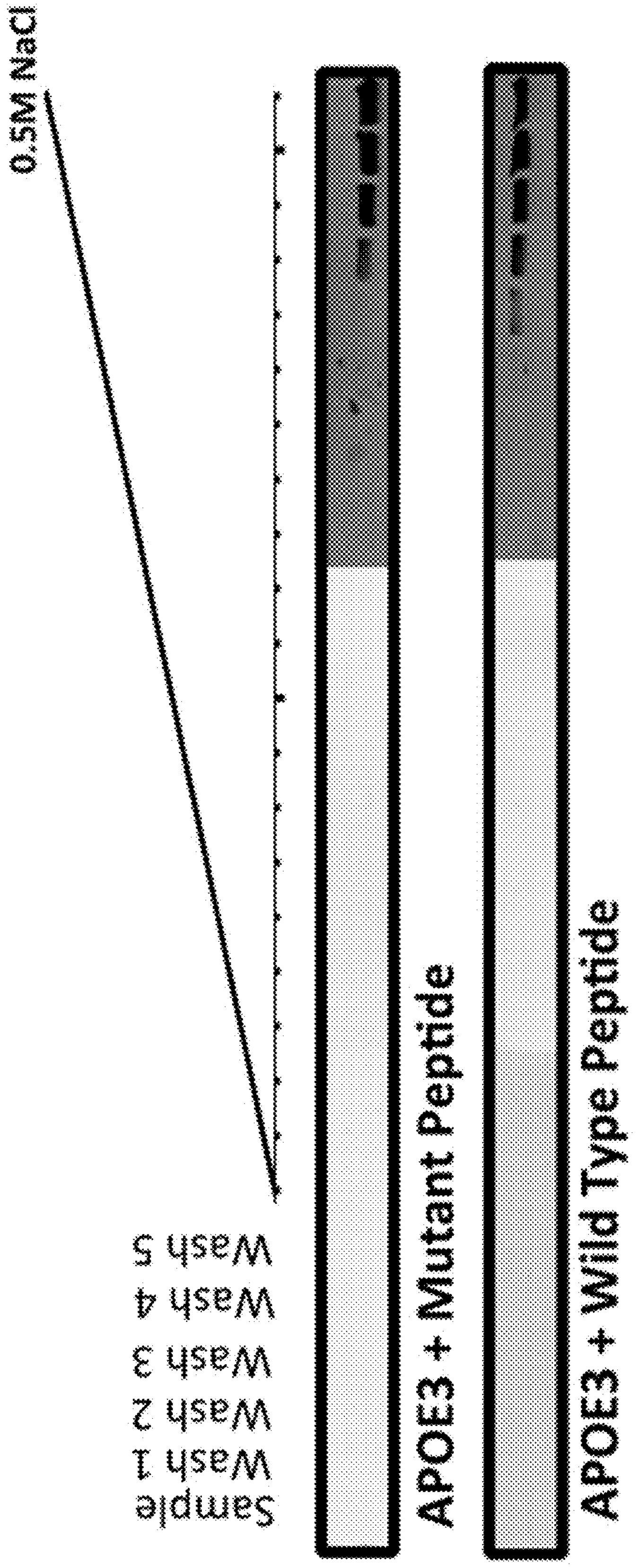
FIG. 16 shows western blot analysis of the heparin-binding affinity of ApoE3 treated with the wild type ApoE3 peptide and the ApoE3ch mutant peptide.

Peptides containing amino acids 130-143 of the wild type ApoE protein and ApoEch mutant protein, respectively, were generated. To examine the effect of these peptides on the binding between wild type ApoE3 recombinant protein and heparin sepharose, a peptide competition assay was carried out as described in materials and methods. As shown in FIG. 16, the wild type ApoE peptide resulted in a one-fraction shift of wild type ApoE3 recombinant protein binding, suggesting that this peptide can compete with wild type full-length ApoE3 for binding to heparin. These results suggest that ApoE fragments containing amino acids 130-143 of the wild type ApoE protein may be used to change the binding properties of ApoE to heparin, thereby preventing or treating Alzheimer's disease or related dementias or neurodegeneration.

To increase protein stability of the peptides, C-terminal and N-terminal fusion proteins containing the heparin-binding domain of human ApoE (wild type and the R136S mutant version) or a site of allosteric modulation of the heparin-binding domain were generated using the backbone Fc IgG2 constructs pfuse-hfc1 and pfcn-hg2 (Invivogen). The human ApoE fragments excluded the sites for APOE2 and APOE4 variants. Administration of ApoE fragments with an R at position 136 may compete with endogenous ApoE for interaction with binding partners including HSPG leading to protection against neurodegeneration. Administration of ApoE fragments with an S at position 136 may bind molecules that do not bind to the wild type ApoE, leading to protection against neurodegeneration. The amino acid sequences for the fragments from the wild type and the R136S mutant ApoE used to generate the fusion proteins are shown below (the R136 position is bolded and double underlined).

Downstream of R136 Fragment

```
WT
                                    (SEQ ID NO: 57)
STEELRVRLASHLRKLRKRLLRDADDLQK
Mutant
                                    (SEQ ID NO: 58)
STEELRVSLASHLRKLRKRLLRDADDLQK
```

Upstream of R136 Fragment

```
WT
                                    (SEQ ID NO: 59)
RLVQYRGEVQAMLGQSTEELRVRLASHLRKL
Mutant
                                    (SEQ ID NO: 60)
RLVQYRGEVQAMLGQSTEELRVSLASHLRKL
```

Figure 17A:
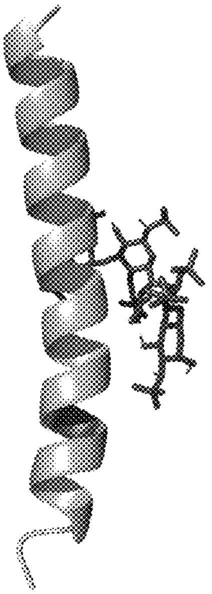
FIGS. 17A-17D show modeling of the interaction of ApoE fragments with heparin.
Figure 17B:
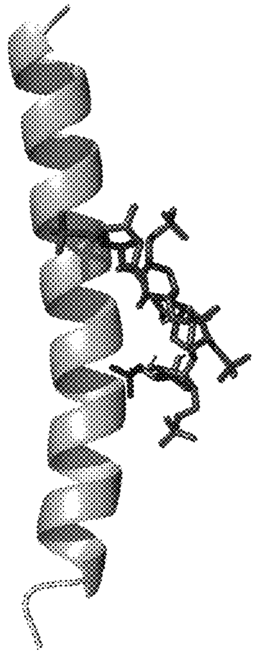
Figure 17C:
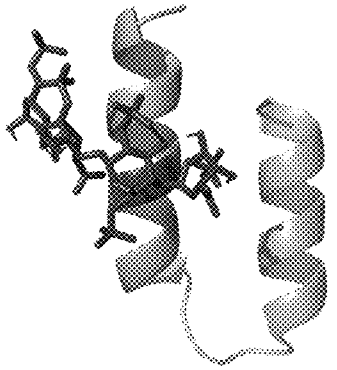
Figure 17D:
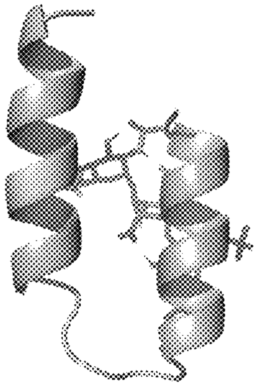

FIGS. 17A-17D show models of the interaction of ApoE fragments with heparin. FIG. 17A shows a model of the wild type ApoE fragment (downstream of R136 fragment, helix) interacting with heparin. FIG. 17B shows a model of the fragment of ApoE R136S (downstream of R136 fragment, helix) interacting with heparin. FIG. 17C shows a model of the wild type ApoE fragment (upstream of R136 fragment, helix) interacting with heparin. FIG. 17D shows a model of the fragment of ApoE R136S (upstream of R136 fragment, helix) interacting with heparin.

The nucleic acid and amino acid sequences for exemplary fusion protein constructs containing either the downstream of R136 fragment or the upstream of R136 fragment are shown below.

```
184Q pfcn-hg2 ApoE 114-144
Nucleic acid sequence
                                                        (SEQ ID NO: 81)
   1 GGATCTGCGA TCGCTCCGGT GCCCGTCAGT GGGCAGAGCG CACATCGCCC ACAGTCCCCG
  61 AGAAGTTGGG GGGAGGGGTC GGCAATTGAA CGGGTGCCTA GAGAAGGTGG CGCGGGGTAA
 121 ACTGGGAAAG TGATGTCGTG TACTGGCTCC GCCTTTTTCC CGAGGGTGGG GGAGAACCGT
 181 ATATAAGTGC AGTAGTCGCC GTGAACGTTC TTTTTCGCAA CGGGTTTGCC GCCAGAACAC
 241 AGCTGAAGCT TCGAGGGGCT CGCATCTCTC CTTCACGCGC CCGCCGCCCT ACCTGAGGCC
 301 GCCATCCACG CCGGTTGAGT CGCGTTCTGC CGCCTCCCGC CTGTGGTGCC TCCTGAACTG
 361 CGTCCGCCGT CTAGGTAAGT TTAAAGCTCA GGTCGAGACC GGGCCTTTGT CCGGCGCTCC
 421 CTTGGAGCCT ACCTAGACTC AGCCGGCTCT CCACGCTTTG CCTGACCCtg cttgctcaac
 481 tctacgTCTT TGTTTCGTTT TCTGTTCTGC GCCGTTACAG ATCCAAGCTG TGACCGGCGC
 541 CTACCTGAGA TCACCGGCGA AGGAGGGCCA CCATGTACAG GATGCAACTC CTGTCTTGCA
 601 TTGCACTAAG TCTTGCACTT GTCACGAATT CGGCACCTCT CGAGCGCAAA TCTAGTGTCG
 661 AGTGCCCACC GTGCCCAGCA CCACCTGTGG CAGGACCGTC AGTCTTCCTC TTCCCCCCAA
 721 AACCCAAGGA CACCCTCATG ATCTCCCGGA CCCCTGAGGT CACGTGCGTG GTGGTGGACG
 781 TGAGCCACGA AGACCCCGAG GTCCAGTTCA ACTGGTACGT GGACGGCGTG GAGGTGCATA
 841 ATGCCAAGAC AAAGCCACGG GAGGAGCAGT TCAACAGCAC GTTCCGTGTG GTCAGCGTCC
 901 TCACCGTTGT GCACCAGGAC TGGCTGAACG GCAAGGAGTA CAAGTGCAAG GTCTCCAACA
 961 AAGGCCTCCC AGCCCCCATC GAGAAAACCA TCTCCAAAAC CAAAGGGCAG CCCCGAGAAC
1021 CACAGGTGTA CACCCTGCCC CCATCCCGGG AGGAGATGAC CAAGAACCAG GTCAGCCTGA
1081 CCTGCCTGGT CAAAGGCTTC TACCCCAGCG ACATCGCCGT GGAGTGGGAG AGCAATGGGC
1141 AGCCGGAGAA CAACTACAAG ACCACGCCTC CCATGCTGGA CTCCGACGGC TCCTTCTTCC
1201 TCTACAGCAA GCTCACCGTG GACAAGAGCA GGTGGCAGCA GGGGAACGTC TTCTCATGCT
1261 CCGTGATGCA TGAGGCTCTG CACAACCACT ACACGCAGAA GAGCCTCTCC CTGTCTCCGG
1321 GTGCACGTAC GCGCCTGGTG CAGTACCGCG GCGAGGTGCA GGCCATGCTC GGCCAGAGCA
```

-continued

1381 CCGAGGAGCT GCGGGTGCGC CTCGCCTCCC ACCTGCGCAA GCTGtgaTAT CTCGAGCTAG
1441 CTGGCCAGAC ATGATAAGAT ACATTGATGA GTTTGGACAA ACCACAACTA GAATGCAGTG
1501 AAAAAAATGC TTTATTTGTG AAATTTGTGA TGCTATTGCT TTATTTGTAA CCATTATAAG
1561 CTGCAATAAA CAAGTTAACA ACAACAATTG CATTCATTTT ATGTTTCAGG TTCAGGGGGA
1621 GGTGTGGGAG GTTTTTTAAA GCAAGTAAAA CCTCTACAAA TGTGGTATGG AATTAATTCT
1681 AAAATACAGC ATAGCAAAAC TTTAACCTCC AAATCAAGCC TCTACTTGAA TCCTTTTCTG
1741 AGGGATGAAT AAGGCATAGG CATCAGGGGC TGTTGCCAAT GTGCATTAGC TGTTTGCAGC
1801 CTCACCTTCT TTCATGGAGT TTAAGATATA GTGTATTTTC CCAAGGTTTG AACTAGCTCT
1861 TCATTTCTTT ATGTTTTAAA TGCACTGACC TCCCACATTC CCTTTTTAGT AAAATATTCA
1921 GAAATAATTT AAATACATCA TTGCAATGAA AATAAATGTT TTTTATTAGG CAGAATCCAG
1981 ATGCTCAAGG CCCTTCATAA TATCCCCCAG TTTAGTAGTT GGACTTAGGG AACAAAGGAA
2041 CCTTTAATAG AAATTGGACA GCAAGAAAGC GAGCTTCTAG CTTATCCTCA GTCCTGCTCC
2101 TCTGCCACAA AGTGCACGCA GTTGCCGGCC GGGTCGCGCA GGGCGAACTC CCGCCCCCAC
2161 GGCTGCTCGC CGATCTCGGT CATGGCCGGC CCGGAGGCGT CCCGGAAGTT CGTGGACACG
2221 ACCTCCGACC ACTCGGCGTA CAGCTCGTCC AGGCCGCGCA CCCACACCCA GGCCAGGGTG
2281 TTGTCCGGCA CCACCTGGTC CTGGACCGCG CTGATGAACA GGGTCACGTC GTCCCGGACC
2341 ACACCGGCGA AGTCGTCCTC CACGAAGTCC CGGGAGAACC CGAGCCGGTC GGTCCAGAAC
2401 TCGACCGCTC CGGCGACGTC GCGCGCGGTG AGCACCGGAA CGGCACTGGT CAACTTGGCC
2461 ATGATGGCTC CTCctgtcag gagaggaaag agaagaaggt tagtacaatt gCTATAGTGA
2521 GTTGTATTAT ACTATGCAGA TATACTATGC CAATGATTAA TTGTCAAACT AGGGCTGCAg
2581 ggttcatagt gccacttttc ctgcactgcc ccatctcctg cccacccttt cccaggcata
2641 gacagtcagt gacttacCAA ACTCACAGGA GGGAGAAGGC AGAAGCTTGA GACAGACCCG
2701 CGGGACCGCC GAACTGCGAG GGGACGTGGC TAGGGCGGCT TCTTTTATGG TGCGCCGGCC
2761 CTCGGAGGCA GGGCGCTCGG GGAGGCCTAG CGGCCAATCT GCGGTGGCAG GAGGCGGGGC
2821 CGAAGGCCGT GCCTGACCAA TCCGGAGCAC ATAGGAGTCT CAGCCCCCCG CCCCAAAGCA
2881 AGGGGAAGTC ACGCGCCTGT AGCGCCAGCG TGTTGTGAAA TGGGGGCTTG GGGGGGTTGG
2941 GGCCCTGACT AGTCAAAACA AACTCCCATT GACGTCAATG GGGTGGAGAC TTGGAAATCC
3001 CCGTGAGTCA AACCGCTATC CACGCCCATT GATGTACTGC CAAAACCGCA TCATCATGGT
3061 AATAGCGATG ACTAATACGT AGATGTACTG CCAAGTAGGA AAGTCCCATA AGGTCATGTA
3121 CTGGGCATAA TGCCAGGCGG GCCATTTACC GTCATTGACG TCAATAGGGG GCGTACTTGG
3181 CATATGATAC ACTTGATGTA CTGCCAAGTG GGCAGTTTAC CGTAAATACT CCACCCATTG
3241 ACGTCAATGG AAAGTCCCTA TTGGCGTTAC TATGGGAACA TACGTCATTA TTGACGTCAA
3301 TGGGCGGGGG TCGTTGGGCG GTCAGCCAGG CGGGCCATTT ACCGTAAGTT ATGTAACGCC
3361 TGCAGGTTAA TTAAGAACAT GTGAGCAAAA GGCCAGCAAA AGGCCAGGAA CCGTAAAAAG
3421 GCCGCGTTGC TGGCGTTTTT CCATAGGCTC CGCCCCCCTG ACGAGCATCA CAAAAATCGA
3481 CGCTCAAGTC AGAGGTGGCG AAACCCGACA GGACTATAAA GATACCAGGC GTTTCCCCCT
3541 GGAAGCTCCC TCGTGCGCTC TCCTGTTCCG ACCCTGCCGC TTACCGGATA CCTGTCCGCC
3601 TTTCTCCCTT CGGGAAGCGT GGCGCTTTCT CATAGCTCAC GCTGTAGGTA TCTCAGTTCG
3661 GTGTAGGTCG TTCGCTCCAA GCTGGGCTGT GTGCACGAAC CCCCCGTTCA GCCCGACCGC
3721 TGCGCCTTAT CCGGTAACTA TCGTCTTGAG TCCAACCCGG TAAGACACGA CTTATCGCCA
3781 CTGGCAGCAG CCACTGGTAA CAGGATTAGC AGAGCGAGGT ATGTAGGCGG TGCTACAGAG
3841 TTCTTGAAGT GGTGGCCTAA CTACGGCTAC ACTAGAAGAA CAGTATTTGG TATCTGCGCT
3901 CTGCTGAAGC CAGTTACCTT CGGAAAAAGA GTTGGTAGCT CTTGATCCGG CAAACAAACC
3961 ACCGCTGGTA GCGGTGGTTT TTTTGTTTGC AAGCAGCAGA TTACGCGCAG AAAAAAAGGA
4021 TCTCAAGAAG ATCCTTTGAT CTTTTCTACG GGGTCTGACG CTCAGTGGAA CGAAAACTCA
4081 CGTTAAGGGA TTTTGGTCAT GGCTAGTTAA TTAACATTTA AATCAGCGGC CGCAATAAAA
4141 TATCTTTATT TTCATTACAT CTGTGTGTTG GTTTTTTGTG TGAATCGTAA CTAACATACG
4201 CTCTCCATCA AAACAAAACG AAACAAAACA AACTAGCAAA ATAGGCTGTC CCCAGTGCAA
4261 GTGCAGGTGC CAGAACATTT CTCTATCGAA Amino acid sequence (SEQ ID NO: 82)

MYRMQLLSCIALSLALVTNSAPLERKSSVECPPCPAPPVAGPSVFLFPP
KPKDTLMISRTPEVTCVVVDVSHEDPEVQFNWYVDGVEVEINAKTKPREEQF
NSTFRVVSVLTVVHQDWLNGKEYKCKVSNKGLPAPIEKTISKTKGQPREPQV
YTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGARTRL
VQYRGEVQAMLGQSTEELRVRLASHLRKL 184R pfcn-hg2 ApoE 114-144 R1365
Nucleic acid sequence (SEQ ID NO: 83)

1 GGATCTGCGA TCGCTCCGGT GCCCGTCAGT GGGCAGAGCG CACATCGCCC ACAGTCCCCG
61 AGAAGTTGGG GGGAGGGGTC GGCAATTGAA CGGGTGCCTA GAGAAGGTGG CGCGGGGTAA
121 ACTGGGAAAG TGATGTCGTG TACTGGCTCC GCCTTTTTCC CGAGGGTGGG GGAGAACCGT
181 ATATAAGTGC AGTAGTCGCC GTGAACGTTC TTTTTCGCAA CGGGTTTGCC GCCAGAACAC
241 AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG
361 CGTCCGCCGT CTAGGTAAGT TTAAAGCTCA GGTCGAGACC GGGCCTTTGT CCGGCGCTCC
421 CTTGGAGCCT ACCTAGACTC AGCCGGCTCT CCACGCTTTG CCTGACCCTg cttgctcaac
481 tctacgTCTT TGTTTCGTTT TCTGTTCTGC GCCGTTACAG ATCCAAGCTG TGACCGGCGC
541 CTACCTGAGA TCACCGGCGA AGGAGGGCCA CCATGTACAG GATGCAACTC CTGTCTTGCA
601 TTGCACTAAG TCTTGCACTT GTCACGAATT CGGCACCTCT CGAGCGCAAA TCTAGTGTCG
661 AGTGCCCACC GTGCCCAGCA CCACCTGTGG CAGGACCGTC AGTCTTCCTC TTCCCCCCAA
721 AACCCAAGGA CACCCTCATG ATCTCCCGGA CCCCTGAGGT CACGTGCGTG GTGGTGGACG
781 TGAGCCACGA AGACCCCGAG GTCCAGTTCA ACTGGTACGT GGACGGCGTG GAGGTGCATA
841 ATGCCAAGAC AAAGCCACGG GAGGAGCAGT TCAACAGCAC GTTCCGTGTG GTCAGCGTCC
901 TCACCGTTGT GCACCAGGAC TGGCTGAACG GCAAGGAGTA CAAGTGCAAG GTCTCCAACA
961 AAGGCCTCCC AGCCCCCATC GAGAAAACCA TCTCCAAAAC CAAAGGGCAG CCCCGAGAAC
1021 CACAGGTGTA CACCCTGCCC CCATCCCGGG AGGAGATGAC CAAGAACCAG GTCAGCCTGA
1081 CCTGCCTGGT CAAAGGCTTC TACCCCAGCG ACATCGCCGT GGAGTGGGAG AGCAATGGGC -continued

```
1141 AGCCGGAGAA CAACTACAAG ACCACGCCTC CCATGCTGGA CTCCGACGGC TCCTTCTTCC
1201 TCTACAGCAA GCTCACCGTG GACAAGAGCA GGTGGCAGCA GGGGAACGTC TTCTCATGCT
1261 CCGTGATGCA TGAGGCTCTG CACAACCACT ACACGCAGAA GAGCCTCTCC CTGTCTCCGG
1321 GTGCACGTAC GCGCCTGGTG CAGTACCGCG GCGAGGTGCA GGCCATGCTC GGCCAGAGCA
1381 CCGAGGAGCT GCGGGTGaGC CTCGCCTCCC ACCTGCGCAA GCTGtgaTAT CTCGAGCTAG
1441 CTGGCCAGAC ATGATAAGAT ACATTGATGA GTTTGGACAA ACCACAACTA GAATGCAGTG
1501 AAAAAAATGC TTTATTTGTG AAATTTGTGA TGCTATTGCT TTATTTGTAA CCATTATAAG
1561 CTGCAATAAA CAAGTTAACA ACAACAATTG CATTCATTTT ATGTTTCAGG TTCAGGGGGA
1621 GGTGTGGGAG GTTTTTTAAA GCAAGTAAAA CCTCTACAAA TGTGGTATGG AATTAATTCT
1681 AAAATACAGC ATAGCAAAAC TTTAACCTCC AAATCAAGCC TCTACTTGAA TCCTTTTCTG
1741 AGGGATGAAT AAGGCATAGG CATCAGGGGC TGTTGCCAAT GTGCATTAGC TGTTTGCAGC
1801 CTCACCTTCT TTCATGGAGT TTAAGATATA GTGTATTTTC CCAAGGTTTG AACTAGCTCT
1861 TCATTTCTTT ATGTTTTAAA TGCACTGACC TCCCACATTC CCTTTTTAGT AAAATATTCA
1921 GAAATAATTT AAATACATCA TTGCAATGAA AATAAATGTT TTTTATTAGG CAGAATCCAG
1981 ATGCTCAAGG CCCTTCATAA TATCCCCCAG TTTAGTAGTT GGACTTAGGG AACAAAGGAA
2041 CCTTTAATAG AAATTGGACA GCAAGAAAGC GAGCTTCTAG CTTATCCTCA GTCCTGCTCC
2101 TCTGCCACAA AGTGCACGCA GTTGCCGGCC GGGTCGCGCA GGGCGAACTC CCGCCCCCAC
2161 GGCTGCTCGC CGATCTCGGT CATGGCCGGC CCGGAGGCGT CCCGGAAGTT CGTGGACACG
2221 ACCTCCGACC ACTCGGCGTA CAGCTCGTCC AGGCCGCGCA CCCACACCCA GGCCAGGGTG
2281 TTGTCCGGCA CCACCTGGTC CTGGACCGCG CTGATGAACA GGGTCACGTC GTCCCGGACC
2341 ACACCGGCGA AGTCGTCCTC CACGAAGTCC CGGGAGAACC CGAGCCGGTC GGTCCAGAAC
2401 TCGACCGCTC CGGCGACGTC GCGCGCGGTG AGCACCGGAA CGGCACTGGT CAACTTGGCC
2461 ATGATGGCTC CTCctgtcag gagaggaaag agaagaaggt tagtacaatt gCTATAGTGA
2521 GTTGTATTAT ACTATGCAGA TATACTATGC CAATGATTAA TTGTCAAACT AGGGCTGCAg
2581 ggttcatagt gccacttttc ctgcactgcc ccatctcctg cccacccttt cccaggcata
2641 gacagtcagt gacttacCAA ACTCACAGGA GGGAGAAGGC AGAAGCTTGA GACAGACCCG
2701 CGGGACCGCC GAACTGCGAG GGGACGTGGC TAGGGCGGCT TCTTTTATGG TGCGCCGGCC
2761 CTCGGAGGCA GGGCGCTCGG GGAGGCCTAG CGGCCAATCT GCGGTGGCAG GAGGCGGGGC
2821 CGAAGGCCGT GCCTGACCAA TCCGGAGCAC ATAGGAGTCT CAGCCCCCCG CCCCAAAGCA
2881 AGGGGAAGTC ACGCGCCTGT AGCGCCAGCG TGTTGTGAAA TGGGGGCTTG GGGGGGTTGG
2941 GGCCCTGACT AGTCAAAACA AACTCCCATT GACGTCAATG GGGTGGAGAC TTGGAAATCC
3001 CCGTGAGTCA AACCGCTATC CACGCCCATT GATGTACTGC CAAAACCGCA TCATCATGGT
3061 AATAGCGATG ACTAATACGT AGATGTACTG CCAAGTAGGA AAGTCCCATA AGGTCATGTA
3121 CTGGGCATAA TGCCAGGCGG GCCATTTACC GTCATTGACG TCAATAGGGG GCGTACTTGG
3181 CATATGATAC ACTTGATGTA CTGCCAAGTG GGCAGTTTAC CGTAAATACT CCACCCATTG
3241 ACGTCAATGG AAAGTCCCTA TTGGCGTTAC TATGGGAACA TACGTCATTA TTGACGTCAA
3301 TGGGCGGGGG TCGTTGGGCG GTCAGCCAGG CGGGCCATTT ACCGTAAGTT ATGTAACGCC
3361 TGCAGGTTAA TTAAGAACAT GTGAGCAAAA GGCCAGCAAA AGGCCAGGAA CCGTAAAAAG
3421 GCCGCGTTGC TGGCGTTTTT CCATAGGCTC CGCCCCCCTG ACGAGCATCA CAAAAATCGA
3481 CGCTCAAGTC AGAGGTGGCG AAACCCGACA GGACTATAAA GATACCAGGC GTTTCCCCCT
3541 GGAAGCTCCC TCGTGCGCTC TCCTGTTCCG ACCCTGCCGC TTACCGGATA CCTGTCCGCC
3601 TTTCTCCCTT CGGGAAGCGT GGCGCTTTCT CATAGCTCAC GCTGTAGGTA TCTCAGTTCG
3661 GTGTAGGTCG TTCGCTCCAA GCTGGGCTGT GTGCACGAAC CCCCCGTTCA GCCCGACCGC
3721 TGCGCCTTAT CCGGTAACTA TCGTCTTGAG TCCAACCCGG TAAGACACGA CTTATCGCCA
3781 CTGGCAGCAG CCACTGGTAA CAGGATTAGC AGAGCGAGGT ATGTAGGCGG TGCTACAGAG
3841 TTCTTGAAGT GGTGGCCTAA CTACGGCTAC ACTAGAAGAA CAGTATTTGG TATCTGCGCT
3901 CTGCTGAAGC CAGTTACCTT CGGAAAAAGA GTTGGTAGCT CTTGATCCGG CAAACAAACC
3961 ACCGCTGGTA GCGGTGGTTT TTTTGTTTGC AAGCAGCAGA TTACGCGCAG AAAAAAAGGA
4021 TCTCAAGAAG ATCCTTTGAT CTTTTCTACG GGGTCTGACG CTCAGTGGAA CGAAAACTCA
4081 CGTTAAGGGA TTTTGGTCAT GGCTAGTTAA TTAACATTTA AATCAGCGGC CGCAATAAAA
4141 TATCTTTATT TTCATTACAT CTGTGTGTTG GTTTTTTGTG TGAATCGTAA CTAACATACG
4201 CTCTCCATCA AAACAAAACG AAACAAAACA AACTAGCAAA ATAGGCTGTC CCCAGTGCAA
4261 GTGCAGGTGC CAGAACATTT CTCTATCGAA
```

Amino acid sequence (SEQ ID NO: 84)

```
MYRMQLLSCIALSLALVTNSAPLERKSSVECPPCPAPPVAGPSVFLFPP
KPKDTLMISRTPEVTCVVVDVSHEDPEVQFNWYVDGVEVEINAKTKPREEQF
NSTFRVVSVLTVVHQDWLNGKEYKCKVSNKGLPAPIEKTISKTKGQPREPQV
YTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGARTRL
VQYRGEVQAMLGQSTEELRVSLASHLRKL
```

197F pfuse hfc2 ApoE 114-144
Nucleic acid sequence (SEQ ID NO: 85)

```
  1 GGATCTGCGA TCGCTCCGGT GCCCGTCAGT GGGCAGAGCG CACATCGCCC ACAGTCCCCG
 61 AGAAGTTGGG GGGAGGGGTC GGCAATTGAA CGGGTGCCTA GAGAAGGTGG CGCGGGGTAA
121 ACTGGGAAAG TGATGTCGTG TACTGGCTCC GCCTTTTTCC CGAGGGTGGG GGAGAACCGT
181 ATATAAGTGC AGTAGTCGCC GTGAACGTTC TTTTTCGCAA CGGGTTTGCC GCCAGAACAC
241 AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG
361 CGTCCGCCGT CTAGGTAAGT TTAAAGCTCA GGTCGAGACC GGGCCTTTGT CCGGCGCTCC
421 CTTGGAGCCT ACCTAGACTC AGCCGGCTCT CCACGCTTTG CCTGACCCTG CTTGCTCAAC
481 TCTACGTCTT TGTTTCGTTT TCTGTTCTGC GCCGTTACAG ATCCAAGCTG TGACCGGCGC
541 CTACCTGAGA TCAccggcGA AGGAGGGCCA CCATGTACAG GATGCAACTC CTGTCTTGCA
601 TTGCACTAAG TCTTGCACTT GTCACGAATT CGATaCGCCT GGTGCAGTAC CGCGGCGAGG
661 TGCAGGCCAT GCTCGGCCAG AGtACtGAGG AGCTGCGGGT GCGCCTCGCC TCCCACCTGC
721 GCAAGCTGat ATCGGCCATG GTTAGATCTG TGGAGTGCCC ACCTTGCCCA GCACCACCTG
781 TGGCAGGACC TTCAGTCTTC CTCTTCCCCC CAAAACCCAA GGACACCCTG ATGATCTCCA
841 GAACCCCTGA GGTCACGTGC GTGGTGGTGG ACGTGAGCCA CGAAGACCCC GAGGTCCAGT
```

-continued

```
 901 TCAACTGGTA CGTGGACGGC ATGGAGGTGC ATAATGCCAA GACAAAGCCA CGGGAGGAGC
 961 AGTTCAACAG CACGTTCCGT GTGGTCAGCG TCCTCACCGT CGTGCACCAG GACTGGCTGA
1021 ACGGCAAGGA GTACAAGTGC AAGGTCTCCA ACAAAGGCCT CCCAGCCCCC ATCGAGAAAA
1081 CCATCTCCAA AACCAAAGGG CAGCCCCGAG AACCACAGGT GTACACCCTG CCCCCATCCC
1141 GGGAGGAGAT GACCAAGAAC CAGGTCAGCC TGACCTGCCT GGTCAAAGGC TTCTACCCCA
1201 GCGACATCGC CGTGGAGTGG GAGAGCAATG GGCAGCCGGA GAACAACTAC AAGACCACAC
1261 CTCCCATGCT GGACTCCGAC GGCTCCTTCT TCCTCTACAG CAAGCTCACC GTGGACAAGA
1321 GCAGGTGGCA GCAGGGGAAC GTCTTCTCAT GCTCCGTGAT GCATGAGGCT CTGCACAACC
1381 ACTACACACA GAAGAGCCTC TCCCTGTCTC CGGGTAAATG AgtgccacgG CTAGCTGGCC
1441 AGACATGATA AGATACATTG ATGAGTTTGG ACAAACCACA ACTAGAATGC AGTGAAAAAA
1501 ATGCTTTATT TGTGAAATTT GTGATGCTAT TGCTTTATTT GTAACCATTA TAAGCTGCAA
1561 TAAACAAGTT AACAACAACA ATTGCATTCA TTTTATGTTT CAGGTTCAGG GGGAGGTGTG
1621 GGAGGTTTTT TAAAGCAAGT AAAACCTCTA CAAATGTGGT ATGGAATTAA TTCTAAAATA
1681 CAGCATAGCA AAACTTTAAC CTCCAAATCA AGCCTCTACT TGAATCCTTT TCTGAGGGAT
1741 GAATAAGGCA TAGGCATCAG GGGCTGTTGC CAATGTGCAT TAGCTGTTTG CAGCCTCACC
1801 TTCTTTCATG GAGTTTAAGA TATAGTGTAT TTTCCCAAGG TTTGAACTAG CTCTTCATTT
1861 CTTTATGTTT TAAATGCACT GACCTCCCAC ATTCCCTTTT TAGTAAAATA TTCAGAAATA
1921 ATTTAAATAC ATCATTGCAA TGAAAATAAA TGTTTTTTAT TAGGCAGAAT CCAGATGCTC
1981 AAGGCCCTTC ATAATATCCC CCAGTTTAGT AGTTGGACTT AGGGAACAAA GGAACCTTTA
2041 ATAGAAATTG GACAGCAAGA AAGCGAGCTT CTAGCTTATC CTCAGTCCTG CTCCTCTGCC
2101 ACAAAGTGCA CGCAGTTGCC GGCCGGGTCG CGCAGGGCGA ACTCCCGCCC CCACGGCTGC
2161 TCGCCGATCT CGGTCATGGC CGGCCCGGAG GCGTCCCGGA AGTTCGTGGA CACGACCTCC
2221 GACCACTCGG CGTACAGCTC GTCCAGGCCG CGCACCCACA CCCAGGCCAG GGTGTTGTCC
2281 GGCACCACCT GGTCCTGGAC CGCGCTGATG AACAGGGTCA CGTCGTCCCG GACCACACCG
2341 GCGAAGTCGT CCTCCACGAA GTCCCGGGAG AACCCGAGCC GGTCGGTCCA GAACTCGACC
2401 GCTCCGGCGA CGTCGCGCGC GGTGAGCACC GGAACGGCAC TGGTCAACTT GGCCATGATG
2461 GCTCCTCctg tcaggagagg aaagagaaga aggttagtac aattgCTATA GTGAGTTGTA
2521 TTATACTATG CAGATATACT ATGCCAATGA TTAATTGTCA AACTAGGGCT GCAgggttca
2581 tagtgccact tttcctgcac tgccccatct cctgcccacc ctttcccagg catagacagt
2641 cagtgactta cCAAACTCAC AGGAGGGAGA AGGCAGAAGC TTGAGACAGA CCCGCGGGAC
2701 CGCCGAACTG CGAGGGGACG TGGCTAGGGC GGCTTCTTTT ATGGTGCGCC GGCCCTCGGA
2761 GGCAGGGCGC TCGGGGAGGC CTAGCGGCCA ATCTGCGGTG GCAGGAGGCG GGGCCGAAGG
2821 CCGTGCCTGA CCAATCCGGA GCACATAGGA GTCTCAGCCC CCCGCCCCAA AGCAAGGGGA
2881 AGTCACGCGC CTGTAGCGCC AGCGTGTTGT GAAATGGGGG CTTGGGGGGG TTGGGGCCCT
2941 GACTAGTCAA AACAAACTCC CATTGACGTC AATGGGGTGG AGACTTGGAA ATCCCCGTGA
3001 GTCAAACCGC TATCCACGCC CATTGATGTA CTGCCAAAAC CGCATCATCA TGGTAATAGC
3061 GATGACTAAT ACGTAGATGT ACTGCCAAGT AGGAAAGTCC CATAAGGTCA TGTACTGGGC
3121 ATAATGCCAG GCGGGCCATT TACCGTCATT GACGTCAATA GGGGGCGTAC TTGGCATATG
3181 ATACACTTGA TGTACTGCCA AGTGGGCAGT TTACCGTAAA TACTCCACCC ATTGACGTCA
3241 ATGGAAAGTC CCTATTGGCG TTACTATGGG AACATACGTC ATTATTGACG TCAATGGGCG
3301 GGGGTCGTTG GGCGGTCAGC CAGGCGGGCC ATTTACCGTA AGTTATGTAA CGCCTGCAGG
3361 TTAATTAAGA ACATGTGAGC AAAAGGCCAG CAAAAGGCCA GGAACCGTAA AAAGGCCGCG
3421 TTGCTGGCGT TTTTCCATAG GCTCCGCCCC CCTGACGAGC ATCACAAAAA TCGACGCTCA
3481 AGTCAGAGGT GGCGAAACCC GACAGGACTA TAAAGATACC AGGCGTTTCC CCCTGGAAGC
3541 TCCCTCGTGC GCTCTCCTGT TCCGACCCTG CCGCTTACCG GATACCTGTC CGCCTTTCTC
3601 CCTTCGGGAA GCGTGGCGCT TTCTCATAGC TCACGCTGTA GGTATCTCAG TTCGGTGTAG
3661 GTCGTTCGCT CCAAGCTGGG CTGTGTGCAC GAACCCCCCG TTCAGCCCGA CCGCTGCGCC
3721 TTATCCGGTA ACTATCGTCT TGAGTCCAAC CCGGTAAGAC ACGACTTATC GCCACTGGCA
3781 GCAGCCACTG GTAACAGGAT TAGCAGAGCG AGGTATGTAG GCGGTGCTAC AGAGTTCTTG
3841 AAGTGGTGGC CTAACTACGG CTACACTAGA AGAACAGTAT TTGGTATCTG CGCTCTGCTG
3901 AAGCCAGTTA CCTTCGGAAA AAGAGTTGGT AGCTCTTGAT CCGGCAAACA AACCACCGCT
3961 GGTAGCGGTG GTTTTTTTGT TTGCAAGCAG CAGATTACGC GCAGAAAAAA AGGATCTCAA
4021 GAAGATCCTT TGATCTTTTC TACGGGGTCT GACGCTCAGT GGAACGAAAA CTCACGTTAA
4081 GGGATTTTGG TCATGGCTAG TTAATTAACA TTTAAATCAG CGGCCGCAAT AAAATATCTT
4141 TATTTTCATT ACATCTGTGT GTTGGTTTTT TGTGTGAATC GTAACTAACA TACGCTCTCC
4201 ATCAAAACAA AACGAAACAA AACAAACTAG CAAAATAGGC TGTCCCCAGT GCAAGTGCAG
4261 GTGCCAGAAC ATTTCTCTAT CGAA
```

Amino acid sequence (SEQ ID NO: 86)

```
MYRMQLLSCIALSLALVTNSIRLVQYRGEVQAMLGQSTEELRVRLAS
HLRKLISAMVRSVECPPCPAPPVAGPSVFLFPPKPKDTLMISRTPEVTCVVVDV
SHEDPEVQFNWYVDGMEVEINAKTKPREEQFNSTFRVVSVLTVVHQDWLNG
KEYKCKVSNKGLPAPIEKTISKTKGQPREPQVYTLPPSREEMTKNQVSLTCLV
KGFYPSDIAVEWESNGQPENNYKTTPPMLDSDGSFFLYSKLTVDKSRWQQGN
VFSCSVMHEALHNHYTQKSLSLSPGK
```

197G pfuse-hfc2 ApoE 114-144 R136S

Nucleic acid sequence (SEQ ID NO: 87)

```
  1 GGATCTGCGA TCGCTCCGGT GCCCGTCAGT GGGCAGAGCG CACATCGCCC ACAGTCCCCG
 61 AGAAGTTGGG GGGAGGGGTC GGCAATTGAA CGGGTGCCTA GAGAAGGTGG CGCGGGGTAA
121 ACTGGGAAAG TGATGTCGTG TACTGGCTCC GCCTTTTTCC CGAGGGTGGG GGAGAACCGT
181 ATATAAGTGC AGTAGTCGCC GTGAACGTTC TTTTTCGCAA CGGGTTTGCC GCCAGAACAC
241 AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG
361 CGTCCGCCGT CTAGGTAAGT TTAAAGCTCA GGTCGAGACC GGGCCTTTGT CCGGCGCTCC
421 CTTGGAGCCT ACCTAGACTC AGCCGGCTCT CCACGCTTTG CCTGACCCTG CTTGCTCAAC
481 TCTACGTCTT TGTTTCGTTT TCTGTTCTGC GCCGTTACAG ATCCAAGCTG TGACCGGCGC
541 CTACCTGAGA TCAccggcGA AGGAGGGCCA CCATGTACAG GATGCAACTC CTGTCTTGCA
601 TTGCACTAAG TCTTGCACTT GTCACGAATT CGATaCGCCT GGTGCAGTAC CGCGGCGAGG
```

-continued

```
 661 TGCAGGCCAT GCTCGGCCAG AGtActGAGG AGCTGCGGGT GaGCCTCGCC TCCCACCTGC
 721 GCAAGCTGat ATCGGCCATG GTTAGATCTG TGGAGTGCCC ACCTTGCCCA GCACCACCTG
 781 TGGCAGGACC TTCAGTCTTC CTCTTCCCCC CAAAACCCAA GGACACCCTG ATGATCTCCA
 841 GAACCCCTGA GGTCACGTGC GTGGTGGTGG ACGTGAGCCA CGAAGACCCC GAGGTCCAGT
 901 TCAACTGGTA CGTGGACGGC ATGGAGGTGC ATAATGCCAA GACAAAGCCA CGGGAGGAGC
 961 AGTTCAACAG CACGTTCCGT GTGGTCAGCG TCCTCACCGT CGTGCACCAG GACTGGCTGA
1021 ACGGCAAGGA GTACAAGTGC AAGGTCTCCA ACAAAGGCCT CCCAGCCCCC ATCGAGAAAA
1081 CCATCTCCAA AACCAAAGGG CAGCCCCGAG AACCACAGGT GTACACCCTG CCCCCATCCC
1141 GGGAGGAGAT GACCAAGAAC CAGGTCAGCC TGACCTGCCT GGTCAAAGGC TTCTACCCCA
1201 GCGACATCGC CGTGGAGTGG GAGAGCAATG GGCAGCCGGA GAACAACTAC AAGACCACAC
1261 CTCCCATGCT GGACTCCGAC GGCTCCTTCT TCCTCTACAG CAAGCTCACC GTGGACAAGA
1321 GCAGGTGGCA GCAGGGGAAC GTCTTCTCAT GCTCCGTGAT GCATGAGGCT CTGCACAACC
1381 ACTACACACA GAAGAGCCTC TCCCTGTCTC CGGGTAAATG AgtgccacgG CTAGCTGGCC
1441 AGACATGATA AGATACATTG ATGAGTTTGG ACAAACCACA ACTAGAATGC AGTGAAAAAA
1501 ATGCTTTATT TGTGAAATTT GTGATGCTAT TGCTTTATTT GTAACCATTA TAAGCTGCAA
1561 TAAACAAGTT AACAACAACA ATTGCATTCA TTTTATGTTT CAGGTTCAGG GGGAGGTGTG
1621 GGAGGTTTTT TAAAGCAAGT AAAACCTCTA CAAATGTGGT ATGGAATTAA TTCTAAAATA
1681 CAGCATAGCA AAACTTTAAC CTCCAAATCA AGCCTCTACT TGAATCCTTT TCTGAGGGAT
1741 GAATAAGGCA TAGGCATCAG GGGCTGTTGC CAATGTGCAT TAGCTGTTTG CAGCCTCACC
1801 TTCTTTCATG GAGTTTAAGA TATAGTGTAT TTTCCCAAGG TTTGAACTAG CTCTTCATTT
1861 CTTTATGTTT TAAATGCACT GACCTCCCAC ATTCCCTTTT TAGTAAAATA TTCAGAAATA
1921 ATTTAAATAC ATCATTGCAA TGAAAATAAA TGTTTTTTAT TAGGCAGAAT CCAGATGCTC
1981 AAGGCCCTTC ATAATATCCC CCAGTTTAGT AGTTGGACTT AGGGAACAAA GGAACCTTTA
2041 ATAGAAATTG GACAGCAAGA AAGCGAGCTT CTAGCTTATC CTCAGTCCTG CTCCTCTGCC
2101 ACAAAGTGCA CGCAGTTGCC GGCCGGGTCG CGCAGGGCGA ACTCCCGCCC CCACGGCTGC
2161 TCGCCGATCT CGGTCATGGC CGGCCCGGAG GCGTCCCGGA AGTTCGTGGA CACGACCTCC
2221 GACCACTCGG CGTACAGCTC GTCCAGGCCG CGCACCCACA CCCAGGCCAG GGTGTTGTCC
2281 GGCACCACCT GGTCCTGGAC CGCGCTGATG AACAGGGTCA CGTCGTCCCG GACCACACCG
2341 GCGAAGTCGT CCTCCACGAA GTCCCGGGAG AACCCGAGCC GGTCGGTCCA GAACTCGACC
2401 GCTCCGGCGA CGTCGCGCGC GGTGAGCACC GGAACGGCAC TGGTCAACTT GGCCATGATG
2461 GCTCCTCctg tcaggagagg aaagagaaga aggttagtac aattgCTATA GTGAGTTGTA
2521 TTATACTATG CAGATATACT ATGCCAATGA TTAATTGTCA AACTAGGGCT GCAgggttca
2581 tagtgccact tttcctgcac tgccccatct cctgcccacc ctttcccagg catagacagt
2641 cagtgactta cCAAACTCAC AGGAGGGAGA AGGCAGAAGC TTGAGACAGA CCCGCGGGAC
2701 CGCCGAACTG CGAGGGGACG TGGCTAGGGC GGCTTCTTTT ATGGTGCGCC GGCCCTCGGA
2761 GGCAGGGCGC TCGGGGAGGC CTAGCGGCCA ATCTGCGGTG GCAGGAGGCG GGGCCGAAGG
2821 CCGTGCCTGA CCAATCCGGA GCACATAGGA GTCTCAGCCC CCCGCCCCAA AGCAAGGGGA
2881 AGTCACGCGC CTGTAGCGCC AGCGTGTTGT GAAATGGGGG CTTGGGGGGG TTGGGGCCCT
2941 GACTAGTCAA AACAAACTCC CATTGACGTC AATGGGGTGG AGACTTGGAA ATCCCCGTGA
3001 GTCAAACCGC TATCCACGCC CATTGATGTA CTGCCAAAAC CGCATCATCA TGGTAATAGC
3061 GATGACTAAT ACGTAGATGT ACTGCCAAGT AGGAAAGTCC CATAAGGTCA TGTACTGGGC
3121 ATAATGCCAG GCGGGCCATT TACCGTCATT GACGTCAATA GGGGGCGTAC TTGGCATATG
3181 ATACACTTGA TGTACTGCCA AGTGGGCAGT TTACCGTAAA TACTCCACCC ATTGACGTCA
3241 ATGGAAAGTC CCTATTGGCG TTACTATGGG AACATACGTC ATTATTGACG TCAATGGGCG
3301 GGGGTCGTTG GGCGGTCAGC CAGGCGGGCC ATTTACCGTA AGTTATGTAA CGCCTGCAGG
3361 TTAATTAAGA ACATGTGAGC AAAAGGCCAG CAAAAGGCCA GGAACCGTAA AAAGGCCGCG
3421 TTGCTGGCGT TTTTCCATAG GCTCCGCCCC CCTGACGAGC ATCACAAAAA TCGACGCTCA
3481 AGTCAGAGGT GGCGAAACCC GACAGGACTA TAAAGATACC AGGCGTTTCC CCCTGGAAGC
3541 TCCCTCGTGC GCTCTCCTGT TCCGACCCTG CCGCTTACCG GATACCTGTC CGCCTTTCTC
3601 CCTTCGGGAA GCGTGGCGCT TTCTCATAGC TCACGCTGTA GGTATCTCAG TTCGGTGTAG
3661 GTCGTTCGCT CCAAGCTGGG CTGTGTGCAC GAACCCCCCG TTCAGCCCGA CCGCTGCGCC
3721 TTATCCGGTA ACTATCGTCT TGAGTCCAAC CCGGTAAGAC ACGACTTATC GCCACTGGCA
3781 GCAGCCACTG GTAACAGGAT TAGCAGAGCG AGGTATGTAG GCGGTGCTAC AGAGTTCTTG
3841 AAGTGGTGGC CTAACTACGG CTACACTAGA AGAACAGTAT TTGGTATCTG CGCTCTGCTG
3901 AAGCCAGTTA CCTTCGGAAA AAGAGTTGGT AGCTCTTGAT CCGGCAAACA AACCACCGCT
3961 GGTAGCGGTG GTTTTTTTGT TTGCAAGCAG CAGATTACGC GCAGAAAAAA AGGATCTCAA
4021 GAAGATCCTT TGATCTTTTC TACGGGGTCT GACGCTCAGT GGAACGAAAA CTCACGTTAA
4081 GGGATTTTGG TCATGGCTAG TTAATTAACA TTTAAATCAG CGGCCGCAAT AAAATATCTT
4141 TATTTTCATT ACATCTGTGT GTTGGTTTTT TGTGTGAATC GTAACTAACA TACGCTCTCC
4201 ATCAAAACAA AACGAAACAA AACAAACTAG CAAAATAGGC TGTCCCCAGT GCAAGTGCAG
4261 GTGCCAGAAC ATTTCTCTAT CGAA
```

Amino acid sequence (SEQ ID NO: 88)

```
MYRMQLLSCIALSLALVTNSIRLVQYRGEVQAMLGQSTEELRVSLASH
LRKLISAMVRSVECPPCPAPPVAGPSVFLFPPKPKDTLMISRTPEVTCVVVDVS
HEDPEVQFNWYVDGMEVEINAKTKPREEQFNSTFRVVSVLTVVEIQDWLNGK
EYKCKVSNKGLPAPIEKTISKTKGQPREPQVYTLPPSREEMTKNQVSLTCLVK
GFYPSDIAVEWESNGQPENNYKTTPPMLDSDGSFFLYSKLTVDKSRWQQGNV
FSCSVMHEALHNHYTQKSLSLSPGK
```

184U pfcn hg2 ApoE 129-157
Nucleic acid sequence (SEQ ID NO: 89)

```
  1 GGATCTGCGA TCGCTCCGGT GCCCGTCAGT GGGCAGAGCG CACATCGCCC ACAGTCCCCG
 61 AGAAGTTGGG GGGAGGGGTC GGCAATTGAA CGGGTGCCTA GAGAAGGTGG CGCGGGGTAA
121 ACTGGGAAAG TGATGTCGTG TACTGGCTCC GCCTTTTTCC CGAGGGTGGG GGAGAACCGT
181 ATATAAGTGC AGTAGTCGCC GTGAACGTTC TTTTTCGCAA CGGGTTTGCC GCCAGAACAC
241 AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG
361 CGTCCGCCGT CTAGGTAAGT TTAAAGCTCA GGTCGAGACC GGGCCTTTGT CCGGCGCTCC
```

-continued

```
 421 CTTGGAGCCT ACCTAGACTC AGCCGGCTCT CCACGCTTTG CCTGACCCtg cttgctcaac
 481 tctacgTCTT TGTTTCGTTT TCTGTTCTGC GCCGTTACAG ATCCAAGCTG TGACCGGCGC
 541 CTACCTGAGA TCACCGGCGA AGGAGGGCCA CCATGTACAG GATGCAACTC CTGTCTTGCA
 601 TTGCACTAAG TCTTGCACTT GTCACGAATT CGGCACCTCT CGAGCGCAAA TCTAGTGTCG
 661 AGTGCCCACC GTGCCCAGCA CCACCTGTGG CAGGACCGTC AGTCTTCCTC TTCCCCCCAA
 721 AACCCAAGGA CACCCTCATG ATCTCCCGGA CCCCTGAGGT CACGTGCGTG GTGGTGGACG
 781 TGAGCCACGA AGACCCCGAG GTCCAGTTCA ACTGGTACGT GGACGGCGTG GAGGTGCATA
 841 ATGCCAAGAC AAAGCCACGG GAGGAGCAGT TCAACAGCAC GTTCCGTGTG GTCAGCGTCC
 901 TCACCGTTGT GCACCAGGAC TGGCTGAACG GCAAGGAGTA CAAGTGCAAG GTCTCCAACA
 961 AAGGCCTCCC AGCCCCCATC GAGAAAACCA TCTCCAAAAC CAAAGGGCAG CCCCGAGAAC
1021 CACAGGTGTA CACCCTGCCC CCATCCCGGG AGGAGATGAC CAAGAACCAG GTCAGCCTGA
1081 CCTGCCTGGT CAAAGGCTTC TACCCCAGCG ACATCGCCGT GGAGTGGGAG AGCAATGGGC
1141 AGCCGGAGAA CAACTACAAG ACCACGCCTC CCATGCTGGA CTCCGACGGC TCCTTCTTCC
1201 TCTACAGCAA GCTCACCGTG GACAAGAGCA GGTGGCAGCA GGGGAACGTC TTCTCATGCT
1261 CCGTGATGCA TGAGGCTCTG CACAACCACT ACACGCAGAA GAGCCTCTCC CTGTCTCCGG
1321 GTGCACGTAC GAGCACCGAG GAGCTGCGGG TGCGCCTCGC CTCCCACCTG CGCAAGCTGC
1381 GTAAGCGGCT CCTCCGCGAT GCCGATGACC TGCAGAAGtg aTATCTCGAG CTAGCTGGCC
1441 AGACATGATA AGATACATTG ATGAGTTTGG ACAAACCACA ACTAGAATGC AGTGAAAAAA
1501 ATGCTTTATT TGTGAAATTT GTGATGCTAT TGCTTTATTT GTAACCATTA TAAGCTGCAA
1561 TAAACAAGTT AACAACAACA ATTGCATTCA TTTTATGTTT CAGGTTCAGG GGGAGGTGTG
1621 GGAGGTTTTT TAAAGCAAGT AAAACCTCTA CAAATGTGGT ATGGAATTAA TTCTAAAATA
1681 CAGCATAGCA AAACTTTAAC CTCCAAATCA AGCCTCTACT TGAATCCTTT TCTGAGGGAT
1741 GAATAAGGCA TAGGCATCAG GGGCTGTTGC CAATGTGCAT TAGCTGTTTG CAGCCTCACC
1801 TTCTTTCATG GAGTTTAAGA TATAGTGTAT TTTCCCAAGG TTTGAACTAG CTCTTCATTT
1861 CTTTATGTTT TAAATGCACT GACCTCCCAC ATTCCCTTTT TAGTAAAATA TTCAGAAATA
1921 ATTTAAATAC ATCATTGCAA TGAAAATAAA TGTTTTTTAT TAGGCAGAAT CCAGATGCTC
1981 AAGGCCCTTC ATAATATCCC CCAGTTTAGT AGTTGGACTT AGGGAACAAA GGAACCTTTA
2041 ATAGAAATTG GACAGCAAGA AAGCGAGCTT CTAGCTTATC CTCAGTCCTG CTCCTCTGCC
2101 ACAAAGTGCA CGCAGTTGCC GGCCGGGTCG CGCAGGGCGA ACTCCCGCCC CCACGGCTGC
2161 TCGCCGATCT CGGTCATGGC CGGCCCGGAG GCGTCCCGGA AGTTCGTGGA CACGACCTCC
2221 GACCACTCGG CGTACAGCTC GTCCAGGCCG CGCACCCACA CCCAGGCCAG GGTGTTGTCC
2281 GGCACCACCT GGTCCTGGAC CGCGCTGATG AACAGGGTCA CGTCGTCCCG GACCACACCG
2341 GCGAAGTCGT CCTCCACGAA GTCCCGGGAG AACCCGAGCC GGTCGGTCCA GAACTCGACC
2401 GCTCCGGCGA CGTCGCGCGC GGTGAGCACC GGAACGGCAC TGGTCAACTT GGCCATGATG
2461 GCTCCTCctg tcaggagagg aaagagaaga aggttagtac aattgCTATA GTGAGTTGTA
2521 TTATACTATG CAGATATACT ATGCCAATGA TTAATTGTCA AACTAGGGCT GCAgggttca
2581 tagtgccact tttcctgcac tgccccatct cctgccccacc ctttcccagg catagacagt
2641 cagtgactta cCAAACTCAC AGGAGGGAGA AGGCAGAAGC TTGAGACAGA CCCGCGGGAC
2701 CGCCGAACTG CGAGGGGACG TGGCTAGGGC GGCTTCTTTT ATGGTGCGCC GGCCCTCGGA
2761 GGCAGGGCGC TCGGGGAGGC CTAGCGGCCA ATCTGCGGTG GCAGGAGGCG GGGCCGAAGG
2821 CCGTGCCTGA CCAATCCGGA GCACATAGGA GTCTCAGCCC CCCGCCCCAA AGCAAGGGGA
2881 AGTCACGCGC CTGTAGCGCC AGCGTGTTGT GAAATGGGGG CTTGGGGGGG TTGGGGCCCT
2941 GACTAGTCAA AACAAACTCC CATTGACGTC AATGGGGTGG AGACTTGGAA ATCCCCGTGA
3001 GTCAAACCGC TATCCACGCC CATTGATGTA CTGCCAAAAC CGCATCATCA TGGTAATAGC
3061 GATGACTAAT ACGTAGATGT ACTGCCAAGT AGGAAAGTCC CATAAGGTCA TGTACTGGGC
3121 ATAATGCCAG GCGGGCCATT TACCGTCATT GACGTCAATA GGGGGCGTAC TTGGCATATG
3181 ATACACTTGA TGTACTGCCA AGTGGGCAGT TTACCGTAAA TACTCCACCC ATTGACGTCA
3241 ATGGAAAGTC CCTATTGGCG TTACTATGGG AACATACGTC ATTATTGACG TCAATGGGCG
3301 GGGGTCGTTG GGCGGTCAGC CAGGCGGGCC ATTTACCGTA AGTTATGTAA CGCCTGCAGG
3361 TTAATTAAGA ACATGTGAGC AAAAGGCCAG CAAAAGGCCA GGAACCGTAA AAAGGCCGCG
3421 TTGCTGGCGT TTTTCCATAG GCTCCGCCCC CCTGACGAGC ATCACAAAAA TCGACGCTCA
3481 AGTCAGAGGT GGCGAAACCC GACAGGACTA TAAAGATACC AGGCGTTTCC CCCTGGAAGC
3541 TCCCTCGTGC GCTCTCCTGT TCCGACCCTG CCGCTTACCG GATACCTGTC CGCCTTTCTC
3601 CCTTCGGGAA GCGTGGCGCT TTCTCATAGC TCACGCTGTA GGTATCTCAG TTCGGTGTAG
3661 GTCGTTCGCT CCAAGCTGGG CTGTGTGCAC GAACCCCCCG TTCAGCCCGA CCGCTGCGCC
3721 TTATCCGGTA ACTATCGTCT TGAGTCCAAC CCGGTAAGAC ACGACTTATC GCCACTGGCA
3781 GCAGCCACTG GTAACAGGAT TAGCAGAGCG AGGTATGTAG GCGGTGCTAC AGAGTTCTTG
3841 AAGTGGTGGC CTAACTACGG CTACACTAGA AGAACAGTAT TTGGTATCTG CGCTCTGCTG
3901 AAGCCAGTTA CCTTCGGAAA AAGAGTTGGT AGCTCTTGAT CCGGCAAACA AACCACCGCT
3961 GGTAGCGGTG GTTTTTTTGT TTGCAAGCAG CAGATTACGC GCAGAAAAAA AGGATCTCAA
4021 GAAGATCCTT TGATCTTTTC TACGGGGTCT GACGCTCAGT GGAACGAAAA CTCACGTTAA
4081 GGGATTTTGG TCATGGCTAG TTAATTAACA TTTAAATCAG CGGCCGCAAT AAAATATCTT
4141 TATTTTCATT ACATCTGTGT GTTGGTTTTT TGTGTGAATC GTAACTAACA TACGCTCTCC
4201 ATCAAAACAA AACGAAACAA AACAAACTAG CAAAATAGGC TGTCCCCAGT GCAAGTGCAG
4261 GTGCCAGAAC ATTTCTCTAT CGAA
```

Amino acid sequence (SEQ ID NO: 90)

```
MYRMQLLSCIALSLALVTNSAPLERKSSVECPPCPAPPVAGPSVFLFPP
KPKDTLMISRTPEVTCVVVDVSHEDPEVQFNWYVDGVEVEINAKTKPREEQF
NSTFRVVSVLTVVHQDWLNGKEYKCKVSNKGLPAPIEKTISKTKGQPREPQV
YTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGARTSTE
ELRVRLASHLRKLRKRLLRDADDLQK
```

184V pfcn hg2 129-157 R136S
Nucleic acid sequence (SEQ ID NO: 91)

```
   1 GGATCTGCGA TCGCTCCGGT GCCCGTCAGT GGGCAGAGCG CACATCGCCC ACAGTCCCCG
  61 AGAAGTTGGG GGAGGGGTC GGCAATTGAA CGGGTGCCTA GAGAAGGTGG CGCGGGGTAA
 121 ACTGGGAAAG TGATGTCGTG TACTGGCTCC GCCTTTTTCC CGAGGGTGGG GGAGAACCGT
```

-continued

181 ATATAAGTGC AGTAGTCGCC GTGAACGTTC TTTTTCGCAA CGGGTTTGCC GCCAGAACAC
241 AGCTGAAGCT TCGAGGGGCT CGCATCTCTC CTTCACGCGC CCGCCGCCCT ACCTGAGGCC
301 GCCATCCACG CCGGTTGAGT CGCGTTCTGC CGCCTCCCGC CTGTGGTGCC TCCTGAACTG
361 CGTCCGCCGT CTAGGTAAGT TTAAAGCTCA GGTCGAGACC GGGCCTTTGT CCGGCGCTCC
421 CTTGGAGCCT ACCTAGACTC AGCCGGCTCT CCACGCTTTG CCTGACCCtg cttgctcaac
481 tctacgTCTT TGTTTCGTTT TCTGTTCTGC GCCGTTACAG ATCCAAGCTG TGACCGGCGC
541 CTACCTGAGA TCACCGGCGA AGGAGGGCCA CCATGTACAG GATGCAACTC CTGTCTTGCA
601 TTGCACTAAG TCTTGCACTT GTCACGAATT CGGCACCTCT CGAGCGCAAA TCTAGTGTCG
661 AGTGCCCACC GTGCCCAGCA CCACCTGTGG CAGGACCGTC AGTCTTCCTC TTCCCCCCAA
721 AACCCAAGGA CACCCTCATG ATCTCCCGGA CCCCTGAGGT CACGTGCGTG GTGGTGGACG
781 TGAGCCACGA AGACCCCGAG GTCCAGTTCA ACTGGTACGT GGACGGCGTG GAGGTGCATA
841 ATGCCAAGAC AAAGCCACGG GAGGAGCAGT TCAACAGCAC GTTCCGTGTG GTCAGCGTCC
901 TCACCGTTGT GCACCAGGAC TGGCTGAACG GCAAGGAGTA CAAGTGCAAG GTCTCCAACA
961 AAGGCCTCCC AGCCCCCATC GAGAAAACCA TCTCCAAAAC CAAAGGGCAG CCCCGAGAAC
1021 CACAGGTGTA CACCCTGCCC CCATCCCGGG AGGAGATGAC CAAGAACCAG GTCAGCCTGA
1081 CCTGCCTGGT CAAAGGCTTC TACCCCAGCG ACATCGCCGT GGAGTGGGAG AGCAATGGGC
1141 AGCCGGAGAA CAACTACAAG ACCACGCCTC CCATGCTGGA CTCCGACGGC TCCTTCTTCC
1201 TCTACAGCAA GCTCACCGTG GACAAGAGCA GGTGGCAGCA GGGGAACGTC TTCTCATGCT
1261 CCGTGATGCA TGAGGCTCTG CACAACCACT ACACGCAGAA GAGCCTCTCC CTGTCTCCGG
1321 GTGCACGTAC GAGCACCGAG GAGCTGCGGG TGaGCCTCGC CTCCCACCTG CGCAAGCTGC
1381 GTAAGCGGCT CCTCCGCGAT GCCGATGACC TGCAGAAGtg aTATCTCGAG CTAGCTGGCC
1441 AGACATGATA AGATACATTG ATGAGTTTGG ACAAACCACA ACTAGAATGC AGTGAAAAAA
1501 ATGCTTTATT TGTGAAATTT GTGATGCTAT TGCTTTATTT GTAACCATTA TAAGCTGCAA
1561 TAAACAAGTT AACAACAACA ATTGCATTCA TTTTATGTTT CAGGTTCAGG GGGAGGTGTG
1621 GGAGGTTTTT TAAAGCAAGT AAAACCTCTA CAAATGTGGT ATGGAATTAA TTCTAAAATA
1681 CAGCATAGCA AAACTTTAAC CTCCAAATCA AGCCTCTACT TGAATCCTTT TCTGAGGGAT
1741 GAATAAGGCA TAGGCATCAG GGGCTGTTGC CAATGTGCAT TAGCTGTTTG CAGCCTCACC
1801 TTCTTTCATG GAGTTTAAGA TATAGTGTAT TTTCCCAAGG TTTGAACTAG CTCTTCATTT
1861 CTTTATGTTT TAAATGCACT GACCTCCCAC ATTCCCTTTT TAGTAAAATA TTCAGAAATA
1921 ATTTAAATAC ATCATTGCAA TGAAAATAAA TGTTTTTTAT TAGGCAGAAT CCAGATGCTC
1981 AAGGCCCTTC ATAATATCCC CCAGTTTAGT AGTTGGACTT AGGGAACAAA GGAACCTTTA
2041 ATAGAAATTG GACAGCAAGA AAGCGAGCTT CTAGCTTATC CTCAGTCCTG CTCCTCTGCC
2101 ACAAAGTGCA CGCAGTTGCC GGCCGGGTCG CGCAGGGCGA ACTCCCGCCC CCACGGCTGC
2161 TCGCCGATCT CGGTCATGGC CGGCCCGGAG GCGTCCCGGA AGTTCGTGGA CACGACCTCC
2221 GACCACTCGG CGTACAGCTC GTCCAGGCCG CGCACCCACA CCCAGGCCAG GGTGTTGTCC
2281 GGCACCACCT GGTCCTGGAC CGCGCTGATG AACAGGGTCA CGTCGTCCCG GACCACACCG
2341 GCGAAGTCGT CCTCCACGAA GTCCCGGGAG AACCCGAGCC GGTCGGTCCA GAACTCGACC
2401 GCTCCGGCGA CGTCGCGCGC GGTGAGCACC GGAACGGCAC TGGTCAACTT GGCCATGATG
2461 GCTCCTCCtg tcaggagagg aaagagaaga aggttagtac aattgCTATA GTGAGTTGTA
2521 TTATACTATG CAGATATACT ATGCCAATGA TTAATTGTCA AACTAGGGCT GCAgggttca
2581 tagtgccact tttcctgcac tgccccatct cctgcccacc ctttcccagg catagacagt
2641 cagtgactta cCAAACTCAC AGGAGGGAGA AGGCAGAAGC TTGAGACAGA CCCGCGGGAC
2701 CGCCGAACTG CGAGGGGACG TGGCTAGGGC GGCTTCTTTT ATGGTGCGCC GGCCCTCGGA
2761 GGCAGGGCGC TCGGGGAGGC CTAGCGGCCA ATCTGCGGTG GCAGGAGGCG GGGCCGAAGG
2821 CCGTGCCTGA CCAATCCGGA GCACATAGGA GTCTCAGCCC CCCGCCCCAA AGCAAGGGGA
2881 AGTCACGCGC CTGTAGCGCC AGCGTGTTGT GAAATGGGGG CTTGGGGGGG TTGGGGCCCT
2941 GACTAGTCAA AACAAACTCC CATTGACGTC AATGGGGTGG AGACTTGGAA ATCCCCGTGA
3001 GTCAAACCGC TATCCACGCC CATTGATGTA CTGCCAAAAC CGCATCATCA TGGTAATAGC
3061 GATGACTAAT ACGTAGATGT ACTGCCAAGT AGGAAAGTCC CATAAGGTCA TGTACTGGGC
3121 ATAATGCCAG GCGGGCCATT TACCGTCATT GACGTCAATA GGGGGCGTAC TTGGCATATG
3181 ATACACTTGA TGTACTGCCA AGTGGGCAGT TTACCGTAAA TACTCCACCC ATTGACGTCA
3241 ATGGAAAGTC CCTATTGGCG TTACTATGGG AACATACGTC ATTATTGACG TCAATGGGCG
3301 GGGGTCGTTG GGCGGTCAGC CAGGCGGGCC ATTTACCGTA AGTTATGTAA CGCCTGCAGG
3361 TTAATTAAGA ACATGTGAGC AAAAGGCCAG CAAAAGGCCA GGAACCGTAA AAAGGCCGCG
3421 TTGCTGGCGT TTTTCCATAG GCTCCGCCCC CCTGACGAGC ATCACAAAAA TCGACGCTCA
3481 AGTCAGAGGT GGCGAAACCC GACAGGACTA TAAAGATACC AGGCGTTTCC CCCTGGAAGC
3541 TCCCTCGTGC GCTCTCCTGT TCCGACCCTG CCGCTTACCG GATACCTGTC CGCCTTTCTC
3601 CCTTCGGGAA GCGTGGCGCT TTCTCATAGC TCACGCTGTA GGTATCTCAG TTCGGTGTAG
3661 GTCGTTCGCT CCAAGCTGGG CTGTGTGCAC GAACCCCCCG TTCAGCCCGA CCGCTGCGCC
3721 TTATCCGGTA ACTATCGTCT TGAGTCCAAC CCGGTAAGAC ACGACTTATC GCCACTGGCA
3781 GCAGCCACTG GTAACAGGAT TAGCAGAGCG AGGTATGTAG GCGGTGCTAC AGAGTTCTTG
3841 AAGTGGTGGC CTAACTACGG CTACACTAGA AGAACAGTAT TTGGTATCTG CGCTCTGCTG
3901 AAGCCAGTTA CCTTCGGAAA AAGAGTTGGT AGCTCTTGAT CCGGCAAACA AACCACCGCT
3961 GGTAGCGGTG GTTTTTTTGT TTGCAAGCAG CAGATTACGC GCAGAAAAAA AGGATCTCAA
4021 GAAGATCCTT TGATCTTTTC TACGGGGTCT GACGCTCAGT GGAACGAAAA CTCACGTTAA
4081 GGGATTTTGG TCATGGCTAG TTAATTAACA TTTAAATCAG CGGCCGCAAT AAAATATCTT
4141 TATTTTCATT ACATCTGTGT GTTGGTTTTT TGTGTGAATC GTAACTAACA TACGCTCTCC
4201 ATCAAAACAA AACGAAACAA AACAAACTAG CAAAATAGGC TGTCCCCAGT GCAAGTGCAG
4261 GTGCCAGAAC ATTTCTCTAT CGAA Amino acid sequence (SEQ ID NO: 92)

MYRMQLLSCIALSLALVTNSAPLERKSSVECPPCPAPPVAGPSVFLFPP
KPKDTLMISRTPEVTCVVVDVSHEDPEVQFNWYVDGVEVEINAKTKPREEQF
NSTFRVVSVLTVVHQDWLNGKEYKCKVSNKGLPAPIEKTISKTKGQPREPQV
YTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGARTSTE
ELRVSLASHLRKLRKRLLRDADDLQK

-continued 197H pfuse hfc2 ApoE 129-157
Nucleic acid sequence (SEQ ID NO: 93)

```
   1 GGATCTGCGA TCGCTCCGGT GCCCGTCAGT GGGCAGAGCG CACATCGCCC ACAGTCCCCG
  61 AGAAGTTGGG GGGAGGGGTC GGCAATTGAA CGGGTGCCTA GAGAAGGTGG CGCGGGGTAA
 121 ACTGGGAAAG TGATGTCGTG TACTGGCTCC GCCTTTTTCC CGAGGGTGGG GGAGAACCGT
 181 ATATAAGTGC AGTAGTCGCC GTGAACGTTC TTTTTCGCAA CGGGTTTGCC GCCAGAACAC
 241 AGCTGAAGCT TCGAGGGGCT CGCATCTCTC CTTCACGCGC CCGCCGCCCT ACCTGAGGCC
 301 GCCATCCACG CCGGTTGAGT CGCGTTCTGC CGCCTCCCGC CTGTGGTGCC TCCTGAACTG
 361 CGTCCGCCGT CTAGGTAAGT TTAAAGCTCA GGTCGAGACC GGGCCTTTGT CCGGCGCTCC
 421 CTTGGAGCCT ACCTAGACTC AGCCGGCTCT CCACGCTTTG CCTGACCCtg cttgctcaac
 481 tctacgTCTT TGTTTCGTTT TCTGTTCTGC GCCGTTACAG ATCCAAGCTG TGACCGGCGC
 541 CTACCTGAGA TCAccggcGA AGGAGGGCCA CCATGTACAG GATGCAACTC CTGTCTTGCA
 601 TTGCACTAAG TCTTGCACTT GTCACGAATT CGATAAGCAC CGAGGAGCTG CGGGTGCGCC
 661 TCGCCTCCCA CCTGCGCAAG CTGCGTAAGC GGCTCCTCCG CGATGCCGAT GACCTGCAGA
 721 AGatatcgGC CATGGTTAGA TCTGTGGAGT GCCCACCTTG CCCAGCACCA CCTGTGGCAG
 781 GACCTTCAGT CTTCCTCTTC CCCCCAAAAC CCAAGGACAC CCTGATGATC TCCAGAACCC
 841 CTGAGGTCAC GTGCGTGGTG GTGGACGTGA GCCACGAAGA CCCCGAGGTC CAGTTCAACT
 901 GGTACGTGGA CGGCATGGAG GTGCATAATG CCAAGACAAA GCCACGGGAG GAGCAGTTCA
 961 ACAGCACGTT CCGTGTGGTC AGCGTCCTCA CCGTCGTGCA CCAGGACTGG CTGAACGGCA
1021 AGGAGTACAA GTGCAAGGTC TCCAACAAAG GCCTCCCAGC CCCCATCGAG AAAACCATCT
1081 CCAAAACCAA AGGGCAGCCC CGAGAACCAC AGGTGTACAC CCTGCCCCCA TCCCGGGAGG
1141 AGATGACCAA GAACCAGGTC AGCCTGACCT GCCTGGTCAA AGGCTTCTAC CCCAGCGACA
1201 TCGCCGTGGA GTGGGAGAGC AATGGGCAGC CGGAGAACAA CTACAAGACC ACACCTCCCA
1261 TGCTGGACTC CGACGGCTCC TTCTTCCTCT ACAGCAAGCT CACCGTGGAC AAGAGCAGGT
1321 GGCAGCAGGG GAACGTCTTC TCATGCTCCG TGATGCATGA GGCTCTGCAC AACCACTACA
1381 CACAGAAGAG CCTCTCCCTG TCTCCGGGTA AATGAgtgcc acgGCTAGCT GGCCAGACAT
1441 GATAAGATAC ATTGATGAGT TTGGACAAAC CACAACTAGA ATGCAGTGAA AAAAATGCTT
1501 TATTTGTGAA ATTTGTGATG CTATTGCTTT ATTTGTAACC ATTATAAGCT GCAATAAACA
1561 AGTTAACAAC AACAATTGCA TTCATTTTAT GTTTCAGGTT CAGGGGGAGG TGTGGGAGGT
1621 TTTTTAAAGC AAGTAAAACC TCTACAAATG TGGTATGGAA TTAATTCTAA AATACAGCAT
1681 AGCAAAACTT TAACCTCCAA ATCAAGCCTC TACTTGAATC CTTTTCTGAG GGATGAATAA
1741 GGCATAGGCA TCAGGGGCTG TTGCCAATGT GCATTAGCTG TTTGCAGCCT CACCTTCTTT
1801 CATGGAGTTT AAGATATAGT GTATTTTCCC AAGGTTTGAA CTAGCTCTTC ATTTCTTTAT
1861 GTTTTAAATG CACTGACCTC CCACATTCCC TTTTTAGTAA AATATTCAGA AATAATTTAA
1921 ATACATCATT GCAATGAAAA TAAATGTTTT TTATTAGGCA GAATCCAGAT GCTCAAGGCC
1981 CTTCATAATA TCCCCCAGTT TAGTAGTTGG ACTTAGGGAA CAAAGGAACC TTTAATAGAA
2041 ATTGGACAGC AAGAAAGCGA GCTTCTAGCT TATCCTCAGT CCTGCTCCTC TGCCACAAAG
2101 TGCACGCAGT TGCCGGCCGG GTCGCGCAGG GCGAACTCCC GCCCCCACGG CTGCTCGCCG
2161 ATCTCGGTCA TGGCCGGCCC GGAGGCGTCC CGGAAGTTCG TGGACACGAC CTCCGACCAC
2221 TCGGCGTACA GCTCGTCCAG GCCGCGCACC CACACCCAGG CCAGGGTGTT GTCCGGCACC
2281 ACCTGGTCCT GGACCGCGCT GATGAACAGG GTCACGTCGT CCCGGACCAC ACCGGCGAAG
2341 TCGTCCTCCA CGAAGTCCCG GGAGAACCCG AGCCGGTCGG TCCAGAACTC GACCGCTCCG
2401 GCGACGTCGC GCGCGGTGAG CACCGGAACG GCACTGGTCA ACTTGGCCAT GATGGCTCCT
2461 Cctgtcagga gaggaaagag aagaaggtta gtacaattgC TATAGTGAGT TGTATTATAC
2521 TATGCAGATA TACTATGCCA ATGATTAATT GTCAAACTAG GGCTGCAggg ttcatagtgc
2581 cacttttcct gcactgcccc atctcctgcc caccctttcc caggcataga cagtcagtga
2641 cttacCAAAC TCACAGGAGG GAGAAGGCAG AAGCTTGAGA CAGACCCGCG GGACCGCCGA
2701 ACTGCGAGGG GACGTGGCTA GGGCGGCTTC TTTTATGGTG CGCCGGCCCT CGGAGGCAGG
2761 GCGCTCGGGG AGGCCTAGCG GCCAATCTGC GGTGGCAGGA GGCGGGGCCG AAGGCCGTGC
2821 CTGACCAATC CGGAGCACAT AGGAGTCTCA GCCCCCCGCC CCAAAGCAAG GGGAAGTCAC
2881 GCGCCTGTAG CGCCAGCGTG TTGTGAAATG GGGGCTTGGG GGGGTTGGGG CCCTGACTAG
2941 TCAAAACAAA CTCCCATTGA CGTCAATGGG GTGGAGACTT GGAAATCCCC GTGAGTCAAA
3001 CCGCTATCCA CGCCCATTGA TGTACTGCCA AAACCGCATC ATCATGGTAA TAGCGATGAC
3061 TAATACGTAG ATGTACTGCC AAGTAGGAAA GTCCCATAAG GTCATGTACT GGGCATAATG
3121 CCAGGCGGGC CATTTACCGT CATTGACGTC AATAGGGGGC GTACTTGGCA TATGATACAC
3181 TTGATGTACT GCCAAGTGGG CAGTTTACCG TAAATACTCC ACCCATTGAC GTCAATGGAA
3241 AGTCCCTATT GGCGTTACTA TGGGAACATA CGTCATTATT GACGTCAATG GGCGGGGGTC
3301 GTTGGGCGGT CAGCCAGGCG GGCCATTTAC CGTAAGTTAT GTAACGCCTG CAGGTTAATT
3361 AAGAACATGT GAGCAAAAGG CCAGCAAAAG GCCAGGAACC GTAAAAAGGC CGCGTTGCTG
3421 GCGTTTTTCC ATAGGCTCCG CCCCCCTGAC GAGCATCACA AAAATCGACG CTCAAGTCAG
3481 AGGTGGCGAA ACCCGACAGG ACTATAAAGA TACCAGGCGT TTCCCCCTGG AAGCTCCCTC
3541 GTGCGCTCTC CTGTTCCGAC CCTGCCGCTT ACCGGATACC TGTCCGCCTT TCTCCCTTCG
3601 GGAAGCGTGG CGCTTTCTCA TAGCTCACGC TGTAGGTATC TCAGTTCGGT GTAGGTCGTT
3661 CGCTCCAAGC TGGGCTGTGT GCACGAACCC CCCGTTCAGC CCGACCGCTG CGCCTTATCC
3721 GGTAACTATC GTCTTGAGTC CAACCCGGTA AGACACGACT TATCGCCACT GGCAGCAGCC
3781 ACTGGTAACA GGATTAGCAG AGCGAGGTAT GTAGGCGGTG CTACAGAGTT CTTGAAGTGG
3841 TGGCCTAACT ACGGCTACAC TAGAAGAACA GTATTTGGTA TCTGCGCTCT GCTGAAGCCA
3901 GTTACCTTCG GAAAAAGAGT TGGTAGCTCT TGATCCGGCA AACAAACCAC CGCTGGTAGC
3961 GGTGGTTTTT TTGTTTGCAA GCAGCAGATT ACGCGCAGAA AAAAAGGATC TCAAGAAGAT
4021 CCTTTGATCT TTTCTACGGG GTCTGACGCT CAGTGGAACG AAAACTCACG TTAAGGGATT
4081 TTGGTCATGG CTAGTTAATT AACATTTAAA TCAGCGGCCG CAATAAAATA TCTTTATTTT
4141 CATTACATCT GTGTGTTGGT TTTTTGTGTG AATCGTAACT AACATACGCT CTCCATCAAA
4201 ACAAAACGAA ACAAAACAAA CTAGCAAAAT AGGCTGTCCC CAGTGCAAGT GCAGGTGCCA
4261 GAACATTTCT CTATCGAA
```

Amino acid sequence (SEQ ID NO: 94)

MYRMQLLSCIALSLALVTNSISTEELRVRLASHLRKLRKRLLRDADDL
QKISAMVRSVECPPCPAPPVAGPSVFLFPPKPKDTLMISRTPEVTCVVVDVSHE

-continued

DPEVQFNWYVDGMEVHNAKTKPREEQFNSTFRVVSVLTVVEIQDWLNGKEY
KCKVSNKGLPAPIEKTISKTKGQPREPQVYTLPPSREEMTKNQVSLTCLVKGF
YPSDIAVEWESNGQPENNYKTTPPMLDSDGSFFLYSKLTVDKSRWQQGNVFS
CSVMHEALHNHYTQKSLSLSPGK 1971 pfuse hfc2 ApoE 129-157 R136S
Nucleic acid sequence (SEQ ID NO: 95)

```
   1 GGATCTGCGA TCGCTCCGGT GCCCGTCAGT GGGCAGAGCG CACATCGCCC ACAGTCCCCG
  61 AGAAGTTGGG GGGAGGGGTC GGCAATTGAA CGGGTGCCTA GAGAAGGTGG CGCGGGGTAA
 121 ACTGGGAAAG TGATGTCGTG TACTGGCTCC GCCTTTTTCC CGAGGGTGGG GGAGAACCGT
 181 ATATAAGTGC AGTAGTCGCC GTGAACGTTC TTTTTCGCAA CGGGTTTGCC GCCAGAACAC
 241 AGCTGAAGCT TCGAGGGGCT CGCATCTCTC CTTCACGCGC CCGCCGCCCT ACCTGAGGCC
 301 GCCATCCACG CCGGTTGAGT CGCGTTCTGC CGCCTCCCGC CTGTGGTGCC TCCTGAACTG
 361 CGTCCGCCGT CTAGGTAAGT TTAAAGCTCA GGTCGAGACC GGGCCTTTGT CCGGCGCTCC
 421 CTTGGAGCCT ACCTAGACTC AGCCGGCTCT CCACGCTTTG CCTGACCCtg cttgctcaac
 481 tctacgTCTT TGTTTCGTTT TCTGTTCTGC GCCGTTACAG ATCCAAGCTG TGACCGGCGC
 541 CTACCTGAGA TCAccggcGA AGGAGGGCCA CCATGTACAG GATGCAACTC CTGTCTTGCA
 601 TTGCACTAAG TCTTGCACTT GTCACGAATT CGATAAGCAC CGAGGAGCTG CGGGTGaGCC
 661 TCGCCTCCCA CCTGCGCAAG CTGCGTAAGC GGCTCCTCCG CGATGCCGAT GACCTGCAGA
 721 AGatatcgGC CATGGTTAGA TCTGTGGAGT GCCCACCTTG CCCAGCACCA CCTGTGGCAG
 781 GACCTTCAGT CTTCCTCTTC CCCCCAAAAC CCAAGGACAC CCTGATGATC TCCAGAACCC
 841 CTGAGGTCAC GTGCGTGGTG GTGGACGTGA GCCACGAAGA CCCCGAGGTC CAGTTCAACT
 901 GGTACGTGGA CGGCATGGAG GTGCATAATG CCAAGACAAA GCCACGGGAG GAGCAGTTCA
 961 ACAGCACGTT CCGTGTGGTC AGCGTCCTCA CCGTCGTGCA CCAGGACTGG CTGAACGGCA
1021 AGGAGTACAA GTGCAAGGTC TCCAACAAAG GCCTCCCAGC CCCCATCGAG AAAACCATCT
1081 CCAAAACCAA AGGGCAGCCC CGAGAACCAC AGGTGTACAC CCTGCCCCCA TCCCGGGAGG
1141 AGATGACCAA GAACCAGGTC AGCCTGACCT GCCTGGTCAA AGGCTTCTAC CCCAGCGACA
1201 TCGCCGTGGA GTGGGAGAGC AATGGGCAGC CGGAGAACAA CTACAAGACC ACACCTCCCA
1261 TGCTGGACTC CGACGGCTCC TTCTTCCTCT ACAGCAAGCT CACCGTGGAC AAGAGCAGGT
1321 GGCAGCAGGG GAACGTCTTC TCATGCTCCG TGATGCATGA GGCTCTGCAC AACCACTACA
1381 CACAGAAGAG CCTCTCCCTG TCTCCGGGTA AATGAgtgcc acgGCTAGCT GGCCAGACAT
1441 GATAAGATAC ATTGATGAGT TTGGACAAAC CACAACTAGA ATGCAGTGAA AAAAATGCTT
1501 TATTTGTGAA ATTTGTGATG CTATTGCTTT ATTTGTAACC ATTATAAGCT GCAATAAACA
1561 AGTTAACAAC AACAATTGCA TTCATTTTAT GTTTCAGGTT CAGGGGGAGG TGTGGGAGGT
1621 TTTTTAAAGC AAGTAAAACC TCTACAAATG TGGTATGGAA TTAATTCTAA AATACAGCAT
1681 AGCAAAACTT TAACCTCCAA ATCAAGCCTC TACTTGAATC CTTTTCTGAG GGATGAATAA
1741 GGCATAGGCA TCAGGGGCTG TTGCCAATGT GCATTAGCTG TTTGCAGCCT CACCTTCTTT
1801 CATGGAGTTT AAGATATAGT GTATTTTCCC AAGGTTTGAA CTAGCTCTTC ATTTCTTTAT
1861 GTTTTAAATG CACTGACCTC CCACATTCCC TTTTTAGTAA AATATTCAGA AATAATTTAA
1921 ATACATCATT GCAATGAAAA TAAATGTTTT TTATTAGGCA GAATCCAGAT GCTCAAGGCC
1981 CTTCATAATA TCCCCCAGTT TAGTAGTTGG ACTTAGGGAA CAAAGGAACC TTTAATAGAA
2041 ATTGGACAGC AAGAAAGCGA GCTTCTAGCT TATCCTCAGT CCTGCTCCTC TGCCACAAAG
2101 TGCACGCAGT TGCCGGCCGG GTCGCGCAGG GCGAACTCCC GCCCCCACGG CTGCTCGCCG
2161 ATCTCGGTCA TGGCCGGCCC GGAGGCGTCC CGGAAGTTCG TGGACACGAC CTCCGACCAC
2221 TCGGCGTACA GCTCGTCCAG GCCGCGCACC CACACCCAGG CCAGGGTGTT GTCCGGCACC
2281 ACCTGGTCCT GGACCGCGCT GATGAACAGG GTCACGTCGT CCCGGACCAC ACCGGCGAAG
2341 TCGTCCTCCA CGAAGTCCCG GGAGAACCCG AGCCGGTCGG TCCAGAACTC GACCGCTCCG
2401 GCGACGTCGC GCGCGGTGAG CACCGGAACG GCACTGGTCA ACTTGGCCAT GATGGCTCCT
2461 Cctgtcagga gaggaaagag aagaaggtta gtacaattgC TATAGTGAGT TGTATTATAC
2521 TATGCAGATA TACTATGCCA ATGATTAATT GTCAAACTAG GGCTGCAggg ttcatagtgc
2581 cacttttcct gcactgcccc atctcctgcc caccctttcc caggcataga cagtcagtga
2641 cttacCAAAC TCACAGGAGG GAGAAGGCAG AAGCTTGAGA CAGACCCGCG GGACCGCCGA
2701 ACTGCGAGGG GACGTGGCTA GGGCGGCTTC TTTTATGGTG CGCCGGCCCT CGGAGGCAGG
2761 GCGCTCGGGG AGGCCTAGCG GCCAATCTGC GGTGGCAGGA GGCGGGGCCG AAGGCCGTGC
2821 CTGACCAATC CGGAGCACAT AGGAGTCTCA GCCCCCCGCC CCAAAGCAAG GGGAAGTCAC
2881 GCGCCTGTAG CGCCAGCGTG TTGTGAAATG GGGGCTTGGG GGGGTTGGGG CCCTGACTAG
2941 TCAAAACAAA CTCCCATTGA CGTCAATGGG GTGGAGACTT GGAAATCCCC GTGAGTCAAA
3001 CCGCTATCCA CGCCCATTGA TGTACTGCCA AAACCGCATC ATCATGGTAA TAGCGATGAC
3061 TAATACGTAG ATGTACTGCC AAGTAGGAAA GTCCCATAAG GTCATGTACT GGGCATAATG
3121 CCAGGCGGGC CATTTACCGT CATTGACGTC AATAGGGGGC GTACTTGGCA TATGATACAC
3181 TTGATGTACT GCCAAGTGGG CAGTTTACCG TAAATACTCC ACCCATTGAC GTCAATGGAA
3241 AGTCCCTATT GGCGTTACTA TGGGAACATA CGTCATTATT GACGTCAATG GGCGGGGGTC
3301 GTTGGGCGGT CAGCCAGGCG GGCCATTTAC CGTAAGTTAT GTAACGCCTG CAGGTTAATT
3361 AAGAACATGT GAGCAAAAGG CCAGCAAAAG GCCAGGAACC GTAAAAAGGC CGCGTTGCTG
3421 GCGTTTTTCC ATAGGCTCCG CCCCCCTGAC GAGCATCACA AAAATCGACG CTCAAGTCAG
3481 AGGTGGCGAA ACCCGACAGG ACTATAAAGA TACCAGGCGT TTCCCCCTGG AAGCTCCCTC
3541 GTGCGCTCTC CTGTTCCGAC CCTGCCGCTT ACCGGATACC TGTCCGCCTT TCTCCCTTCG
3601 GGAAGCGTGG CGCTTTCTCA TAGCTCACGC TGTAGGTATC TCAGTTCGGT GTAGGTCGTT
3661 CGCTCCAAGC TGGGCTGTGT GCACGAACCC CCCGTTCAGC CCGACCGCTG CGCCTTATCC
3721 GGTAACTATC GTCTTGAGTC CAACCCGGTA AGACACGACT TATCGCCACT GGCAGCAGCC
3781 ACTGGTAACA GGATTAGCAG AGCGAGGTAT GTAGGCGGTG CTACAGAGTT CTTGAAGTGG
3841 TGGCCTAACT ACGGCTACAC TAGAAGAACA GTATTTGGTA TCTGCGCTCT GCTGAAGCCA
3901 GTTACCTTCG GAAAAAGAGT TGGTAGCTCT TGATCCGGCA AACAAACCAC CGCTGGTAGC
3961 GGTGGTTTTT TTGTTTGCAA GCAGCAGATT ACGCGCAGAA AAAAAGGATC TCAAGAAGAT
```

-continued

```
4021 CCTTTGATCT TTTCTACGGG GTCTGACGCT CAGTGGAACG AAAACTCACG TTAAGGGATT
4081 TTGGTCATGG CTAGTTAATT AACATTTAAA TCAGCGGCCG CAATAAAATA TCTTTATTTT
4141 CATTACATCT GTGTGTTGGT TTTTTGTGTG AATCGTAACT AACATACGCT CTCCATCAAA
4201 ACAAAACGAA ACAAAACAAA CTAGCAAAAT AGGCTGTCCC CAGTGCAAGT GCAGGTGCCA
4261 GAACATTTCT CTATCGAA
```

Amino acid sequence (SEQ ID NO: 96)

```
MYRMQLLSCIALSLALVTNSISTEELRVSLASHLRKLRKRLLRDADDL
QKISAMVRSVECPPCPAPPVAGPSVFLFPPKPKDTLMISRTPEVTCVVVDVSHE
DPEVQFNWYVDGMEVHNAKTKPREEQFNSTFRVVSVLTVVHQDWLNGKEY
KCKVSNKGLPAPIEKTISKTKGQPREPQVYTLPPSREEMTKNQVSLTCLVKGF
YPSDIAVEWESNGQPENNYKTTPPMLDSDGSFFLYSKLTVDKSRWQQGNVFS
CSVMHEALHNHYTQKSLSLSPGK
```

Example 5: CRISPR-Cas9 Mediated Editing and Base Editing of APOE

To introduce the R136S mutation in APOE using CRISPR-Cas9, gRNA sequences were designed (Table 7). In one example, a gRNA sequence is cloned into lentiCRISPR v2 using 2 oligos to form a linker containing the 20 base sequence that is cloned into the BsmB1 site downstream of the U6 promoter. To support repair, a template was designed with 2 additional silent mutations. The template has 50 bases flanking the area with the mutations. An exemplary template sequence is as follows:

(SEQ ID NO: 65)

CGCCTGGTGCAGTACCGCGGCGAGGTGCAGGCCATGCTCGGCCAGAGCAC aGAGGAGCT*c*CGcGTGaGtCTCGCaagCCACCTGCGCAAGCTGCGTAAGC

GGCTCCTCCGCGATGCCGATGACCTGC where silent mutations to abolish PAM motifs are double underlined, the codon corresponding to the R136S mutation is bolded, and silent mutation to generate SacI site for cleaving PCR products from clones that received the template is italicized.

TABLE 7 gRNA designs for introducing R136S mutation

| Plasmid | gRNA | SEQ ID NO: | Distance From DSB | ON target score | OFF target score |
|---|---|---|---|---|---|
| 18401 | CTTACGCAGCTTGCGCAGGT | 69 | 16 | 61.2 | 90.5 |
| 18402 | GCTTGCGCAGGTGGGAGGCG | 70 | 6 | 59.5 | 53.9 |
| 18403 | ACGCAGCTTGCGCAGGTGGG | 71 | 13 | 59.4 | 62.9 |
| 18404 | CCAGAGCACCGAGGAGCTGC | 72 | 9 | 49.3 | 42.7 |
| Optional 18405 | GCCAGAGCACCGAGGAGCTG | 73 | 10 | 52.8 | 33.7 |
| Optional 18406 | GAGGCGCACCCGCAGCTCCT | 74 | 11 | 51.1 | 60.5 |

Without wishing to be bound by theory, a proposed mechanism for the APOE3ch mutation is loss of function (e.g. in binding to HSPG). Accordingly, gRNA sequences were designed to "knockout" APOE using CRISPR-Cas9 (Table 8). The gRNAs are designed to target exon 3 (amino acids 1-61) of ApoE. In an example, a gRNA sequence is cloned into lentiCRISPR v2 by ordering 2 oligos to form a linker containing the 20 base sequence that is cloned into BsmB1 site downstream of the U6 promoter. Repair is done by non-homologous end joining (NHEJ), which is an error-prone process and often results in short insertions or deletions leading to APOE knockout.

TABLE 8 gRNA designs for APOE knockout

| Plasmid | gRNA | SEQ ID NO: | Break at amino acid | ON target score | OFF target score |
|---|---|---|---|---|---|
| 184Q1 | AGCTGCGCCAGCAGACCGAG | 75 | 18 | 66.3 | 74.4 |
| 184Q2 | CCAGGCCAAGGTGGAGCAAG | 76 | 3 | 65.6 | 49.3 |
| 184Q3 | CACAGGATGCCAGGCCAAGG | 77 | 1 | 65.4 | 44.5 |
| 184Q4 | ACAGTGTCTGCACCCAGCGC | 78 | 38 | 60.6 | 71.4 |
| 184Q5 | GGCCAAGGTGGAGCAAGCGG | 79 | 5 | 59.3 | 71.3 |

A R136H mutation in APOE is predicted to have a similar effect as the R136S mutation. Accordingly, to introduce a R136H mutation in APOE using base editing techniques, the following gRNA was designed (Table 9). The gRNA sequence GAGGCGCACCCGCAGCTCCT (SEQ ID NO: 80) is cloned into pLenti sgRNA (addgene 71409), using 2 oligos to form a linker containing the 20 base sequence that is cloned into BsmB1 site downstream of the U6 promoter. Plasmid Addgene base editor plasmid pCMV-BE3 (#73021) is used to produce base editing.

TABLE 9 gRNA design for APOE base editing

| gRNA | SEQ ID NO: | R136H change | Base editing score | OFF target score |
|---|---|---|---|---|
| GAGGCGCACCCGCAGCTCCT | 80 | CGC→CAC | 4.6 | 60.5 |

Example 6: High-Throughput Screening of Molecules that Modify ApoE and Heparin Binding To screen for molecules that affect ApoE and heparin binding, ApoE proteins are pre-incubated with candidate polypeptides, small molecules, nucleic acids, lipids or carbohydrates. The pre-incubated ApoE proteins are introduced to heparin-coated surfaces (such as plates or columns), allowed to bind to heparin/HSPG/GAG, and unbound ApoE and candidate molecules are washed off. Alternatively, heparin-coated surfaces (such as plates) can be pre-incubated with candidate molecules, before applying ApoE proteins. The levels of ApoE bound to heparin are detected using antibodies, protein assays, or fluorescence, and the effect of the candidate molecules on ApoE/heparin binding are assessed. Candidate molecules that reduce ApoE/heparin binding may represent novel therapeutics for prevention or treatment of cognitive decline associated with dementia and/or mild cognitive impairment in a human subject in need of such treatments. An example of such molecules include EZ-482 (See, e.g. Mondal et al. Biochemistry 55 (18): 2613-21, 2016. The structure of EZ-482 is shown below).

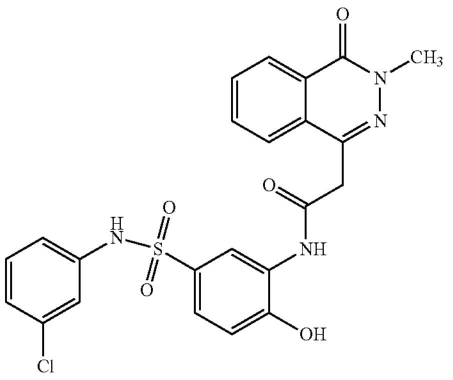 [SMILES: Cn1nc(CC(=O)Nc2cc(S(=O)(=O)Nc3cccc(Cl)c3)ccc2O)c2ccccc2c1=O]

Example 7: High-Throughput Screening of Molecules that Modify ApoE and Anti-ApoE Antibody Binding To screen for molecules that affect ApoE and anti-ApoE antibody binding, ApoE proteins are pre-incubated with candidate polypeptides, small molecules, nucleic acids, lipids or carbohydrates. The pre-incubated ApoE proteins are introduced to surfaces (such as plates or columns) coated with antibodies that bind to the HSPG-binding sites of ApoE (any of the anti-ApoE antibodies as described herein), allowed to bind to the antibodies, and unbound ApoE and candidate molecules are washed off. Alternatively, heparin-coated surfaces (such as plates) can be pre-incubated with candidate molecules, before applying ApoE proteins. The levels of ApoE bound to anti-ApoE antibodies are detected using antibodies, protein assays, or fluorescence, and the effect of the candidate molecules on the binding are assessed. Candidate molecules that increase or reduce ApoE/heparin binding may represent novel therapeutics for prevention or treatment of cognitive decline associated with dementia and/or mild cognitive impairment in a human subject in need of such treatments.

Example 8: Antibody Characterization

Antibodies that bind to wild type ApoE and ApoEch mutant were further evaluated using heparin-affinity chromatography, western blotting, subclones analysis, monoclonal antibody screening, screening for selectivity between huApoE3 and msApoE, and in vivo subretinal injections.

Methods

Chromatography Experiments

His-tagged recombinant ApoE peptide (50 μg/mL) was incubated 3 h R·T. with each antibody individually at 1:10 dilution in 20 mM Tris HCl buffer (pH 7.5). Samples were tested for heparin binding using the heparin sepharose column. Briefly, the column was allowed to reach R·T. and washed 5 times with 20 mM Tris-HCL. Protein input was loaded onto the column upon collecting 10 μL for WB experiments. Input was recycled through the column 5 times. Flow-through was collected and the column was subsequently washed 5 times and recovered fractions were labeled as "washes". 1 mL fractions were retrieved for each 0.05 M step of the NaCl salt gradient from 0 to 1 M. 5 M fraction was also tested to ensure complete release of the protein from the column. WB or ELISA were used to test changes in ApoE binding to heparin.

Western Blotting

Samples for WB analyses were prepared by diluting 10 μL of each fraction in 4× sample buffer (Laemmli's SDS-Sample buffer, BP-110R, Boston bioproducts), 4 μL DTT (Sigma Aldrich), and 16 μL 1×RIPA buffer. Electrophoresis was performed under denaturing conditions, using a vertical electrophoretic chamber (Biorad). Bands separated on 4-20% precast gels (Biorad) using constant voltage (15' 70V, 1 h 100V). Transfer of the proteins was performed on nitrocellulose membranes (Millipore) at 70 V constant voltage for 1 h. Membranes were blocked 1 h R·T. using Odyssey blocking buffer (Licor) and membranes were washed 3×10' with TBS-0.05% Tween 20 (Thermo fisher) prior incubation with primary antibody (Anti-His, rb, 1:5000, Novus biological) and secondary antibody (Donkey anti-rb-800, 1:10000, Licor). Image acquisition was done using Odyssey scanner. Data was analyzed using Image J. Data was normalized by the input and expressed normalized intensities over fraction number (0=input, 1-27=increasing 0.05 M NaCl step gradient in 20 mM Tris HCl pH 7.5, 28=5 M NaCl in 20 mM Tris HCl pH 7.5).

ELISA

To test selectivity of the antibodies for huApoE3WT, huApoE3ch or msApoE, anti-his ELISA coated plates were incubated with 0.0025 μg/μL of the target protein for 2 h at R·T. under gentle shaking. Wells were washed 5 times with 1× wash buffer (R&D) and subsequently incubated with serial dilutions of Innovagen antibody of interest over night at 4° C. on a shaker (100 μL/well). The following day, wells were washed 5 times with sample buffer and incubated for 45 minutes using Rabbit-anti-mouse HRP-conjugated buffer (1:10,000; 100 μL/well; Abcam). After 5 more washes, plates were incubated with chromogen A+B 1:1 to initiate the colorimetric reaction (100 μL/well). The reaction was stopped with 2 N sulfidric acid (R&D stop solution., 50 μL/well) and absorbance detected at 450 nm spectroscopically.

Antibodies designed against the heparin binding domain of APOE were tested for affinity to APOE3 and APOEch mutant recombinant protein using an ELISA. The Ni-NTA HisSorb Plates (Qiagen) plates were washed 3 times with wash buffer 1 (DY008), the APOE recombinant proteins were suspended in buffer (DY008) to give a final concentration of 0.5 ug/ml. The plates were incubated with 200 μl for 2 hours. The plate was then washed 5 times with 1× wash buffer (DY008), the plates were then incubated with antibodies in a serial dilution series from 1:1000 to 1:32000 and incubated overnight at 4° C. The plate is then washed 5 times in 1× wash buffer (DY008). The plates were then incubated with Anti-mouse HRP (Abcam; ab97046) (1:10000) for 45 minutes. The plate was then washed 5 times in 1× wash buffer to ensure complete removal of unbound secondary antibody. The Sulfuric acid from the ELISA reagent kit (DY008) was warmed to 37° C. prior to addition of 100 μl of tetramethylbenzidine (Millipore) initiating the detection phase of the reaction. After a 5-mins incubation, sulfuric acid was added to terminate the reaction. The plate was then read using Synery 2 microplate reader (BioTek Instrument. Inc) and the Gen5 version1.11 software).

Results

Figure 18A:
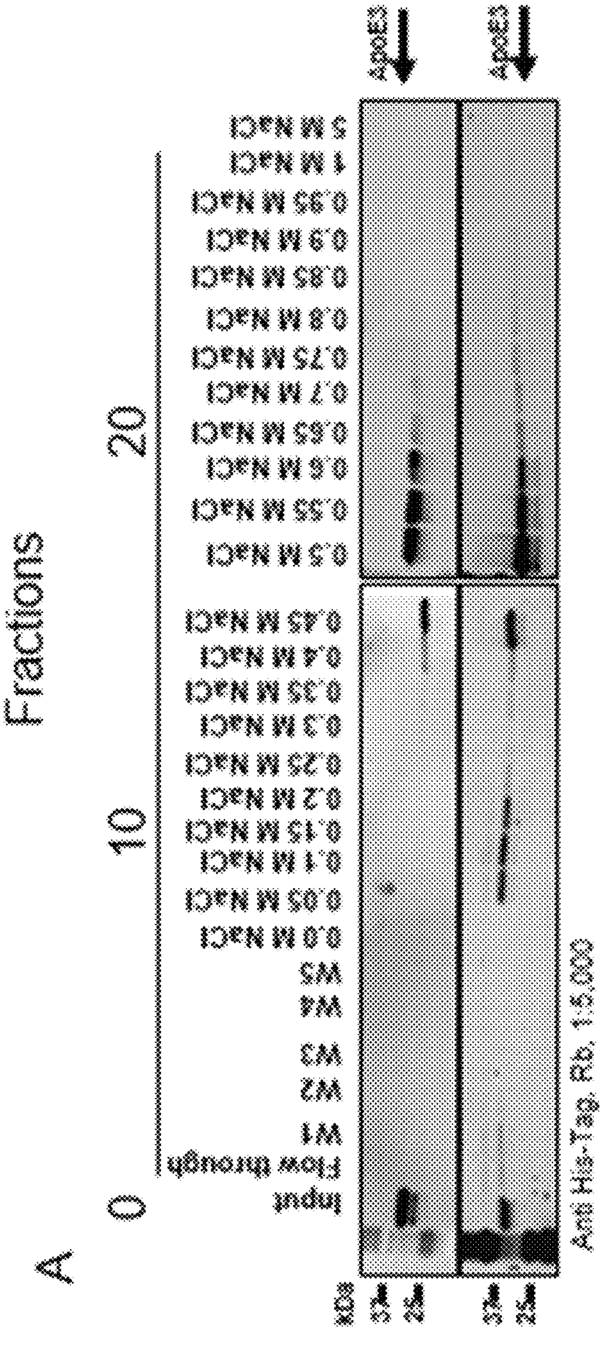
FIGS. 18A-18B show heparin-affinity chromatography and western blot analysis of antibody 1H4.
Figure 18B:
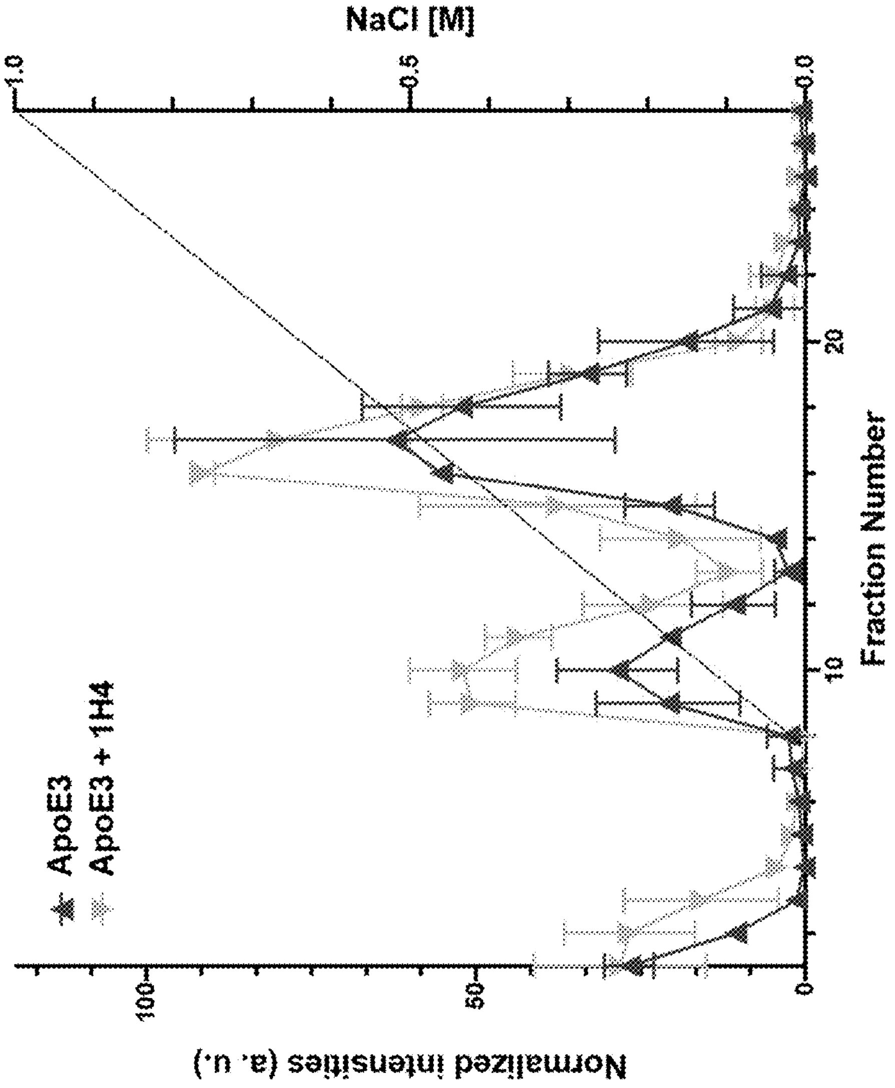
Figure 19:
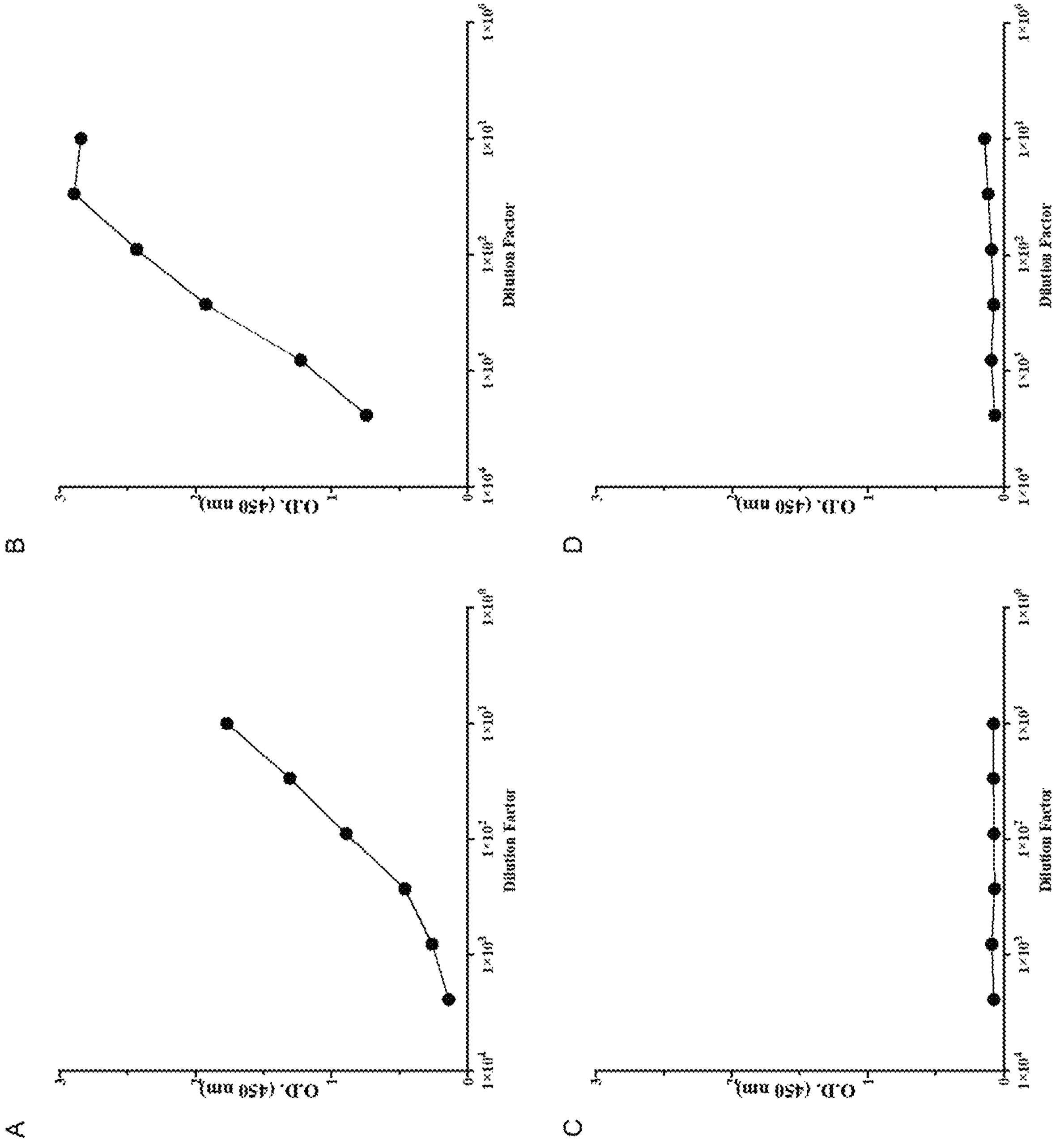
FIGS. 19A-19D show ELISA results of 1H4-2 serum tested with ApoE3 WT full-length protein (A), ApoE3 WT peptide (B), ApoE3ch full length protein (C), and ApoE3ch peptide (D).

Antibody 1H4 was evaluated using heparin-affinity chromatography and western blotting. ApoE3 was incubated either with negative control (vehicle, top blots) or 1H4 (bottom blots) and each fraction was subjected to heparin-affinity chromatography and western blotting (FIG. 18A). ApoE3 positive bands are indicated by the arrows and detected using the antibody anti his-tag (rb, 1:5,000) that specifically detects the his-tag of the recombinant human APOE. FIG. 18B shows quantification of WB blotting bands detected by the antibody anti hi-tag as shown in FIG. 18A. Intensities were normalized to the input. These results show that ApoE3 binding to heparin was reduced in the presence of the antibody, and that antibody 1H4 competes with ApoE for heparin binding. N=2 independent experiments.

Figure 20:
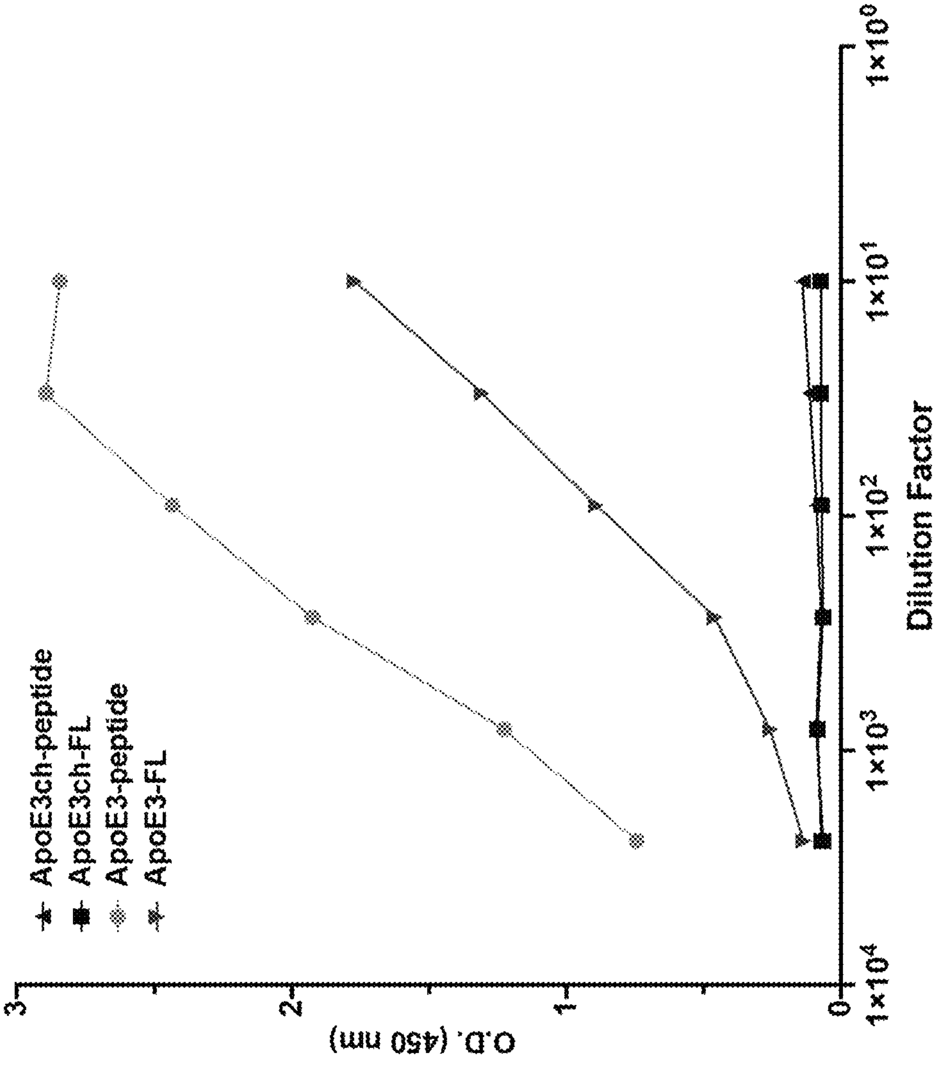
FIG. 20 shows ELISA results of 1H4-2 serum tested with ApoE3 WT full-length protein, ApoE3 WT peptide, ApoE3ch full length protein, and ApoE3ch peptide.

Next, subclone analysis of 1H4 serum was carried out. FIGS. 19A-19D show ELISA results of 1H4-2 serum tested with ApoE3 WT full-length protein (A), ApoE3 WT peptide (B), ApoE3ch full length protein (C), and ApoE3ch peptide (D). The results are expressed as optical density at 450 nm over dilution factor of the serum tested. FIG. 20 is a diagram comparing the results shown in FIGS. 19A-19D.

Figure 21:
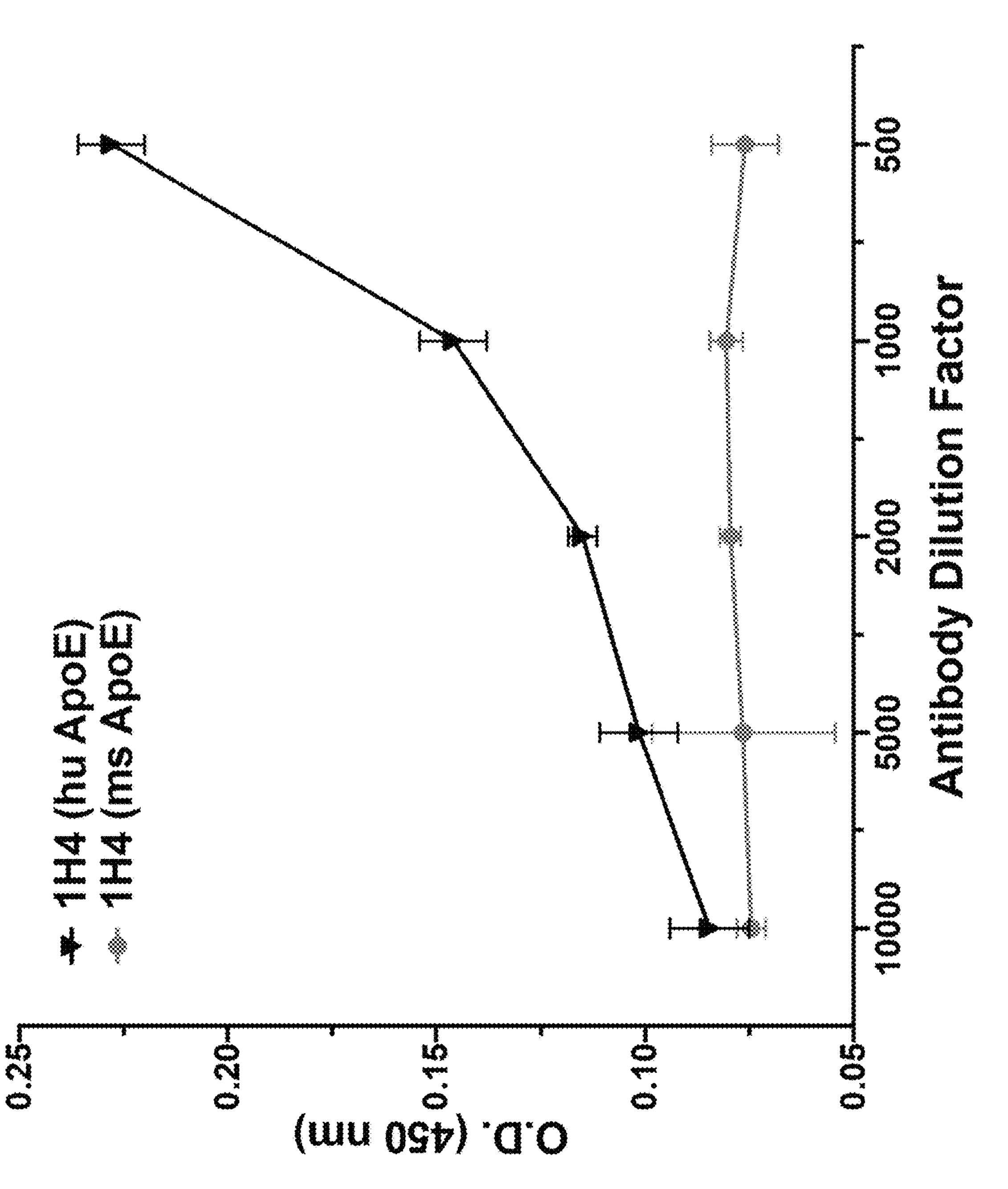
FIG. 21 shows representative ELISA profiles of serial dilutions of the antibody 1H4 incubated either with human recombinant ApoE3 or mouse recombinant ApoE3.

FIG. 21 shows representative ELISA profiles of serial dilutions of the antibody 1H4 incubated either with human recombinant ApoE3 or mouse recombinant ApoE3. The results show that the antibody preferentially binds to the human protein and not to the mouse, and that antibody 1H4 is selective for human ApoE. The results are shown as averaged optical densities detected at 450 nm±s.e. m. (n=2).

Figure 22:
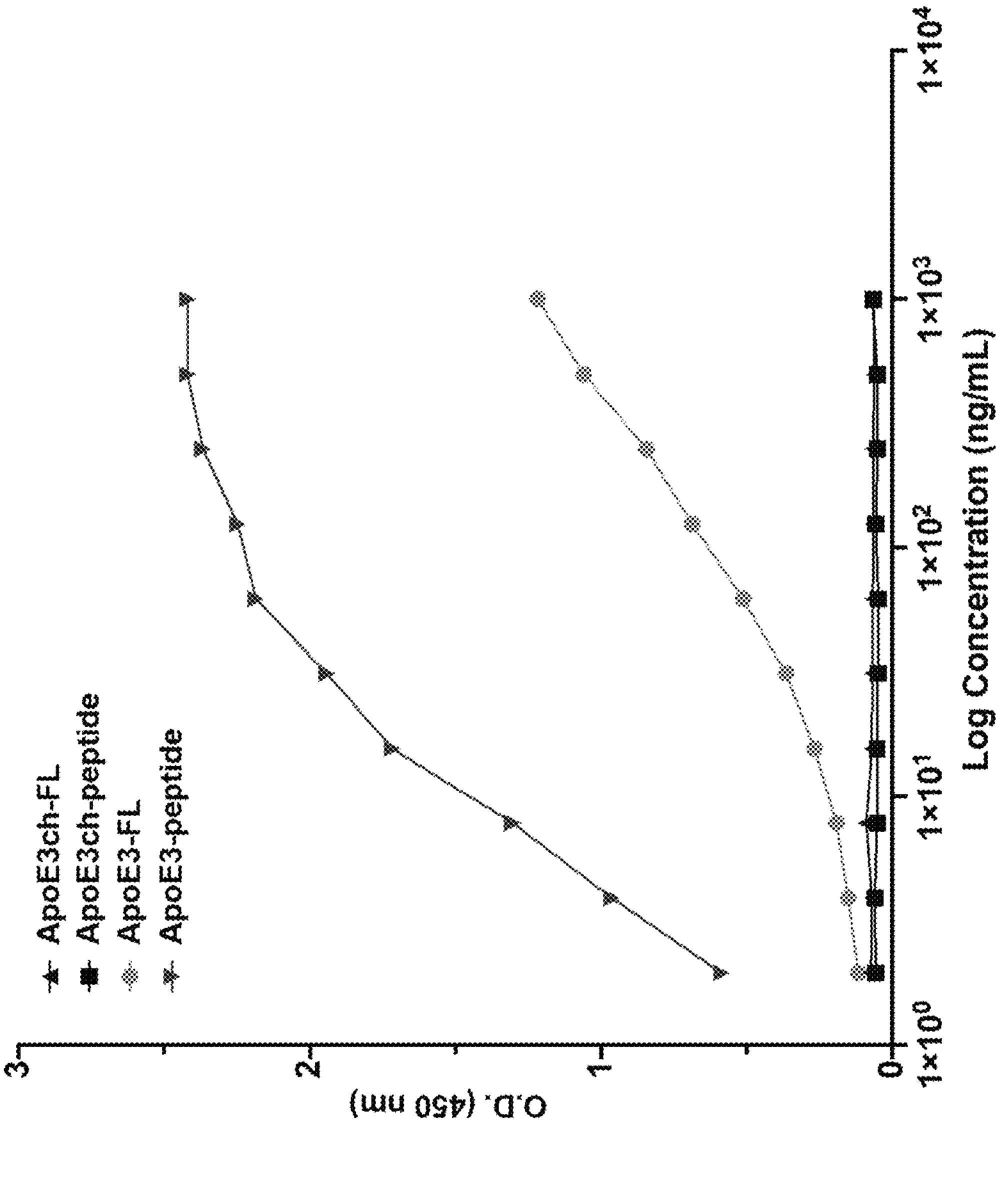
FIG. 22 shows ELISA results for the monoclonal 1H4 antibody purified from cloned hybridoma.

Next, monoclonal 1H4 antibody was purified from cloned hybridoma, and subjected to ELISA evaluation. FIG. 22 shows results from the ELISA experiments.

Antibody 7C11 was evaluated using heparin-affinity chromatography, western blotting, quantitative ELISA for chromatography fractions, and competitive ELISA for binding analyses.

Figure 23A:
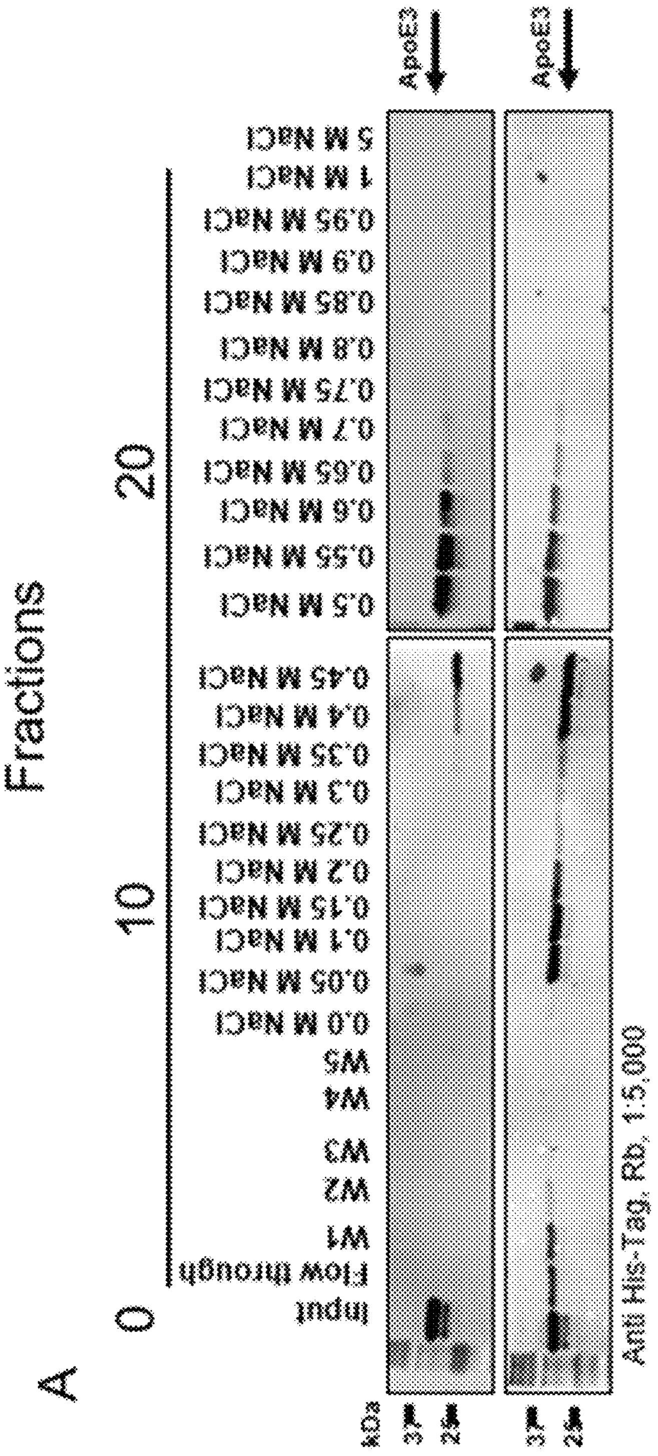
FIGS. 23A and 23B show heparin-affinity chromatography and western blot analysis of antibody 7C11.
Figure 23B:
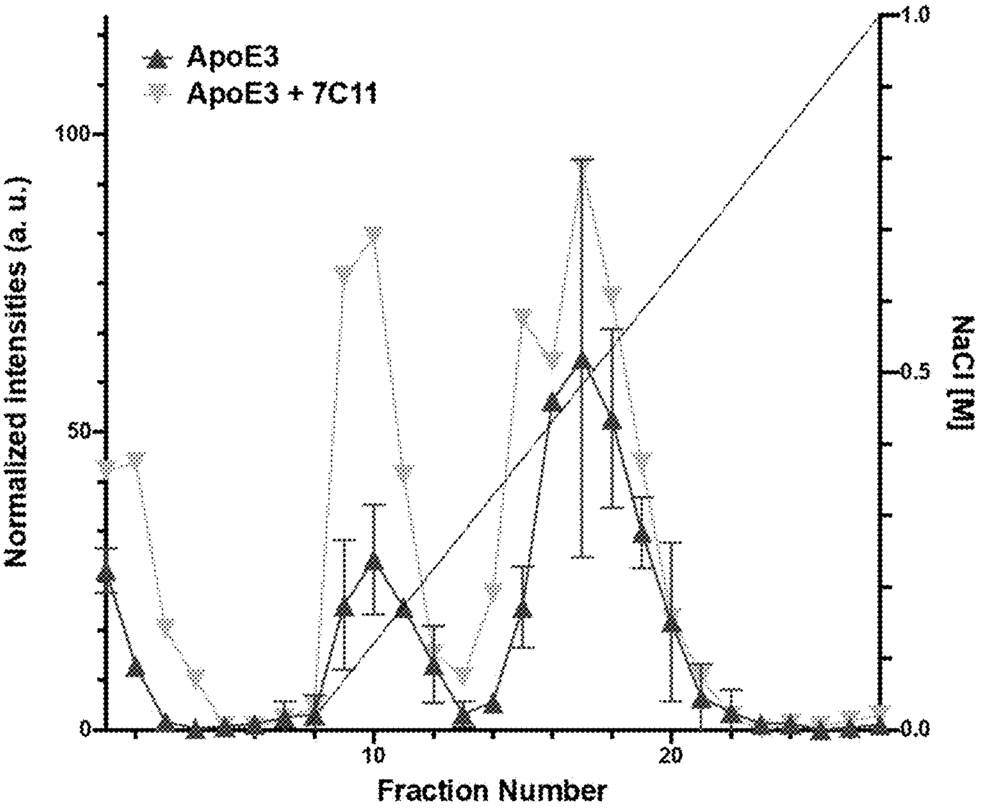
Figure 24:
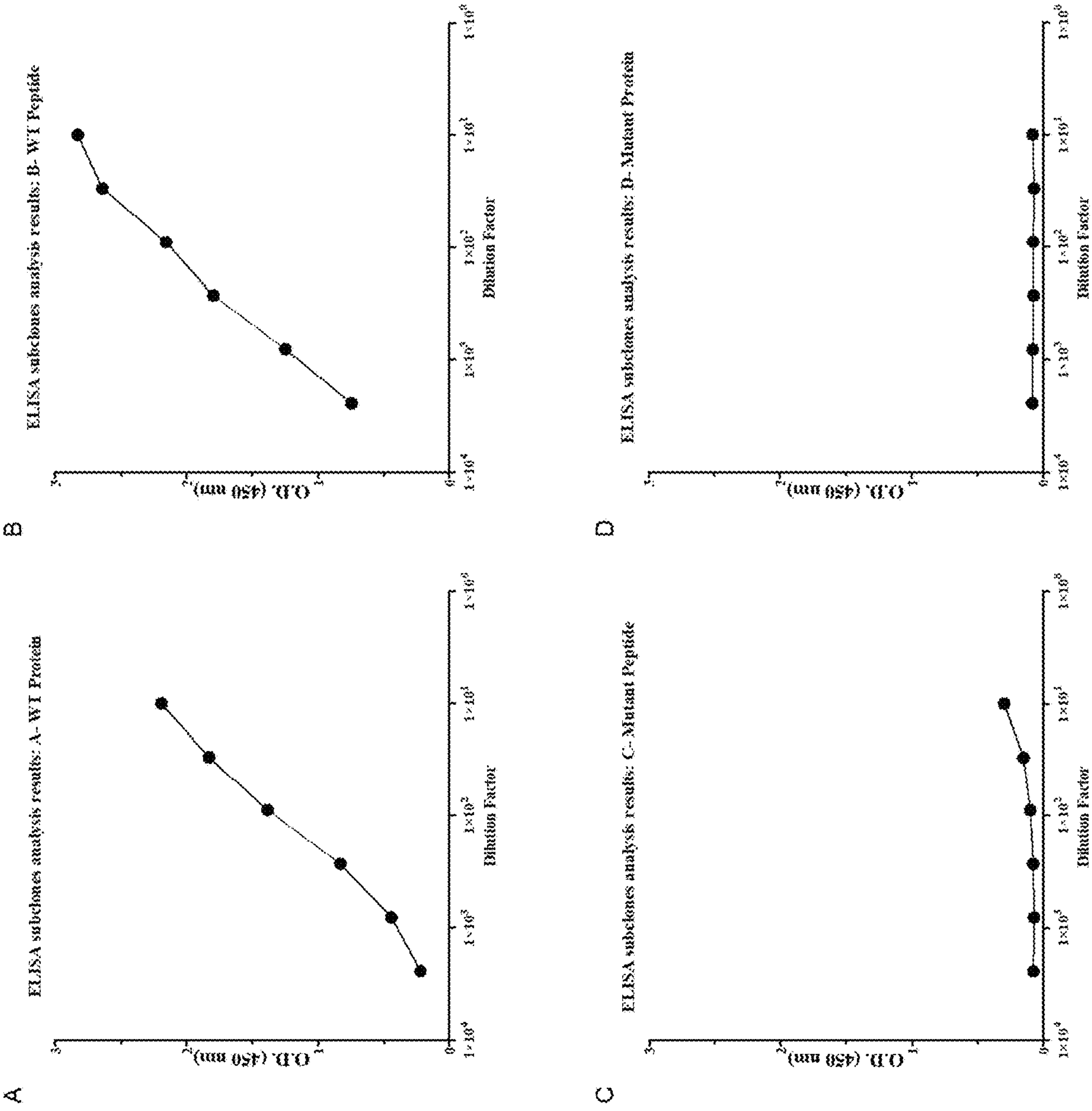
FIGS. 24A-24D show ELISA results from testing the 7C11-1 serum with ApoE3 WT full-length protein (A), ApoE3 WT peptide (B), ApoE3ch full length protein (C), or ApoE3ch peptide (D).

Heparin affinity chromatography fractions of ApoE3 incubated either with negative control (vehicle, top blots) or the antibody 7C11 (bottom blots) and subjected to western blotting (FIG. 23A). ApoE3 positive bands are indicated by the arrows and detected using the antibody anti his-tag (rb, 1:5,000) that specifically detects the his-tag of the recombinant peptide. FIG. 23B shows quantification of the WB blotting bands detected by the antibody anti hi-tag as shown in FIG. 23A.

Intensities were normalized to the input. These results show that ApoE3 binding to heparin was reduced in the presence of the antibody, and that 7C11 competes with ApoE for heparin binding.

Figure 25:
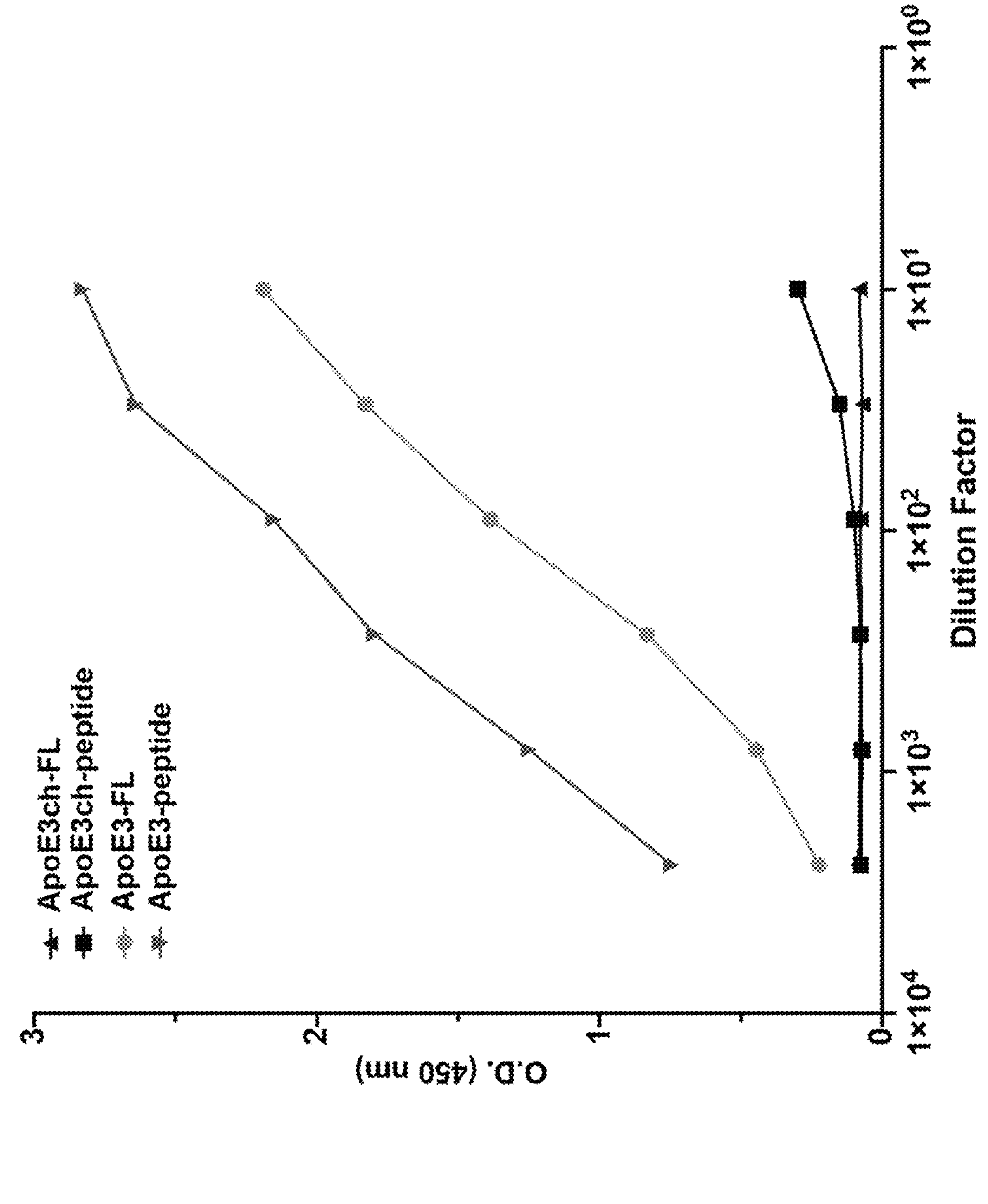
FIG. 25 shows ELISA results from testing the 7C11-1 serum with ApoE3 WT full-length protein, ApoE3 WT peptide, ApoE3ch full length protein, or ApoE3ch peptide.
Figure 26:
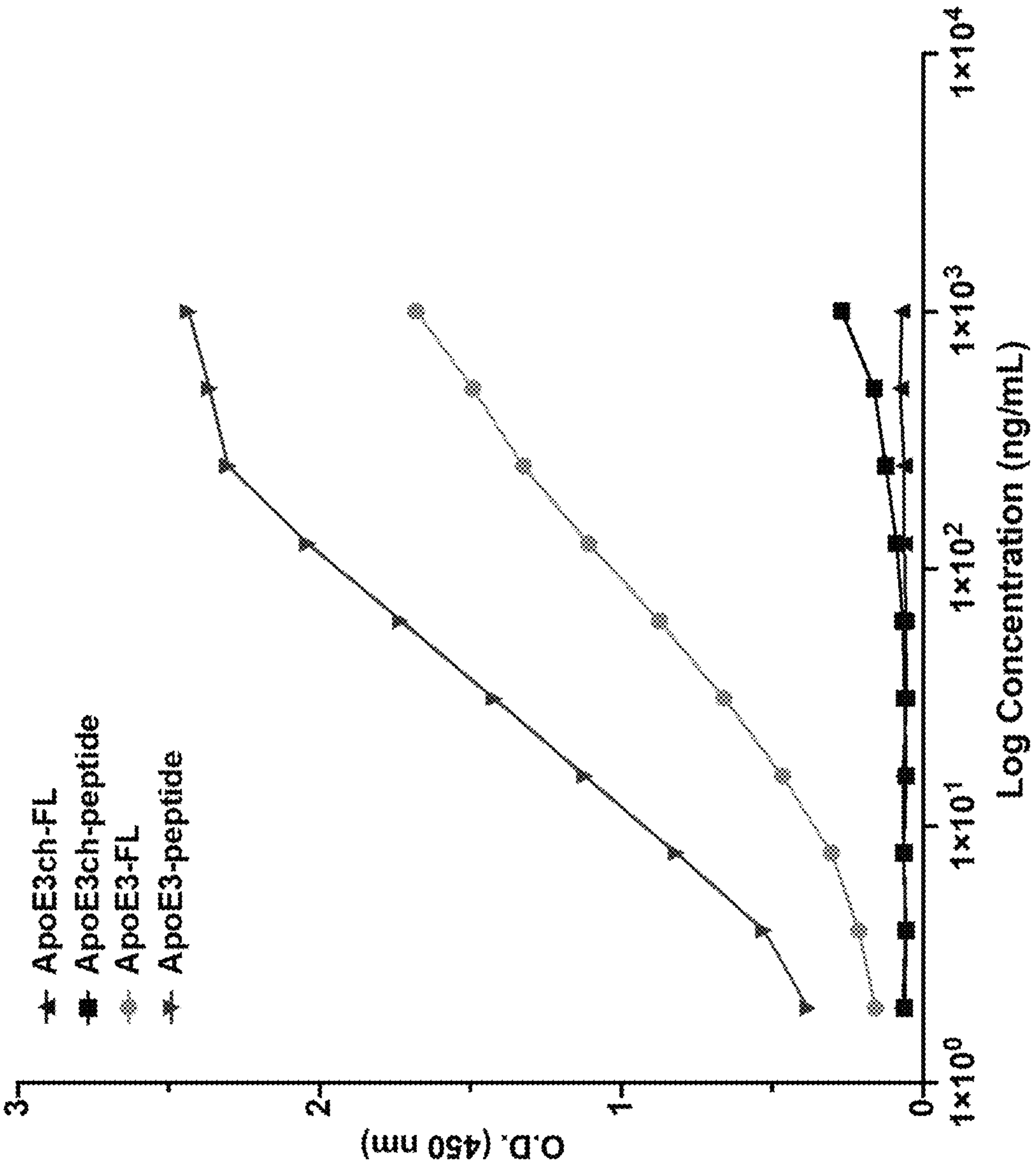
FIG. 26 shows ELISA results for the monoclonal 7C11-1 antibody purified from cloned hybridoma.

Next, subclone analysis of 7C11-1 serum was carried out. FIGS. 24A-24D show ELISA results from testing the 7C11-1 serum with ApoE3 WT full-length protein (A), ApoE3 WT peptide (B), ApoE3ch full length protein (C), or ApoE3ch peptide (D). The results are shown as optical density at 450 nm over dilution factor of the serum tested. FIG. 25 is a diagram comparing the results shown in FIGS. 19A-19D. Next, monoclonal 7C11-1 antibody was purified from cloned hybridoma, and subjected to ELISA evaluation. FIG. 26 shows results from the ELISA experiments.

Figure 27:
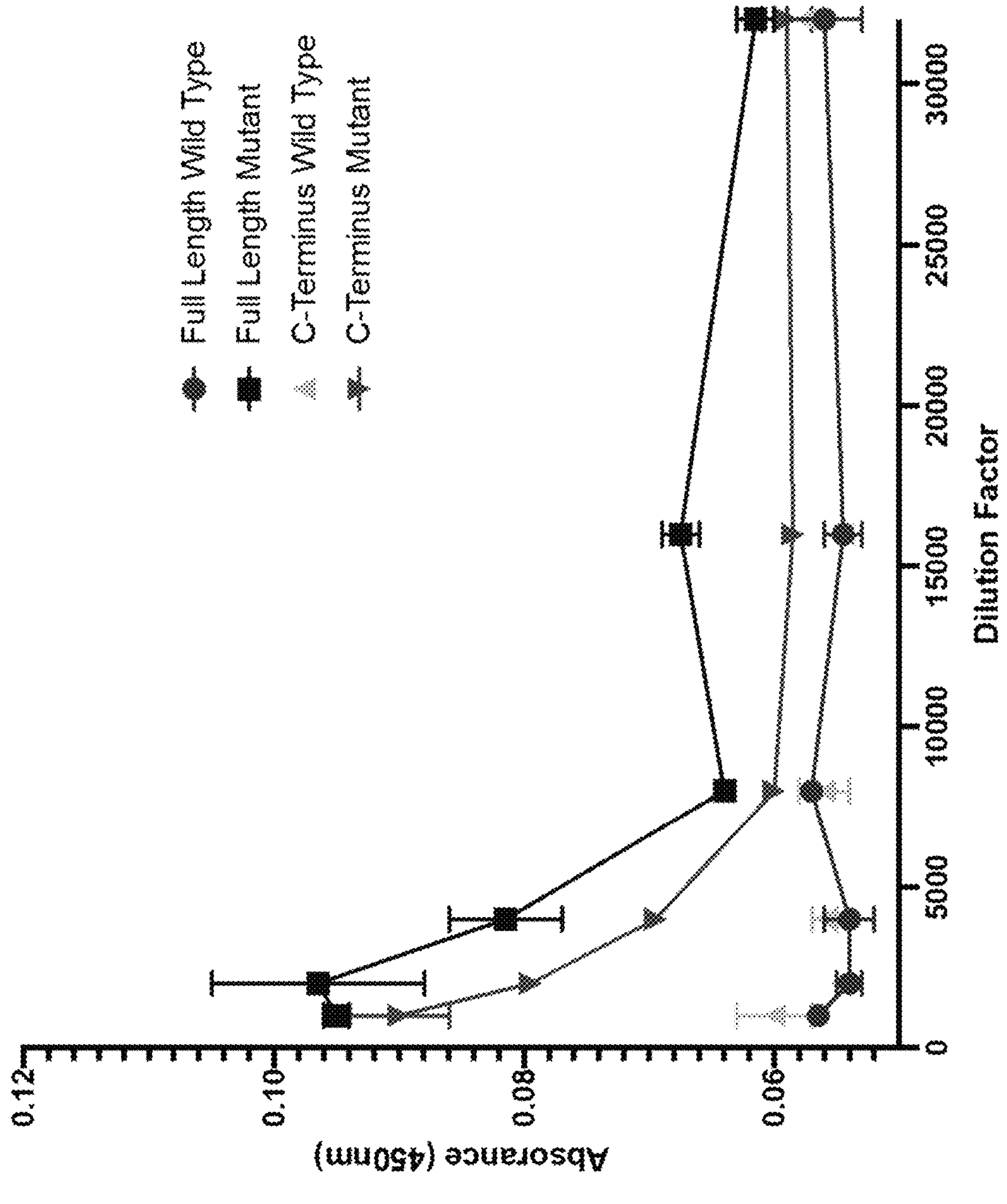
FIG. 27 shows results from ELISA screening of the 19G10-2 antibody against the heparin binding domain of APOE3 Wild Type (WT) and APOE3ch Mutant recombinant protein.

The 19G10-2 antibody was further evaluated using Heparin-Affinity chromatography, Western Blotting, Quantitative ELISA for chromatography fractions, and ELISA for binding analyses. ELISA screening of the 19G10-2 antibody was performed against the heparin binding domain of APOE3 Wild Type (WT) and APOE3ch Mutant recombinant protein. As shown in FIG. 27, the 19G10-2 antibody displays specificity towards both the full length and c-terminal domain of the APOE3ch (amino acids 125 to 299) mutant recombinant protein and some interaction with APOE3 WT.

Figure 28A:
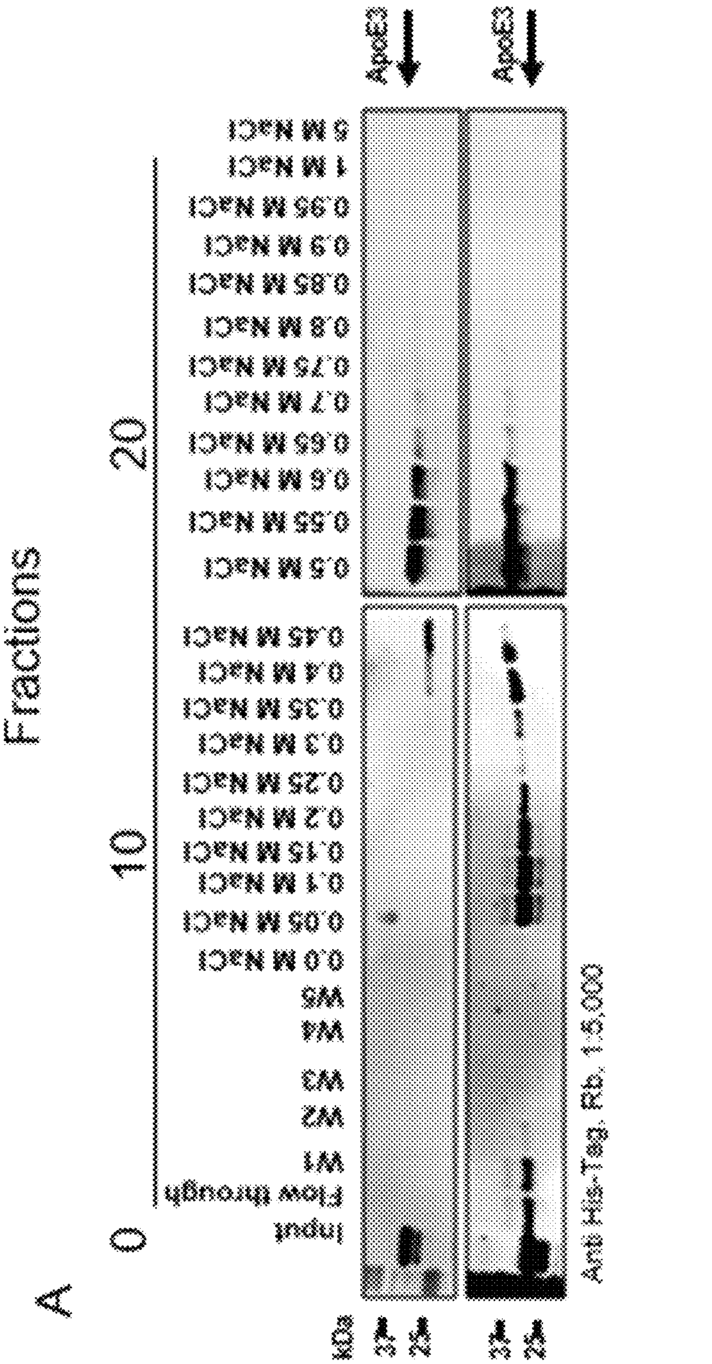
FIGS. 28A and 28B show heparin-affinity chromatography and western blot analysis of antibody 19G10-2.
Figure 28B:
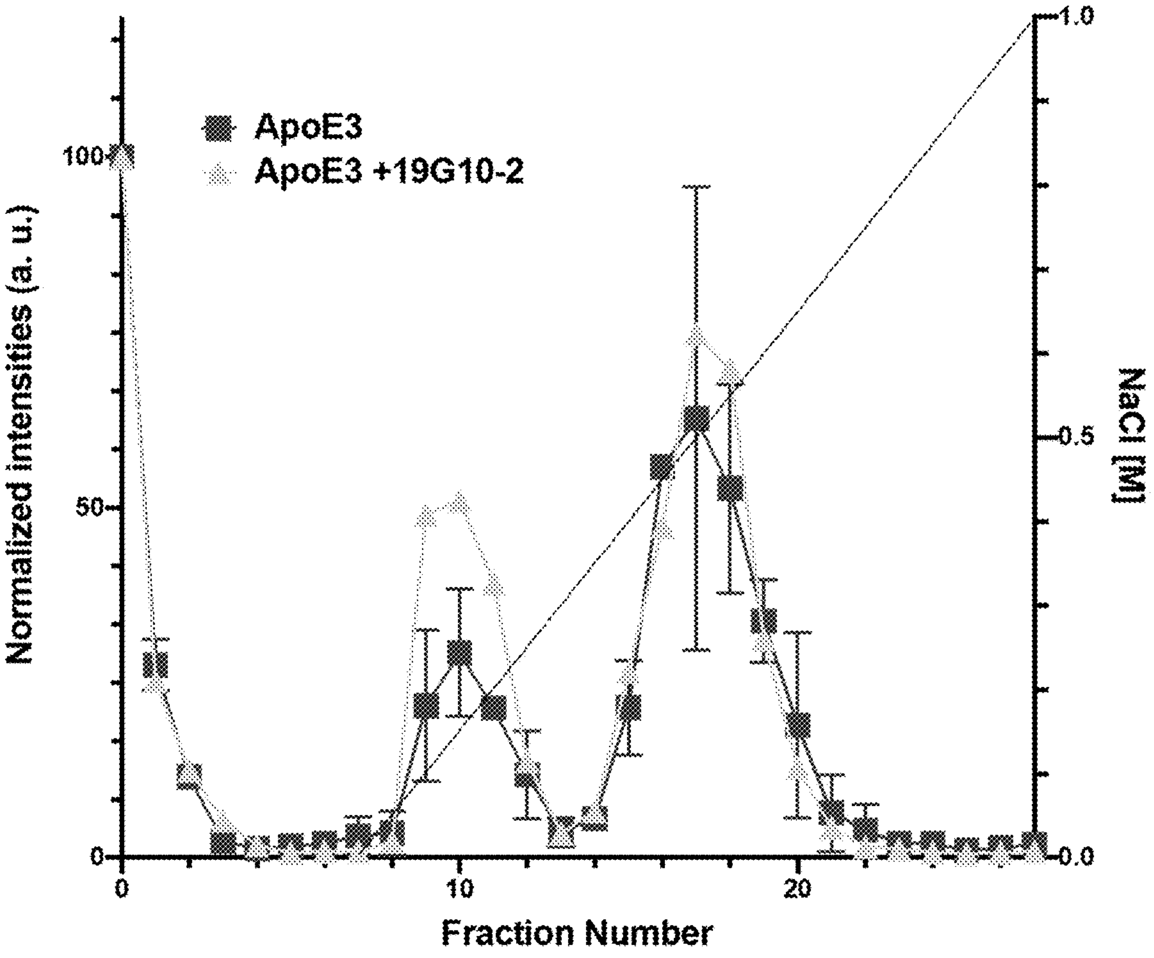

Heparin affinity chromatography fractions of ApoE3 incubated either with negative control (vehicle, top blots) or the antibody 19G10-2 (bottom blots) were subjected to ELISA analysis (FIG. 28A). ApoE3 positive bands are indicated by the arrows and detected using the antibody anti his-tag (rb, 1:5,000) that specifically detects the his-tag of the recombinant peptide. FIG. 28B shows quantification of WB blotting bands detected by the antibody anti hi-tag as shown in FIG. 28A. Intensities were normalized to the input. These results show that despite being designed against the ApoE3ch-HSPG domain, 19G10-2 competes with wild type ApoE for heparin binding and resulted in reduced ApoE3 binding to heparin. Without wishing to be bound by theory, antibody 19G10-2 may recognize and/or stabilize a conformation specific feature of APOE (e.g. an APOE polymer or aggregate) that is less likely to bind heparin/HSPG/GAG.

Figure 29:
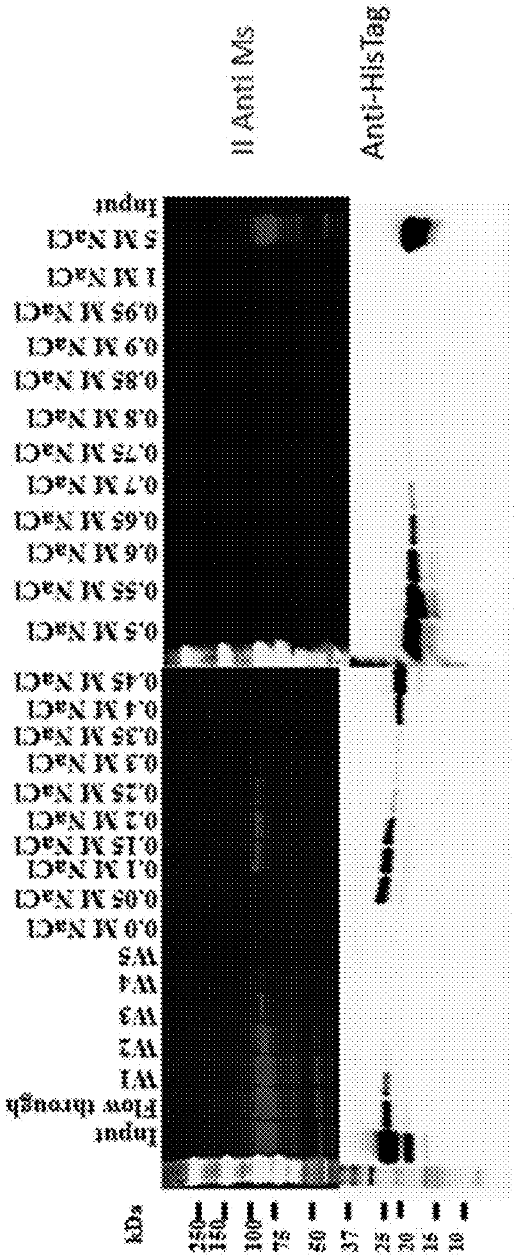
FIG. 29 shows western blotting of ApoE3 WT incubated with 19G10-2 serum antibody.

FIG. 29 shows western blotting of ApoE3 WT incubated with 19G10-2 serum antibody. Top blots: membranes probed with secondary anti-mouse to detect 19G10-2 antibody. Bottom membranes were incubated with anti his-tag as described previously to detect ApoE3 positive fractions. This analysis demonstrates that antibody-APOE complexes (left side of the blots; top and bottom) do not bind to heparin, while free APOE bind to heparin with high affinity (right side of the blot; bottom).

Figure 30:
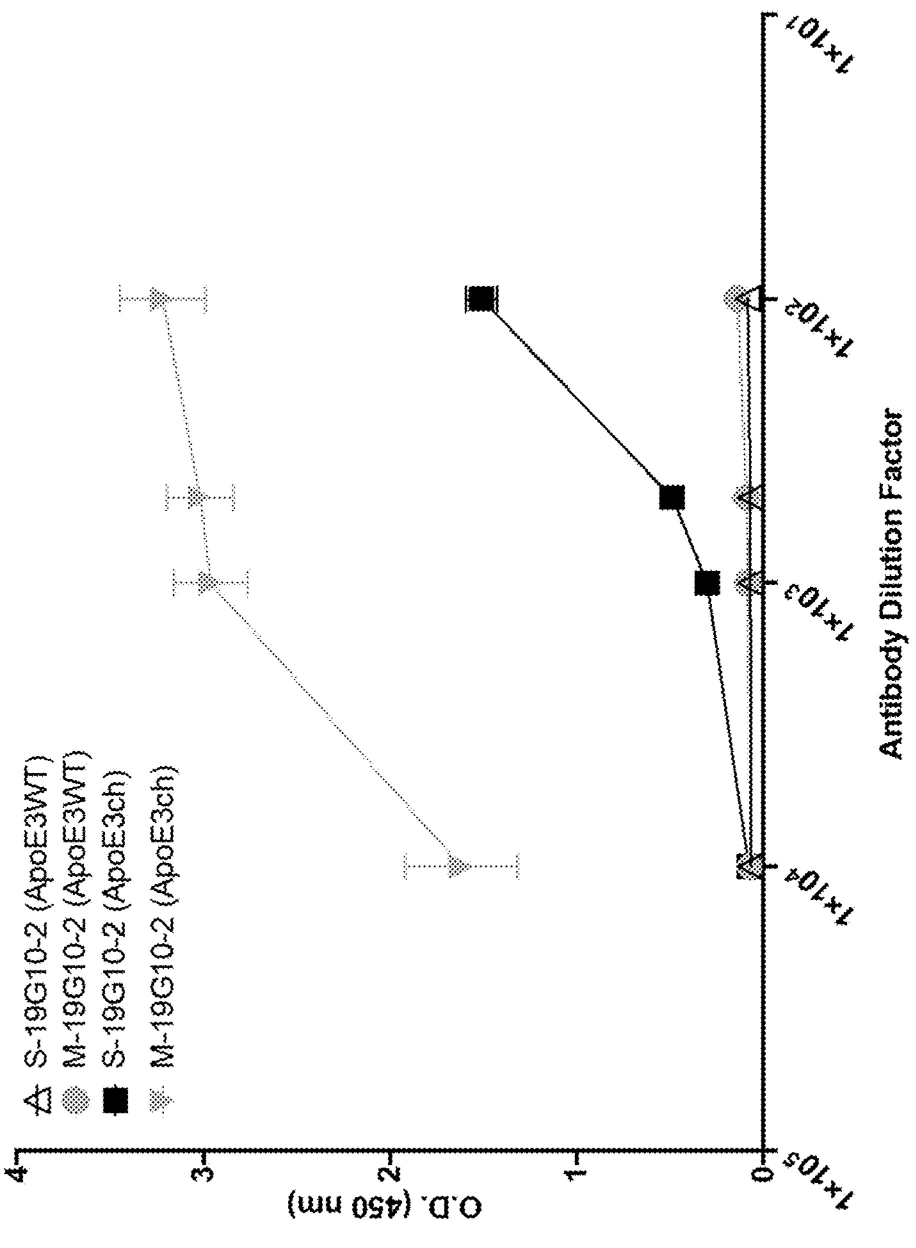
FIG. 30 is representative ELISA showing the differences in binding of both serum and monoclonal antibody hybridoma supernatant 19G10-2 for ApoE3WT or ApoE3ch.
Figure 31:
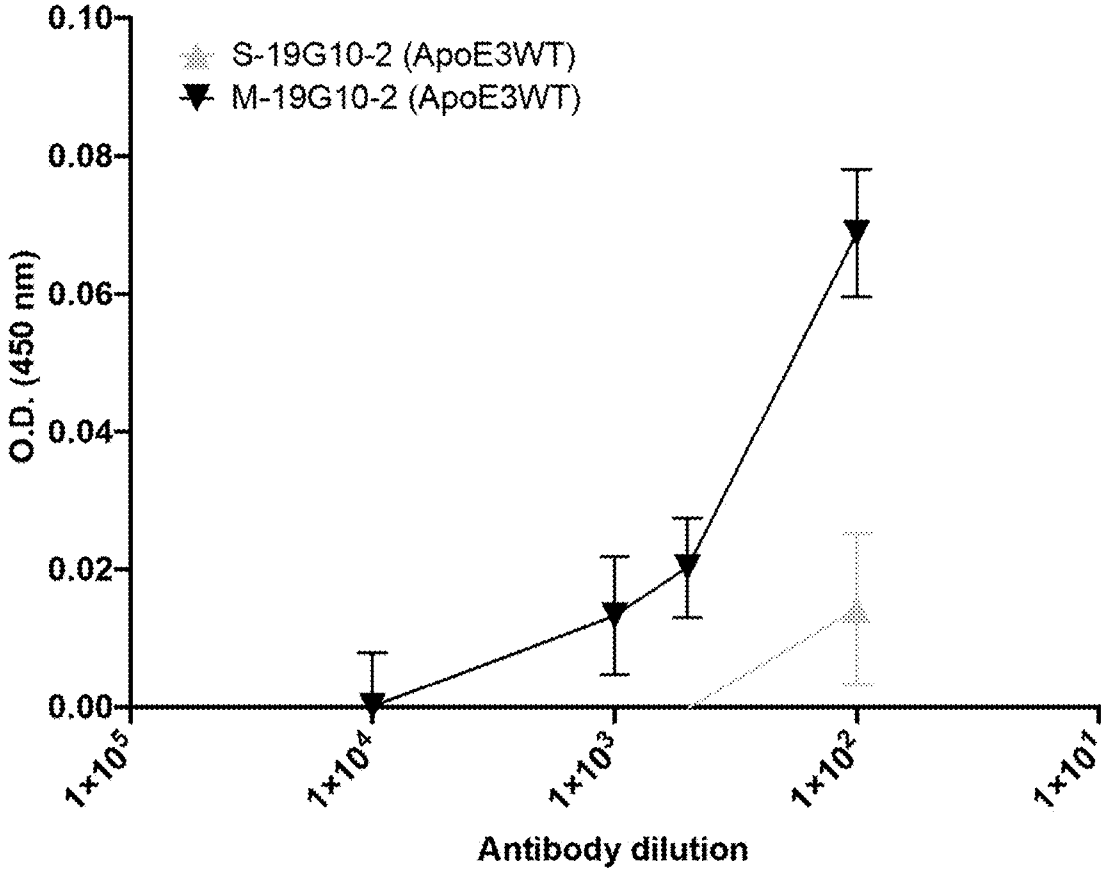
FIG. 31 is an enlargement of the Y axes in FIG. 30.
Figure 32:
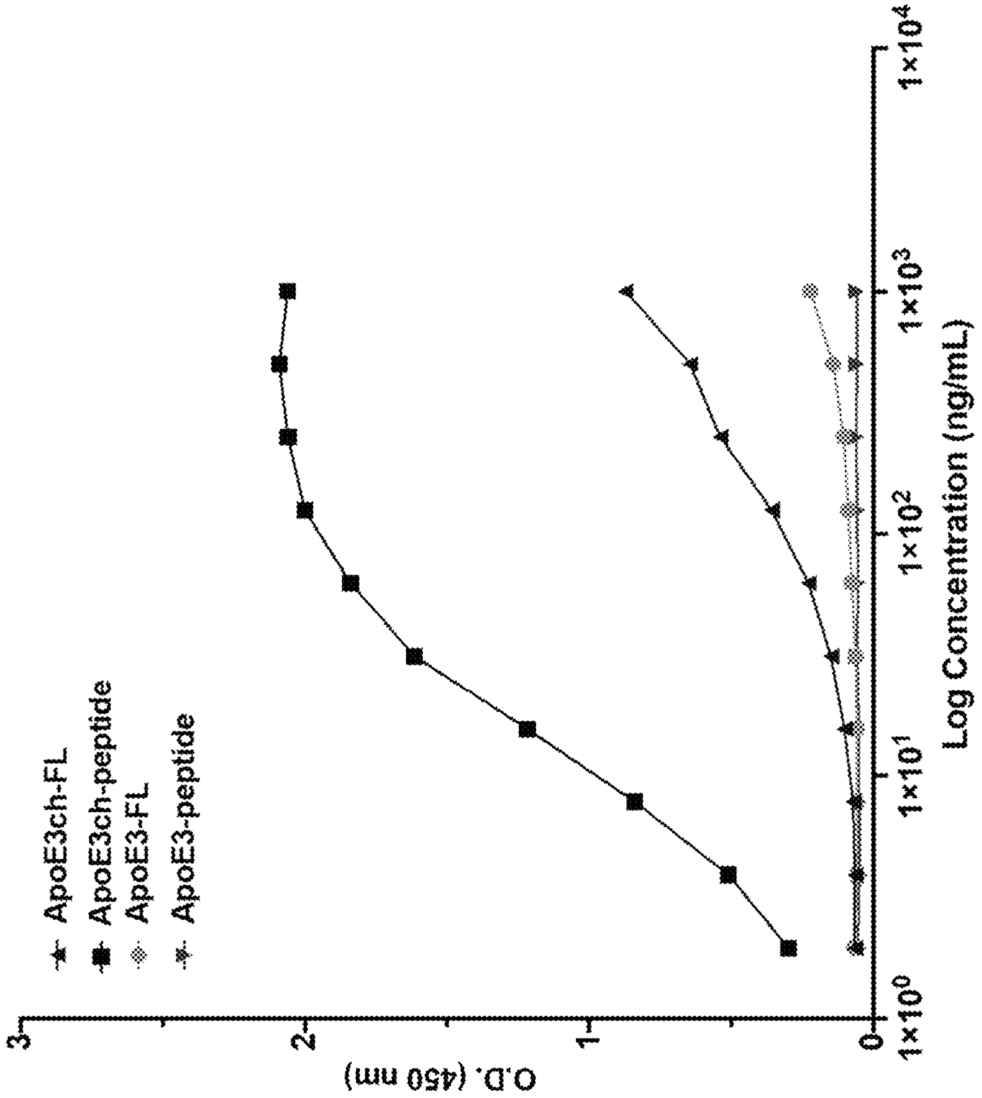
FIG. 32 shows ELISA results for the monoclonal 19G10-2 antibody purified from cloned hybridoma.

FIG. 30 is representative ELISA showing the differences in binding of both serumand monoclonal antibody hybridoma supernatant 19G10-2 for ApoE3WT or ApoE3ch. Data confirms the preponderant selectivity of this antibody for the ApoE3ch variant. FIG. 31 is an enlargement of the Y axes showing some limited binding profiles of the antibody 19G10-2 (serum, grey profile; monoclonal, black binding profile) in the presence of ApoE3WT. Next, monoclonal 19G10-2 antibody was purified from cloned hybridoma, and subjected to ELISA evaluation. FIG. 32 shows results from the ELISA experiments. A signal of recognition of the full-length WT APOE higher than that of the WT ApoE peptide suggest binding of a conformation-specific feature.

Figure 33:
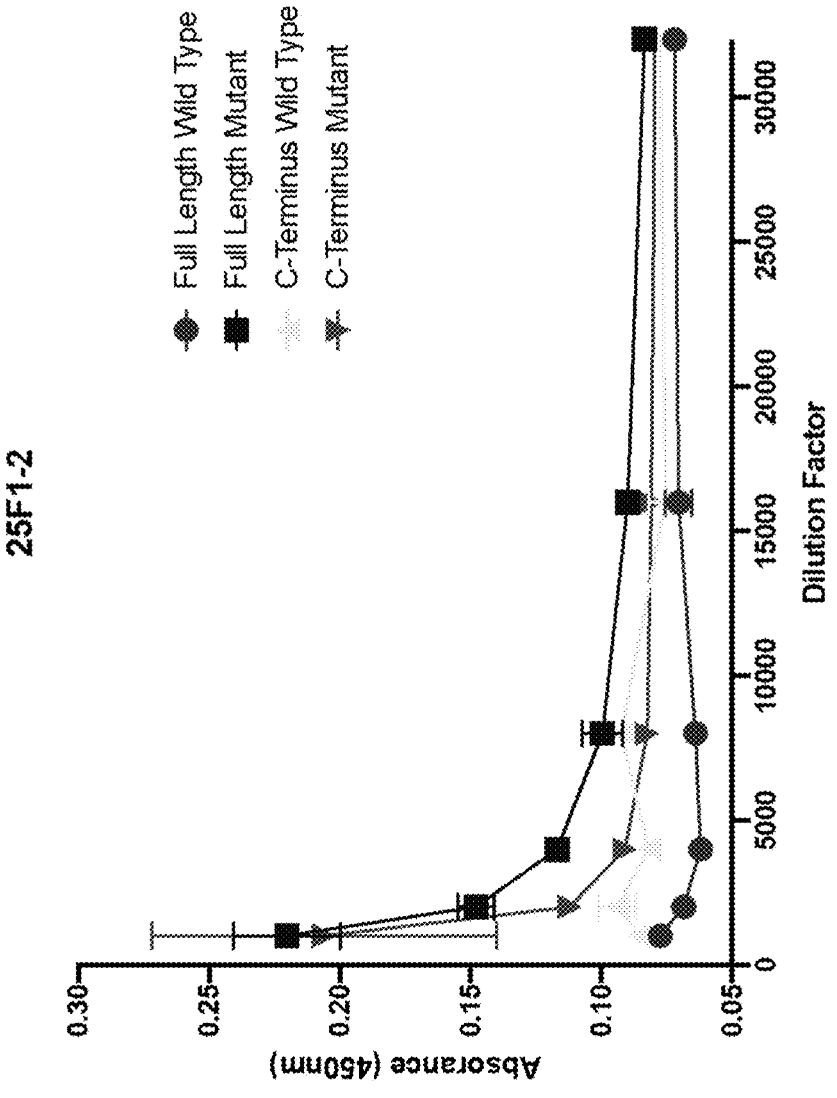
FIG. 33 shows results from ELISA screening of the 25F1-2 antibody against the heparin binding domain of APOE3 Wild Type (WT) and APOE3ch Mutant recombinant protein.

The 25F1-2 antibody was further evaluated using Heparin-Affinity chromatography, Western Blotting, Quantitative ELISA for chromatography fractions, and ELISA for binding analyses. FIG. 33 shows ELISA screening of the 25F1-2 antibody against the heparin binding domain of APOE3 Wild Type (WT) and APOE3ch Mutant recombinant protein. As shown in FIG. 33, the 25F1-2 antibody shows high affinity for the APOE3 mutant full length and c terminal protein, however, it does not appear to have strong binding to the c-terminus of the APOE3WT protein and showed limited interaction with APOE3 WT full length protein. The results are displayed as optical density at 450 nm over dilution factor of the serum tested.

Figure 34A:
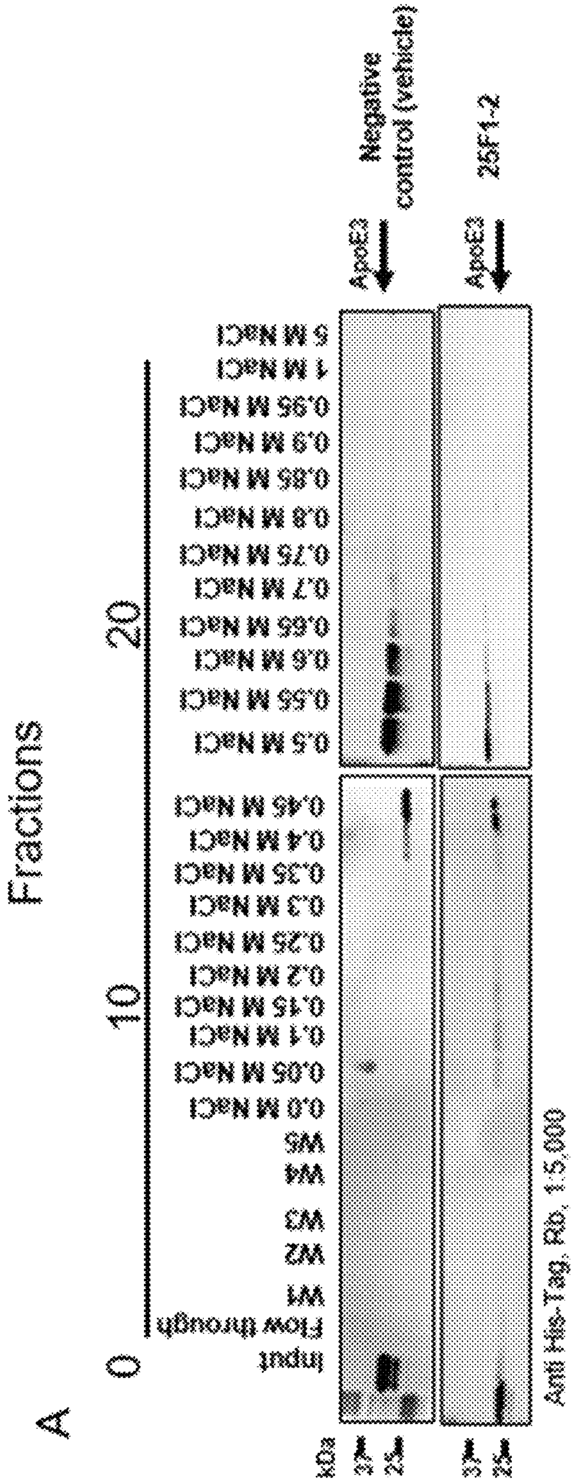
FIGS. 34A and 34B show heparin-affinity chromatography and western blot analysis of antibody 25F1-2.
Figure 34B:
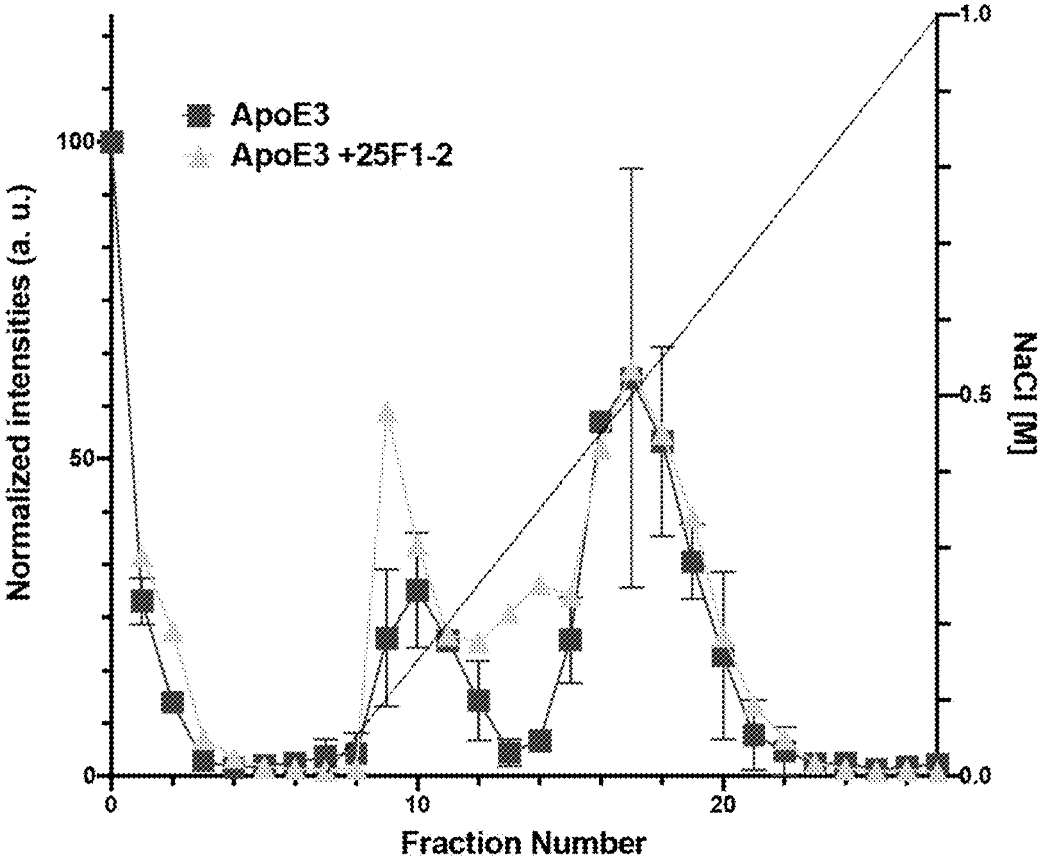

Heparin affinity chromatography fractions of ApoE3 incubated either with negative control (vehicle, top blots) or the antibody 25F1-2 (bottom blots) were subjected to western blotting (FIG. 34A). ApoE3 positive bands are indicated by the arrows and detected using the antibody anti his-tag (rb, 1:5,000) that specifically detects the his-tag of the recombinant peptide. FIG. 34B shows quantification of WB blotting bands detected by the antibody anti hi-tag as shown in FIG. 34A. Intensities were normalized to the input. These results show that despite being designed against the ApoE3ch-HSPG domain, 25F1-2 competes with wild type ApoE for heparin binding and resulted in reduced ApoE3 binding to heparin.

Figure 35:
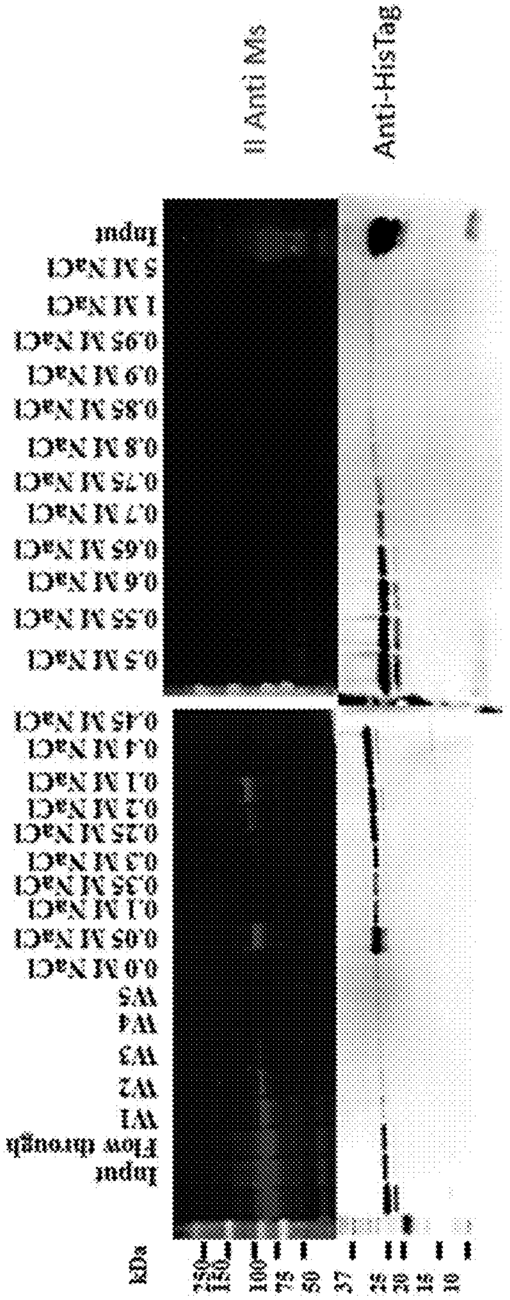
FIG. 35 shows western blotting of ApoE3 WT incubated with the 25F1-2 monoclonal antibody.

FIG. 35 shows western blotting of ApoE3 WT incubated with the 25F1-2 monoclonal antibody. Top blots: membranes probed with secondary anti-mouse to detect 25F1-2. Bottom membranes were incubated with anti his-tag as described previously to detect ApoE3 positive fractions. This analysis demonstrates that antibody-APOE complexes (left blots; top and bottom) do not bind to heparin, while free ApoE bind to heparin with high affinity (right blot, bottom).

Figure 36:
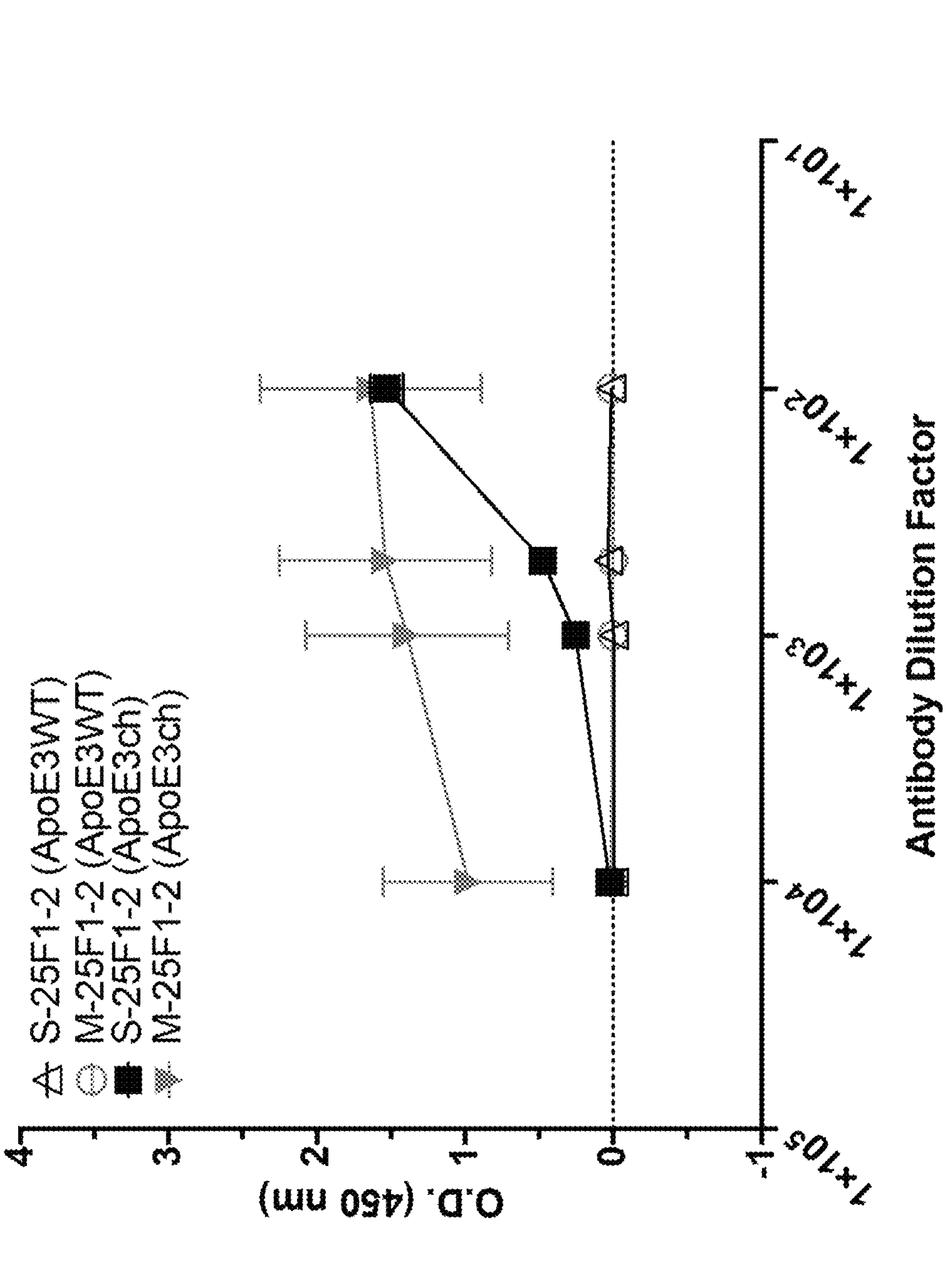
FIG. 36 is representative ELISA showing the differences in binding of both 25F1-2 serum and monoclonal antibody hybridoma supernatant 25F1-2 for ApoE3WT or ApoE3ch.
Figure 37:
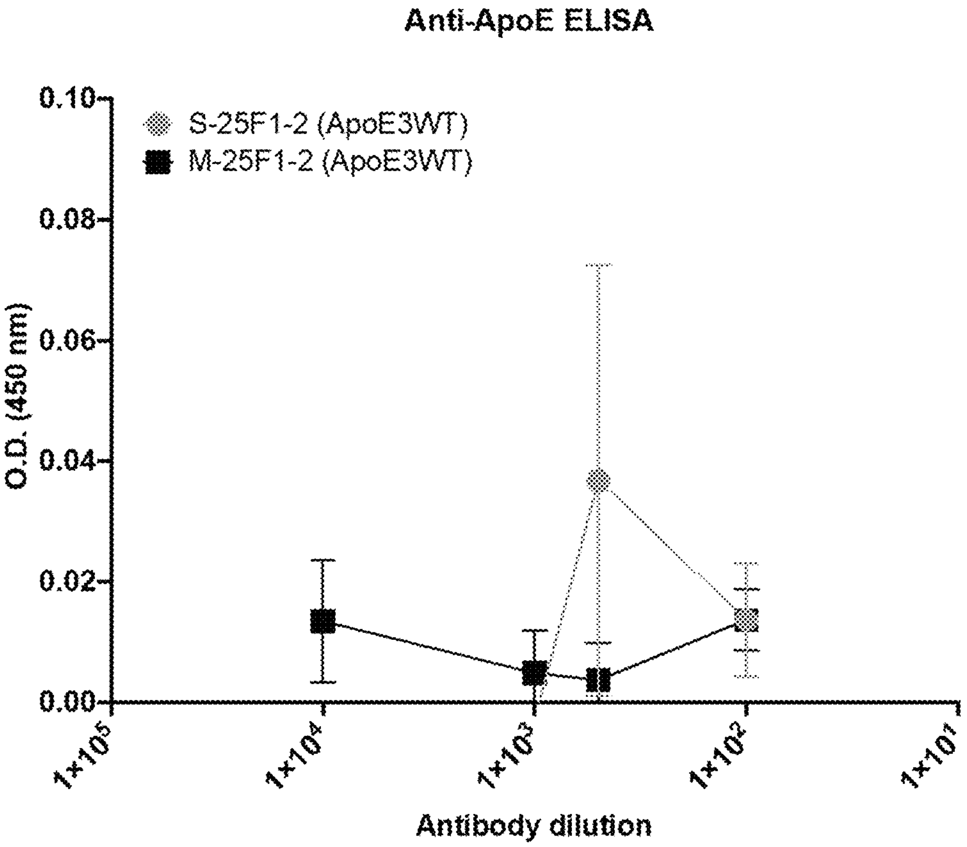
FIG. 37 is an enlargement of the Y axes of FIG. 36.
Figure 38:
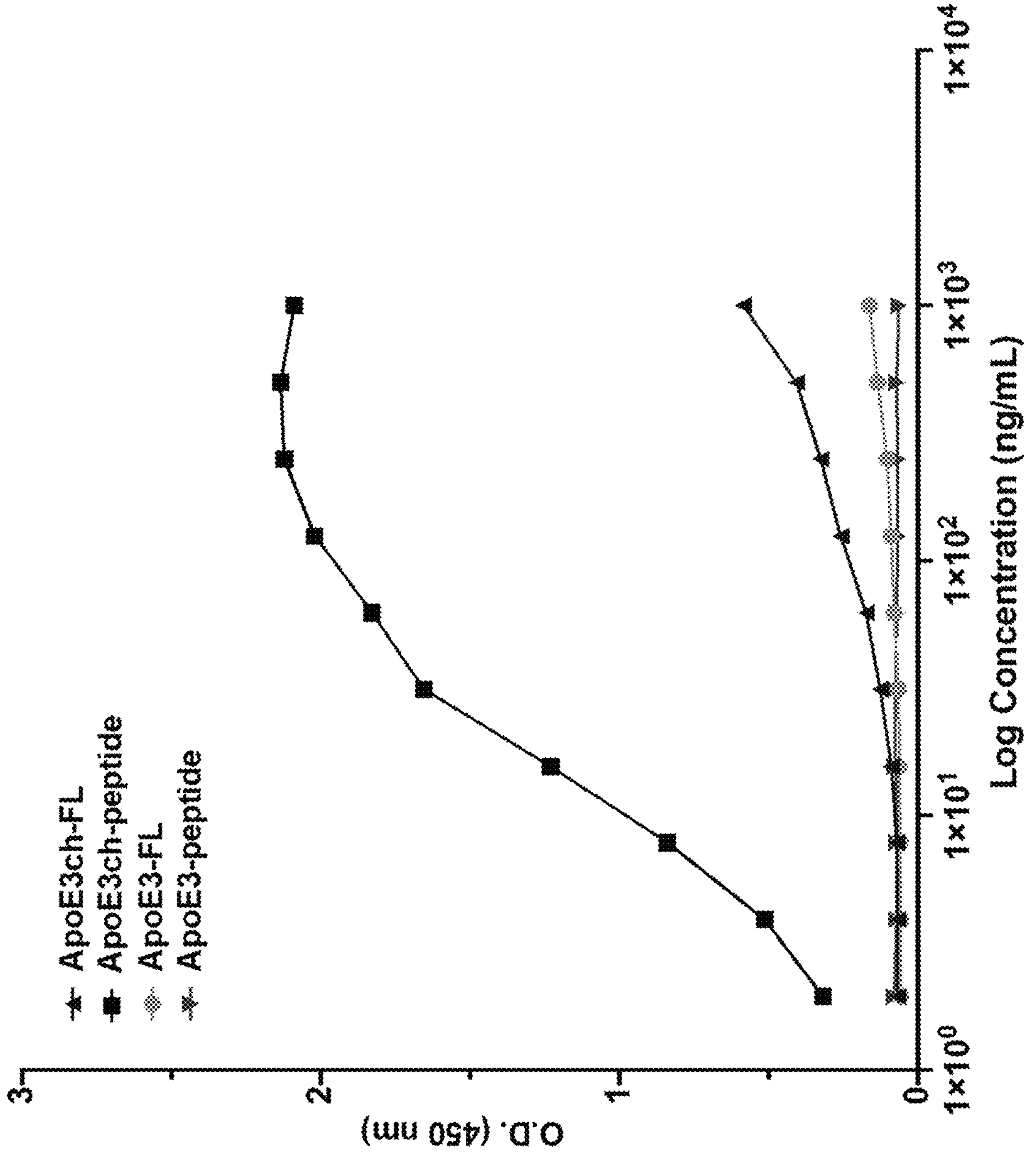
FIG. 38 shows ELISA results for the monoclonal 25F1-2 antibody purified from cloned hybridoma.

FIG. 36 is representative ELISA showing the differences in binding of both 25F1-2 serum and monoclonal antibody hybridoma supernatant 25F1-2 for ApoE3WT or ApoE3ch. These results confirms the preponderant selectivity of this antibody for the ApoE3ch variant. FIG. 37 is an enlargement of the Y axes of FIG. 36, showing the binding profiles of the antibody 25F1-2 in the presence of ApoE3WT. Next, monoclonal 25F1-2 antibody was purified from cloned hybridoma, and subjected to ELISA evaluation. FIG. 38 shows results from the ELISA experiments. A signal of some recognition of the full-length WT APOE higher than that of the WT ApoE peptide suggest binding of a conformation-specific feature.

Figure 39:
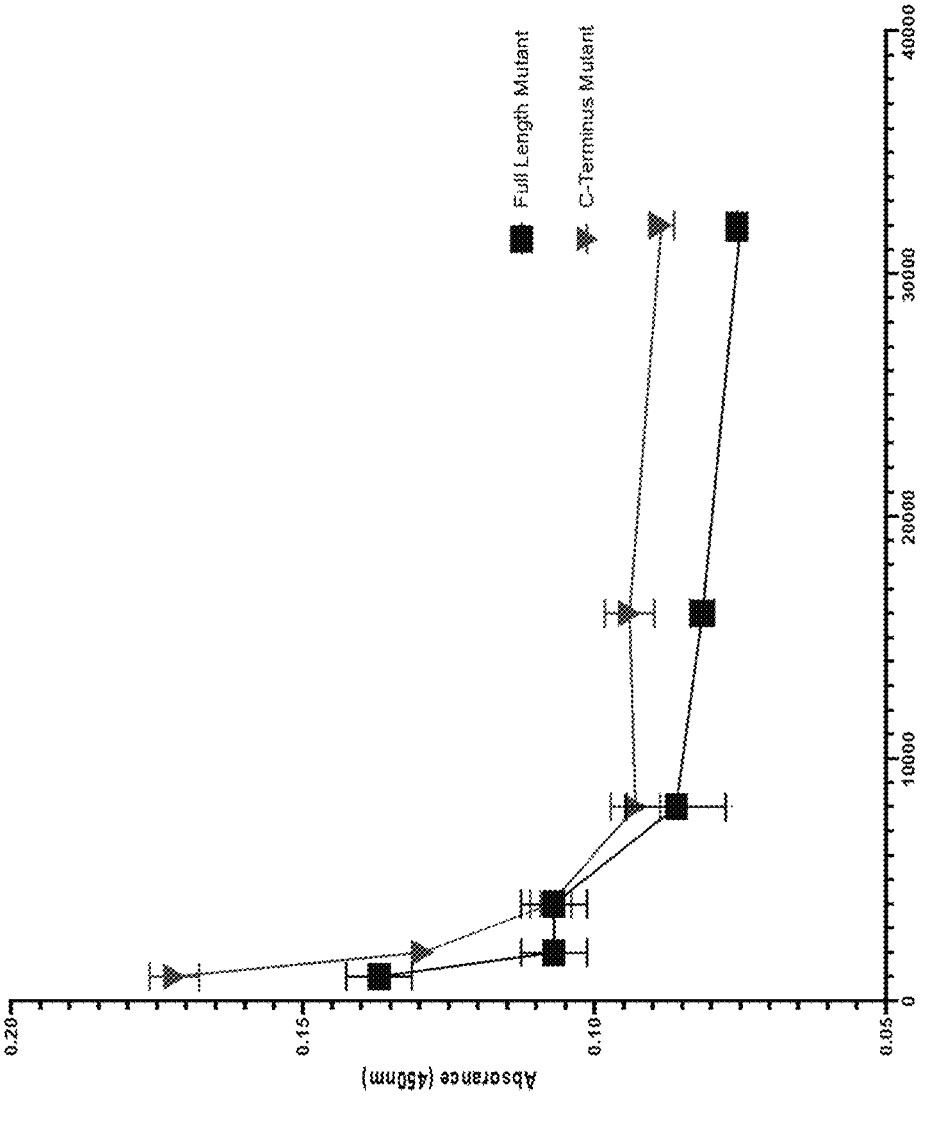
FIG. 39 shows ELISA screening of the 1343 antibody against the heparin binding domain of APOE3 Wild Type (WT) and APOE3ch Mutant recombinant protein.
Figure 40:
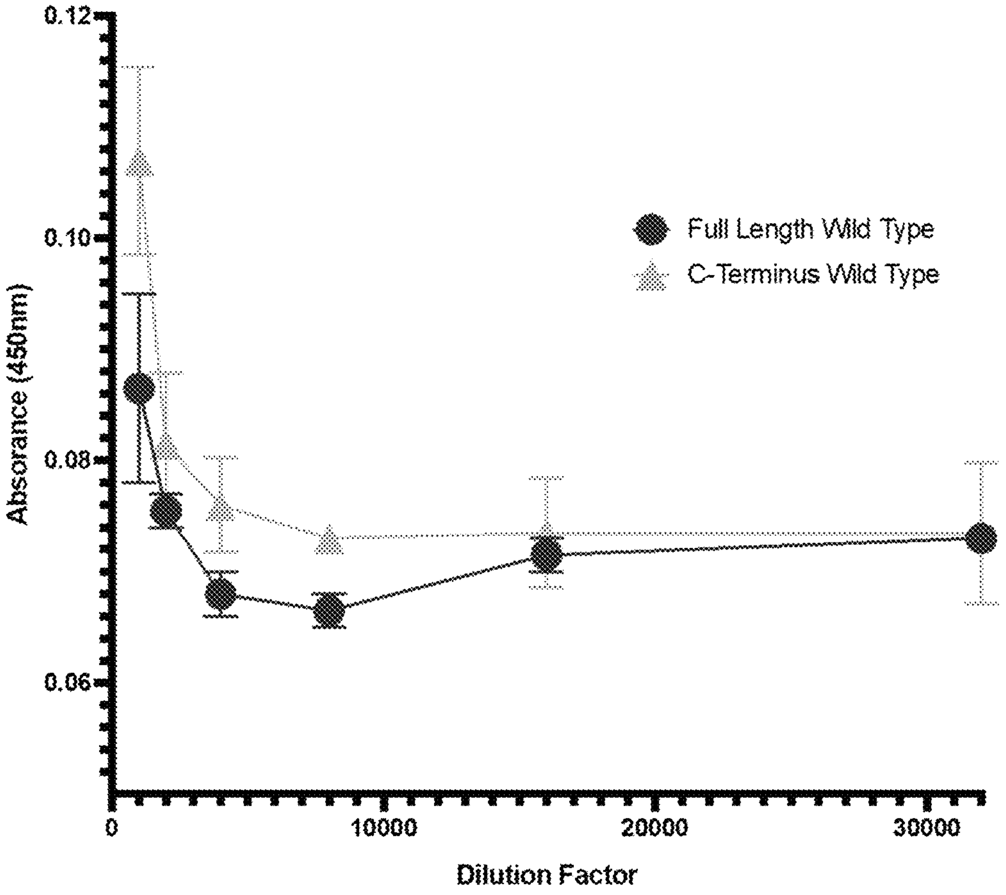
FIG. 40 shows ELISA screening of the 1343 antibody against the heparin binding domain of APOE3 Wild Type (WT) and APOE3ch Mutant recombinant protein.

The mouse antibody 1343ab (renamed from 23B2) was evaluated using heparin-affinity chromatography and western blotting, and quantitative ELISA for chromatography fractions. FIGS. 39 and 40 show ELISA screening of the 1343 antibody against the heparin binding domain of APOE3 Wild Type (WT) and APOE3ch Mutant recombinant protein. 1343 displayed reactivity to both the APOE3 WT and APOE3ch mutant C-Terminus and full-length recombinant APOE proteins (mutant refers to Christchurch mutant).

Figure 41A:
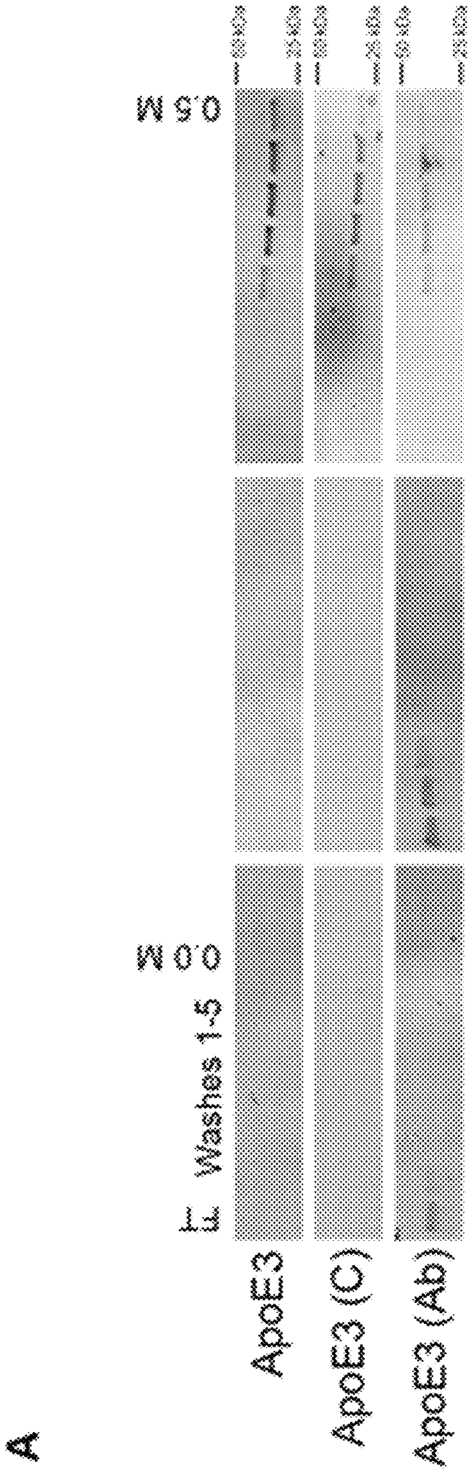
FIG. 41A shows western blot analysis of ApoE in protein fractions eluted from heparin columns in the presence or absence of the 1343 antibody.
Figure 41B:
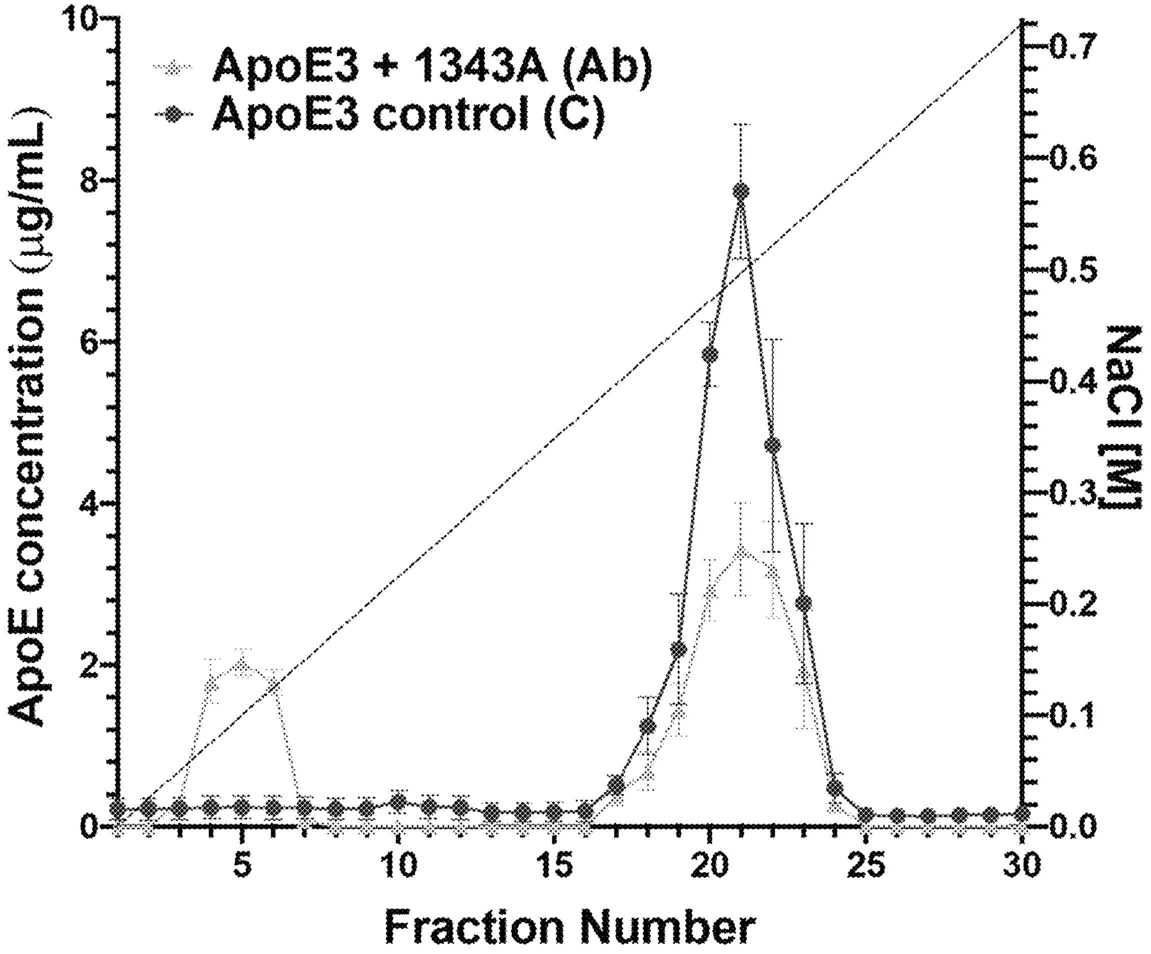
FIG. 41B shows ELISA analysis of the fractions.

ApoE in protein fractions eluted from heparin columns using an increasing NaCl gradient in the presence or absence of the 1343 was subjected to western blotting (FIG. 41A). Individual blots were cropped between 25 to 50 kDa. Blank spaces separate individual blots. FT=flow through. An ELISA was carried out to quantify differences in the NaCl elution patterns of different ApoE in the presence and absence of 1343 (FIG. 41B). N=3 columns per isoform in independent experiments were analyzed side-by-side twice on different days to quantify differences. Error bars depict standard error of mean.

Upon validation, CDR sequences from mouse antibodies 1H4-2, 7C11-1, 19G10-2, 25F1-2, and 1343ab were grafted into human IgG backbones (IgG2 or IgG4) to generate humanized counterparts.

Example 9: In Vivo Validation of ApoE Antibodies

An intraocular model of inducible APOE-dependent Tau hyperphosphorylation (paired helical filament formation) was generated. This model was used to test the ability for the ApoE antibodies to inhibit Tau pathology, which is a marker of neurodegeneration. FIG. 42A shows an exemplary experimental outline.

Briefly, his-tagged recombinant human APOE3 was injected intravitreally into a B6; C3-Tg (Prnp-MAPT*P301S) PS19Vle/J mouse (Jackson lab 008169) (Yoshiyama et al. 53 (3): 337-51, 2007). This mouse model contains a human tau P301S mutation and is a validated animal model for Alzheimer's disease and other tauopathies such as frontotemporal dementia (See e.g. Bugiani et al. 58 (6): 667-77, 1999). Mice injected with PBS were used as control.

As shown in FIG. 42B, in the control retina of 6-week old mice, paired helical filaments of phosphorylated tau (PHF) are absent from ganglion cells and their axon fibers (signal inside vessels labeled with isolectin B4 are background signal). In contrast, administration of recombinant human APOE3 (his tagged) triggered robust formation of PHF detected with the AT8 antibody. PHF are robust in ganglion cell axons (arrows) and in the ganglion cell bodies. Human APOE was detected around the ganglion cell bodies using anti-His antibody.

Figures 43A, 43B, 43C, 43D, 43E:
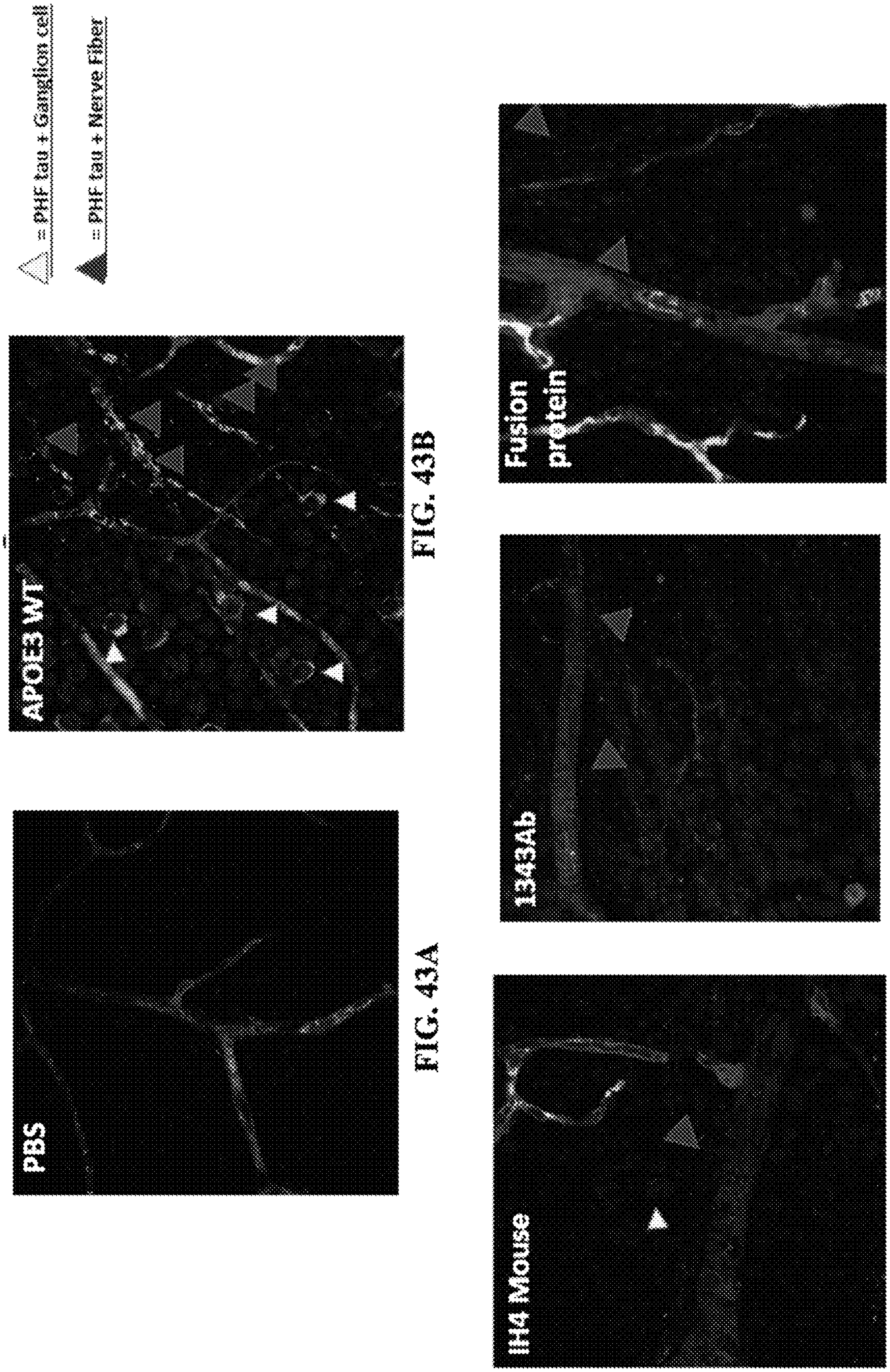
FIGS. 43A-43I show PHF tau in control retina as compared to retina injected with either the mouse 1H4-2 antibody or the humanized 1343Ah antibody.
Figure 43F:
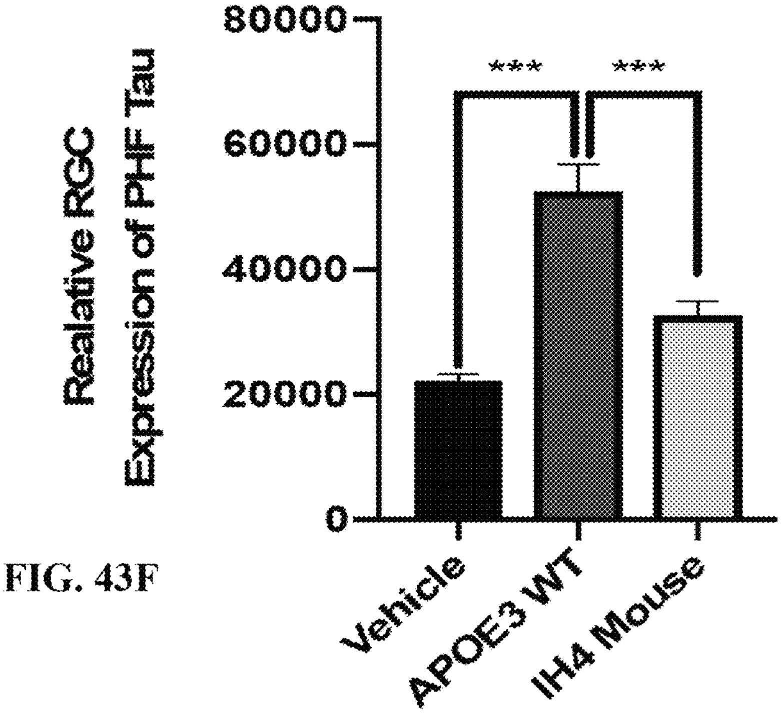
Figure 43G:
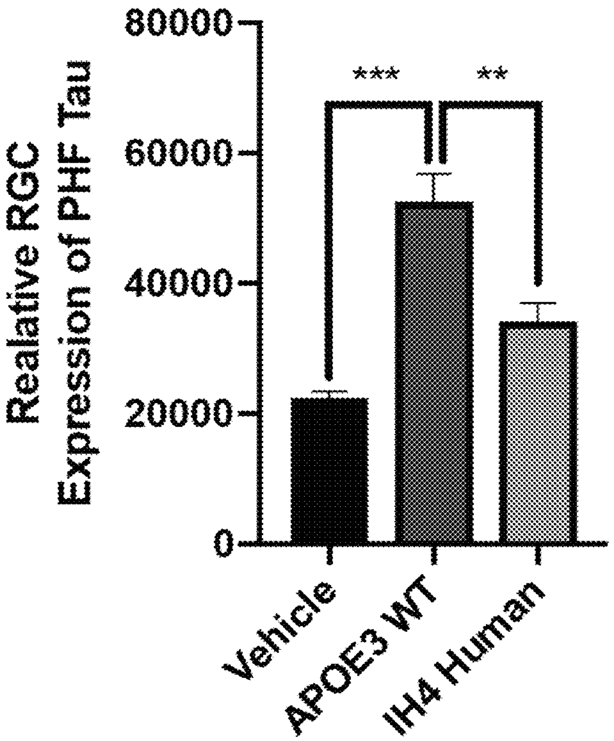
Figure 43I:
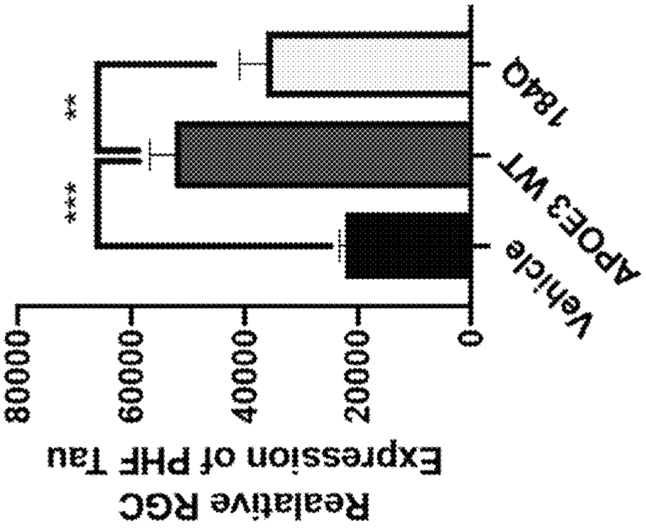
Figure 43H:
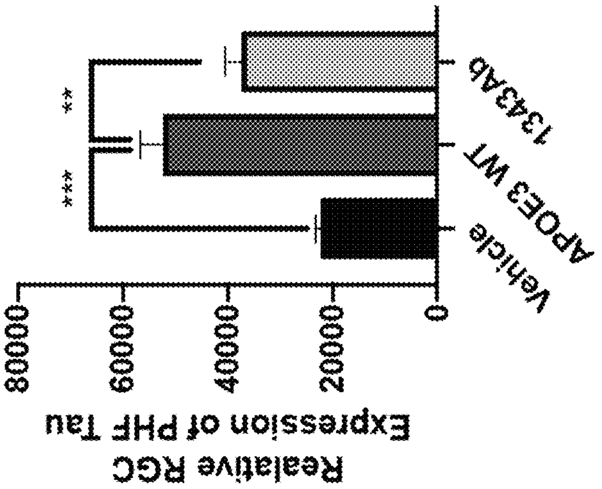

The mouse 1H4-2 antibody and the humanized 1343Ah antibody were injected intravitreally into the eye of mice from the above mouse model (final volume 2 μL). The animals were sacrificed on day 3 post injection and retinas were dissected and immunolabeled. Retinas were stained with DAPI, Isolectin, and AT8 (pTAU), which recognizes phosphorylated paired helical filament tau (PHF tau). Retinas were imaged using the SP8 confocal microscope. As shown in FIGS. 43B, 43C, 43F and 43G, APOE3 WT resulted in a significant increase in PHF Tau, which is significantly reduced by 1H4-2 (* $p<0.001$). Similarly, administration of the humanized 1H4-2 IgG2/kappa recombinant monoclonal antibody effectively reduced APOE-dependent induction of PHF tau pathology in vivo (FIG. 43H; $p<0.01$, *$p<0.001$). As shown in FIGS. 43D and 43H, PHF Tau level was significantly reduced by the humanized 1343Ah ($p<0.01$, ***$p<0.001$).

The similarity of the efficacy between the mouse monoclonal antibody and the corresponding humanized antibody confirms the affinity of the binding domain for ApoE or ApoEch, and that the binding property is retained during humanization. This shows the binding properties of the CDRs are transferable from the original mouse IgG1 to other proteins including human IgG2.

Figure 44:
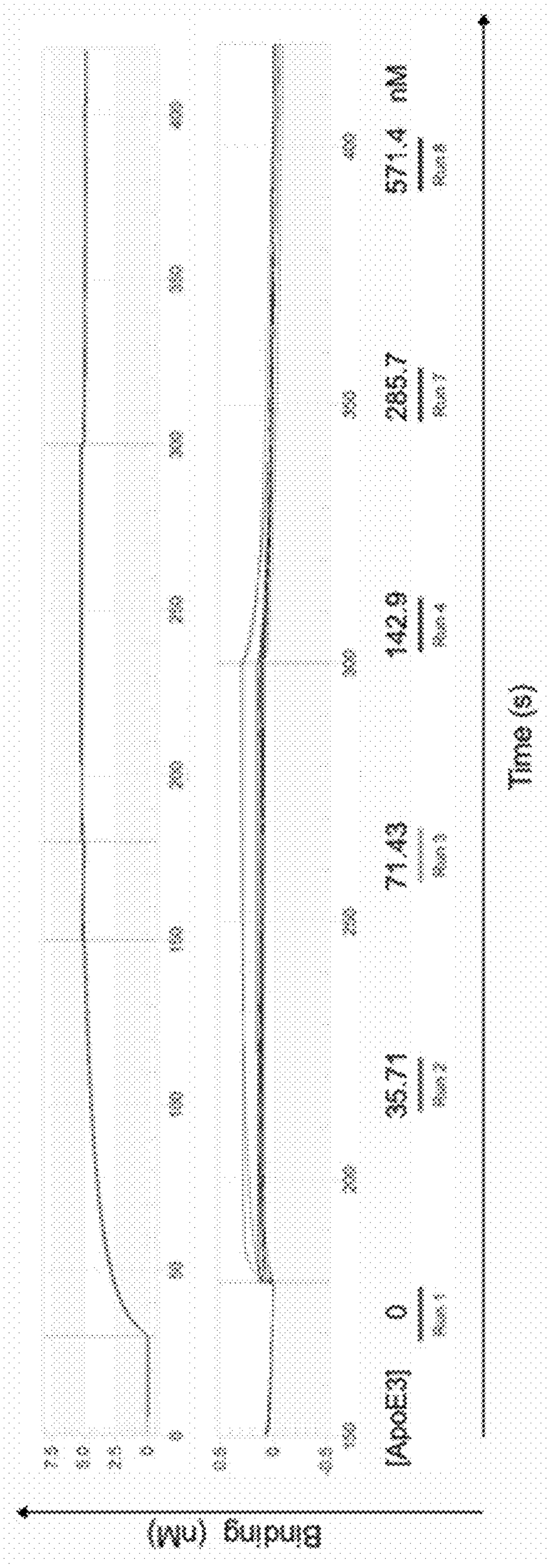
FIG. 44 shows representative binding measurements of increasing concentrations (nM) of ApoE3 protein to 1H4 on the protein A biosensor.

The binding affinity between ApoE3 and the monoclonal antibody 1H4 (mAb 1H4) was determined using the advanced kinetic module of the BLItz system (Blitz Pro, FB-609928, ver. 1.3.1.3). Briefly, a protein A biosensor was loaded with mAb 1H4 and both association and dissociation constants were determined at increasing concentrations of the full length ApoE3 protein (Innovagen) from 0 to 571.4 nM. The following running settings were used: 30 s initial baseline in the experimental media, 120 s loading of the ligand (mAb 1H4) on the biosensors, 30 s new baseline before association (120 s) and dissociation (120 s) steps. A total of 6 runs of 420 s at 2200 rpm and room temperature were conducted to determine the binding parameters of ApoE3. Global fitting and step corrections of the dissociation experiments were performed using the BLItz software (ver. 1.1.0.7). FIG. 44 shows representative binding measurements of increasing concentrations (nM) of ApoE3 protein to 1H4 on protein A biosensor. KD, Ka and Kd were measured (table 10) and calculated using the BLItz system. Top panel is representative of the association steps, the bottom panel is representative of the dissociation steps of the binding kinetic. The X and Y axes depicts time in second and binding in nM, respectively.

| Run Index | Con. ApoE3 (nM) | KD (nM) | ka (1/Ms) | Ka Error | kd (1/s) | kd Error |
|---|---|---|---|---|---|---|
| 1 | 0 | | | | | |
| 2 | 35.71 | 14.28 | 2900000 | 0.04142 | 0.001119 | 0.1543 |
| 3 | 71.43 | 14.28 | 2900000 | 0.04142 | 0.001119 | 0.1425 |
| 4 | 142.9 | 14.28 | 2900000 | 0.04142 | 0.001119 | 0.3063 |
| 7 | 285.7 | 14.28 | 2900000 | 0.04142 | 0.001119 | 0.09633 |
| 8 | 571.4 | 14.28 | 2900000 | 0.04142 | 0.001119 | 0.146 |

| Run Index | Con. ApoE3 (nM) | KD (nM) | ka (1/Ms) | Ka Error | kd (1/s) | kd Error |
|---|---|---|---|---|---|---|
| 1 | 0 | | | | | |
| 2 | 35.71 | 14.28 | 2900000 | 0.04142 | 0.001119 | 0.1543 |
| 3 | 71.43 | 14.28 | 2900000 | 0.04142 | 0.001119 | 0.1425 |
| 4 | 142.9 | 14.28 | 2900000 | 0.04142 | 0.001119 | 0.3063 |
| 7 | 285.7 | 14.28 | 2900000 | 0.04142 | 0.001119 | 0.09633 |
| 8 | 571.4 | 14.28 | 2900000 | 0.04142 | 0.001119 | 0.146 |

| Run Index | Con. ApoE3 (nM) | Rmax | Rmax Error | R Equilibrium |
|---|---|---|---|---|
| 1 | 0 | | | |
| 2 | 35.71 | 0.1543 | 0.005199 | 0.1102 |
| 3 | 71.43 | 0.1425 | 0.003305 | 0.1187 |
| 4 | 142.9 | 0.3063 | 0.003587 | 0.2785 |
| 7 | 285.7 | 0.09633 | 0.001949 | 0.09174 |
| 8 | 571.4 | 0.146 | 0.001883 | 0.1425 |

Example 10: In Vivo Validation of APOE Fragment Fusion Proteins

Next, a fusion protein containing an APOE fragment that includes the HSPG-binding domain, and the Fc region of a human IgG was tested using a similar in vivo model. Briefly, 0.78 μg of recombinant full-length APOE was used to induce tau pathology. 0.14 μg of the fusion protein was injected intravitreally in to the mice. As shown in FIGS. 43E and 43I, the fusion protein diminished APOE-dependent tau pathology in neurons.

Example 11: Sequences of Chimeric Antibodies

The sequences of the chimeric antibodies where CDRs were transferred from mouse to human IgG2 or IgG4 are shown below:

Normal font = vector
Italicized = Signal peptide
underlined = VL/VH
double underlined = Constant part (human Kappa/IgG4/IgG2)

Sequences of expression vectors for mAb 1H4 IgG2/kappa:
>p1H4.VL.hk
(SEQ ID NO: 97)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACCA*TGTACAGGATGCAACTCCTGTCTTGCATTGCACTAAGTCTTGCACTTGTCAC*
*GAATTCA*GACAACGTGCTGACACAGAGCCCTGCCAGCCTGGCTGTTTCTCTGGGACAGAGAG
CCACCATCAGCTGCAAGGCCAGCCAGAGCGTTGACTACGACGGCGACAGCTACATGAACTGG
TATCAGCAGAAGCCCGGCCAGCCACCTAAGGTGTTCATCTACGCCGCCAGCAACCTGGAAAG
CGGCATCCCTGCCAGATTTTCTGGCTCTGGCAGCGGCACCGACTTCACCCTGAATATCCATC
CTGTGGAAGAAGAGGACGCCGCCACCTACTACTGCCAGCAGAGCAATGAGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGG
CTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGT
GATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGAC
TCTGGGGTTCGCGAAATGACCGACCAAGCGACGCCCAACCTGCCATCACGAGATTTCGATTC
CACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGTATACCGTCGA
CCTCTAGCTAGAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATG

-continued

AGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACA
TGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAA
AGTGCCACCTGACGTCGACGGATCGGGAGATCTCCCGATCCCCTATGGTCGACTCTCAGTAC
AATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATG
AAGAATCTGCTTAGG

>p1H4.VE.hIgG2

(SEQ ID NO: 98)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTC*GGAAGTGAAGCTGGTGGAAAGCGGCGGAGGTGTTGTTCAGCCTGGCGGATCTCTGA
AGCTGAGCTGTGCCGCCAGCGGCTTCACCTTTAGCAGCTACACAATGAGCTGGGTCCGACAG
ACCCCTGAGAAGAGACTGGAATGGGTCGCCAAGATCCGGAACGGCGGAGGCATCACCTACTA
CCTGGATACCCTGAAGGGCAGATTCACCATCAGCCGGGACAACGCCAAGAACACCCTGTACC
TGCAGATGAGCAGCCTGAAGTCCGAGGACACCGCCATCTACTTTTGCGCCAGACACTACTAC
GGCAGCGAGGACTACTTCGACTATTGGGGCCAGGGCACCACACTGACCGTTAGCTCTGCTAG
CACCAAGGGCCCATCGGTCTTCCCCCTGGCGCCCTGCTCCAGGAGCACCTCCGAGAGCACAG
CGGCCCTGGGCTGCCTGGTCAAGGACTACTTCCCCGAACCGGTGACGGTGTCGTGGAACTCA
GGCGCTCTGACCAGCGGCGTGCACACCTTCCCAGCTGTCCTACAGTCCTCAGGACTCTACTC
CCTCAGCAGCGTGGTGACCGTGCCCTCCAGCAACTTCGGCACCCAGACCTACACCTGCAACG
TAGATCACAAGCCCAGCAACACCAAGGTGGACAAGACAGTTGAGCGCAAATGTTGTGTCGAG
TGCCCACCGTGCCCAGCACCACCTGTGGCAGGACCGTCAGTCTTCCTCTTCCCCCCAAAACC
CAAGGACACCCTCATGATCTCCCGGACCCCTGAGGTCACGTGCGTGGTGGTGGACGTGAGCC
ACGAAGACCCCGAGGTCCAGTTCAACTGGTACGTGGACGGCGTGGAGGTGCATAATGCCAAG
ACAAAGCCACGGGAGGAGCAGTTCAACAGCACGTTCCGTGTGGTCAGCGTCCTCACCGTTGT
GCACCAGGACTGGCTGAACGGCAAGGAGTACAAGTGCAAGGTCTCCAACAAAGGCCTCCCAG
CCCCCATCGAGAAAACCATCTCCAAAACCAAAGGGCAGCCCCGAGAACCACAGGTGTACACC
CTGCCCCCATCCCGGGAGGAGATGACCAAGAACCAGGTCAGCCTGACCTGCCTGGTCAAAGG
CTTCTACCCCAGCGACATCGCCGTGGAGTGGGAGAGCAATGGGCAGCCGGAGAACAACTACA
AGACCACGCCTCCCATGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCA
CAACCACTACACGCAGAAGAGCCTCTCCCTGTCTCCGGGTAAATGACCTAGCGTGGCATCTA
GACACTCTCGAGAAGGGTTCGATCCCTACCGGTTAGTAATGAGTTTGATATCTCGACAATCA
ACCTCTGGATTACAAAATTTGTGAAAGATTGACTGGTATTCTTAACTATGTTGCTCCTTTTA
CGCTATGTGGATACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTTGTGGCCCGTTGT
CAGGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGGAA

-continued

CTCATCGCCGCCTGCCTTGCCCGCTGCTGGACAGGGGCTCGGCTGTTGGGCACTGACAATTC
CGTGGTGTTGTCGGGGAAGCTGACGTCCTTTCCATGGCTGCTCGCCTGTGTTGCCACCTGGA
TTCTGCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACGAGTCG
GATCTCCCTTTGGGCCGCCTCCCCGCCTGGAAACGGGGGAGGCTAACTGAAACACGGAAGGA
GACAATACCGGAAGGAACCCGCGCTATGACGGCAATAAAAAGACAGAATAAAACGCACGGGT
GTTGGGTCGTTTGTTCATAAACGCGGGGTTCGGTCCCAGGGCTGGCACTCTGTCGATACCCC
ACCGAGACCCCATTGGGGCCAATACGCCCGCGTTTCTTCCTTTTCCCCACCCCACCCCCCAA
GTTCGGGTGAAGGCCCAGGGCTCGCAGCCAACGTCGGGGCGGCAGGCCCTGCCATAGCAGAT
CTGCGCAGCTGGGGCTCTAGGGGGTATCCCCACGCGCCCTGTAGCGGCGCATTAAGCGCGGC
GGGTGTGGTGGTTACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGTCAAGCTCTAAATCGG
GGCATCCCTTTAGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCTCG
GTCTATTCTTTTGATTTATAAGGGATTTTGGGGATTTCGGCCTATTGGTTAAAAAATGAGCT
GATTTAACAAAAATTTAACGCGAATTAATTCTGTGGAATGTGTGTCAGTTAGGGTGTGGAAA
GTCCCCAGGCTCCCCAGCAGGCAGAAGTATGCAAAGCATGCATCTCAATTAGTCAGCAACCA
GGTGTGGAAAGTCCCCAGGCTCCCCAGCAGGCAGAAGTATGCAAAGCATGCATCTCAATTAG
TCAGCAACCATAGTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCGAGGCCGCCTCTG
CCTCTGAGCTATTCCAGAAGTAGTGAGGAGGCTTTTTTGGAGGCCTAGGCTTTTGCAAAAAG
CTCCCGGGAGCTTGTATATCCATTTTCGGATCTGATCAAGAGACAGGATGAGGATCGTTTCG
CATGATTGAACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCTGTCAGCG
CAGGGGCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCTCGACG
TTGTCACTGAAGCGGGAAGGGACTGGCTGCTATTGGGCGAAGTGCCGGGGCAGGATCTCCTG
TCATCTCACCTTGCTCCTGCCGAGAAAGTATCCATCATGGCTGATGCAATGCGGCGGCTGCA
TACGCTTGATCCGGCTACCTGCCCATTCGACCACCAAGCGAAACATCGCATCGAGCGAGCAC
GTACTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGTCGT
GACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGAT
ATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAGCGGGACTCT
GGGGTTCGCGAAATGACCGACCAAGCGACGCCCAACCTGCCATCACGAGATTTCGATTCCAC
CGCCGCCTTCTATGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTTATTGCAGCTTAT
AATGGTTACAAATAAAGCAATAGCATCACAAATTTCACAAATAAAGCATTTTTTTCACTGCA
TTCTAGTTGTGGTTTGTCCAAACTCATCAATGTATCTTATCATGTCTGTATACCGTCGACCT
CTAGCTAGAGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCC
GACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCT
CAATGCTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCT
AGATCCTTTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATCTG
GCCCCAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATTCAGC
TCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGC
GTCAATACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAA
AACAGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGT
GCCACCTGACGTCGACGGATCGGGAGATCTCCCGATCCCCTATGGTCGACTCTCAGTACAAT
CTGCTCTGATGCCGCATAGTTAAGCCAGTATCTGCTCCCTGCTTGTGTGTTGGAGGTCGCTG
AGTAGTGCGCGAGCAAAATTTAAGCTACAACAAGGCAAGGCTTGACCGACAATTGCATGAAG
AATCTGCTTAGG

-continued

Sequences of expression vectors for mAb 1343Ah IgG2/kappa:
>p1343Ah.VL.hk (SEQ ID NO: 99)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTCA*GACATCGTGCTGACACAGAGCCCTGCCAGCCTGGCTGTTTCTCTGGGACAGAGAG
CCACCATCAGCTGCAAGGCCAGCCAGAGCGTTGACTACGACGGCGAGAACTACATGAACTGG
TATCAGCAGAAGCCCGGACAGAGCCCCAAGCTGCTGATCTACGTGGCCAGCAATCTGGAAAG
CGGCATCCCCGCCAGATTTTCTGGCAGCGGAAGCGGCACCGACTTCACCCTGAATATCCATC
CTGTGGAAGAAGAGGACGCCGCCACCTACTACTGCCAGCAGTCCAATCTGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGG
CTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGT
GATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGAC
TCTGGGGTTCGCGAAATGACCGACCAAGCGACGCCCAACCTGCCATCACGAGATTTCGATTC
CACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGTATACCGTCGA
CCTCTAGCTAGAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATG
AGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACA
TGTGAGCAAAGGCCAGCAAAAGGCCAGGAACCGTAAAAAGGCCGCGTTGCTGGCGTTTTTC

-continued

CATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAA
AGTGCCACCTGACGTCGACGGATCGGGAGATCTCCCGATCCCCTATGGTCGACTCTCAGTAC
AATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATG
AAGAATCTGCTTAGG

>p1343Ah.VH.hIgG2

(SEQ ID NO: 100)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTC*GGAGGTCCAGCTGCAGCAGTCTGGCGCCGAACTTGTTAGACCTGGCGCTCTGGTCA
AGCTGAGCTGTAAAGCCAGCGGCTTCAACATCAAGGACTACCATCTGCACTGGGTCAAGCAG
AGGCCTGAGCAGGGACTCGAGTGGATCGGCTGGATCGACCCCGAGAACGGCAACGTGATCTA
CGACCCCAAGTTCCAGGGCAAAGCCACCATGACCGTGGTCACCAGCAGCAACACAGCCTACC
TGCAGCTGAGAAGCCTGACCAGCGAAGATACCGCCGTGTACTTCTGCACCAGAGGCACAGCC
AGAGCCAGCTTCGATTATTGGGGCCAGGGCACCAGCCTGACCGTTTCTTCTGCTAGCACCAA
GGGCCCATCGGTCTTCCCCCTGGCGCCCTGCTCCAGGAGCACCTCCGAGAGCACAGCGGCCC
TGGGCTGCCTGGTCAAGGACTACTTCCCCGAACCGGTGACGGTGTCGTGGAACTCAGGCGCT
CTGACCAGCGGCGTGCACACCTTCCCAGCTGTCCTACAGTCCTCAGGACTCTACTCCCTCAG
CAGCGTGGTGACCGTGCCCTCCAGCAACTTCGGCACCCAGACCTACACCTGCAACGTAGATC
ACAAGCCCAGCAACACCAAGGTGGACAAGACAGTTGAGCGCAAATGTTGTGTCGAGTGCCCA
CCGTGCCCAGCACCACCTGTGGCAGGACCGTCAGTCTTCCTCTTCCCCCCAAAACCCAAGGA
CACCCTCATGATCTCCCGGACCCCTGAGGTCACGTGCGTGGTGGTGGACGTGAGCCACGAAG
ACCCCGAGGTCCAGTTCAACTGGTACGTGGACGGCGTGGAGGTGCATAATGCCAAGACAAAG
CCACGGGAGGAGCAGTTCAACAGCACGTTCCGTGTGGTCAGCGTCCTCACCGTTGTGCACCA
GGACTGGCTGAACGGCAAGGAGTACAAGTGCAAGGTCTCCAACAAAGGCCTCCCAGCCCCCA
TCGAGAAAACCATCTCCAAAACCAAAGGGCAGCCCCGAGAACCACAGGTGTACACCCTGCCC
CCATCCCGGGAGGAGATGACCAAGAACCAGGTCAGCCTGACCTGCCTGGTCAAAGGCTTCTA
CCCCAGCGACATCGCCGTGGAGTGGGAGAGCAATGGGCAGCCGGAGAACAACTACAAGACCA
CGCCTCCCATGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTCTGCACAACCA
CTACACGCAGAAGAGCCTCTCCCTGTCTCCGGGTAAATGACCTAGCGTGGCATCTAGACACT
CTCGAGAAGGGTTCGATCCCTACCGGTTAGTAATGAGTTTGATATCTCGACAATCAACCTCT
GGATTACAAAATTTGTGAAAGATTGACTGGTATTCTTAACTATGTTGCTCCTTTTACGCTAT
GTGGATACGCTGCTTTAATGCCTTTGTATCATGCTATTGCTTCCCGTATGGCTTTCATTTTC
TCCTCCTTGTATAAATCCTGGTTGCTGTCTCTTTATGAGGAGTTGTGGCCCGTTGTCAGGCA
ACGTGGCGTGGTGTGCACTGTGTTTGCTGACGCAACCCCCACTGGTTGGGGCATTGCCACCA
CCTGTCAGCTCCTTTCCGGGACTTTCGCTTTCCCCCTCCCTATTGCCACGGCGGAACTCATC
GCCGCCTGCCTTGCCCGCTGCTGGACAGGGGCTCGGCTGTTGGGCACTGACAATTCCGTGGT
GTTGTCGGGGAAGCTGACGTCCTTTCCATGGCTGCTCGCCTGTGTTGCCACCTGGATTCTGC
GCGGGACGTCCTTCTGCTACGTCCCTTCGGCCCTCAATCCAGCGGACCTTCCTTCCCGCGGC
CTGCTGCCGGCTCTGCGGCCTCTTCCGCGTCTTCGCCTTCGCCCTCAGACGAGTCGGATCTC
CCTTTGGGCCGCCTCCCCGCCTGGAAACGGGGGAGGCTAACTGAAACACGGAAGGAGACAAT

-continued

ACCGGAAGGAACCCGCGCTATGACGGCAATAAAAAGACAGAATAAAACGCACGGGTGTTGGG
TCGTTTGTTCATAAACGCGGGGTTCGGTCCCAGGGCTGGCACTCTGTCGATACCCCACCGAG
ACCCCATTGGGGCCAATACGCCCGCGTTTCTTCCTTTTCCCCACCCCACCCCCCAAGTTCGG
GTGAAGGCCCAGGGCTCGCAGCCAACGTCGGGGCGGCAGGCCCTGCCATAGCAGATCTGCGC
AGCTGGGGCTCTAGGGGGTATCCCCACGCGCCCTGTAGCGGCGCATTAAGCGCGGCGGGTGT
GGTGGTTACGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCGGGGCATC
CCTTTAGGGTTCCGATTTAGTGCTTTACGGCACCTCGACCCCAAAAAACTTGATTAGGGTGA
TGGTTCACGTAGTGGGCCATCGCCCTGATAGACGGTTTTTCGCCCTTTGACGTTGGAGTCCA
CGTTCTTTAATAGTGGACTCTTGTTCCAAACTGGAACAACACTCAACCCTATCTCGGTCTAT
TCTTTTGATTTATAAGGGATTTTGGGGATTTCGGCCTATTGGTTAAAAAATGAGCTGATTTA
ACAAAAATTTAACGCGAATTAATTCTGTGGAATGTGTGTCAGTTAGGGTGTGGAAAGTCCCC
AGGCTCCCCAGCAGGCAGAAGTATGCAAAGCATGCATCTCAATTAGTCAGCAACCAGGTGTG
GAAAGTCCCCAGGCTCCCCAGCAGGCAGAAGTATGCAAAGCATGCATCTCAATTAGTCAGCA
ACCATAGTCCCGCCCCTAACTCCGCCCATCCCGCCCCTAACTCCGCCCAGTTCCGCCCATTC
TCCGCCCCATGGCTGACTAATTTTTTTTATTTATGCAGAGGCCGAGGCCGCCTCTGCCTCTG
AGCTATTCCAGAAGTAGTGAGGAGGCTTTTTTGGAGGCCTAGGCTTTTGCAAAAAGCTCCCG
GGAGCTTGTATATCCATTTTCGGATCTGATCAAGAGACAGGATGAGGATCGTTTCGCATGAT
TGAACAAGATGGATTGCACGCAGGTTCTCCGGCCGCTTGGGTGGAGAGGCTATTCGGCTATG
ACTGGGCACAACAGACAATCGGCTGCTCTGATGCCGCCGTGTTCCGGCTGTCAGCGCAGGGG
CGCCCGGTTCTTTTTGTCAAGACCGACCTGTCCGGTGCCCTGAATGAACTGCAGGACGAGGC
AGCGCGGCTATCGTGGCTGGCCACGACGGGCGTTCCTTGCGCAGCTGTGCTCGACGTTGTCA
CTGAAGCGGGAAGGGACTGGCTGCTATTGGGCGAAGTGCCGGGGCAGGATCTCCTGTCATCT
CACCTTGCTCCTGCCGAGAAAGTATCCATCATGGCTGATGCAATGCGGCGGCTGCATACGCT
TGATCCGGCTACCTGCCCATTCGACCACCAAGCGAAACATCGCATCGAGCGAGCACGTACTC
GGATGGAAGCCGGTCTTGTCGATCAGGATGATCTGGACGAAGAGCATCAGGGGCTCGCGCCA
GCCGAACTGTTCGCCAGGCTCAAGGCGCGCATGCCCGACGGCGAGGATCTCGTCGTGACCCA
TGGCGATGCCTGCTTGCCGAATATCATGGTGGAAAATGGCCGCTTTTCTGGATTCATCGACT
GTGGCCGGCTGGGTGTGGCGGACCGCTATCAGGACATAGCGTTGGCTACCCGTGATATTGCT
GAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGGTT
CGCGAAATGACCGACCAAGCGACGCCCAACCTGCCATCACGAGATTTCGATTCCACCGCCGC
CTTCTATGAAAGGTTGGGCTTCGGAATCGTTTTCCGGGACGCCGGCTGGATGATCCTCCAGC
GCGGGGATCTCATGCTGGAGTTCTTCGCCCACCCCAACTTGTTTATTGCAGCTTATAATGGT
TACAAATAAAGCAATAGCATCACAAATTTCACAAATAAAGCATTTTTTTCACTGCATTCTAG
TTGTGGTTTGTCCAAACTCATCAATGTATCTTATCATGTCTGTATACCGTCGACCTCTAGCT
AGAGCTTGGCGTAATCATGGTCATAGCTGTTTCCTGTGTGAAATTGTTATCCGCTCACAATT
CCACACAACATACGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGGCGCTCTTCCGCT
TCCTCGCTCACTGACTCGCTGCGCTCGGTCGTTCGGCTGCGGCGAGCGGTATCAGCTCACTC
AAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGC
TCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCGAGGTAT
GTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGATCC
TTTTAAATTAAAAATGAAGTTTTAAATCAATCTAAAGTATATATGAGTAAACTTGGTCTGAC
AGTTACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCCCCA
GTGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGCGCAACGTTGTTG
CCATTGCTACAGGCATCGTGGTGTCACGCTCGTCGTTTGGTATGGCTTCATTCAGCTCCGGT
TCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAG
CACTGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTCAAT
ACGGGATAATACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGG
AAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTGCCACC
TGACGTCGACGGATCGGGAGATCTCCCGATCCCCTATGGTCGACTCTCAGTACAATCTGCTC
TGATGCCGCATAGTTAAGCCAGTATCTGCTCCCTGCTTGTGTGTTGGAGGTCGCTGAGTAGT
GCGCGAGCAAAATTTAAGCTACAACAAGGCAAGGCTTGACCGACAATTGCATGAAGAATCTG
CTTAGG

-continued

Sequences of expression vectors for mAb 19G10 IgG4/kappa:
>p19G10.VL.hk (SEQ ID NO: 101)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTCA*GACATCGTGCTGACACAGAGCCCTGCCAGCCTGGCTGTTTCTCTGGGACAGAGAG
CCACCATCAGCTGCAAGGCCAGCCAGAGCGTTGACTACGACGGCGACAGCTACATGAACTGG
TATCAGCAGAAGTCCGGCCAGCCTCCTAAGCTGCTGATCTACGCCGCCAGCAATCTGGAAAG
CGGCATCCCTGCCAGATTTTCCGGCTCTGGCAGCGGCACCGACTTCACCCTGAATATCCATC
CTGTGGAAGAAGAGGACGCCGCCACCTACTACTGCCAGCAGAGCAATGTGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGG
CTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGT
GATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGAC
TCTGGGGTTCGCGAAATGACCGACCAAGCGACGCCCAACCTGCCATCACGAGATTTCGATTC
CACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGTATACCGTCGA
CCTCTAGCTAGAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATG
AGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACA

-continued

TGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAA
AGTGCCACCTGACGTCGACGGATCGGGAGATCTCCCGATCCCCTATGGTCGACTCTCAGTAC
AATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATG
AAGAATCTGCTTAGG

>p19G10.VH.hIgG4

(SEQ ID NO: 102)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTC*GGAGGTCCAGCTGCAGCAGTCTGGCGCCGAACTTGTTAGACCTGGCGCTCTGGTCA
AGCTGAGCTGTAAAGCCAGCGGCTTCAACATCAAGGACTACCACATGCACTGGGTCAAAGAG
CGGCCTGAGCAGGGACTCGAGTGGATCGGATGGATCGACCCCGAGAACGGCAACACTATGTA
CGACCCCAAGTTCCAGGGCAAAGCCAGCATCACCGCCGACACCTCTAGCAACACAGCCTACC
TGCAGCTGAGCAGCCTGACCTCTGAAGATACCGCCGTGTACTACTGCGTGCGGGGAACAGCC
AGAGCCAGCTTTGATTATTGGGGCCAGGGCACCACACTGACCGTGTCATCTGCTAGCACCAA
GGGCCCATCGGTCTTCCCCCTGGCGCCCTGCTCCAGGAGCACCTCCGAGAGCACAGCCGCCC
TGGGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTCAG
CAGCGTGGTGACCGTGCCCTCCAGCAGCTTGGGCACGAAGACCTACACCTGCAACGTAGATC
ACAAGCCCAGCAACACCAAGGTGGACAAGAGAGTTGAGTCCAAATATGGTCCCCCATGCCCA
TCATGCCCAGCACCTGAGTTCCTGGGGGGACCATCAGTCTTCCTGTTCCCCCCAAAACCCAA
GGACACTCTCATGATCTCCCGGACCCCTGAGGTCACGTGCGTGGTGGTGGACGTGAGCCAGG
AAGACCCCGAGGTCCAGTTCAACTGGTACGTGGATGGCGTGGAGGTGCATAATGCCAAGACA
AAGCCGCGGGAGGAGCAGTTCAACAGCACGTACCGTGTGGTCAGCGTCCTCACCGTCCTGCA
CCAGGACTGGCTGAACGGCAAGGAGTACAAGTGCAAGGTCTCCAACAAAGGCCTCCCGTCCT
CCATCGAGAAAACCATCTCCAAAGCCAAAGGGCAGCCCCGAGAGCCACAGGTGTACACCCTG
CCCCCATCCCAGGAGGAGATGACCAAGAACCAGGTCAGCCTGACCTGCCTGGTCAAAGGCTT
CTACCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAGGCTAACCGTGGAC
AAGAGCAGGTGGCAGGAGGGGAATGTCTTCTCATGCTCCGTGATGCATGAGGCTCTGCACAA
CCACTACACACAGAAGAGCCTCTCCCTGTCTCTGGGTAAATAACCTAGCGTGGCATCTAGAC
ACTCTCGAGAAGGGTTCGATCCCTACCGGTTAGTAATGAGTTTGATATCTCGACAATCAACC
TCTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCATT
TTCTCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGACAATTCCGT
GGTGTTGTCGGGGAAGCTGACGTCCTTTCCATGGCTGCTCGCCTGTGTTGCCACCTGGATTC
TGCGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGGAT

-continued

CTCCCTTTGGGCCGCCTCCCCGCCTGGAAACGGGGGAGGCTAACTGAAACACGGAAGGAGAC
AATACCGGAAGGAACCCGCGCTATGACGGCAATAAAAAGACAGAATAAAACGCACGGGTGTT
GGGTCGTTTGTTCATAAACGCGGGGTTCGGTCCCAGGGCTGGCACTCTGTCGATACCCCACC
GAGACCCCATTGGGGCCAATACGCCCGCGTTTCTTCCTTTTCCCCACCCCACCCCCCAAGTT
CGGGTGAAGGCCCAGGGCTCGCAGCCAACGTCGGGGCGGCAGGCCCTGCCATAGCAGATCTG
CGCAGCTGGGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGCTCCTTTCG
CTTTCTTCCCTTCCTTTCTCGCCACGTTCGCCGGCTTTCCCCGTCAAGCTCTAAATCGGGGC
ATCCCTTTAGGGTTCCGATTTAGTGCTTTACGGCACCTCGACCCCAAAAAACTTGATTAGGG
TGATGGTTCACGTAGTGGGCCATCGCCCTGATAGACGGTTTTTCGCCCTTTGACGTTGGAGT
CCACGTTCTTTAATAGTGGACTCTTGTTCCAAACTGGAACAACACTCAACCCTATCTCGGTC
TATTCTTTTGATTTATAAGGGATTTTGGGGATTTCGGCCTATTGGTTAAAAAATGAGCTGAT
TTAACAAAAATTTAACGCGAATTAATTCTGTGGAATGTGTGTCAGTTAGGGTGTGGAAAGTC
CCCAGGCTCCCCAGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCGCCCA
TTCTCCGCCCCATGGCTGACTAATTTTTTTTATTTATGCAGAGGCCGAGGCCGCCTCTGCCT
CTGAGCTATTCCAGAAGTAGTGAGGAGGCTTTTTTGGAGGCCTAGGCTTTTGCAAAAAGCTC
CCGGGAGCTTGTATATCCATTTTCGGATCTGATCAAGAGACAGGATGAGGATCGTTTCGCAT
GATTGAACAAGATGGATTGCACGCAGGTTCTCCGGCCGCTTGGGTGGAGAGGCTATTCGGCT
ATGACTGGGCACAACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGAACTGCAGGACGA
GGCAGCGCGGCTATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAGGATCTCCTGTCA
TCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTCGCG
CCAGCCGAACTGTTCGCCAGGCTCAAGGCGCGCATGCCCGACGGCGAGGATCTCGTCGTGAC
CCATGGCGATGCCTGCTTGCCGAATATCATGGTGGAAAATGGCCGCTTTTCTGGATTCATCG
ACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAGCGGGACTCTGGG
GTTCGCGAAATGACCGACCAAGCGACGCCCAACCTGCCATCACGAGATTTCGATTCCACCGC
CGCCTTCTATGAAAGGTTGGGCTTCGGAATCGTTTTCCGGGACGCCGGCTGGATGATCCTCC
AGCGCGGGGATCTCATGCTGGAGTTCTTCGCCCACCCCAACTTGTTTATTGCAGCTTATAAT
GGTTACAAATAAAGCAATAGCATCACAAATTTCACAAATAAAGCATTTTTTTCACTGCATTC
TAGTTGTGGTTTGTCCAAACTCATCAATGTATCTTATCATGTCTGTATACCGTCGACCTCTA
GCTAGAGCTTGGCGTAATCATGGTCATAGCTGTTTCCTGTGTGAAATTGTTATCCGCTCACA
ATTCCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAA
TGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCCGAAAAGTGCC
ACCTGACGTCGACGGATCGGGAGATCTCCCGATCCCCTATGGTCGACTCTCAGTACAATCTG
CTCTGATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATGAAGAAT
CTGCTTAGG

-continued

Sequences of expression vectors for mAb 25F1 IgG4/kappa:
>p25F1.VL.hk (SEQ ID NO: 103)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTCA*GACATCGTGCTGACACAGAGCCCTGCCAGCCTGGCTGTTTCTCTGGGACAGAGAG
CCACCATCAGCTGCAAGGCCAGCCAGAGCGTTGACTACGACGGCGACACCTACATGAACTGG
TATCAGCAGAAGCCCGGCCAGCCACCTAAGCTGCTGATCTACACAGCCAGCAACCTGGAAAG
CGGCATCCCCGCCAGATTTTCTGGCAGCGGAAGCGGCACCGACTTCACCCTGAATATCCATC
CTGTGGAAGAGGTGGACGCCGCCACCTACTACTGCCAGCAGAGCAATGAGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGG
CTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGT
GATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGAC
TCTGGGGTTCGCGAAATGACCGACCAAGCGACGCCCAACCTGCCATCACGAGATTTCGATTC
CACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGTATACCGTCGA
CCTCTAGCTAGAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATG
AGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACA

-continued

TGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAA
AGTGCCACCTGACGTCGACGGATCGGGAGATCTCCCGATCCCCTATGGTCGACTCTCAGTAC
AATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATG
AAGAATCTGCTTAGG

>p20F1.VE.hIgG4

(SEQ ID NO: 104)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTC*GGAGGTCCAGCTGCAGCAGTCTGGCGCCGAACTTGTTAGACCTGGCGCTCTGGTCA
AGTGGTCCTGTAAAGCCAGCGGCTTCAACATCAAGGACTACCACATCCACTGGGTCAAGCAG
AGGCCTGAGCAGGGCCTCGATTGGATCGGCTGGATCGACCCCGAGATCGACAAGACCCTGTA
CGACCCCAAGTTCCAGGGCAAAGCCAGAATCACCGCCGACACCAGCAGCAACACAGCCTACC
TGCAACTGAGCAGCCTGACCAGCGAAGATACCGCCGTGTACTACTGCGCCAGAGGAACAGCC
AGAGCCAGCTTCGATTATTGGGGCCAGGGCACCACACTGACCGTGTCATCTGCTAGCACCAA
GGGCCCATCGGTCTTCCCCCTGGCGCCCTGCTCCAGGAGCACCTCCGAGAGCACAGCCGCCC
TGGGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTCAG
CAGCGTGGTGACCGTGCCCTCCAGCAGCTTGGGCACGAAGACCTACACCTGCAACGTAGATC
ACAAGCCCAGCAACACCAAGGTGGACAAGAGAGTTGAGTCCAAATATGGTCCCCCATGCCCA
TCATGCCCAGCACCTGAGTTCCTGGGGGGACCATCAGTCTTCCTGTTCCCCCCAAAACCCAA
GGACACTCTCATGATCTCCCGGACCCCTGAGGTCACGTGCGTGGTGGTGGACGTGAGCCAGG
AAGACCCCGAGGTCCAGTTCAACTGGTACGTGGATGGCGTGGAGGTGCATAATGCCAAGACA
AAGCCGCGGGAGGAGCAGTTCAACAGCACGTACCGTGTGGTCAGCGTCCTCACCGTCCTGCA
CCAGGACTGGCTGAACGGCAAGGAGTACAAGTGCAAGGTCTCCAACAAAGGCCTCCCGTCCT
CCATCGAGAAAACCATCTCCAAAGCCAAAGGGCAGCCCCGAGAGCCACAGGTGTACACCCTG
CCCCCATCCCAGGAGGAGATGACCAAGAACCAGGTCAGCCTGACCTGCCTGGTCAAAGGCTT
CTACCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAGGCTAACCGTGGAC
AAGAGCAGGTGGCAGGAGGGGAATGTCTTCTCATGCTCCGTGATGCATGAGGCTCTGCACAA
CCACTACACACAGAAGAGCCTCTCCCTGTCTCTGGGTAAATAACCTAGCGTGGCATCTAGAC
ACTCTCGAGAAGGGTTCGATCCCTACCGGTTAGTAATGAGTTTGATATCTCGACAATCAACC
TCTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCATT
TTCTCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTGCCA
CCACCTGTCAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGACAATTCCGT
GGTGTTGTCGGGGAAGCTGACGTCCTTTCCATGGCTGCTCGCCTGTGTTGCCACCTGGATTC
TGCGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCGGAT

-continued

CTCCCTTTGGGCCGCCTCCCCGCCTGGAAACGGGGGAGGCTAACTGAAACACGGAAGGAGAC
AATACCGGAAGGAACCCGCGCTATGACGGCAATAAAAAGACAGAATAAAACGCACGGGTGTT
GGGTCGTTTGTTCATAAACGCGGGGTTCGGTCCCAGGGCTGGCACTCTGTCGATACCCCACC
GAGACCCCATTGGGGCCAATACGCCCGCGTTTCTTCCTTTTCCCCACCCCACCCCCCAAGTT
CGGGTGAAGGCCCAGGGCTCGCAGCCAACGTCGGGGCGGCAGGCCCTGCCATAGCAGATCTG
CGCAGCTGGGGCTCTAGGGGGTATCCCCACGCGCCCTGTAGCGGCGCATTAAGCGCGGCGGG
TGTGGTGGTTACGCGCAGCGTGACCGCTACACTTGCCAGCGCCCTAGCGCCCGCTCCTTTCG
CTTTCTTCCCTTCCTTTCTCGCCACGTTCGCCGGCTTTCCCCGTCAAGCTCTAAATCGGGGC
ATCCCTTTAGGGTTCCGATTTAGTGCTTTACGGCACCTCGACCCCAAAAAACTTGATTAGGG
TGATGGTTCACGTAGTGGGCCATCGCCCTGATAGACGGTTTTTCGCCCTTTGACGTTGGAGT
CCACGTTCTTTAATAGTGGACTCTTGTTCCAAACTGGAACAACACTCAACCCTATCTCGGTC
TATTCTTTTGATTTATAAGGGATTTTGGGGATTTCGGCCTATTGGTTAAAAAATGAGCTGAT
TTAACAAAAATTTAACGCGAATTAATTCTGTGGAATGTGTGTCAGTTAGGGTGTGGAAAGTC
CCCAGGCTCCCCAGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCGCCCA
TTCTCCGCCCCATGGCTGACTAATTTTTTTTATTTATGCAGAGGCCGAGGCCGCCTCTGCCT
CTGAGCTATTCCAGAAGTAGTGAGGAGGCTTTTTTGGAGGCCTAGGCTTTTGCAAAAAGCTC
CCGGGAGCTTGTATATCCATTTTCGGATCTGATCAAGAGACAGGATGAGGATCGTTTCGCAT
GATTGAACAAGATGGATTGCACGCAGGTTCTCCGGCCGCTTGGGTGGAGAGGCTATTCGGCT
ATGACTGGGCACAACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGAACTGCAGGACGA
GGCAGCGCGGCTATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAGGATCTCCTGTCA
TCTCACCTTGCTCCTGCCGAGAAAGTATCCATCATGGCTGATGCAATGCGGCGGCTGCATAC
GCTTGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTCGCG
CCAGCCGAACTGTTCGCCAGGCTCAAGGCGCGCATGCCCGACGGCGAGGATCTCGTCGTGAC
CCATGGCGATGCCTGCTTGCCGAATATCATGGTGGAAAATGGCCGCTTTTCTGGATTCATCG
ACTGTGGCCGGCTGGGTGTGGCGGACCGCTATCAGGACATAGCGTTGGCTACCCGTGATATT
GCTGAAGAGCTTGGCGGCGAATGGGCTGACCGCTTCCTCGTGCTTTACGGTATCGCCGCTCC
CGATTCGCAGCGCATCGCCTTCTATCGCCTTCTTGACGAGTTCTTCTGAGCGGGACTCTGGG
GTTCGCGAAATGACCGACCAAGCGACGCCCAACCTGCCATCACGAGATTTCGATTCCACCGC
CGCCTTCTATGAAAGGTTGGGCTTCGGAATCGTTTTCCGGGACGCCGGCTGGATGATCCTCC
AGCGCGGGGATCTCATGCTGGAGTTCTTCGCCCACCCCAACTTGTTTATTGCAGCTTATAAT
GGTTACAAATAAAGCAATAGCATCACAAATTTCACAAATAAAGCATTTTTTTCACTGCATTC
TAGTTGTGGTTTGTCCAAACTCATCAATGTATCTTATCATGTCTGTATACCGTCGACCTCTA
GCTAGAGCTTGGCGTAATCATGGTCATAGCTGTTTCCTGTGTGAAATTGTTATCCGCTCACA
ATTCCACACAACATACGAGCCGGAAGCATAAAGTGTAAAGCCTGGGGTGCCTAATGAGTGAG
CTAACTCACATTAATTGCGTTGCGCTCACTGCCCGCTTTCCAGTCGGGAAACCTGTCGTGCC
GCTGCATTAATGAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCAA
TGCTCACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCCAACC
CGGTAAGACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTCT
GACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCATCCAGTC
TATTAATTGTTGCCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGGTGAG
TACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTT
CTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAAC
AGGAAGGCAAAATGCCGCAAAAAAGGGAATAAGGGCGACACGGAAATGTTGAATACTCATAC
TCTTCCTTTTTCAATATTATTGAAGCATTTATCAGGGTTATTGTCTCATGAGCGGATACATA
TTTGAATGTATTTAGAAAAATAAACAAATAGGGGTTCCGCGCACATTTCCCCGAAAAGTGCC
ACCTGACGTCGACGGATCGGGAGATCTCCCGATCCCCTATGGTCGACTCTCAGTACAATCTG
CTCTGATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATGAAGAAT
CTGCTTAGG

-continued

Sequences of expression vectors for mAb 7C11.1 IgG2/kappa:
>p7C11.1.VL.hk (SEQ ID NO: 105)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTCA*GACAACGTGCTGACACAGAGCCCTGCCAGCCTGGCTGTTTCTCTGGGACAGAGAG
CCACCATCAGCTGCAAGGCCAGCCAGAGCGTTGACTACGACGGCGACAGCTACATGAACTGG
TATCAGCAGAAGCCCGGCCAGCCACCTAAGGTGTTCATCTACGCCGCCAGCAACCTGGAAAG
CGGCATCCCTGCCAGATTTCTGGCTCTGGCAGCGGCACCAACTTCACCCTGAACATTCACC
CCGTGGAAGAAGAGGACGCCGCCACCTACTACTGCCAGCAGAGCAATGAGGACCCCTGGACA
TTTGGCGGAGGCACCAAGCTGGAAATCAAGCGTACGGTGGCTGCACCATCTGTCTTCATCTT
CCCGCCATCTGATGAGCAGTTGAAATCTGGAACTGCCTCTGTTGTGTGCCTGCTGAATAACT
TCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGAC
GCTGAGCAAAGCAGACTACGAGAAACACAAAGTCTACGCCTGCGAAGTCACCCATCAGGGCC
TGAGCTCGCCCGTCACAAAGAGCTTCAACAGGGGAGAGTGTTAGAGGGAGCTAGCGTGGCAT
CTAGACACTCTCGAGAAGGGTTCGATCCCTACCGGTTAGTAATGAGTTTGATATCTCGACAA
TCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGACAA
TTCCGTGGTGTTGTCGGGGAAGCTGACGTCCTTTCCATGGCTGCTCGCCTGTGTTGCCACCT
GGATTCTGCGCGGGACGTCCTTCTGCTACGTCCCTTCGGCCCTCAATCCAGCGGACCTTCCT
TCCCGCGGCCTGCTGCCGGCTCTGCGGCCTCTTCCGCGTCTTCGCCTTCGCCCTCAGACGAG
TCGGATCTCCCTTTGGGCCGCCTCCCCGCCTGGAAACGGGGGAGGCTAACTGAAACACGGAA
GGAGACAATACCGGAAGGAACCCGCGCTATGACGGCAATAAAAAGACAGAATAAAACGCACG
GGTGTTGGGTCGTTTGTTCATAAACGCGGGGTTCGGTCCCAGGGCTGGCACTCTGTCGATAC
CCCACCGAGACCCCATTGGGGCCAATACGCCCGCGTTTCTTCCTTTTCCCCACCCCACCCCC
CAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGC
GGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGCATCCCTTTAGGGTTCCGATTTAGTGCTTTACGGCACCTCGACCCCAAAAAACTTGA
TTAGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGTCTATTCTTTTGATTTATAAGGGATTTTGGGGATTTCGGCCTATTGGTTAAAAAATGA
GCTGATTTAACAAAAATTTAACGCGAATTAATTCTGTGGAATGTGTGTCAGTTAGGGTGTGG
AAAGTCCCCAGGCTCCCCAGCAGGCAGAAGTATGCAAAGCATGCATCTCAATTAGTCAGCAA
CCAGGTGTGGAAAGTCCCCAGGCTCCCCAGCAGGCAGAAGTATGCAAAGCATGCATCTCAAT
TAGTCAGCAACCATAGTCCCGCCCCTAACTCCGCCCATCCCGCCCCTAACTCCGCCCAGTTC
CGCCCATTCTCCGCCCCATGGCTGACTAATTTTTTTTATTTATGCAGAGGCCGAGGCCGCCT
CTGCCTCTGAGCTATTCCAGAAGTAGTGAGGAGGCTTTTTTGGAGGCCTAGGCTTTTGCAAA
AAGCTCCCGGGAGCTTGTATATCCATTTTCGGATCTGATCAAGAGACAGGATGAGGATCGTT
TCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCA
GCGCAGGGGCGCCCGGTTCTTTTTGTCAAGACCGACCTGTCCGGTGCCCTGAATGAACTGCA
GGACGAGGCAGCGCGGCTATCGTGGCTGGCCACGACGGGCGTTCCTTGCGCAGCTGTGCTCG
ACGTTGTCACTGAAGCGGGAAGGGACTGGCTGCTATTGGGCGAAGTGCCGGGGCAGGATCTC
CTGTCATCTCACCTTGCTCCTGCCGAGAAAGTATCCATCATGGCTGATGCAATGCGGCGGCT
GCATACGCTTGATCCGGCTACCTGCCCATTCGACCACCAAGCGAAACATCGCATCGAGCGAG
CACGTACTCGGATGGAAGCCGGTCTTGTCGATCAGGATGATCTGGACGAAGAGCATCAGGGG
CTCGCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGT
GATATTGCTGAAGAGCTTGGCGGCGAATGGGCTGACCGCTTCCTCGTGCTTTACGGTATCGC
CGCTCCCGATTCGCAGCGCATCGCCTTCTATCGCCTTCTTGACGAGTTCTTCTGAGCGGGAC
TCTGGGGTTCGCGAAATGACCGACCAAGCGACGCCCAACCTGCCATCACGAGATTTCGATTC
CACCGCCGCCTTCTATGAAAGGTTGGGCTTCGGAATCGTTTTCCGGGACGCCGGCTGGATGA
TCCTCCAGCGCGGGGATCTCATGCTGGAGTTCTTCGCCCACCCCAACTTGTTTATTGCAGCT
TATAATGGTTACAAATAAAGCAATAGCATCACAAATTTCACAAATAAAGCATTTTTTTCACT
GCATTCTAGTTGTGGTTTGTCCAAACTCATCAATGTATCTTATCATGTCTGTATACCGTCGA
CCTCTAGCTAGAGCTTGGCGTAATCATGGTCATAGCTGTTTCCTGTGTGAAATTGTTATCCG
CTCACAATTCCACACAACATACGAGCCGGAAGCATAAAGTGTAAAGCCTGGGGTGCCTAATG
AGTGAGCTAACTCACATTAATTGCGTTGCGCTCACTGCCCGCTTTCCAGTCGGGAAACCTGT
CGTGCCAGCTGCATTAATGAATCGGCCAACGCGCGGGGAGAGGCGGTTTGCGTATTGGGCGC
TCTTCCGCTTCCTCGCTCACTGACTCGCTGCGCTCGGTCGTTCGGCTGCGGCGAGCGGTATC
AGCTCACTCAAAGGCGGTAATACGGTTATCCACAGAATCAGGGGATAACGCAGGAAAGAACA

-continued

TGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAAGCGTGGCGCTT
TCTCAATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAG
AAGGACAGTATTTGGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGTTTGCAAGCAGCAG
ATTACGCGCAGAAAAAAAGGATCTCAAGAAGATCCTTTGATCTTTTCTACGGGGTCTGACGC
TCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTC
AGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCTCTTGCCC
GGCGTCAATACGGGATAATACCGCGCCACATAGCAGAACTTTAAAAGTGCTCATCATTGGAA
AACGTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTGAGC
AAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGA
TACATATTTGAATGTATTTAGAAAAATAAACAAATAGGGGTTCCGCGCACATTTCCCCGAAA
AGTGCCACCTGACGTCGACGGATCGGGAGATCTCCCGATCCCCTATGGTCGACTCTCAGTAC
AATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATG
AAGAATCTGCTTAGG

>p7C11.1.VH.hIgG2

(SEQ ID NO: 106)

GTTAGGCGTTTTGCGCTGCTTCGCGATGTACGGGCCAGATATACGCGTTGACATTGATTATT
GACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATG
GGTGGAGTATTTACGGTAAACTGCCCACTTGGCAGTACATCAAGTGTATCATATGCCAAGTA
CGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTG
ACCTCCATAGAAGACACCGGGACCGATCCAGCCTCCGGACTCTAGAGGATCGAACCCTTAAG
CTTGCCACC*ATGTACAGGATGCAACTCCTGTCTTGCATTGCACTAAGTCTTGCACTTGTCAC*
*GAATTC*GGAAGTGAAGCTGGTGGAAAGCGGCGGAGGACTGGTTCAACCTGGCGGATCTCTGA
AGCTGAGCTGTGCCGCCAGCGGCTTCACCTTCAGCAGATACACAATGAGCTGGGTCCGACAG
ACCCCTGAGAAGAGACTGGAATGGGTCGCCAAGATCAGAAACGTCGGCGGCATCACCTACTA
TCCCGACACCGTGAAGGGCAGATTCACCATCTCCAGAGACAACGCCAAGAACACCCTGTACC
TGCAGATGAGCAGCCTGAAGTCCGAGGACACCGCCATGTACTACTGCGCCAGACACTACTAC
GGCAGCGAGGACTACTTCGACTATTGGGGCCAGGGCACCACACTGACCGTTAGCTCTGCTAG
CACCAAGGGCCCATCGGTCTTCCCCCTGGCGCCCTGCTCCAGGAGCACCTCCGAGAGCACAG
CGGCCCTGGGCTGCCTGGTCAAGGACTACTTCCCCGAACCGGTGACGGTGTCGTGGAACTCA
GGCGCTCTGACCAGCGGCGTGCACACCTTCCCAGCTGTCCTACAGTCCTCAGGACTCTACTC
CCTCAGCAGCGTGGTGACCGTGCCCTCCAGCAACTTCGGCACCCAGACCTACACCTGCAACG
TAGATCACAAGCCCAGCAACACCAAGGTGGACAAGACAGTTGAGCGCAAATGTTGTGTCGAG
TGCCCACCGTGCCCAGCACCACCTGTGGCAGGACCGTCAGTCTTCCTCTTCCCCCCAAAACC
CAAGGACACCCTCATGATCTCCCGGACCCCTGAGGTCACGTGCGTGGTGGTGGACGTGAGCC
ACGAAGACCCCGAGGTCCAGTTCAACTGGTACGTGGACGGCGTGGAGGTGCATAATGCCAAG
ACAAAGCCACGGGAGGAGCAGTTCAACAGCACGTTCCGTGTGGTCAGCGTCCTCACCGTTGT
GCACCAGGACTGGCTGAACGGCAAGGAGTACAAGTGCAAGGTCTCCAACAAAGGCCTCCCAG
CCCCCATCGAGAAAACCATCTCCAAAACCAAAGGGCAGCCCCGAGAACCACAGGTGTACACC
CTGCCCCCATCCCGGGAGGAGATGACCAAGAACCAGGTCAGCCTGACCTGCCTGGTCAAAGG
CTTCTACCCCAGCGACATCGCCGTGGAGTGGGAGAGCAATGGGCAGCCGGAGAACAACTACA
AGACCACGCCTCCCATGCTGGACTCCGACGGCTCCTTCTTCCTCTACAGCAAGCTCACCGTG
GACAAGAGCAGGTGGCAGCAGGGGAACGTCTTCTCATGCTCCGTGATGCATGAGGCTCTGCA
CAACCACTACACGCAGAAGAGCCTCTCCCTGTCTCCGGGTAAATGACCTAGCGTGGCATCTA
GACACTCTCGAGAAGGGTTCGATCCCTACCGGTTAGTAATGAGTTTGATATCTCGACAATCA
ACCTCTGGATTACAAAATTTGTGAAAGATTGACTGGTATTCTTAACTATGTTGCTCCTTTTA
CGCTATGTGGATACGCTGCTTTAATGCCTTTGTATCATGCTATTGCTTCCCGTATGGCTTTC
ATTTTCTCCTCCTTGTATAAATCCTGGTTGCTGTCTCTTTATGAGGAGTTGTGGCCCGTTGT
CAGGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGGAA
CTCATCGCCGCCTGCCTTGCCCGCTGCTGGACAGGGGCTCGGCTGTTGGGCACTGACAATTC
CGTGGTGTTGTCGGGGAAGCTGACGTCCTTTCCATGGCTGCTCGCCTGTGTTGCCACCTGGA
TTCTGCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACGAGTCG

-continued

GATCTCCCTTTGGGCCGCCTCCCCGCCTGGAAACGGGGGAGGCTAACTGAAACACGGAAGGA
GACAATACCGGAAGGAACCCGCGCTATGACGGCAATAAAAAGACAGAATAAAACGCACGGGT
GTTGGGTCGTTTGTTCATAAACGCGGGGTTCGGTCCCAGGGCTGGCACTCTGTCGATACCCC
ACCGAGACCCCATTGGGGCCAATACGCCCGCGTTTCTTCCTTTTCCCCACCCCACCCCCCAA
GTTCGGGTGAAGGCCCAGGGCTCGCAGCCAACGTCGGGGCGGCAGGCCCTGCCATAGCAGAT
CTGCGCAGCTGGGGCTCTAGGGGGTATCCCCACGCGCCCTGTAGCGGCGCATTAAGCGCGGC
GGGTGTGGTGGTTACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGTCAAGCTCTAAATCGG
GGCATCCCTTTAGGGTTCCGATTTAGTGCTTTACGGCACCTCGACCCCAAAAAACTTGATTA
GGGTGATGGTTCACGTAGTGGGCCATCGCCCTGATAGACGGTTTTTCGCCCTTTGACGTTGG
AGTCCACGTTCTTTAATAGTGGACTCTTGTTCCAAACTGGAACAACACTCAACCCTATCTCG
GTCTATTCTTTTGATTTATAAGGGATTTTGGGGATTTCGGCCTATTGGTTAAAAAATGAGCT
GATTTAACAAAAATTTAACGCGAATTAATTCTGTGGAATGTGTGTCAGTTAGGGTGTGGAAA
GTCCCCAGGCTCCCCAGCAGGCAGAAGTATGCAAAGCATGCATCTCAATTAGTCAGCAACCA
GGTGTGGAAAGTCCCCAGGCTCCCCAGCAGGCAGAAGTATGCAAAGCATGCATCTCAATTAG
TCAGCAACCATAGTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCGAGGCCGCCTCTG
CCTCTGAGCTATTCCAGAAGTAGTGAGGAGGCTTTTTTGGAGGCCTAGGCTTTTGCAAAAAG
CTCCCGGGAGCTTGTATATCCATTTTCGGATCTGATCAAGAGACAGGATGAGGATCGTTTCG
CATGATTGAACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCTGTCAGCG
CAGGGGCGCCCGGTTCTTTTTGTCAAGACCGACCTGTCCGGTGCCCTGAATGAACTGCAGGA
CGAGGCAGCGCGGCTATCGTGGCTGGCCACGACGGGCGTTCCTTGCGCAGCTGTGCTCGACG
TTGTCACTGAAGCGGGAAGGGACTGGCTGCTATTGGGCGAAGTGCCGGGGCAGGATCTCCTG
TCATCTCACCTTGCTCCTGCCGAGAAAGTATCCATCATGGCTGATGCAATGCGGCGGCTGCA
TACGCTTGATCCGGCTACCTGCCCATTCGACCACCAAGCGAAACATCGCATCGAGCGAGCAC
GTACTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGTCGT
GACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGAT
ATTGCTGAAGAGCTTGGCGGCGAATGGGCTGACCGCTTCCTCGTGCTTTACGGTATCGCCGC
TCCCGATTCGCAGCGCATCGCCTTCTATCGCCTTCTTGACGAGTTCTTCTGAGCGGGACTCT
GGGGTTCGCGAAATGACCGACCAAGCGACGCCCAACCTGCCATCACGAGATTTCGATTCCAC
CGCCGCCTTCTATGAAAGGTTGGGCTTCGGAATCGTTTTCCGGGACGCCGGCTGGATGATCC
TCCAGCGCGGGGATCTCATGCTGGAGTTCTTCGCCCACCCCAACTTGTTTATTGCAGCTTAT
AATGGTTACAAATAAAGCAATAGCATCACAAATTTCACAAATAAAGCATTTTTTTCACTGCA
TTCTAGTTGTGGTTTGTCCAAACTCATCAATGTATCTTATCATGTCTGTATACCGTCGACCT
CTAGCTAGAGCTTGGCGTAATCATGGTCATAGCTGTTTCCTGTGTGAAATTGTTATCCGCTC
ACAATTCCACACAACATACGAGCCGGAAGCATAAAGTGTAAAGCCTGGGGTGCCTAATGAGT
GAGCTAACTCACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGAACATGT
GAGCAAAAGGCCAGCAAAAGGCCAGGAACCGTAAAAAGGCCGCGTTGCTGGCGTTTTTCCAT
AGGCTCCGCCCCCCTGACGAGCATCACAAAAATCGACGCTCAAGTCAGAGGTGGCGAAACCC
GACAGGACTATAAAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGCGTGGCGCTTTCT
CAATGCTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCT
AGATCCTTTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTATTTCGTTC
ATCCATAGTTGCCTGACTCCCCGTCGTGTAGATAACTACGATACGGGAGGGCTTACCATCTG
GCCCCAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATGGCTTCATTCAGC
TCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGT
GAGTACTCAACCAAGTCATTCTGAGAATAGTGTATGCGGCGACCGAGTTGCTCTTGCCCGGC
GTCAATACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAA
AACAGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGT
GCCACCTGACGTCGACGGATCGGGAGATCTCCCGATCCCCTATGGTCGACTCTCAGTACAAT
CTGCTCTGATGCCGCATAGTTAAGCCAGTATCTGCTCCCTGCTTGTGTGTTGGAGGTCGCTG
AGTAGTGCGCGAGCAAAATTTAAGCTACAACAAGGCAAGGCTTGACCGACAATTGCATGAAG
AATCTGCTTAGG

REFERENCES

1. Lendon, C. L., et al. E280A PS-1 mutation causes Alzheimer's disease but age of onset is not modified by ApoE alleles. Hum Mutat 10, 186-195 (1997).
2. Aguirre-Acevedo, D. C., et al. [Validity and reliability of the CERAD-Col neuropsychological battery]. Rev Neurol 45, 655-660 (2007).
3. Yesavage, J. A. Opportunities for and obstacles to treatments for dementias. J Am Geriatr Soc 31, 59-60 (1983).
4. Reisberg, B. Functional assessment staging (FAST). Psychopharmacol Bull 24, 653-659 (1988).
5. Mahley, R. W., Huang, Y. & Rall, S. C., Jr. Pathogenesis of type III hyperlipoproteinemia (dysbetalipoproteinemia). Questions, quandaries, and paradoxes. J Lipid Res 40, 1933-1949 (1999).
6. Fisher, S., et al. A scalable, fully automated process for construction of sequence-ready human exome targeted capture libraries. Genome Biol 12, $R_1$ (2011).
7. Lek, M., et al. Analysis of protein-coding genetic variation in 60,706 humans. Nature 536, 285-291 (2016).
8. Li, H. Aligning sequence reads, clone sequences and assembly contigs with BWA-MEM . . . arXiv: 1303.3997v1 [q-bio.GN] (2013).

9 Kohler, S., et al. The Human Phenotype Ontology project: linking molecular biology and disease through phenotype data. Nucleic Acids Res 42, D966-974 (2014).

10. Smedley, D., et al. A Whole-Genome Analysis Framework for Effective Identification of Pathogenic Regulatory Variants in Mendelian Disease. Am J Hum Genet 99, 595-606 (2016).
11. Chen, J., Li, Q. & Wang, J. Topology of human apolipoprotein E3 uniquely regulates its diverse biological functions. Proc Natl Acad Sci USA 108, 14813-14818 (2011).
12. Rose, A. S., et al. NGL viewer: web-based molecular graphics for large complexes. Bioinformatics 34, 3755-3758 (2018).
13. Zhong, L., et al. A rapid and cost-effective method for genotyping apolipoprotein E gene polymorphism. Mol Neurodegener 11, 2 (2016).
14. Quiroz, Y. T., et al. Association Between Amyloid and Tau Accumulation in Young Adults With Autosomal Dominant Alzheimer Disease. JAMA Neurol (2018).
15. Fleisher, A. S., et al. Associations between biomarkers and age in the presenilin 1 E280A autosomal dominant Alzheimer disease kindred: a cross-sectional study. JAMA Neurol 72, 316-324 (2015).
16. Becker, J. A., et al. Amyloid-β associated cortical thinning in clinically normal elderly. Ann Neurol 69, 1032-1042 (2011).
17. Braak, H., Rüb, U., Schultz, C. & Del Tredici, K. Vulnerability of cortical neurons to Alzheimer's and Parkinson's diseases. J Alzheimers Dis 9, 35-44 (2006).
18. Braak, H. & Braak, E. Diagnostic criteria for neuropathologic assessment of Alzheimer's disease. Neurobiol Aging 18, S85-88 (1997).
19. Johnson, K. A., et al. Tau positron emission tomographic imaging in aging and early Alzheimer disease. Ann Neurol 79, 110-119 (2016).
20. Chien, D. T., et al. Early clinical PET imaging results with the novel PHF-tau radioligand [F-18]-T807. J Alzheimers Dis 34, 457-468 (2013).
21. Wang, L., et al. Evaluation of Tau Imaging in Staging Alzheimer Disease and Revealing Interactions Between beta-Amyloid and Tauopathy. JAMA Neurol 73, 1070-1077 (2016).
22. Logan, J., et al. Graphical analysis of reversible radioligand binding from time-activity measurements applied to [N-11C-methyl]-(−)-cocaine PET studies in human subjects. J Cereb Blood Flow Metab 10, 740-747 (1990).
23. Amariglio, R. E., et al. Subjective cognitive concerns, amyloid-β, and neurodegeneration in clinically normal elderly. Neurology 85, 56-62 (2015).
24. Hedden, T., et al. Disruption of functional connectivity in clinically normal older adults harboring amyloid burden. J Neurosci 29, 12686-12694 (2009).
25. Beecham, G. W., et al. Genome-wide association meta-analysis of neuropathologic features of Alzheimer's disease and related dementias. PLOS Genet 10, e1004606 (2014).
26. Hashimoto, T., et al. Apolipoprotein E, especially apolipoprotein E4, increases the oligomerization of amyloid beta peptide. J Neurosci 32, 15181-15192 (2012).
27. Hudry, E., et al. Gene transfer of human Apoe isoforms results in differential modulation of amyloid deposition and neurotoxicity in mouse brain. Sci Transl Med 5, 212ra161 (2013).
28. Lemere, C. A., et al. The E280A presenilin 1 Alzheimer mutation produces increased A beta 42 deposition and severe cerebellar pathology. Nat Med 2, 1146-1150 (1996).
29. Quiroz, Y. T., et al. Association Between Amyloid and Tau Accumulation in Young Adults With Autosomal Dominant Alzheimer Disease. JAMA Neurol (2018).
30. Acosta-Baena, N., et al. Pre-dementia clinical stages in presenilin 1 E280A familial early-onset Alzheimer's disease: a retrospective cohort study. Lancet Neurol 10, 213-220 (2011).
31. Lopera, F., et al. Clinical features of early-onset Alzheimer disease in a large kindred with an E280A presenilin-1 mutation. JAMA 277, 793-799 (1997).
32. Cacace, R., Sleegers, K. & Van Broeckhoven, C. Molecular genetics of early-onset Alzheimer's disease revisited. Alzheimers Dement 12, 733-748 (2016).
33. Albert, M. S., et al. The diagnosis of mild cognitive impairment due to Alzheimer's disease: recommendations from the National Institute on Aging-Alzheimer's Association workgroups on diagnostic guidelines for Alzheimer's disease. Alzheimers Dement 7, 270-279 (2011).
34. Smedley, D., et al. A Whole-Genome Analysis Framework for Effective Identification of Pathogenic Regulatory Variants in Mendelian Disease. Am J Hum Genet 99, 595-606 (2016).
35. Corder, E. H., et al. Protective effect of apolipoprotein E type 2 allele for late onset Alzheimer disease. Nat Genet 7, 180-184 (1994).
36. Corder, E. H., et al. Gene dose of apolipoprotein E type 4 allele and the risk of Alzheimer's disease in late onset families. Science 261, 921-923 (1993).
37. Farrer, L. A., et al. Effects of age, sex, and ethnicity on the association between apolipoprotein E genotype and Alzheimer disease. A meta-analysis. APOE and Alzheimer Disease Meta Analysis Consortium. JAMA 278, 1349-1356 (1997).
38. Wardell, M. R., Brennan, S. O., Janus, E. D., Fraser, R. & Carrell, R. W. Apolipoprotein E2-Christchurch (136 Arg - - - - Ser). New variant of human apolipoprotein E in a patient with type III hyperlipoproteinemia. J Clin Invest 80, 483-490 (1987).
39. Candas-Estebanez, B., et al. APOE Variants E2, E3, and E4 Can Be Miscalled By Classical PCR-RFLP When The Christchurch Variant Is Also Present. J Clin Lab Anal 31 (2017).

40. Wardell M R, Brennan S O, Janus E D, Fraser R, Carrell R W. Apolipoprotein E2-Christchurch (136 Arg - - - - Ser). New variant of human apolipoprotein E in a patient with type III hyperlipoproteinemia. J Clin Invest 1987; 80:483-90.
41. Velez J I, Lopera F, Sepulveda-Falla D, et al. APOE*E2 allele delays age of onset in PSEN1 E280A Alzheimer's disease. Mol Psychiatry 2016; 21:916-24.
42. Hollingworth P, Harold D, Sims R, et al. Common variants at ABCA7, MS4A6A/MS4A4E, EPHA1, CD33 and CD2AP are associated with Alzheimer's disease. Nat Genet 2011; 43:429-35.
43. Wardell, M. R., Brennan, S. O., Janus, E. D., Fraser, R. & Carrell, R. W. Apolipoprotein E2-Christchurch (136 Arg - - - Ser). New variant of human apolipoprotein E in a patient with type III hyperlipoproteinemia. J Clin Invest 80, 483-490 (1987).
44. Mahley, R. W., Huang, Y. & Rall, S. C., Jr. Pathogenesis of type III hyperlipoproteinemia (dysbetalipoproteinemia). Questions, quandaries, and paradoxes. J Lipid Res 40, 1933-1949 (1999).
45. Mahley R W. Apolipoprotein E: from cardiovascular disease to neurodegenerative disorders. J Mol Med (Berl) 2016; 94:739-46.
46. Romeo S, Pennacchio L A, Fu Y, et al. Population-based resequencing of ANGPTL4 uncovers variations that reduce triglycerides and increase HDL. Nat Genet 2007; 39:513-6.
47. Mahley, R. W. Apolipoprotein E: from cardiovascular disease to neurodegenerative disorders. J Mol Med (Berl) 94, 739-746 (2016).
48. Hashimoto, T., et al. Apolipoprotein E, especially apolipoprotein E4, increases the oligomerization of amyloid beta peptide. J Neurosci 32, 15181-15192 (2012).
49. Walsh, D. M., et al. Naturally secreted oligomers of amyloid beta protein potently inhibit hippocampal long-term potentiation in vivo. Nature 416, 535-539 (2002).
50. Lalli, M. A., et al. Whole-genome sequencing suggests a chemokine gene cluster that modifies age at onset in familial Alzheimer's disease. Mol Psychiatry 20, 1294-1300 (2015).
51. Huynh, T. V., et al. Age-Dependent Effects of apoE Reduction Using Antisense Oligonucleotides in a Model of beta-amyloidosis. Neuron 96, 1013-1023 e1014 (2017).
52. Huynh, T. V., et al. Age-Dependent Effects of apoE Reduction Using Antisense Oligonucleotides in a Model of beta-amyloidosis. Neuron 96, 1013-1023 e1014 (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising an anti-Apolipoprotein E (ApoE) antibody or an antigen-binding fragment thereof, wherein the antibody or the antigen-binding fragment thereof comprises: (a) a heavy chain variable region (VH) that comprises: (i) a heavy chain complementarity determining region 1 (VHCDR1) sequence according to the amino acid sequence of SEQ ID NO: 7, (ii) a heavy chain variable region 2 (VHCDR2) sequence according to the amino acid sequence of SEQ ID NO: 8, and (iii) a heavy chain variable region 3 (VHCDR3) sequence according to the amino acid sequence of SEQ ID NO 9; and (b) a light chain variable region (VL) that comprises: (i) a light chain variable region 1 (VLCDR1) sequence according to the amino acid sequence of SEQ ID NO: 4, (ii) a light chain variable region 2 (VLCDR2) sequence according to the amino acid sequence of SEQ ID NO: 5, and (iii) a light chain variable region 3 (VLCDR3) sequence according to the amino acid sequence of SEQ ID NO: 6.

2. The composition of claim 1, wherein the antibody or the antigen-binding fragment thereof comprises: (a) a VH sequence with at least 80% sequence identity to amino acids 20-139 of the amino acid sequence of SEQ ID NO: 13 and comprises VHCDR1, VHCDR2, and VHCDR3 having the amino acid sequences of SEQ ID NOs: 7, 8, and 9, respectively; and (b) a VL sequence with at least 80% sequence identity to amino acids 21-131 of the amino acid sequence of SEQ ID NO: 12 and comprises VLCDR1, VLCDR2, and VLCDR3 having the amino acid sequences of SEQ ID NOs: 4, 5, and 6, respectively.

3. The composition of claim 2, wherein the antibody or the antigen-binding fragment thereof comprises: (a) a VH sequence with at least 85% sequence identity to amino acids 20-139 of the amino acid sequence of SEQ ID NO: 13 and comprises VHCDR1, VHCDR2, and VHCDR3 having the amino acid sequences of SEQ ID NOs: 7, 8, and 9, respectively; and (b) a VL sequence with at least 85% sequence identity to amino acids 21-131 of the amino acid sequence of SEQ ID NO: 12 and comprises VLCDR1, VLCDR2, and VLCDR3 having the amino acid sequences of SEQ ID NOs: 4, 5, and 6, respectively.

4. The composition of claim 1, wherein the antibody or the antigen-binding fragment thereof is a humanized or chimeric antibody or an antigen-binding fragment thereof.

5. The composition of claim 1, wherein the antibody is a monoclonal antibody, or wherein the antigen binding fragment thereof is a single-chain Fv (scFv), a Fab, a Fab' or a F(ab')2.

6. The composition of claim 1, wherein the antibody is a monoclonal antibody that comprises (i) a mouse IgG1, IgG2a, IgG2b, IgG2c, or IgG3 heavy chain constant region, or (ii) a human IgG1, IgG2, IgG3, or IgG4 heavy chain constant region.

7. A pharmaceutical composition comprising the composition of claim 1 and a pharmaceutically acceptable diluent, carrier or excipient.

8. A composition comprising an isolated polynucleotide or polynucleotides encoding the anti-ApoE antibody or antigen binding fragment thereof of claim 1.

9. A composition a comprising an isolated host cell comprising an isolated polynucleotide or polynucleotides encoding the anti-ApoE antibody or antigen binding fragment thereof of claim 1.

* * * * *